United States Patent
Morris et al.

(10) Patent No.: US 9,149,378 B2
(45) Date of Patent: Oct. 6, 2015

(54) AXIALLY NESTED SLIDE AND LOCK EXPANDABLE DEVICE

(75) Inventors: Andrew Morris, San Diego, CA (US);
Eric Schmid, San Diego, CA (US);
Jeffrey Sheriff, San Marcos, CA (US);
Brandon Felkins, Half Moon Bay, CA (US)

(73) Assignee: REVA MEDICAL, INC., San Diego, CA (US)

( * ) Notice: Subject to any disclaimer, the term of this patent is extended or adjusted under 35 U.S.C. 154(b) by 498 days.

(21) Appl. No.: 12/193,673

(22) Filed: Aug. 18, 2008

(65) Prior Publication Data
US 2009/0030501 A1 Jan. 29, 2009

Related U.S. Application Data

(63) Continuation-in-part of application No. 11/196,800, filed on Aug. 2, 2005.

(51) Int. Cl.
*A61F 2/93* (2013.01)
*A61F 2/92* (2013.01)
*A61F 2/915* (2013.01)
(Continued)

(52) U.S. Cl.
CPC . *A61F 2/92* (2013.01); *A61F 2/915* (2013.01); *A61F 2/91* (2013.01); *A61F 2/93* (2013.01); *A61F 2/94* (2013.01); *A61F 2002/91591* (2013.01); *A61F 2210/0004* (2013.01); *A61F 2210/0014* (2013.01); *A61F 2220/0025* (2013.01); *A61F 2250/001* (2013.01);
(Continued)

(58) Field of Classification Search
CPC ....................................................... A61F 2/93
See application file for complete search history.

(56) References Cited

U.S. PATENT DOCUMENTS

| | | | |
|---|---|---|---|
| 2,361,506 | A | 10/1944 | Gray et al. |
| 3,620,218 | A | 11/1971 | Schmitt |

(Continued)

FOREIGN PATENT DOCUMENTS

| | | |
|---|---|---|
| AU | 2013204977 B2 | 5/2014 |
| CA | 2368659 | 10/2000 |

(Continued)

OTHER PUBLICATIONS

"Intermediate", Online Oxford English Dictionary, date accessed Nov. 1, 2010, p. 1.*

(Continued)

*Primary Examiner* — Thomas J Sweet
*Assistant Examiner* — Rebecca Preston
(74) *Attorney, Agent, or Firm* — Knobbe Martens Olson & Bear LLP

(57) ABSTRACT

The inventions relate generally to expandable medical implants for maintaining support of a body lumen and, in particular, to an axially nested, diametrically expandable, slide and lock vascular device for enlarging an occluded portion of a vessel. The axially nested vascular device desirably achieves both competitive crossing profiles while maintaining other key features, such as, for example, radial strength and luminal patency. The collapsed profile can also be made very thin without compromising radial strength. Thus, the vascular device can advantageously be deployed in small and difficult to reach areas or vessels. The axial nesting substantially eliminates radial overlap between mating structural elements thereby desirably allowing for a low, uniform profile.

58 Claims, 75 Drawing Sheets

(51) Int. Cl.
*A61F 2/94* (2013.01)
*A61F 2/91* (2013.01)

(52) U.S. Cl.
CPC . *A61F2250/0067* (2013.01); *A61F 2250/0098* (2013.01)

(56) References Cited

U.S. PATENT DOCUMENTS

| | | |
|---|---|---|
| 4,261,390 A | 4/1981 | Belofsky |
| 4,383,555 A | 5/1983 | Finley |
| 4,553,545 A | 11/1985 | Maass et al. |
| 4,576,532 A | 3/1986 | Hanson et al. |
| 4,714,508 A | 12/1987 | Chivens et al. |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,762,129 A | 8/1988 | Bonzel |
| 4,776,337 A | 10/1988 | Palmaz |
| 4,788,751 A | 12/1988 | Shely et al. |
| 4,817,600 A | 4/1989 | Herms et al. |
| 4,877,030 A | 10/1989 | Beck et al. |
| 4,922,905 A | 5/1990 | Strecker |
| 4,954,126 A | 9/1990 | Wallstén |
| 4,980,449 A | 12/1990 | Kohn et al. |
| 5,007,926 A | 4/1991 | Derbyshire |
| 5,040,548 A | 8/1991 | Yock |
| 5,059,211 A | 10/1991 | Stack et al. |
| 5,061,273 A | 10/1991 | Yock |
| 5,092,877 A | 3/1992 | Pinchuk |
| 5,099,060 A | 3/1992 | Kohn et al. |
| 5,108,416 A | 4/1992 | Ryan et al. |
| 5,108,417 A | 4/1992 | Sawyer |
| 5,140,094 A | 8/1992 | Kohn et al. |
| 5,151,100 A | 9/1992 | Abele et al. |
| 5,158,548 A | 10/1992 | Lau et al. |
| 5,192,307 A | 3/1993 | Wall |
| 5,194,570 A | 3/1993 | Kohn et al. |
| 5,195,984 A | 3/1993 | Schatz |
| 5,197,978 A | 3/1993 | Hess |
| 5,198,507 A | 3/1993 | Kohn et al. |
| 5,216,115 A | 6/1993 | Kohn et al. |
| 5,230,349 A | 7/1993 | Langberg |
| 5,232,445 A | 8/1993 | Bonzel |
| 5,242,399 A | 9/1993 | Lau et al. |
| 5,242,997 A | 9/1993 | Kohn et al. |
| 5,264,537 A | 11/1993 | Kohn et al. |
| 5,266,073 A | 11/1993 | Wall |
| 5,282,823 A | 2/1994 | Schwartz et al. |
| 5,300,085 A | 4/1994 | Yock |
| 5,306,286 A | 4/1994 | Stack et al. |
| 5,306,294 A | 4/1994 | Winston et al. |
| 5,314,472 A | 5/1994 | Fontaine |
| 5,317,077 A | 5/1994 | Kohn et al. |
| 5,344,426 A | 9/1994 | Lau et al. |
| 5,350,395 A | 9/1994 | Yock |
| 5,397,355 A | 3/1995 | Marin et al. |
| 5,402,554 A | 4/1995 | Oetiker |
| 5,421,955 A | 6/1995 | Lau et al. |
| 5,423,321 A | 6/1995 | Fontenot |
| 5,423,885 A | 6/1995 | Williams |
| 5,441,515 A | 8/1995 | Khosravi et al. |
| 5,443,496 A | 8/1995 | Schwartz et al. |
| 5,443,500 A | 8/1995 | Sigwart |
| 5,445,646 A | 8/1995 | Euteneuer et al. |
| 5,449,382 A | 9/1995 | Dayton |
| 5,451,233 A | 9/1995 | Yock |
| 5,464,450 A | 11/1995 | Buscemi et al. |
| 5,476,508 A | 12/1995 | Amstrup |
| 5,484,449 A | 1/1996 | Amundson et al. |
| 5,490,962 A | 2/1996 | Cima et al. |
| 5,496,275 A | 3/1996 | Sirhan et al. |
| 5,496,346 A | 3/1996 | Horzewski et al. |
| 5,514,154 A | 5/1996 | Lau et al. |
| 5,527,337 A | 6/1996 | Stack et al. |
| 5,545,135 A | 8/1996 | Iacob et al. |
| 5,545,138 A | 8/1996 | Fugoso et al. |
| 5,549,556 A | 8/1996 | Ndondo-Lay et al. |
| 5,549,662 A * | 8/1996 | Fordenbacher ............. 623/1.17 |
| 5,551,954 A | 9/1996 | Buscemi et al. |
| 5,554,182 A | 9/1996 | Dinh et al. |
| 5,556,413 A | 9/1996 | Lam |
| 5,571,166 A | 11/1996 | Dinh et al. |
| 5,575,816 A | 11/1996 | Rudnick et al. |
| 5,578,075 A | 11/1996 | Dayton |
| 5,587,507 A | 12/1996 | Kohn et al. |
| 5,591,172 A | 1/1997 | Bachmann et al. |
| 5,591,223 A | 1/1997 | Lock et al. |
| 5,591,224 A | 1/1997 | Schwartz et al. |
| 5,591,227 A | 1/1997 | Dinh et al. |
| 5,599,352 A | 2/1997 | Dinh et al. |
| 5,603,722 A | 2/1997 | Phan et al. |
| 5,607,463 A | 3/1997 | Schwartz et al. |
| 5,618,299 A | 4/1997 | Khosravi et al. |
| 5,626,600 A | 5/1997 | Horzewski et al. |
| 5,628,785 A | 5/1997 | Schwartz et al. |
| 5,629,077 A | 5/1997 | Turnlund et al. |
| 5,632,771 A | 5/1997 | Boatman et al. |
| 5,643,312 A | 7/1997 | Fischell et al. |
| 5,643,314 A | 7/1997 | Carpenter et al. |
| 5,643,339 A | 7/1997 | Kavteladze et al. |
| 5,649,977 A | 7/1997 | Campbell |
| 5,651,174 A | 7/1997 | Schwartz et al. |
| 5,658,995 A | 8/1997 | Kohn et al. |
| 5,670,602 A | 9/1997 | Kohn et al. |
| 5,681,345 A | 10/1997 | Euteneuer |
| 5,697,967 A | 12/1997 | Dinh et al. |
| 5,707,387 A | 1/1998 | Wijay |
| 5,725,549 A | 3/1998 | Lam |
| 5,733,328 A | 3/1998 | Fordenbacher |
| 5,735,872 A | 4/1998 | Carpenter et al. |
| 5,741,293 A | 4/1998 | Wijay |
| 5,749,888 A | 5/1998 | Yock |
| 5,755,708 A | 5/1998 | Segal |
| 5,759,186 A | 6/1998 | Bachmann et al. |
| 5,766,710 A | 6/1998 | Turnlund et al. |
| 5,769,868 A | 6/1998 | Yock |
| 5,797,951 A | 8/1998 | Mueller |
| 5,799,384 A | 9/1998 | Schwartz et al. |
| 5,800,393 A | 9/1998 | Sahota |
| 5,800,456 A | 9/1998 | Maeda et al. |
| 5,800,507 A | 9/1998 | Schwartz |
| 5,833,707 A | 11/1998 | McIntyre et al. |
| 5,836,965 A | 11/1998 | Jendersee et al. |
| 5,849,034 A | 12/1998 | Schwartz |
| 5,851,217 A | 12/1998 | Wolff et al. |
| 5,851,231 A | 12/1998 | Wolff et al. |
| 5,855,600 A | 1/1999 | Alt |
| 5,855,802 A | 1/1999 | Acciai et al. |
| 5,868,747 A | 2/1999 | Ochoa et al. |
| 5,876,419 A | 3/1999 | Carpenter et al. |
| 5,893,840 A | 4/1999 | Hull et al. |
| 5,906,639 A | 5/1999 | Rudnick et al. |
| 5,910,816 A | 6/1999 | Fontenot et al. |
| 5,921,952 A | 7/1999 | Desmond, III et al. |
| 5,944,726 A | 8/1999 | Blaeser et al. |
| 5,951,586 A | 9/1999 | Berg et al. |
| 5,954,729 A | 9/1999 | Bachmann et al. |
| 5,957,971 A | 9/1999 | Schwartz |
| 5,957,975 A | 9/1999 | Lafont et al. |
| 5,976,181 A | 11/1999 | Whelan et al. |
| 5,984,963 A | 11/1999 | Ryan et al. |
| 5,989,280 A | 11/1999 | Euteneuer et al. |
| 6,007,545 A | 12/1999 | Venturelli |
| 6,015,387 A | 1/2000 | Schwartz et al. |
| 6,019,779 A | 2/2000 | Thorud et al. |
| 6,019,785 A | 2/2000 | Strecker |
| 6,033,436 A | 3/2000 | Steinke et al. |
| 6,036,715 A | 3/2000 | Yock |
| 6,048,521 A | 4/2000 | Kohn et al. |
| 6,059,825 A | 5/2000 | Hobbs et al. |
| 6,063,111 A | 5/2000 | Hieshima et al. |
| 6,080,190 A | 6/2000 | Schwartz |

(56) References Cited

U.S. PATENT DOCUMENTS

| | | |
|---|---|---|
| 6,080,191 A | 6/2000 | Summers |
| 6,093,157 A | 7/2000 | Chandrasekaran |
| 6,120,491 A | 9/2000 | Kohn et al. |
| 6,125,523 A | 10/2000 | Brown et al. |
| 6,132,457 A | 10/2000 | Chobotov |
| 6,156,062 A | 12/2000 | McGuinness |
| 6,159,239 A | 12/2000 | Greenhalgh |
| 6,160,084 A | 12/2000 | Langer et al. |
| 6,171,334 B1 | 1/2001 | Cox |
| 6,174,328 B1 | 1/2001 | Cragg |
| 6,179,878 B1 | 1/2001 | Duerig et al. |
| 6,183,503 B1 | 2/2001 | Hart et al. |
| 6,190,403 B1 | 2/2001 | Fishchell et al. |
| 6,197,789 B1 | 3/2001 | Grainger |
| 6,214,037 B1 | 4/2001 | Mitchell et al. |
| 6,224,626 B1 * | 5/2001 | Steinke ........................ 623/1.16 |
| 6,238,430 B1 | 5/2001 | Klumb et al. |
| 6,258,117 B1 | 7/2001 | Camrud et al. |
| 6,262,079 B1 | 7/2001 | Grainger et al. |
| 6,264,624 B1 | 7/2001 | Desmond, III et al. |
| 6,264,672 B1 | 7/2001 | Fisher |
| 6,280,473 B1 | 8/2001 | Lemperle et al. |
| 6,283,983 B1 | 9/2001 | Makower et al. |
| 6,284,862 B1 | 9/2001 | Kohn et al. |
| 6,287,329 B1 | 9/2001 | Duerig et al. |
| 6,287,333 B1 | 9/2001 | Appling et al. |
| 6,302,907 B1 | 10/2001 | Hijlkema |
| 6,309,350 B1 | 10/2001 | Van Tassel et al. |
| 6,319,277 B1 | 11/2001 | Rudnick et al. |
| 6,319,492 B1 | 11/2001 | Kohn et al. |
| 6,322,586 B1 | 11/2001 | Monroe et al. |
| 6,350,277 B1 | 2/2002 | Kocur |
| 6,359,102 B1 | 3/2002 | Kemnitzer et al. |
| 6,361,558 B1 | 3/2002 | Hieshima et al. |
| 6,383,211 B1 | 5/2002 | Staehle |
| 6,388,043 B1 | 5/2002 | Langer et al. |
| 6,391,032 B2 | 5/2002 | Blaeser et al. |
| 6,406,490 B1 | 6/2002 | Roth |
| 6,409,750 B1 | 6/2002 | Hyodoh et al. |
| 6,409,751 B1 | 6/2002 | Hall et al. |
| 6,409,752 B1 | 6/2002 | Boatman et al. |
| 6,425,915 B1 | 7/2002 | Khosravi et al. |
| 6,447,508 B1 | 9/2002 | Sharkey et al. |
| 6,451,034 B1 | 9/2002 | Gifford, III et al. |
| 6,458,152 B1 | 10/2002 | Khosravi et al. |
| 6,475,477 B1 | 11/2002 | Kohn et al. |
| 6,485,510 B1 | 11/2002 | Camrud et al. |
| 6,488,700 B2 | 12/2002 | Klumb et al. |
| 6,491,704 B2 | 12/2002 | Gifford, III et al. |
| 6,491,705 B2 | 12/2002 | Gifford, III et al. |
| 6,491,938 B2 | 12/2002 | Kunz et al. |
| 6,497,671 B2 | 12/2002 | Ferrera et al. |
| 6,527,791 B2 | 3/2003 | Fisher |
| 6,530,940 B2 | 3/2003 | Fisher |
| 6,530,958 B1 | 3/2003 | Cima et al. |
| 6,562,021 B1 | 5/2003 | Derbin et al. |
| 6,565,582 B2 | 5/2003 | Gifford, III et al. |
| 6,565,596 B1 | 5/2003 | White et al. |
| 6,569,191 B1 | 5/2003 | Hogan |
| 6,569,441 B2 | 5/2003 | Kunz et al. |
| 6,582,458 B1 | 6/2003 | White et al. |
| 6,582,472 B2 | 6/2003 | Hart |
| 6,585,760 B1 | 7/2003 | Fogarty |
| 6,602,497 B1 | 8/2003 | Kohn et al. |
| 6,607,551 B1 | 8/2003 | Sullivan et al. |
| 6,610,086 B1 | 8/2003 | Kock et al. |
| 6,613,073 B1 | 9/2003 | White et al. |
| 6,620,356 B1 | 9/2003 | Wong et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,645,143 B2 | 11/2003 | Van Tassel et al. |
| 6,652,555 B1 | 11/2003 | Van Tassel et al. |
| 6,659,105 B2 | 12/2003 | Burbank et al. |
| 6,676,658 B2 | 1/2004 | Burbank et al. |
| 6,682,541 B1 | 1/2004 | Gifford, III et al. |
| 6,685,736 B1 | 2/2004 | White et al. |
| 6,689,153 B1 | 2/2004 | Skiba |
| 6,689,158 B1 | 2/2004 | White et al. |
| 6,695,857 B2 | 2/2004 | Gifford, III et al. |
| 6,699,257 B2 | 3/2004 | Gifford, III et al. |
| 6,699,280 B2 | 3/2004 | Camrud et al. |
| 6,702,846 B2 | 3/2004 | Mikus et al. |
| 6,709,449 B2 | 3/2004 | Camrud et al. |
| 6,720,402 B2 | 4/2004 | Langer et al. |
| 6,736,838 B1 | 5/2004 | Richter |
| 6,736,844 B1 | 5/2004 | Glatt et al. |
| 6,746,477 B2 | 6/2004 | Moore |
| 6,749,627 B2 | 6/2004 | Thompson et al. |
| 6,786,922 B2 | 9/2004 | Schaeffer |
| 6,790,221 B2 | 9/2004 | Monroe et al. |
| 6,792,979 B2 | 9/2004 | Konya et al. |
| 6,802,849 B2 | 10/2004 | Blaeser et al. |
| 6,821,292 B2 | 11/2004 | Pazienza et al. |
| 6,852,308 B2 | 2/2005 | Kohn et al. |
| 6,869,143 B2 | 3/2005 | Secord |
| 6,878,159 B2 | 4/2005 | Iwasaka et al. |
| 6,878,162 B2 | 4/2005 | Bales et al. |
| 6,916,868 B2 | 7/2005 | Kemnitzer et al. |
| 6,929,709 B2 | 8/2005 | Smith |
| 6,951,053 B2 | 10/2005 | Padilla et al. |
| 6,962,604 B2 | 11/2005 | Hijlkema |
| 6,964,680 B2 | 11/2005 | Shanley |
| 6,974,472 B2 | 12/2005 | Hong et al. |
| 6,974,475 B1 | 12/2005 | Wall |
| 6,991,647 B2 | 1/2006 | Jadhav |
| 7,041,126 B2 | 5/2006 | Shin et al. |
| 7,056,493 B2 | 6/2006 | Kohn et al. |
| 7,077,860 B2 | 7/2006 | Yan et al. |
| 7,128,756 B2 | 10/2006 | Lowe et al. |
| 7,141,063 B2 | 11/2006 | White et al. |
| 7,175,653 B2 | 2/2007 | Gaber |
| 7,229,473 B2 | 6/2007 | Falotico et al. |
| 7,255,710 B2 | 8/2007 | White et al. |
| 7,279,664 B2 | 10/2007 | Weber |
| 7,329,277 B2 | 2/2008 | Addonizio et al. |
| 7,476,232 B2 | 1/2009 | Deal |
| 7,520,893 B2 | 4/2009 | Rivelli |
| 7,553,377 B1 | 6/2009 | Chen et al. |
| 7,556,644 B2 | 7/2009 | Burpee et al. |
| 7,637,939 B2 | 12/2009 | Tischler |
| 7,704,275 B2 | 4/2010 | Schmid et al. |
| 7,722,662 B2 | 5/2010 | Steinke et al. |
| 7,763,065 B2 | 7/2010 | Schmid et al. |
| 7,763,067 B2 | 7/2010 | Bales et al. |
| 7,766,960 B2 | 8/2010 | Alexander et al. |
| 7,780,721 B2 | 8/2010 | Bales et al. |
| 7,812,290 B2 | 10/2010 | Weber |
| 7,846,198 B2 | 12/2010 | Hogendijk |
| 7,947,071 B2 | 5/2011 | Schmid |
| 7,988,721 B2 | 8/2011 | Morris et al. |
| 8,172,894 B2 | 5/2012 | Schmid et al. |
| 8,277,500 B2 | 10/2012 | Schmid et al. |
| 8,292,944 B2 | 10/2012 | Schmid et al. |
| 8,460,363 B2 | 6/2013 | Morris et al. |
| 8,512,394 B2 | 8/2013 | Schmid et al. |
| 8,523,936 B2 | 9/2013 | Schmid et al. |
| 8,540,762 B2 | 9/2013 | Schmid et al. |
| 8,545,547 B2 | 10/2013 | Schmid et al. |
| 8,617,235 B2 | 12/2013 | Schmid et al. |
| 2001/0010015 A1 | 7/2001 | Hijlkema |
| 2001/0020173 A1 | 9/2001 | Klumb et al. |
| 2001/0029378 A1 | 10/2001 | Blaeser et al. |
| 2001/0044561 A1 | 11/2001 | Uneyama et al. |
| 2002/0010504 A1 | 1/2002 | Alt et al. |
| 2002/0040238 A1 | 4/2002 | Rudnick et al. |
| 2002/0052641 A1 | 5/2002 | Monroe et al. |
| 2002/0072656 A1 | 6/2002 | Van Tassel et al. |
| 2002/0077693 A1 | 6/2002 | Barclay et al. |
| 2002/0082682 A1 | 6/2002 | Barclay et al. |
| 2002/0095204 A1 | 7/2002 | Thompson et al. |
| 2002/0099431 A1 | 7/2002 | Armstrong et al. |
| 2002/0111669 A1 | 8/2002 | Pazienza et al. |
| 2002/0116044 A1 | 8/2002 | Cottone et al. |

(56) References Cited

U.S. PATENT DOCUMENTS

| | | |
|---|---|---|
| 2002/0120322 A1 | 8/2002 | Thompson et al. |
| 2002/0120323 A1 | 8/2002 | Thompson et al. |
| 2002/0123791 A1 | 9/2002 | Harrison |
| 2002/0138081 A1 | 9/2002 | Blaeser et al. |
| 2002/0138126 A1 | 9/2002 | Camrud et al. |
| 2002/0147489 A1 | 10/2002 | Hong et al. |
| 2002/0151967 A1 | 10/2002 | Mikus et al. |
| 2002/0156456 A1 | 10/2002 | Fisher |
| 2002/0156457 A1 | 10/2002 | Fisher |
| 2002/0193870 A1 | 12/2002 | Jang |
| 2003/0045923 A1 | 3/2003 | Bashiri |
| 2003/0069633 A1 | 4/2003 | Richter et al. |
| 2003/0074043 A1 | 4/2003 | Thompson |
| 2003/0078649 A1 | 4/2003 | Camrud et al. |
| 2003/0120334 A1 | 6/2003 | Gerberding |
| 2003/0176914 A1 | 9/2003 | Rabkin et al. |
| 2003/0199969 A1 | 10/2003 | Steinke et al. |
| 2003/0208262 A1 | 11/2003 | Gaber |
| 2003/0211135 A1 | 11/2003 | Greenhalgh et al. |
| 2003/0212451 A1 | 11/2003 | Cox et al. |
| 2003/0220682 A1 | 11/2003 | Kujawski |
| 2004/0024446 A1 | 2/2004 | Smith |
| 2004/0044401 A1 | 3/2004 | Bales et al. |
| 2004/0054400 A1 | 3/2004 | Granada |
| 2004/0062788 A1 | 4/2004 | Richter |
| 2004/0068316 A1 | 4/2004 | Schaeffer |
| 2004/0086458 A1 | 5/2004 | Kohn et al. |
| 2004/0086462 A1 | 5/2004 | Kohn et al. |
| 2004/0093073 A1 | 5/2004 | Lowe et al. |
| 2004/0093076 A1 | 5/2004 | White et al. |
| 2004/0097959 A1 | 5/2004 | Thompson |
| 2004/0106971 A1 | 6/2004 | Schwartz et al. |
| 2004/0106977 A1 | 6/2004 | Sullivan et al. |
| 2004/0133260 A1 | 7/2004 | Schwartz et al. |
| 2004/0143319 A1 | 7/2004 | Schwartz et al. |
| 2004/0167616 A1 | 8/2004 | Camrud et al. |
| 2004/0186551 A1 | 9/2004 | Kao et al. |
| 2004/0186556 A1 | 9/2004 | Hogendijk et al. |
| 2004/0186557 A1 | 9/2004 | Gambale et al. |
| 2004/0191175 A1 | 9/2004 | Kohn et al. |
| 2004/0193251 A1 | 9/2004 | Rudnick et al. |
| 2004/0224003 A1 | 11/2004 | Schultz |
| 2004/0236401 A1 | 11/2004 | Shin et al. |
| 2004/0243217 A1 | 12/2004 | Andersen et al. |
| 2004/0243218 A1 | 12/2004 | Schaeffer |
| 2005/0038497 A1 | 2/2005 | Neuendorf et al. |
| 2005/0038503 A1 | 2/2005 | Greenhalgh et al. |
| 2005/0106119 A1 | 5/2005 | Brandom et al. |
| 2005/0123481 A1 | 6/2005 | Kohn et al. |
| 2005/0165203 A1 | 7/2005 | Kohn et al. |
| 2005/0203615 A1 | 9/2005 | Forster et al. |
| 2005/0216076 A1 | 9/2005 | Kveen et al. |
| 2005/0246010 A1 | 11/2005 | Alexander et al. |
| 2006/0020324 A1* | 1/2006 | Schmid et al. ............... 623/1.16 |
| 2006/0024266 A1 | 2/2006 | Brandom et al. |
| 2006/0026815 A1 | 2/2006 | Padilla et al. |
| 2006/0030934 A1 | 2/2006 | Hogendijk et al. |
| 2006/0034769 A1 | 2/2006 | Kohn et al. |
| 2006/0036316 A1 | 2/2006 | Zeltinger et al. |
| 2006/0079955 A1 | 4/2006 | Brown |
| 2006/0115449 A1 | 6/2006 | Pacetti |
| 2006/0136041 A1 | 6/2006 | Schmid et al. |
| 2006/0182779 A1 | 8/2006 | Brandom et al. |
| 2006/0204440 A1 | 9/2006 | Kohn et al. |
| 2007/0010870 A1 | 1/2007 | Alt et al. |
| 2007/0032854 A1 | 2/2007 | Schmid et al. |
| 2007/0032857 A1 | 2/2007 | Schmid et al. |
| 2007/0061004 A1 | 3/2007 | Steinke |
| 2007/0142901 A1 | 6/2007 | Steinke |
| 2007/0250148 A1 | 10/2007 | Perry et al. |
| 2007/0270939 A1 | 11/2007 | Hood et al. |
| 2008/0046066 A1 | 2/2008 | Jenson et al. |
| 2008/0051868 A1 | 2/2008 | Cottone et al. |
| 2008/0051873 A1 | 2/2008 | Cottone et al. |
| 2008/0051874 A1 | 2/2008 | Cottone et al. |
| 2008/0051875 A1 | 2/2008 | Cottone et al. |
| 2008/0071355 A1 | 3/2008 | Weber |
| 2008/0114391 A1 | 5/2008 | Dieck et al. |
| 2008/0183275 A1 | 7/2008 | Schmid et al. |
| 2008/0195190 A1 | 8/2008 | Bland et al. |
| 2008/0221664 A1 | 9/2008 | Bales et al. |
| 2008/0221665 A1 | 9/2008 | Peckham et al. |
| 2008/0262599 A1 | 10/2008 | Caro et al. |
| 2008/0269869 A1 | 10/2008 | Cho |
| 2008/0288050 A1 | 11/2008 | Addonizio et al. |
| 2009/0143853 A1 | 6/2009 | Morris et al. |
| 2009/0187239 A1 | 7/2009 | Goto |
| 2010/0004725 A1 | 1/2010 | Zipse et al. |
| 2010/0042203 A1 | 2/2010 | Cottone et al. |
| 2010/0114297 A1 | 5/2010 | Calisse |
| 2010/0131048 A1 | 5/2010 | Schmid et al. |
| 2010/0280593 A1 | 11/2010 | Richter |
| 2010/0292773 A1 | 11/2010 | Schmid et al. |
| 2010/0324662 A1 | 12/2010 | Addonizio et al. |
| 2011/0172759 A1 | 7/2011 | Schmid et al. |
| 2011/0245909 A1 | 10/2011 | Schmid et al. |
| 2013/0253631 A1 | 9/2013 | Schmid et al. |
| 2014/0025159 A1 | 1/2014 | Morris et al. |
| 2014/0067042 A1 | 3/2014 | Schmid et al. |
| 2014/0094897 A1 | 4/2014 | Schmid et al. |

FOREIGN PATENT DOCUMENTS

| | | |
|---|---|---|
| CA | 2590672 | 4/2014 |
| CN | 102245127 B | 6/2014 |
| EP | 0712614 | 5/1996 |
| EP | 0756853 | 2/1997 |
| JP | 07-000531 | 1/1995 |
| JP | 08-196641 | 8/1996 |
| JP | 08-336598 | 12/1996 |
| JP | 9-313617 | 12/1997 |
| JP | 2007-185363 | 7/2007 |
| JP | 5559798 | 6/2014 |
| WO | WO 90/14046 A1 | 11/1990 |
| WO | WO 94/21196 A2 | 9/1994 |
| WO | WO 94/21196 A3 | 2/1995 |
| WO | WO 96/14030 A1 | 5/1996 |
| WO | WO 97/07751 A1 | 3/1997 |
| WO | WO 97/42911 A1 | 11/1997 |
| WO | WO 98/22045 | 5/1998 |
| WO | WO 98/22073 A2 | 5/1998 |
| WO | WO 98/41169 A1 | 9/1998 |
| WO | WO 98/22073 A3 | 2/1999 |
| WO | WO 99/08740 A1 | 2/1999 |
| WO | WO 99/15106 A1 | 4/1999 |
| WO | WO 99/40874 A1 | 8/1999 |
| WO | WO 99/65421 A2 | 12/1999 |
| WO | WO 96/65421 A3 | 1/2000 |
| WO | WO 00/09195 A1 | 2/2000 |
| WO | WO 00/10623 A1 | 3/2000 |
| WO | WO 00/30565 A1 | 6/2000 |
| WO | WO 00/59405 A1 | 10/2000 |
| WO | WO 00/62708 A1 | 10/2000 |
| WO | WO 00/71058 A1 | 11/2000 |
| WO | WO 01/24735 A1 | 4/2001 |
| WO | WO 01/35864 A1 | 5/2001 |
| WO | WO 01/51114 A2 | 7/2001 |
| WO | WO 01/70298 A2 | 9/2001 |
| WO | WO 01/87180 A2 | 11/2001 |
| WO | WO 01/51114 A3 | 1/2002 |
| WO | WO 01/70298 A3 | 2/2002 |
| WO | WO 00/62708 C2 | 6/2002 |
| WO | WO 01/87180 A3 | 6/2002 |
| WO | WO 02/47582 A2 | 6/2002 |
| WO | WO 02/053204 A2 | 7/2002 |
| WO | WO 02/054990 A2 | 7/2002 |
| WO | WO 02/47582 A3 | 10/2002 |
| WO | WO 02/054990 A3 | 11/2002 |
| WO | WO 02/053204 A3 | 3/2003 |
| WO | WO 03/022178 A1 | 3/2003 |
| WO | WO 03/047464 A2 | 6/2003 |
| WO | WO 03/057076 A1 | 7/2003 |
| WO | WO 03/047464 A3 | 9/2003 |
| WO | WO 03/047464 C2 | 11/2003 |

(56) References Cited

FOREIGN PATENT DOCUMENTS

| WO | WO 03/094798 A1 | 11/2003 |
|---|---|---|
| WO | WO 03/099161 A2 | 12/2003 |
| WO | WO 03/099161 A3 | 2/2004 |
| WO | WO 2004/019820 A1 | 3/2004 |
| WO | WO 2004/026112 A2 | 4/2004 |
| WO | WO 2004/032803 A1 | 4/2004 |
| WO | WO 2004/026112 C2 | 6/2004 |
| WO | WO 2004/026112 A3 | 10/2004 |
| WO | WO 2004-087015 | 10/2004 |
| WO | WO 2004/096340 A1 | 11/2004 |
| WO | WO 2004/110312 A1 | 12/2004 |
| WO | WO 2006/010636 A1 | 2/2006 |
| WO | WO 2006/014596 A1 | 2/2006 |
| WO | WO 2006/014699 A1 | 2/2006 |
| WO | WO 2006/020616 A1 | 2/2006 |
| WO | WO 2006/107608 A1 | 10/2006 |
| WO | WO 2007/016409 A1 | 2/2007 |
| WO | WO 2007/084444 A2 | 7/2007 |
| WO | WO 2010-022005 | 2/2010 |
| WO | WO 2010-042879 | 4/2010 |
| WO | WO 2011/127452 A1 | 10/2011 |

OTHER PUBLICATIONS

Office Action received in corresponding Canadian Application No. 2615708, mailed Jun. 22, 2009, 4 pages.
International Search Report and Written Opinion in related International application No. PCT/US2006/029566, mailed Dec. 28, 2006, 13 pp.
Asahara, T. "Local delivery of vascular endothelial growth factor accelerates reendothelialization and attenuates intimal hyperplasia in balloon-insured rate carotid artery," *Circulation* 91: 2793-2801, 1995.
Autieri, M.V. et al. "Antisense oligonucleotides to the p65 subunit of NF-Kb inhibit human vascualr smooth muscle cell adherence and proliferation and prevent neointima formation in rat carotid arteries," *Biochemical and Biophysical Research Communications* 213: 827-836, 1995.
Brauner, R. "Controlled periadverntitial administration of verapamil inhibits neointimal smooth muscle cell proliferation and ameliorates vasomotor abnormalities in experimental vein bypass grafts," *The Journal of Thoracic and Cardiovascular Surgery* 114: 53-63, 1997.
Carmeliet, P. et al. "Inhibitory role of plasminogen activator inhibitor-1 in arterial wound healing and neointima formation," *Circulation* 96: 3180-3191, 1997.
Epstein, S.E. et al. "Cytotoxic effects of a recombinant chimeric toxin on rapidly proliferating vascular smooth muscle cells," *Circulation* 84: 778-787, 1991.
Hu, Y. "Inhibition of neointima hyperplasia of mouse vein grafts by locally applied suramin," *Circulation* 100: 861-868, 1999.
Kurisu, Y. et al. "Protective effect of beraprost sodium, a stable prostacyclin analogue, on cardiac allograft vasculopathy in rats," *Hiroshima Journal of Medical Science* 56: 11-19, 1997.
Morishita, R. et al. "Novel in vitro gene transfer method for study of local modulators in vascular smooth muscle cells," *Hypertension* 21: 894-899, 1993.
Nerem, R.M. et al. "Tissue engineering and the vascular system, synthetic biodegradable polymer scaffolds," pp. 164-185, 1997.
Von Der Leyen, H.E. et al. "Gene therapy neointimal vascular lesion: in vivo transfer of endothelial cell nitric oxide synthase gene," *PNAS USA* 92:1137-1141, 1995.
Yasukawa, H. "Inhibition of intimal hyperplasia after balloon injury by antibodies to intercellular adhesion molecule-1 and lymphocyte funtion, Associated antigen-1," *Circulation* 95: 1515-1522, 1997.
Balcon, R. et al., *Recommendations on stent manufacture, implantation and utilization*, European Heart Journal, Oct. 1997, vol. 18, pp. 1536-1547.
Charles, Roger et al., *Ceramide-Coated Balloon Catheters Limit Neointimal Hyperplasia After Stretch Injury in Carotid Arteries*, Circulation Research, 2000; 87; pp. 282-288.
Coroneos, Emmanuel et al., *Differential Regulation of Sphingomyelinase and Ceramidase Activities by Growth Factors and Cytokines*, The Journal of Biological Chemistry, Oct. 6, 1995, vol. 270, No. 40, pp. 23305-23309.
Coroneos, Emmanuel et al., *Sphingolipid metabolites differentially regulate extracellular signal-regulated kinase and stress-activated protein kinase cascades*, Biochem. J., 1196; 316, pp. 13-17 (Printed in Great Britain).
Jacobs, Leila S. et al., *Sphingolipids as mediators of effects of platelet-derived growth factor in vascular smooth muscle cells*, Am J Physiol (American Physiological Society), 1993, pp. C740-C747.
Tanguay, Jean Francois et al., *Current Status of Biodegradable Stents*, Cardiology Clinics, Contemporary Interventional Techniques, Nov. 1994, vol. 12, No. 4, pp. 699-713, W.B. Saunders Company.
Nikol, S. et al., *Molecular biology and post-angioplasty restenosis*, Atherosclerosis, 1996; 123, pp. 17-31.
Phillips, Paul S. MD, et al., *The Stenter's Notebook*, 1998, (entire book), Physicians' Press, Birmingham, Michigan.
Ratner, Buddy D. et al., *Biomaterials Science, An Introducation to Materials in Medicine*, 2nd Edition, 2004, (entire book), Elsevier Acadmeic Press.
Serruys, Patrick W. et al., *Handbook of Coronary Stents*, Fourth Edition, 2002, (entire book), Martin Dunitz Ltd.
Atala, Anthony et al., *Synthetic Biodegradable Polymer Scaffolds*, 1997, (entire book), Birkhauser Boston.
Office Action received in corresponding Russian Application No. 2008107557, mailed Dec. 27, 2010.
Office Action received in corresponding Canadian Application No. 2615708, mailed Feb. 2, 2011.
International Search Report in corresponding International Application No. PCT/US2009/054087, mailed Sep. 30, 2009.
International Preliminary Report on Patentability in corresponding International Application No. PCT/US2009/054087, mailed Mar. 3, 2011.
Office Action received in corresponding Chinese Application No. 200680033304.1, mailed Dec. 11, 2009.
International Preliminary Report on Patentability in corresponding PCT Application No. PCT/US2006/029566, dated Feb. 5, 2008.
Office Action received in corresponding Australian Application No. 2006275662, dated Apr. 11, 2012, 2 pages.
Office Action received in corresponding Australian Application No. 2009282633, dated Apr. 26, 2013, 3 pages.
Office Action received in corresponding Chinese Application No. 200680033304.1, issued Feb. 14, 2012.
Rejection Decision received in corresponding Chinese Application No. 200680033304.1, issued Sep. 29, 2012, 7 pages.
Reexamination Notification issued by the Patent Reexamination Board received in corresponding Chinese Application No. 200680033304.1, issued Dec. 5, 2013, 12 pages.
Office Action received in corresponding Japanese Application No. 2008-525061, mailed Sep. 7, 2011.
Office Action received in corresponding Japanese Application No. 2011-523913, mailed Jun. 18, 2013, 6 pages.
Office Action received in corresponding Japanese Application No. 2008-525061, mailed Jun. 5, 2012.
Rejection Decision received in corresponding Chinese Application No. 200680033304.1, issued Sep. 29, 2012.
Office Action received in corresponding Japanese Application No. 2011-523913, mailed Jun. 18, 2013.
Reexamination Notification issued by the Patent Reexamination Board received in corresponding Chinese Application No. 200680033304.1, issued Jun. 10, 2014, 3 pages.
Office Action received in corresponding Japanese Application No. 2011-523913, mailed Mar. 11, 2014, 4 pages.

* cited by examiner

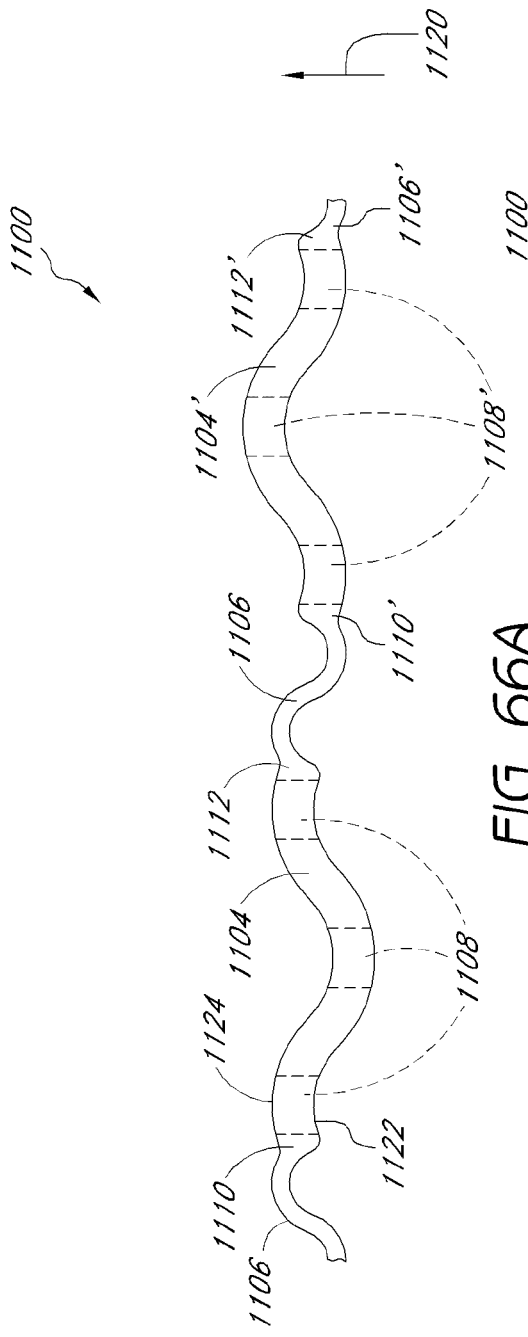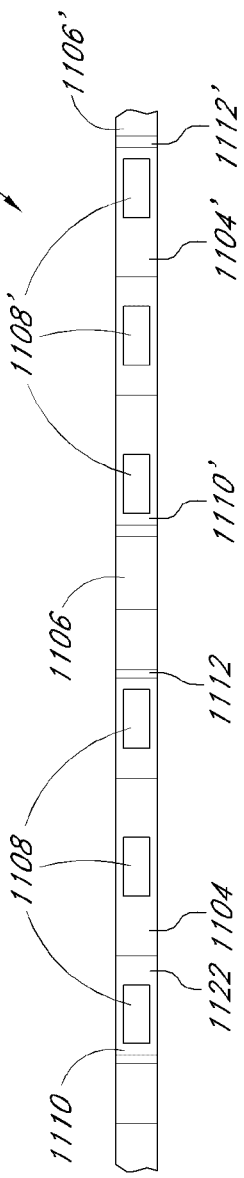
FIG. 66A
FIG. 66B

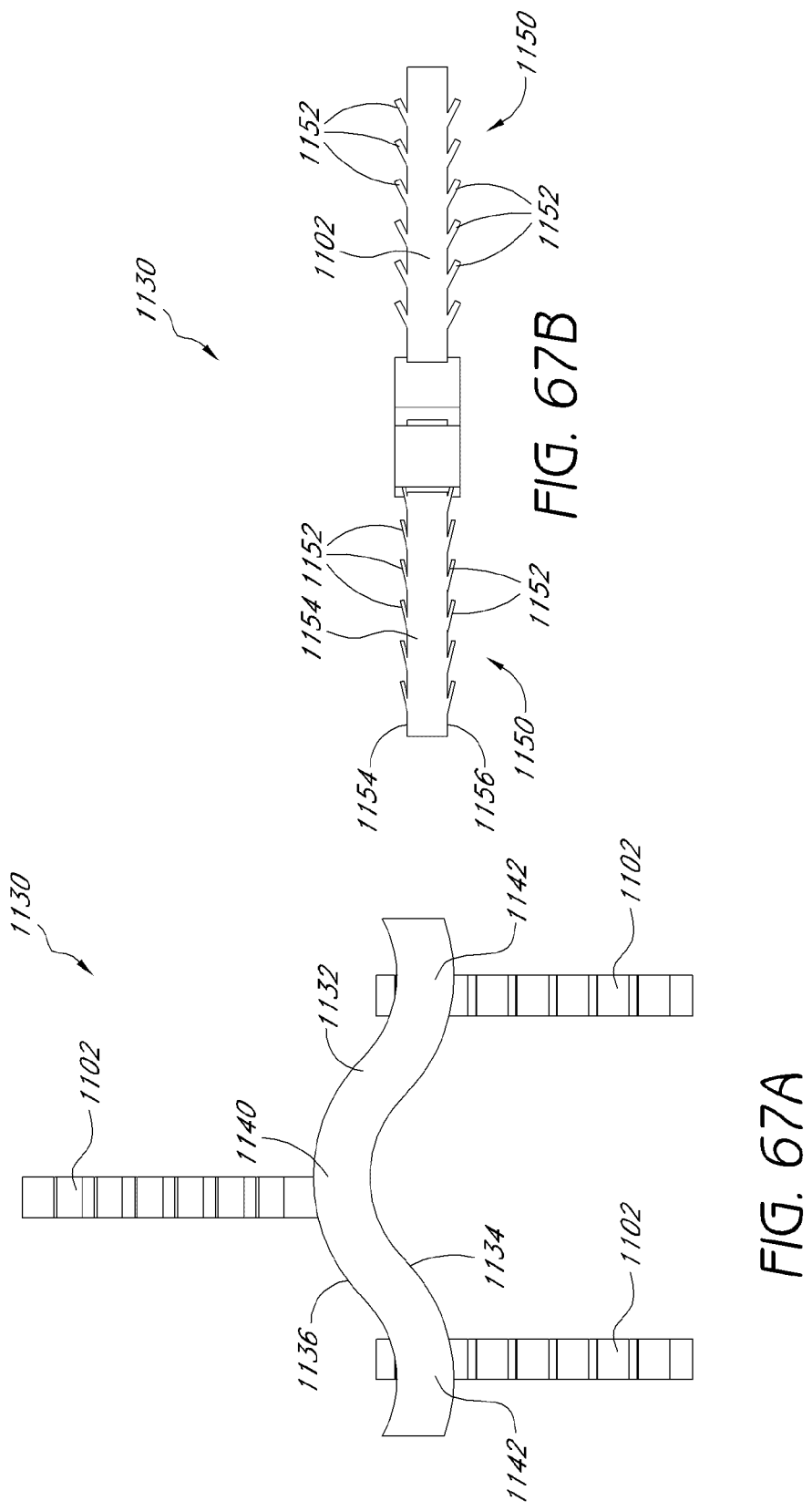

AXIALLY NESTED SLIDE AND LOCK EXPANDABLE DEVICE

CROSS-REFERENCE TO RELATED APPLICATIONS

This application is a continuation-in-part of U.S. application Ser. No. 11/196,800, filed Aug. 2, 2005, the entirety of which is hereby incorporated herein by reference.

BACKGROUND OF THE INVENTIONS

1. Field of the Inventions

The inventions relate generally to expandable medical implants for maintaining support of a body lumen. More particularly, the inventions relate to a predominantly axially nested, diametrically expandable, slide and lock device for enlarging a portion of a body lumen.

2. Description of the Related Art

Stents or expandable stent grafts are implanted in a variety of body lumens in an effort to maintain their patency. The body lumens no matter how large or small may be vascular and nonvascular. These devices are typically intraluminally implanted by use of a catheter, which is inserted at an easily accessible location and then advanced to the deployment site. The stent is initially in a radially compressed or collapsed state to enable it to be maneuvered through the lumen. Once in position, the stent is deployed which, depending on its configuration, may be achieved either automatically or manually, by for example, the inflation of a balloon about which the stent is carried on the catheter.

An important and frequent use of stents is the treatment of blood vessels in situations where part of the vessel wall or stenotic plaque blocks or occludes fluid flow in the vessel. Often, a balloon catheter is utilized in a percutaneous transluminal coronary angioplasty procedure to enlarge the occluded portion of the vessel. However, the dilation of the occlusion can cause fissuring of atherosclerotic plaque and damage to the endothelium and underlying smooth muscle cell layer, potentially leading to immediate problems from flap formation or perforations in the vessel wall, as well as long-term problems with restenosis of the dilated vessel. Implantation of stents can provide support for such problems and prevent re-closure of the vessel or provide patch repair for a perforated vessel. Further, the stent may overcome the tendency of diseased vessel walls to collapse, thereby maintaining a more normal flow of blood through that vessel. Stents are also now being used in other clinical conditions such as in patients with unstable vulnerable plaque lesions.

As stents are normally employed to hold open an otherwise blocked, constricted or occluded lumen, a stent must exhibit sufficient radial or hoop strength in its expanded state to effectively counter the anticipated forces. It is, however, simultaneously necessary for the stent to be as compact as possible in its collapsed state in order to facilitate its advancement through the lumen. As a result, it is advantageous for a stent to have as large an expansion ratio as possible.

An additional consideration is the longitudinal flexibility of the device. Such characteristic is important not only in maneuvering the stent into position, which may require the traversal of substantial convolutions of the vasculature, but also to better conform to any curvature of the vasculature at the deployment site. At the same time it is, however, necessary for the stent to nonetheless exhibit sufficient radial strength to provide the necessary support for the lumen walls upon deployment.

Another problem inherent in many prior art stent configurations is the longitudinal contraction that such structures typically undergo as they are radially expanded. This not only reduces the effective length of the stent in its deployed state but may cause abrasion trauma to be inflicted on the vessel walls during expansion.

A number of very different approaches have been previously devised in an effort to address these various requirements. A popular approach calls for the stent to be constructed wholly of wire. The wire is bent, woven and/or coiled to define a generally cylindrical structure in a configuration that has the ability to undergo radial expansion. The use of wire has a number of disadvantages associated therewith including for example, its substantially constant cross-section which may cause greater or lesser than an ideal amount of material to be concentrated at certain locations along the stent. Additionally, wire has limitations with respect to the shapes it can be formed into thus limiting the expansion ratio, coverage area, flexibility and strength that can ultimately be attained therewith.

As an alternative to wire-based structures, stents have been constructed from tube stock. By selectively removing material from such tubular starting material, a desired degree of flexibility and expandability can be imparted to the structure. Etching techniques as well as laser-cutting processes are utilized to remove material from the tube. Laser cutting provides for a high degree of precision and accuracy with which very well defined patterns of material can be removed from the tube to conversely leave very precisely and accurately defined patterns of material in tact. The performance of such stent is very much a function of the pattern of material which remains (i.e., design) and material thickness. The selection of a particular pattern has a profound effect on the coverage area, expansion ratio and strength of the resulting stent as well as its longitudinal flexibility and longitudinal dimensional stability during expansion.

While the tube-based stents offer many advantages over the wire-based designs, it is nonetheless desirable to improve upon such designs in an effort to further enhance longitudinal flexibility and longitudinal dimensional stability during radial expansion without sacrificing radial hoop strength.

One stent design described by Fordenbacher, see e.g., U.S. Pat. Nos. 5,549,662 and 5,733,328, employs a plurality of elongated parallel stent components, each having a longitudinal backbone that spans the entire axial length of the stent and a plurality of opposing circumferential elements or fingers extending therefrom. The circumferential elements from one stent component weave into paired slots in the longitudinal backbone of an adjacent stent component. This weave-like interlocking configuration, wherein a circumferential element passes through the first slot in a pair and then weaves back through the second slot in the pair, is essential to Fordenbacher's goal of permitting radial expansion without material deformation. In addition, sufficient members of circumferential elements in the Fordenbacher stent may provide adequate scaffolding. Unfortunately, the circumferential elements have free ends, protruding from the paired slots. Moreover, the circumferential elements weaving through the paired slots also necessarily stand off from the lumen wall. Both the free ends and the stand off may pose significant risks of thrombosis and/or restenosis. Moreover, this stent design would tend to be rather inflexible as a result of the plurality of longitudinal backbones.

Some stents employ "jelly roll" designs, wherein a sheet is rolled upon itself with a high degree of overlap in the collapsed state and a decreasing overlap as the stent unrolls to an expanded state. Examples of such designs are described in U.S. Pat. No. 5,421,955 to Lau, U.S. Pat. Nos. 5,441,515 and 5,618,299 to Khosravi, and U.S. Pat. No. 5,443,500 to Sigwart. The disadvantage of these designs is that they tend to exhibit very poor longitudinal flexibility. In a modified design that exhibits improved longitudinal flexibility, multiple short rolls are coupled longitudinally. See e.g., U.S. Pat. No. 5,649,977 to Campbell and U.S. Pat. Nos. 5,643,314 and 5,735,872 to Carpenter. However, these coupled rolls lack vessel support between adjacent rolls. Furthermore, these designs exhibit extensive overlapping of stent elements in multiple layers, which makes the delivery profile rather thick.

Various types of stents, including those referenced above, are often described based on their means for expansion. For additional information, a variety of stents types are described by Balcon et al., "Recommendations on Stent Manufacture, Implantation and Utilization," European Heart Journal (1997), vol. 18, pages 1536-1547, and Phillips, et al., "The Stenter's Notebook," Physician's Press (1998), Birmingham, Mich.

Balloon expandable stents are manufactured in the collapsed condition and are expanded to a desired diameter with a balloon. The expandable stent structure may be held in the expanded condition by mechanical deformation of the stent as taught in, for example, U.S. Pat. No. 4,733,665 to Palmaz. Alternatively, balloon expandable stents may be held in the expanded condition by engagement of the stent walls with respect to one another as disclosed in, for example, U.S. Pat. No. 4,740,207 to Kreamer, U.S. Pat. No. 4,877,030 to Beck et al., and U.S. Pat. No. 5,007,926 to Derbyshire. Further still, the stent may be held in the expanded condition by one-way engagement of the stent walls together with tissue growth into the stent, as disclosed in U.S. Pat. No. 5,059,211 to Stack et al.

Although balloon expandable stents are the first stent type to be widely used in clinical applications, it is well recognized that balloon expandable stents have a variety of shortcomings which may limit their effectiveness in many important applications. For example, balloon expandable stents often exhibit substantial recoil (i.e., a reduction in diameter) immediately following deflation of the inflatable balloon. Accordingly, it may be necessary to over-inflate the balloon during deployment of the stent to compensate for the subsequent recoil. This is disadvantageous because it has been found that over-inflation may damage the blood vessel. Furthermore, a deployed balloon expandable stent may exhibit chronic recoil over time, thereby reducing the patency of the lumen. Still further, balloon expandable stents often exhibit foreshortening (i.e., a reduction in length) during expansion, thereby creating undesirable stresses along the vessel wall and making stent placement less precise. Still further, many balloon expandable stents, such as the original Palmaz-Schatz stent and later variations, are configured with an expandable mesh having relatively jagged terminal prongs, which increases the risk of injury to the vessel, thrombosis and/or restenosis.

Self-expanding stents are manufactured with a diameter approximately equal to, or larger than, the vessel diameter and are collapsed and constrained at a smaller diameter for delivery to the treatment site. Self-expanding stents are commonly placed within a sheath or sleeve to constrain the stent in the collapsed condition during delivery. After the treatment site is reached, the constraint mechanism is removed and the stent self-expands to the expanded condition. Most commonly, self-expanding stents are made of Nitinol or other shape memory alloy. One of the first self-expanding stents used clinically is the braided "WallStent," as described in U.S. Pat. No. 4,954,126 to Wallsten. Another example of a self-expanding stent is disclosed in U.S. Pat. No. 5,192,307 to Wall wherein a stent-like prosthesis is formed of plastic or sheet metal that is expandable or contractible for placement.

Heat expandable stents are similar in nature to self-expanding stents. However, this type of stent utilizes the application of heat to produce expansion of the stent structure. Stents of this type may be formed of a shape memory alloy, such as Nitinol or other materials, such as polymers, that must go through a thermal transition to achieve a dimensional change. Heat expandable stents are often delivered to the affected area on a catheter capable of receiving a heated fluid. Heated saline or other fluid may be passed through the portion of the catheter on which the stent is located, thereby transferring heat to the stent and causing the stent to expand. However, heat expandable stents have not gained widespread popularity due to the complexity of the devices, unreliable expansion properties and difficulties in maintaining the stent in its expanded state. Still further, it has been found that the application of heat during stent deployment may damage the blood vessel.

In summary, although a wide variety of stents have been proposed over the years for maintaining the patency of a body lumen, none of the existing schemes has been capable of overcoming most or all of the above described shortcomings. As a result, clinicians are forced to weigh advantages against shortcomings when selecting a stent type to use in a particular application. Accordingly, there remains a need for an improved stent: one that is compact and flexible enough when collapsed to permit uncomplicated delivery to the affected area; one that is sufficiently flexible upon deployment to conform to the shape of the affected body lumen; one that expands uniformly to a desired diameter, without change in length; one that maintains the expanded size, without significant recoil; and one that has sufficient scaffolding to provide a clear through-lumen.

SUMMARY

For purposes of summarizing the inventions, certain aspects, advantages and novel features of the inventions have been described herein above. Of course, it is to be understood that not necessarily all such advantages may be achieved in accordance with any particular embodiment of the inventions. Thus, the inventions may be embodied or carried out in a manner that achieves or optimizes one advantage or group of advantages as taught or suggested herein without necessarily achieving other advantages as may be taught or suggested herein.

Some embodiments provide a diametrically expanding, slide and lock vascular device, prosthesis or stent comprising elements or members that do not substantially overlap each other in the radial direction, i.e., do not lay (nest) upon each other in the deployed state. In the nested (non-expanded, undeployed, predilated) position, the radial thickness of two overlapping elements is less than about two times the nominal material thickness. Overlap in the non-deployed state is generally acceptable as long a suitable crossing profile is achieved while in the deployed state there is desirably substantially no, minimal or reduced overlap.

During manufacture and assembly of the axially nested embodiments, the device structural elements are substantially majorly or primarily positioned side by side (axially) in the predilated or non-expanded state to substantially reduce or minimize the device crossing profile and bulk in both the undeployed (non-expanded, predilated) and deployed (expanded, dilated) states. Advantageously, by substantially reducing or eliminating the excess bulk typically encountered with a radially nesting device design, embodiments of the inventions can be used to achieve competitive devices and crossing profiles with a wide variety of materials at a wide variety of thicknesses, thereby desirably allowing for optimum device design and performance.

Many conventional slide and lock vascular devices comprise elements that overlap each other in the radial direction, i.e., lay upon each other. This feature can limit that thickness of material that can be employed as well as the number of elements that can be employed. As the thickness or element number increases, competitive features of the device may be compromised, such as crossing profile. To provide acceptable crossing profiles, the thicknesses and the number of elements employed in these radially nesting devices is often reduced, which can have an impact on such features as reliability and device radial strength.

Embodiments of the inventions provide an axially nested vascular device to achieve both competitive crossing profiles while maintaining other key features, such as, for example, radial strength and luminal patency. Advantageously, an axially nested device design allows for use of thicker materials to maintain radial strength, as needed or desired.

Embodiments of the inventions can utilize a number of features to create slide and lock mechanisms that allow for controlled and predictable device expansion. For example, deflectable and non-deflectable elements and members can be employed to achieve desired deployment and lock out performance. The skilled artisan will appreciate that a variety of mechanisms, features and/or geometries can readily be included to achieve the desired deployment and lock out performance. For example, mechanisms can be employed that incorporate the bulk of the structural element, or smaller localized sub-elements can be employed.

Some embodiments provide a slide-and-lock stent that comprises a tubular member that is expandable from a collapsed state to an expanded state. The tubular member comprises at least one slide-and-lock section, comprising separate first and second axially nested, slidably coupled structural elements, at least one of which comprises a deflectable structure configured to deflect during expansion from the collapsed state to the expanded state, thereby resisting recoil, and wherein no portion of either structural elements weaves through paired slots in the other structural element.

In preferred variations, the deflectable structure is configured to deflect axially. Alternatively, the deflectable structure is configured to deflect radially.

Some embodiments provide a slide-and-lock stent that comprises a tubular member. The tubular member is expandable from a collapsed diameter to an expanded diameter. The tubular member comprises a first circumferential slide-and-lock section and a second circumferential slide-and-lock section. The slide-and-lock sections are longitudinally arranged and linked. Each of the slide-and-lock sections comprises a first axial element and a second axial element. The corresponding axial elements of each slide-and-lock section are spatially offset and connected by an interlocking articulating mechanism. Each of the first axial elements comprises a first rib with least one axially outwardly extending tooth and each of the second axial elements comprises a second rib with at least one axially inwardly extending tooth. Corresponding outwardly and inwardly extending teeth engage one another during expansion and are configured to permit one-way sliding between the corresponding first and second axial elements such that at least one of the corresponding first and second ribs is axially and temporarily deflected during expansion from the collapsed diameter to the expanded diameter.

Some embodiments provide a slide-and-lock stent that comprises a tubular member. The tubular member is expandable from a first diameter to a second diameter. The tubular member comprises a first circumferential section and a second circumferential section. The circumferential sections are longitudinally arranged. A linkage section connects the circumferential sections and is configured to provide flexibility. Each of the circumferential sections comprises a first slide-and-lock element and a second slide-and-lock element. The corresponding slide-and-lock elements of each circumferential section are radially connected by a slidable articulating mechanism. Each of the first slide-and-lock elements comprises at least one tooth and each of the second slide-and-lock elements comprises at least one radially extending tooth. During expansion the teeth of the first slide-and-lock elements engage corresponding radially extending teeth of the second slide and lock sections. The teeth are configured to permit one-way sliding between the corresponding first and second slide-and-lock elements such that at least a portion of the corresponding first and second slide-and-lock elements is radially deflected during expansion from the first diameter to the second diameter.

Some embodiments provide a slide-and-lock stent that comprises a tubular member. The tubular member is expandable from a collapsed state to an expanded state and comprises a lumen. The tubular member comprises at least one slide-and-lock section. The slide-and-lock section comprises at least one first structural element and at least one second structural element that are radially interlocked with an articulating mechanism such as to provide circumferential relative motion between the first structural element and the second structural element. The articulating mechanism is configured to permit one-way sliding between the first structural element and the second structural element such that at least a portion of the first structural element and/or at least a portion of the second structural element is elastically deflected during expansion from the collapsed state to the expanded state. Advantageously, the radial interlocking between the structural elements substantially eliminates radial overlap and allows for a substantially clear through-lumen such that substantially no structure protrudes into the lumen in either the collapsed or the expanded state.

In some embodiments, the stent can be configured such that one or more interconnection members thereof comprise a stop member for limiting expansion of the stent. For example, the stop member can be disposed at a distal end of the interconnection member. The engagement aperture of the linkage section can define a first passing profile and the stop member defines a second passing profile being greater than the first passing profile. Thus, as the interconnection member passes through the engagement aperture during expansion, the movement of the interconnection member relative to the engagement aperture can be limited by the stop member.

In embodiments of the inventions, structural elements can be linked together and interlocking elements captured through a wide variety of techniques. For example, channels can be created or added that allow the elements to slide within, between or therethrough. Other examples include, but are not limited to, capture straps, overhanging elements, covers, tongue-groove configurations and other suitable geometries, that can be employed or created through a wide variety of techniques to provide for linkage and capture of elements.

Embodiments of the inventions provide an improved stent: one that desirably is small enough and flexible enough when collapsed to permit uncomplicated delivery to the affected area; one that is sufficiently flexible upon deployment to conform to the shape of the affected body lumen; one that expands uniformly to a desired diameter, without change in length; one that maintains the expanded size, without significant recoil; one that has sufficient scaffolding to provide a clear through-lumen; one that supports endothelialization or covering of the stent with vessel lining, which in turn minimizes the risk of thrombosis; and one that has a greater capacity to deliver therapeutic agents to minimize injury, treat restenosis and other vascular diseases.

Stents in accordance with embodiments of the inventions can be fabricated or created using a wide variety of manufacturing methods, techniques and procedures. These include, but are not limited to, lasing, laser processing, milling, stamping, forming, casting, molding, laminating, bonding, welding, adhesively fixing, and the like, among others.

In some embodiments, stent features and mechanisms are created in a generally two dimensional geometry and further processed, for example by utilizing, but not limited to, bonding, lamination and the like, into three dimensional designs and features. In other embodiments, stent features and mechanisms are directly created into three dimensional shapes, for example by utilizing, but not limited to, processes such as injection molding and the like.

In preferred variations to the above-described stents, the stent further comprises a material selected from the group consisting of metal and polymer. Preferably, the polymer comprises a bioresorbable polymer. More preferably, the polymer comprises a radiopaque, bioresorbable polymer. In one aspect, the polymer forms a coating on at least a portion of the stent. The polymer coating may further comprise a biocompatible, bioresorbable polymer adapted to promote a selected biological response.

A method for re-treatment of a body lumen is disclosed in accordance with another embodiment of the present inventions. The method comprises the steps of: deploying to a region of the body lumen any of the above described stents, wherein the stent is made from a bioresorbable polymer, and resides at the region for a period of time; and administering to the region, after the period of time, a second treatment, such as for example, treatments selected from the group consisting of a second stent of any kind, angioplasty, arthrectomy, surgical bypass, radiation, ablation, local drug infusion, etc., or any subsequent intervention or treatment.

In preferred variations to the above-described stents, the stent further comprises a therapeutic agent.

In preferred variations to the above-described stents, the stent further comprises a layered material. Preferably, the layered material comprises a bioresorbable polymer.

One key design aspect of embodiments of a slide and lock vascular device is its deployment ratio, that is, the ratio of final maximum diameter to initial compacted diameter. Depending upon the particular design being pursued or the application being addressed, the deployment ratio may vary. Advantageously, the stent of embodiments of the inventions allows the number of elements to be increased or decreased, that is, varied, as needed or desired, to achieve optimization of the deployment ratio as well as device performance, crossing profile, flexibility, among others. This desirably adds to the device versatility and utility.

In preferred variations to the above-described stents, a cross-sectional geometry of at least a portion of the stent is tapered so as to produce generally desirable blood flow characteristics when the stent is placed in a blood vessel lumen.

In preferred variations to the above-described stents, the stent further comprises a retractable sheath sized for enclosing the tubular member during delivery to a treatment site.

In preferred variations to the above-described stents, the stent further comprises a solid wall region. The solid wall region may further comprise an opening.

In preferred variations to the above-described stents, the stent further comprises a polymeric sheath.

A system for treating a site within a vessel is also disclosed. The system comprises a catheter having a deployment means, and any of the above-described stents, wherein the catheter is adapted to deliver the stent to the site and the deployment means is adapted to deploy the stent. In preferred variations, the catheter is selected from the group consisting of over-the-wire catheters, coaxial rapid-exchange catheters, and multi-exchange delivery catheters.

All of these embodiments are intended to be within the scope of the inventions herein disclosed. These and other embodiments of the inventions will become readily apparent to those skilled in the art from the following detailed description of the preferred embodiments having reference to the attached figures, the inventions not being limited to any particular preferred embodiment(s) disclosed.

BRIEF DESCRIPTION OF THE DRAWINGS

Having thus summarized the general nature of the inventions and some of its features and advantages, certain preferred embodiments and modifications thereof will become apparent to those skilled in the art from the detailed description herein having reference to the figures that follow, of which:

FIG. 66A is a top view of an elongate linkage section of the axially nested stent of FIG. 66, in accordance with an embodiment.

FIG. 66B is a side view of the elongate linkage section of FIG. 66A.

FIG. 67A is a top view of an interconnection member of the stent of FIG. 66, in accordance with an embodiment.

FIG. 67B is a side view of the interconnection member of FIG. 67A.

DETAILED DESCRIPTION OF THE PREFERRED EMBODIMENTS

Figure 1:
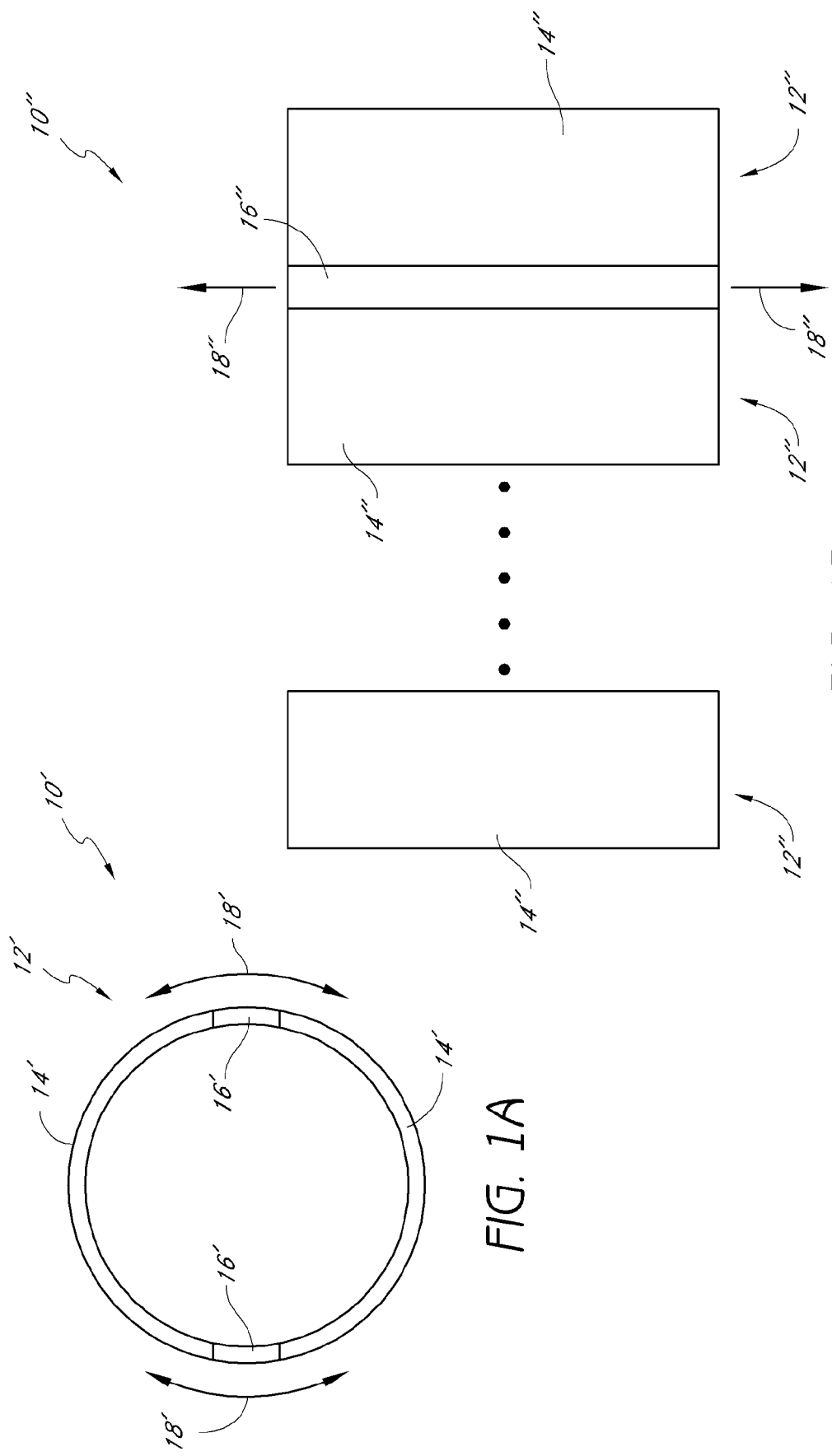
FIG. 1A is a simplified schematic end view of an axially nested slide and lock stent illustrating features and advantages in accordance with an embodiment of the inventions.
FIG. 1B is a simplified schematic side view of an axially nested slide and lock stent illustrating features and advantages in accordance with another embodiment of the inventions.

While the description sets forth various embodiment specific details, it will be appreciated that the description is illustrative only and should not be construed in any way as limiting the inventions. Furthermore, various applications of the inventions, and modifications thereto, which may occur to those who are skilled in the art, are also encompassed by the general concepts described herein.

The term "stent" is used herein to designate embodiments for placement in (1) vascular body lumens (i.e., arteries and/or veins) such as coronary vessels, neurovascular vessels and peripheral vessels for instance renal, iliac, femoral, popliteal, subclavian and carotid; and in (2) nonvascular body lumens such as those treated currently i.e., digestive lumens (e.g., gastrointestinal, duodenum and esophagus, biliary ducts), respiratory lumens (e.g., tracheal and bronchial), and urinary lumens (e.g., urethra); (3) additionally such embodiments may be useful in lumens of other body systems such as the reproductive, endocrine, hematopoietic and/or the integumentary, musculoskeletal/orthopedic and nervous systems (including auditory and ophthalmic applications); and, (4) finally, stent embodiments may be useful for expanding an obstructed lumen and for inducing an obstruction (e.g., as in the case of aneurysms).

In the following description of the present inventions, the term "stent" may be used interchangeably with the term "prosthesis" and should be interpreted broadly to include a wide variety of devices configured for supporting a segment of a body passageway. Furthermore, it should be understood that the term "body passageway" encompasses any lumen or duct within a body, such as those described herein.

Still further, it should be understood that the term "shape-memory material" is a broad term that includes a variety of known shape memory alloys, such as nickel-titanium alloys, as well as any other materials that return to a previously defined shape after undergoing substantial plastic deformation.

In one preferred embodiment, the assembled stent generally comprises a tubular member having a length in the longitudinal axis and a diameter in the circumferential axis sized for insertion into the body lumen. The tubular member is preferably formed with a "clear through-lumen," which is defined as having little or no structure protruding into the lumen in either the collapsed or expanded condition.

In many of the embodiments illustrated and described herein, the intraluminal stent is preferably provided with "slide-and-lock elements" generally referred to herein as "axial elements." The axial elements are slidably interconnected with circumferentially adjacent axial elements in a manner wherein the stent exhibits mono-directional axial expansion from an axially collapsed state to an axially expanded state, e.g., during deployment. The axial elements are preferably configured to provide a ratcheting effect such that the stent is maintained (i.e., "locked-out") in the expanded diameter after deployment within the body passage. More particularly, the structures (e.g., axial elements) may flex or bend; however, unlike conventional balloon expandable stents, no substantial plastic deformation of the elements are required during expansion of the stent from a collapsed diameter to an expanded diameter. Elements of this type are generally referred to herein as "non-deforming elements." Accordingly, the term "non-deforming element" is intended to generally describe a structure that substantially maintains its original dimensions (i.e., length and width) during deployment of the stent. Each axial element is preferably formed as a flat sheet that is cut or otherwise shaped to provide a slide-and-lock mechanism.

The phrase "weaves through paired slots" has the meaning described in U.S. Pat. Nos. 5,549,662 and 5,733,328. As used herein, this phrase describes a particular slidable coupling or articulation between stent components, wherein a portion of one stent component passes through one of a pair of slots in another stent component, and then passes back through the second of the pair of slots, creating a weave-like interlocking configuration. Preferred embodiments of the present inventions employ slidable couplings or articulations between stent components that avoid weave-like configurations, such that in these preferred embodiments, no portion of a stent component weaves through paired slots in another stent component.

The term "radial strength," as used herein, describes the external pressure that a stent is able to withstand without incurring clinically significant damage. Due to their high radial strength, balloon expandable stents are commonly used in the coronary arteries to ensure patency of the vessel. During deployment in a body lumen, the inflation of the balloon can be regulated for expanding the stent to a particular desired diameter. Accordingly, balloon expandable stents may be used in applications wherein precise placement and sizing are important. Balloon expandable stents may be used for direct stenting applications, where there is no pre-dilation of the vessel before stent deployment, or in prosthetic applications, following a pre-dilation procedure (e.g., balloon angioplasty). During direct stenting, the expansion of the inflatable balloon dilates the vessel while also expanding the stent.

In another preferred embodiment, the stent further comprises a tubular member formed from a biocompatible and preferably, bioresorbable polymer, such as those disclosed in co-pending U.S. application Ser. No. 10/952,202; incorporated herein in its entirety by reference. It is also understood that the various polymer formulae employed may include homopolymers and heteropolymers, which includes stereoisomers. Homopolymer is used herein to designate a polymer comprised of all the same type of monomers. Heteropolymer is used herein to designate a polymer comprised of two or more different types of monomer which is also called a co-polymer. A heteropolymer or co-polymer may be of a kind known as block, random and alternating. Further with respect to the presentation of the various polymer formulae, products according to embodiments of the present inventions may be comprised of a homopolymer, heteropolymer and/or a blend of such polymers.

The term "bioresorbable" is used herein to designate polymers that undergo biodegradation (through the action of water and/or enzymes to be chemically degraded) and at least some of the degradation products are eliminated and/or absorbed by the body. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography). The term, "inherently radiopaque", is used herein to designate polymer that is intrinsically radiopaque due to the covalent bonding of halogen species to the polymer. Accordingly, the term does encompass a polymer which is simply blended with a halogenated species or other radiopacifying agents such as metals and their complexes.

In another preferred variation, the stent further comprises an amount of a therapeutic agent (for example, a pharmaceutical agent and/or a biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, tissues or cell lines or synthetic analogs of such molecules, including antibodies, growth factors, interleukins and interferons; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

In some embodiments, the design features of the axial elements can be varied to customize the functional features of strength, compliance, radius of curvature at deployment and expansion ratio. In some embodiments, the stent comprises a resorbable material and vanishes when its job is done. In some embodiments, the stent serves as a therapeutic delivery platform.

The stent preferably comprises at least one longitudinal module, which consists of a series of axial elements, including one or more slide-and-lock axial elements and optionally one or more passive axial elements, linked in the longitudinal axis by flexible coupling portions. Preferably, the axial elements from two or more similar longitudinal modules are slidably connected to circumferentially adjacent axial elements. Of course, single module (or jellyroll-type) embodiments are also encompassed within the scope of the present disclosure. Each module is preferably a discrete, unitary structure that does not stretch or otherwise exhibit any substantial permanent deformation during stent deployment.

Some embodiments relate to an axially expandable stent used to open, or to expand a targeted area in a body lumen. In some embodiments, the assembled stent comprises a tubular member having a length in the longitudinal axis and a diameter in the circumferential or axial axis, of appropriate size to be inserted into the body lumen. The length and diameter of the tubular member may vary considerably for deployment in different selected target lumens depending on the number and configuration of the structural components, described below. The tubular member is adjustable from at least a first collapsed diameter to at least a second expanded diameter. One or more stops and engaging elements or tabs are incorporated into the structural components of the tubular member whereby recoil (i.e., collapse from an expanded diameter to a more collapsed diameter) is minimized to less than about 5%.

The tubular member in accordance with some embodiments has a "clear through-lumen," which is defined as having no structural elements protruding into the lumen in either the collapsed or expanded diameters. Further, the tubular member has smooth marginal edges to minimize the trauma of edge effects. The tubular member is preferably thin-walled (wall thickness depending on the selected materials ranging from less than about 0.010 inches for plastic and degradable materials to less than about 0.002 inches for metal materials) and flexible (e.g., less than about 0.01 Newtons force/millimeter deflection) to facilitate delivery to small vessels and through tortuous vasculature.

Stents according to aspects of the present inventions are preferably formed with walls for providing a low crossing profile and for allowing excellent longitudinal flexibility. In preferred embodiments, the wall thickness is about 0.0001 inches to about 0.0250 inches, and more preferably about 0.0010 to about 0.0100 inches. However, the wall thickness depends, at least in part, on the selected material. For example, the thickness may be less than about 0.0080 inches for plastic and degradable materials and may be less than about 0.0020 inches for metal materials. More particularly, for a 3.00 mm stent application, when a plastic material is used, the thickness is preferably in the range of about 0.0040 inches to about 0.0085 inches. However, a stent having various diameters may employ different thicknesses for biliary and other peripheral vascular applications. The above thickness ranges have been found to provide preferred characteristics through all aspects of the device including assembly and deployment. However, it will be appreciated that the above thickness ranges should not be limiting with respect to the scope of the inventions and that the teachings of the present inventions may be applied to devices having dimensions not discussed herein.

Some aspects are also disclosed in co-pending U.S. patent application Ser. Nos. 11/016,269, 60/601,526, 10/655,338, 10/773,756, 10/897,235; each of which is incorporated herein in its entirety by reference thereto.

The preferred embodiments of the inventions described herein relate generally to expandable medical implants for maintaining support of a body lumen and, in particular, to an axially nested, diametrically expandable, slide and lock vascular device for enlarging an occluded portion of a vessel.

While the description sets forth various embodiment specific details, it will be appreciated that the description is illustrative only and should not be construed in any way as limiting the inventions. Furthermore, various applications of the inventions, and modifications thereto, which may occur to those who are skilled in the art, are also encompassed by the general concepts described herein.

Some embodiments relate to an expandable stent having a plurality of longitudinally arranged sections, segments or frames. The sections have a plurality of axially nesting sliding and locking elements permitting one-way sliding of the elements from a collapsed diameter to an expanded/deployed diameter, but inhibiting recoil from the expanded diameter. In some embodiments, the stent comprises a polymer and is fabricated by a combination of laminating and laser cutting a plurality of layers. Advantageously, the stent substantially reduces or minimizes overlap between the structural elements and thus desirably reduces the effective wall thickness of the stent. Another advantage is that the stent design elements and interlocks can be varied to customize the functional features of strength, compliance, radius of curvature at deployment and expansion ratio. In some embodiments, the stent comprises a resorbable material and vanishes when its job is done. In some embodiments, the stent serves as a delivery platform for therapeutic agents such as pharmaceutical compounds or biological materials.

Some embodiments relate to a radially expandable stent used to open, or to expand a targeted area in a body lumen. Some embodiments relate to a radially expandable stent used as a drug delivery platform to treat vascular conditions. In some embodiments, the assembled stent comprises a tubular member having a length in the longitudinal axis and a diameter in the radial axis, of appropriate size to be inserted into the body lumen. The length and diameter of the tubular member may vary considerably for deployment in different selected target lumens depending on the number and configuration of the structural components, described below. The tubular member is adjustable from at least a first collapsed diameter to at least a second expanded diameter. One or more stops, teeth, slots or grooves and engaging elements, tabs, teeth or tongues are incorporated into the structural components of the tubular member whereby recoil (i.e., collapse from an expanded diameter to a more collapsed diameter) is minimized to less than about 5%.

The tubular member in accordance with some embodiments has a "clear through-lumen," which is defined as having no structural elements protruding into the lumen in either the collapsed or expanded diameters. Further, the tubular member has smooth marginal edges to minimize the trauma of edge effects. The tubular member is preferably thin-walled (wall thickness depending on the selected materials and intended vessel size to be treated ranging from less than about 0.009 inches for plastic and resorbable materials to less than about 0.0008 inches for metal materials) and flexible to facilitate delivery to small vessels and through tortuous vasculature. The thin walled design can also minimize blood turbulence and thus risk of thrombosis. The thin profile of the deployed tubular member in accordance with some embodiments also facilitates more rapid endothelialization of the stent.

In some embodiments, the wall of the tubular member comprises at least one section, which comprises at least one sliding and locking structural element. Preferably, a plurality of sections are connected in the longitudinal axis via linkage elements which couple at least some of the structural elements between adjacent sections. The structural elements are configured within each section so as to generally define the circumference of the tubular member. In some embodiments, each structural element within a section is a discrete, unitary structure. In some embodiments, the tubular member comprises an integral unit including one or more sections with one or more structural elements. In one embodiment, each structural element comprises one or more circumferential ribs bowed in the radial axis to form a fraction of the total circumference of the tubular member.

At least some of the structural elements have at least one articulating mechanism (e.g., deflecting or non-deflecting) for providing slidable engagement between adjacent circumferentially offset structural elements and/or adjacent axially offset structural elements. In one embodiment, the articulating mechanism includes a tongue and groove configuration. The articulating between structural elements is such that a locking or ratcheting mechanism is formed, whereby the adjacent elements may slide circumferentially in one direction but are substantially prevented from sliding circumferentially in an opposite direction. Accordingly, the tubular member may be radially expanded from a smaller diameter to a larger diameter, but advantageously recoil to a smaller diameter is minimized by the locking mechanism. The amount of recoil can be customized for the application by adjusting the configuration of the articulating locking mechanism. In one embodiment, the recoil is less than about 5%.

Some features and arrangements of embodiments of stents are disclosed in U.S. Pat. Nos. 6,033,436, 6,224,626 and 6,623,521 each issued to Steinke, the disclosures of each one of which are hereby incorporated in their entirety by reference thereto.

Embodiments and Design Features of the Device

FIG. 1A schematically depicts an end view of one embodiment of a vascular device, prosthesis or stent 10' generally comprising one or more longitudinally arranged sections, segments or frames 12'. Each section 12' includes two or more structural elements 14' that are radially or circumferentially coupled to other structural elements 14' of the same section 12' by one-way slide and lock articulating mechanisms 16'.

The articulating mechanisms 16' allow one-way expansion of the section 12' from a first collapsed diameter to a second expanded diameter. During expansion, there is circumferential relative motion between the structural elements 14' as generally shown by arrows 18' such that one or both of the structural elements 14' slidably move apart.

As described in more detail below, even though the structural elements 14' of the same section 12' are radially or circumferentially coupled, the sections 12' and structural elements 14' are designed and configured such that there is minimal or reduced overlapping in the radial or circumferential direction between the structural elements 14' in both the non-expanded and expanded states. Thus, the structural elements 14' are referred to as being axially, longitudinally or non-radially nested.

FIG. 1B schematically depicts a side view of another embodiment of a vascular device, prosthesis or stent 10" generally comprising two or more longitudinally arranged sections, segments or frames 12". Each section 12" includes one or more structural elements 14". Structural elements 14" of adjacent sections 12" are axially or longitudinally coupled to one another by one-way slide and lock articulating mechanisms 16".

The articulating mechanisms 16" allow one-way expansion of the sections 12" from a first collapsed diameter to a second expanded diameter. During expansion, there is circumferential relative motion between the structural elements 14" as generally shown by arrows 18" such that one or both of the structural elements 14" slidably move.

As described in more detail below, the axial or longitudinal coupling between the structural elements 14" of adjacent sections 12", and the design and configuration of the sections 12" and structural elements 14" are such that there is minimal or reduced overlapping in the radial or circumferential direction between the structural elements 14" in both the non-expanded and expanded states. Thus, the structural elements 14" are referred to as being axially, longitudinally or non-radially nested.

Advantageously, the axially nested embodiments of FIGS. 1A and 1B, and others as described, taught or suggested herein, allow suitable crossing profiles (e.g. luminal size) while maintaining desirable radial strength and luminal patency. In the non-expanded state, there is also minimal or reduced overlap between structural elements, so that the luminal size facilitates insertion of a guiding catheter balloon or the like to expand the vascular device. The collapsed profile can also be made very thin without compromising radial strength. Thus, the stent of embodiments of the inventions can be deployed in small and difficult to reach vessels, such as the intercranial vessels distal to the carotids and the remote coronary vessels.

The axially nested embodiments of FIGS. 1A and 1B, and others as described, taught or suggested herein advantageously significantly minimizes radial stacking (overlap), thus reducing material thickness of the stent in the nondeployed and deployed configurations and thus desirably reduces the effective wall thickness of the deployed stent. Stated differently, the stent substantially eliminates radial overlap between mating structural elements thereby desirably allowing for a low, uniform profile.

Figure 2:
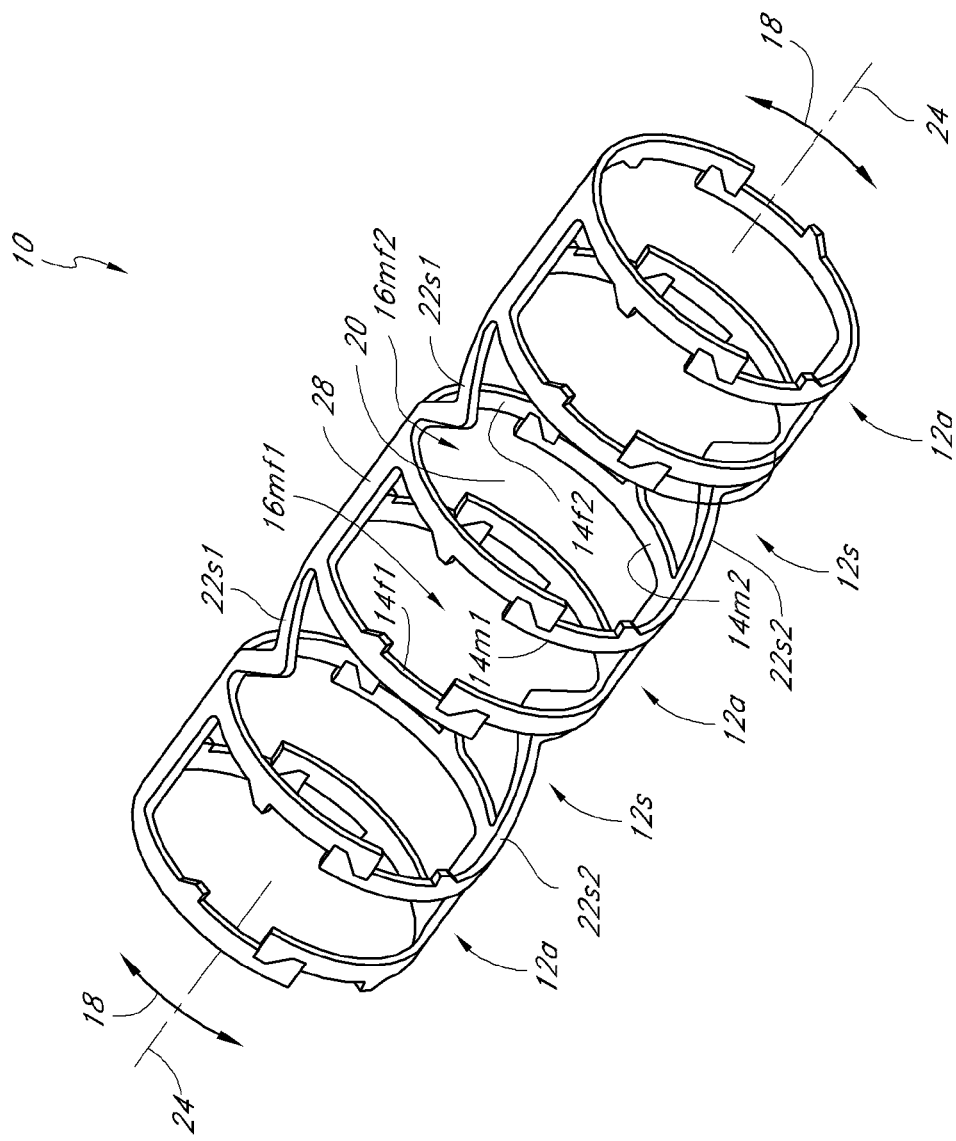
FIG. 2 is a simplified perspective view of an axially nested slide and lock stent in an expanded state illustrating features and advantages in accordance with an embodiment of the inventions.

FIG. 2 shows one embodiment of an axially nested slide and lock vascular device, prosthesis or stent 10 having a tubular form with a wall comprising a plurality of generally longitudinally arranged linked circumferential sections, segments or frames 12a, 12s. The stent 10 has a through lumen 20 which is expandable from a first diameter to a second diameter. The stent 10 and/or the lumen 20 have a generally longitudinal axis 24.

The stent 10 comprises alternatingly arranged slide and lock sections 12a and linkage sections 12s. Each section 12a includes a pair of male structural elements 14m1, 14m2 and a pair of female structural elements 14f1, 14f2 that respectively slidingly mate via respective interlocking articulating mechanisms 16mf1, 16mf2. In modified embodiments, fewer or more structural elements may be efficaciously utilized, as needed or desired.

Each linkage section 12s includes a pair of spring elements 22s1, 22s2 with the spring elements 22s1 connected to adjacent female structural elements 14f1, 14f2 and the spring elements 22s2 connected to adjacent male structural elements 14m1, 14m2. As described further below, the spring elements 22 can allow expansion of the sections 12s and also allow for deflection of ribs of the structural elements 14 during stent expansion. The spring elements 22 also allow for flexibility in the non-deployed and deployed states. In modified embodiments, fewer or more spring elements may be efficaciously utilized, as needed or desired.

During stent expansion, there is circumferential relative motion between the mating male structural elements 14m1, 14m2 and female structural elements 14/1, 14/2 as generally shown by arrows 18. One or both of the mating male-female structural elements 14m1, 14/1 and 14m2, 14/2 may slidably move apart.

Figure 3:
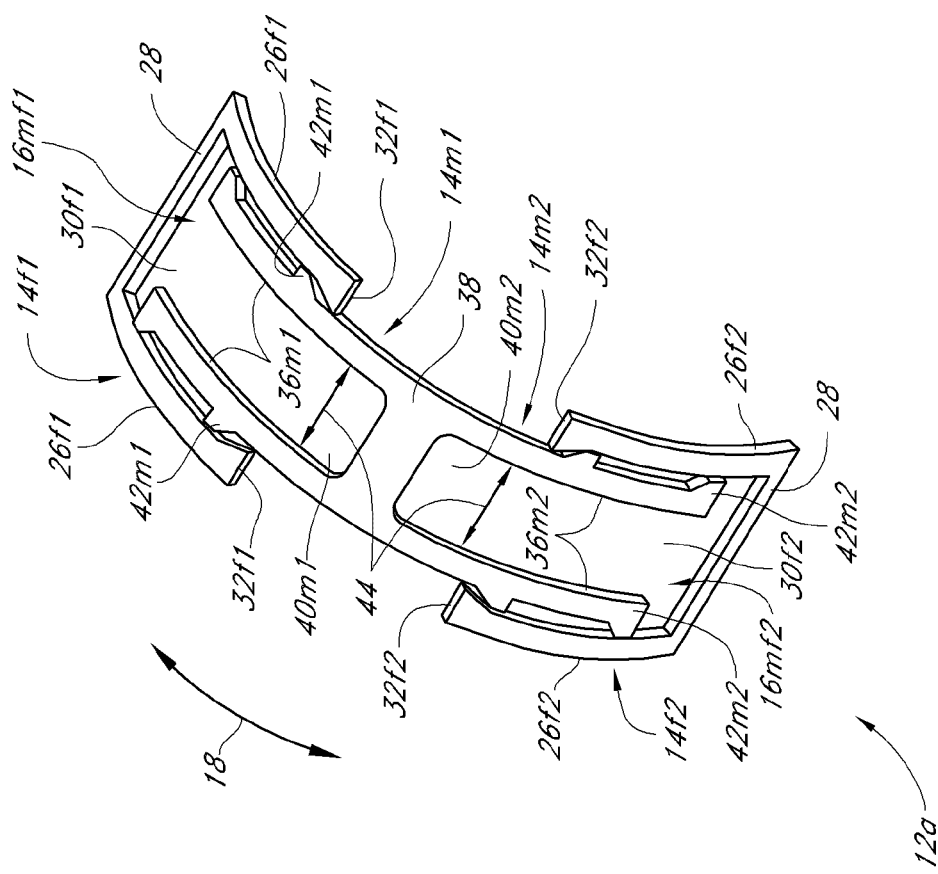
FIG. 3 is a simplified partially exploded perspective view of an undeployed section of the stent of FIG. 2 illustrating features and advantages in accordance with an embodiment of the inventions.
Figure 4:
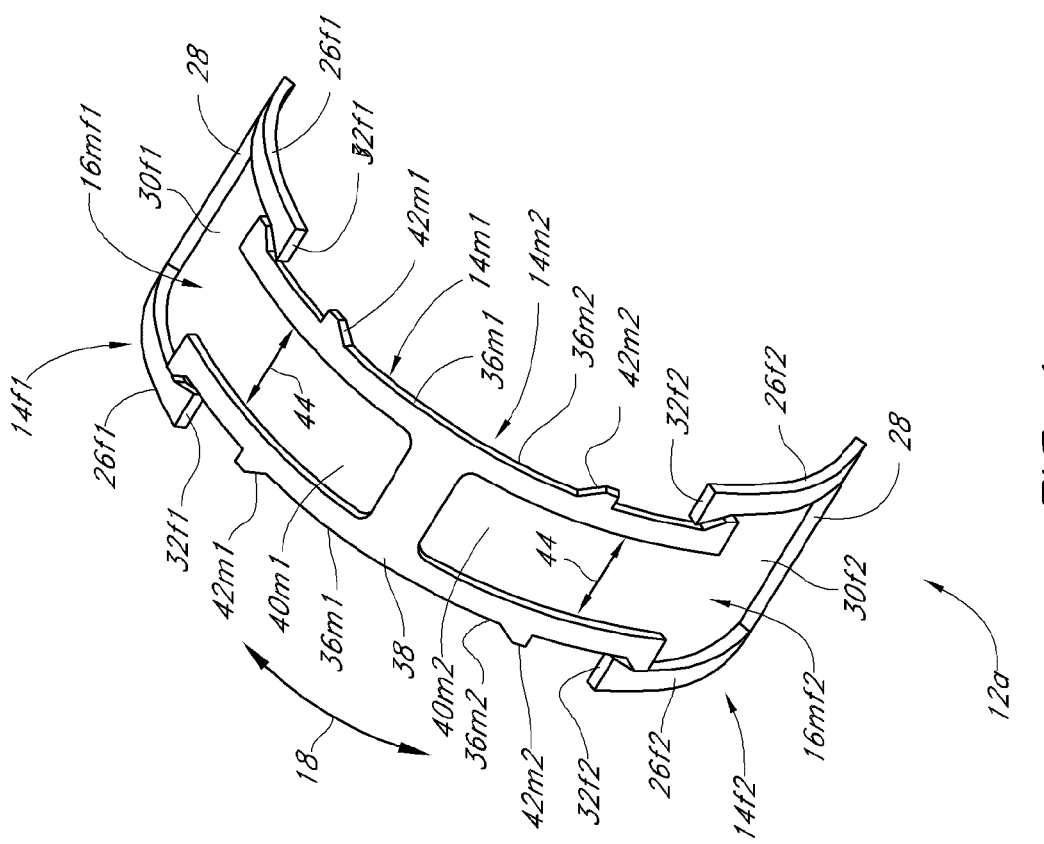
FIG. 4 is a simplified partially exploded perspective view of a deployed section of the stent of FIG. 2 illustrating features and advantages in accordance with an embodiment of the inventions.

FIGS. 3 and 4 are partially exploded views of one of the sections 12a. FIG. 3 shows the section 12a in a collapsed or undeployed state and FIG. 4 shows the section 12a in an expanded or deployed state.

The female structural element 14/1 generally comprises a pair of spaced ribs or arms 26/1 to form a gap 30/1 therebetween. Each of the ribs 26/1 includes an inwardly extending end stop, tooth or tab 32/1 that engage the male structural element 14m1.

The female structural element 14/2 generally comprises a pair of spaced ribs or arms 26/2 to form a gap 30/2 therebetween. Each of the ribs 26/2 includes an inwardly extending end stop, tooth or tab 32/2 that engage the male structural element 14m2.

The female structural elements 14/1, 14/2 share a common end portion 28 to which the ribs 26/1 and 26/2 are connected. In one embodiment, the female structural elements 14/1, 14/2 comprise an integral unit. In modified embodiments, the female structural elements 14/1, 14/2 can efficaciously be connected by other techniques, as needed or desired.

The male structural element 14m1 generally comprises a pair of spaced ribs or arms 36m1 to form a gap 40m1 therebetween. In the collapsed state (FIG. 3), the ribs 36m1 extend into the gap 30/1 between the female ribs 26/1. Each of the ribs 36m1 includes a plurality of outwardly extending spaced stops, teeth or tabs 42m1 that engage the female structural element 14/1 and its stops 32/1.

The male structural element 14m2 generally comprises a pair of spaced ribs or arms 36m2 to form a gap 40m2 therebetween. In the collapsed state (FIG. 3), the ribs 36m2 extend into the gap 30/2 between the female ribs 26/2. Each of the ribs 36m2 includes a plurality of outwardly extending spaced stops, teeth or tabs 42m2 that engage the female structural element 14/2 and its stops 32/2.

The male structural elements 14m1, 14m2 share a common end portion 38 to which the ribs 36m1 and 36m2 are connected. In one embodiment, the male structural elements 14m1, 14m2 comprise an integral unit. In modified embodiments, the male structural elements 14m1, 14m2 can efficaciously be connected by other techniques, as needed or desired.

During expansion, there is circumferential relative motion between the male set of ribs 36m1 and female set of ribs 26/1 with one or both of the sets slidably moving apart. Similarly, there is circumferential relative motion between the male set of ribs 36m2 and female set of ribs 26/2 with one or both of the sets slidably moving apart. The motion is generally denoted by arrows 18.

As illustrated by FIGS. 3 and 4, during expansion, the stops 32/1, 32/2 and the respective stops 42m1, 42m2 cross one another. This is accomplished by utilizing an axially deflecting mechanism. Thus, during "cross-over" the male ribs 36m1 and/or the female ribs 26/1 are respectively deflected outwards and inwards and then resume their original undeflected position. This axial motion is generally denoted by arrows 44.

Similarly, during "cross-over" the male ribs 36m2 and/or the female ribs 26/2 are respectively deflected outwards and inwards and then resume their original undeflected position with their axial motion being generally denoted by the arrows 44. In one embodiment, the spring elements 22s1, 22s2 facilitate this rib deflection by providing a resilient biasing mechanism to achieve substantially elastic rib deflection or deformation.

As indicated above, either the male ribs 36m1, 36m2, the female ribs 26/1, 26/2, both or any other suitable combination of ribs may axially deflect to achieve the desired expansion and other deployment characteristics. The axial deflection is caused by the generation of a generally axial or longitudinal force when the female stops 32/1, 32/2 and respective male stops 42m1, 42m2 slide over, engage or abut one another. As discussed further below, at full expansion, a capture mechanism is provided to limit further stent expansion.

Advantageously, there is substantially no or minimal overlap between nesting male structural elements 14m1, 14m2 and respective female structural elements 14/1, 14/2 in both the collapsed state (see, for example, FIG. 3) and the expanded state (see, for example, FIG. 4). The male ribs 36m1, 36m2 and respective female ribs 26/1, 26/2 of a given section 12a are axially and/or radially displaced from one another and from the ribs or elements of adjacent sections. Thus, the structural elements 14 are referred to as being axially nested since their radial overlap is substantially reduced or minimal.

Figure 5:
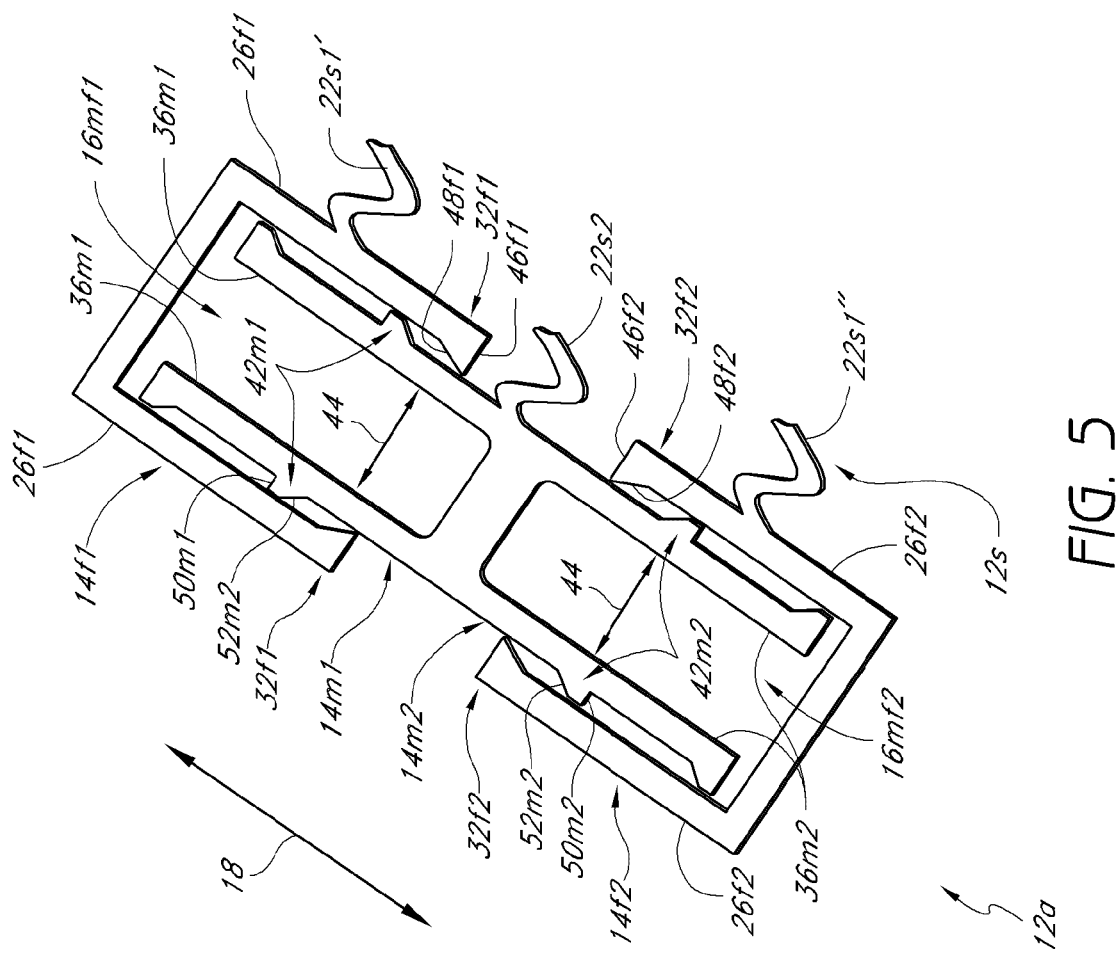
FIG. 5 is a simplified planar perspective view of sections of the stent of FIG. 2 illustrating features and advantages in accordance with an embodiment of the inventions.

FIG. 5 shows a planar view of the active slide and lock section 12a connected to an adjacent linkage section 12s. The linkage section 12s includes three elements 22s1', 22s1" and 22s2 some or all of which may be spring elements.

In the embodiment of FIG. 5, two independent spring elements 22s1', 22s1" of the linkage section 12s are connected to a respective one of the female structural elements 14/1, 14/2 and one spring element 22s2 of the same linkage section 12s is connected to both the male structural elements 14m1, 14m2. In modified embodiments, any suitable number of spring elements 22s and/or rigid elements may be connected to the male and female structural elements 14m, 14f with efficacy, as needed or desired, to control the rib deflection and stent deployment characteristics.

The female stops 32/1, 32/2 are configured so that they have generally flat respective end surfaces 46/1, 46/2 to substantially reduce or minimize recoil and generally tapered respective engaging surfaces 48/1, 48/2 to facilitate one-way sliding. Similarly, the male stops 42m1, 42m2 are configured so that they have generally flat respective end surfaces 50m1, 50m2 to substantially reduce or minimize recoil and generally tapered respective engaging surfaces 52m1, 52m2 to facilitate one-way sliding. Other suitable configurations that inhibit undesirable recoil and facilitate one-way expansion may be efficaciously utilized, as needed or desired.

Figure 6:
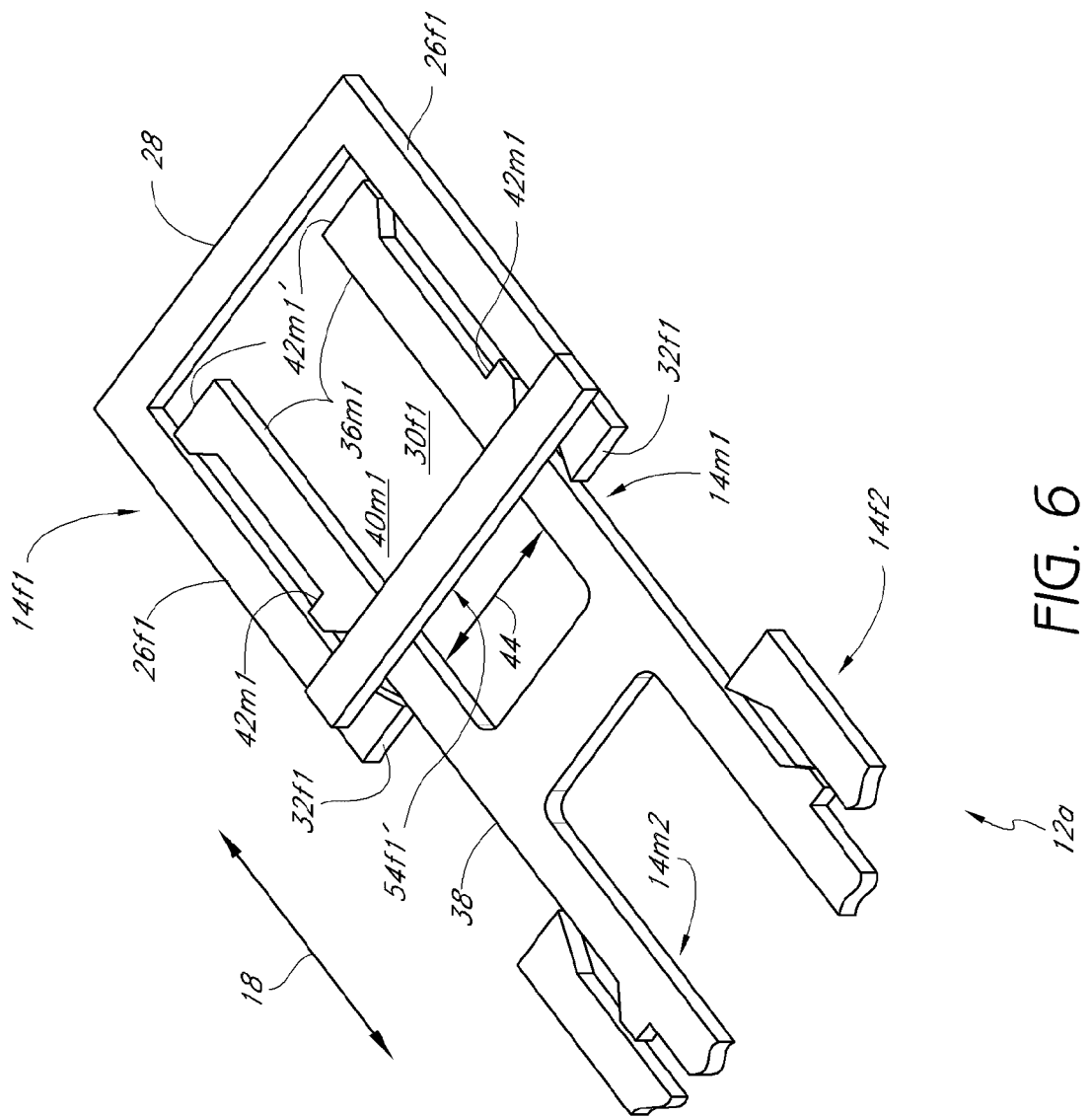
FIG. 6 is a simplified planar perspective partial view of a section of the stent of FIG. 2 with a capture mechanism illustrating features and advantages in accordance with an embodiment of the inventions.

FIG. 6 shows one embodiment of the female structural element 14/1 including a capture mechanism, device or strap 54/1' to provide profile capture, containment or control during stent expansion. A similar or other suitable capture mechanism can also be associated with the other female structural element 14/2.

The capture strap 54/1' is connected to the female ribs 26/1 and extends therebetween. In one embodiment, the female structural element 14/1 including the capture strap 54/1' comprise an integral unit. In modified embodiments, the capture strap, member or element 54/1' can efficaciously be connected to the ribs 26/1 by other techniques, as needed or desired.

In the illustrated embodiment of FIG. 6, the capture strap 54/1' is located substantially adjacent to the open end of the gap 30/1 formed between the female ribs 26/1 and substantially adjacent to the end stops 32/1. The capture strap 54/1' permits sliding relative motion between itself (and hence the female structural element 14/1) and the male structural element 14m1 such that the male ribs 36m1 desirably do not jump out of their track during stent deployment.

The female end stops 32/1 and the male end stops 42m1' are configured to provide engagement that stops further stent expansion. The end stops 42m1' are located adjacent to the open end of the gap 40m1 formed between the ribs 36m1. Any one of a number of suitable locking or lock-out mechanisms may be utilized to control the maximum stent expansion such as tongue and groove arrangements and the like, among others.

Figure 7:
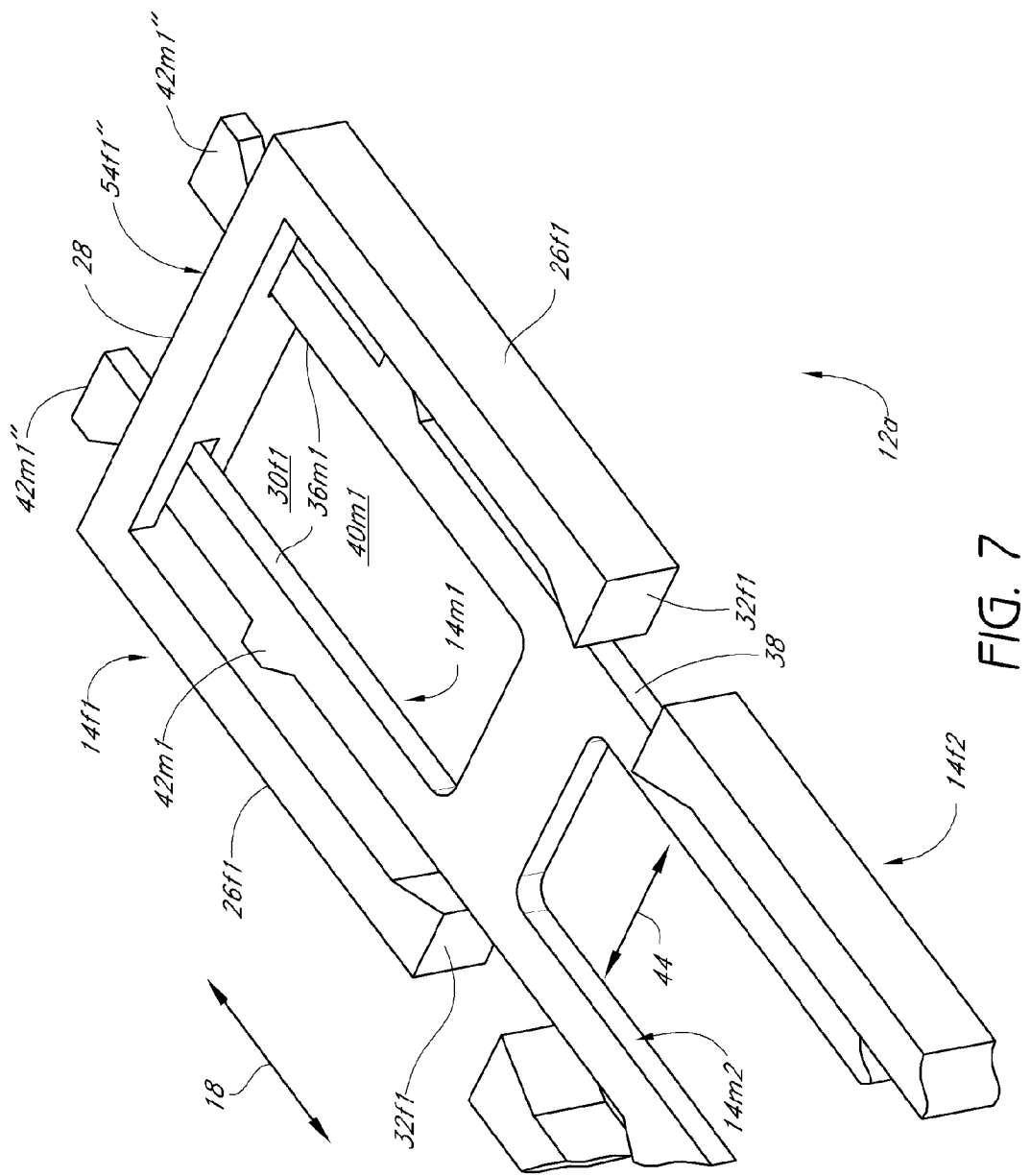
FIG. 7 is a simplified planar perspective partial view of a section of the stent of FIG. 2 with a capture mechanism illustrating features and advantages in accordance with another embodiment of the inventions.
Figure 8:
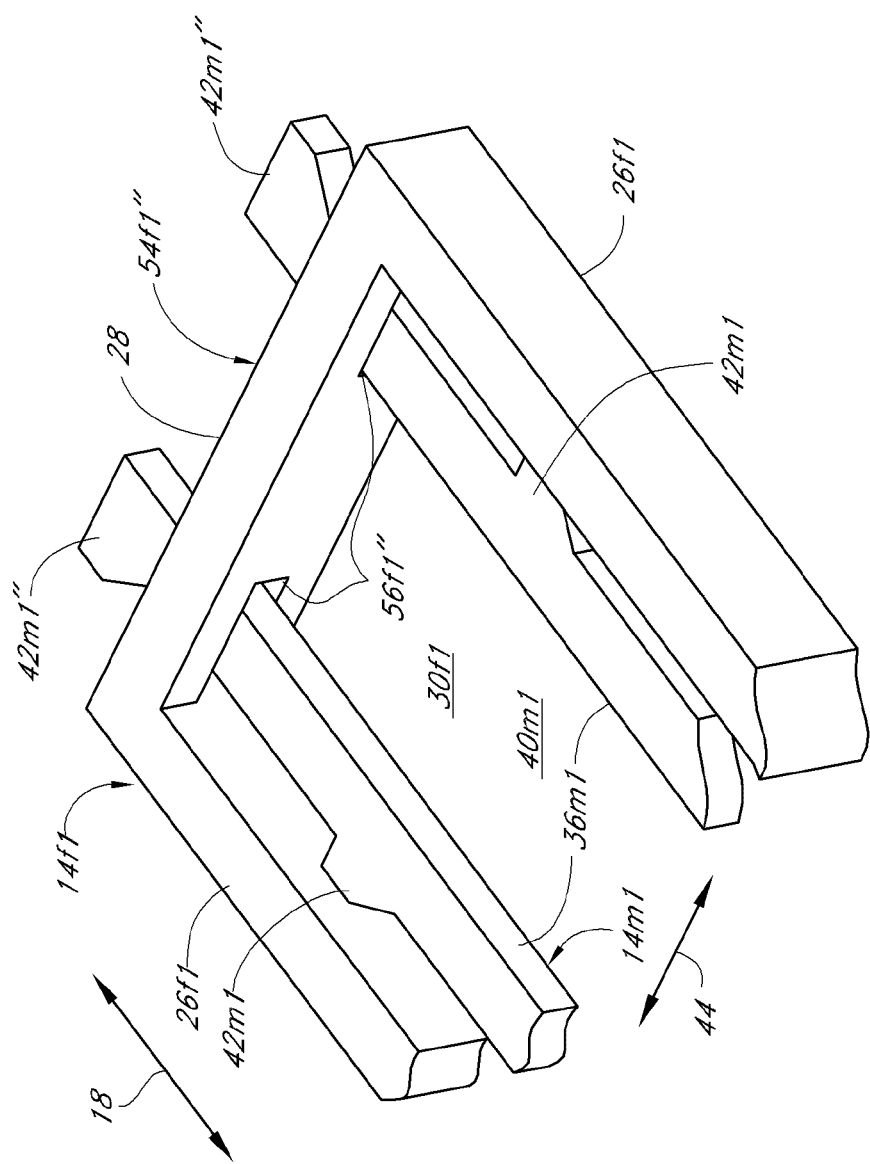
FIG. 8 is a simplified planar enlarged perspective view of the capture mechanism of FIG. 7.

FIGS. 7 and 8 show another embodiment of a capture mechanism, device or strap 54/1" incorporated with the female structural element 14/1 to provide profile control in the non-deployed or collapsed state. A similar or other suitable capture mechanism can also be associated with the other female structural element 14/2. The capture strap 54/1" may be used in conjunction with the capture strap 54/1' (FIG. 6) or independently, as needed or desired.

The capture strap 54/1" is connected to the female ribs 26/1 and extends therebetween. In one embodiment, the female structural element 14/1 including the capture strap 54/1" comprise an integral unit. In modified embodiments, the capture strap 54/1" can efficaciously be connected to the ribs 26/1 by other techniques, as needed or desired.

In the illustrated embodiment of FIGS. 7 and 8, the capture strap, member or element 54/1" is located substantially adjacent to the closed end of the gap 30/1 formed between the female ribs 26/1 and substantially at the end portion 28. The capture strap 54/1" holds the male ribs 36/1 in place in the deployed state and prevents them from jumping out. This desirably maintains the stent profile.

In the embodiment of FIGS. 7 and 8, the end portion capture strap 54/1" includes a pair of spaced slots or grooves 56/1" through which respective male ribs 36m1 extend. The slots 56/1" are configured to allow slidable relative motion between the ribs 36m1 and slots 56/1" thereby allowing the end stops 42m1" to pass therethrough during stent expansion or deployment. Grooves or tracks may be provided on the inwardly facing surfaces of the female ribs 26/1 that engage the male stops 42m1, 42m1" during stent expansion, thereby preventing the male ribs 36m1 from jumping out and disturbing the stent profile.

The female end stops 32/1 and the male end stops 42m1" are configured to provide engagement that stops further stent expansion. The end stops 42m1" are located adjacent to the open end of the gap 40m1 formed between the ribs 36m1. Any one of a number of suitable locking or lock-out mechanisms may be utilized to control the maximum stent expansion such as tongue and groove arrangements and the like, among others.

Figure 9:
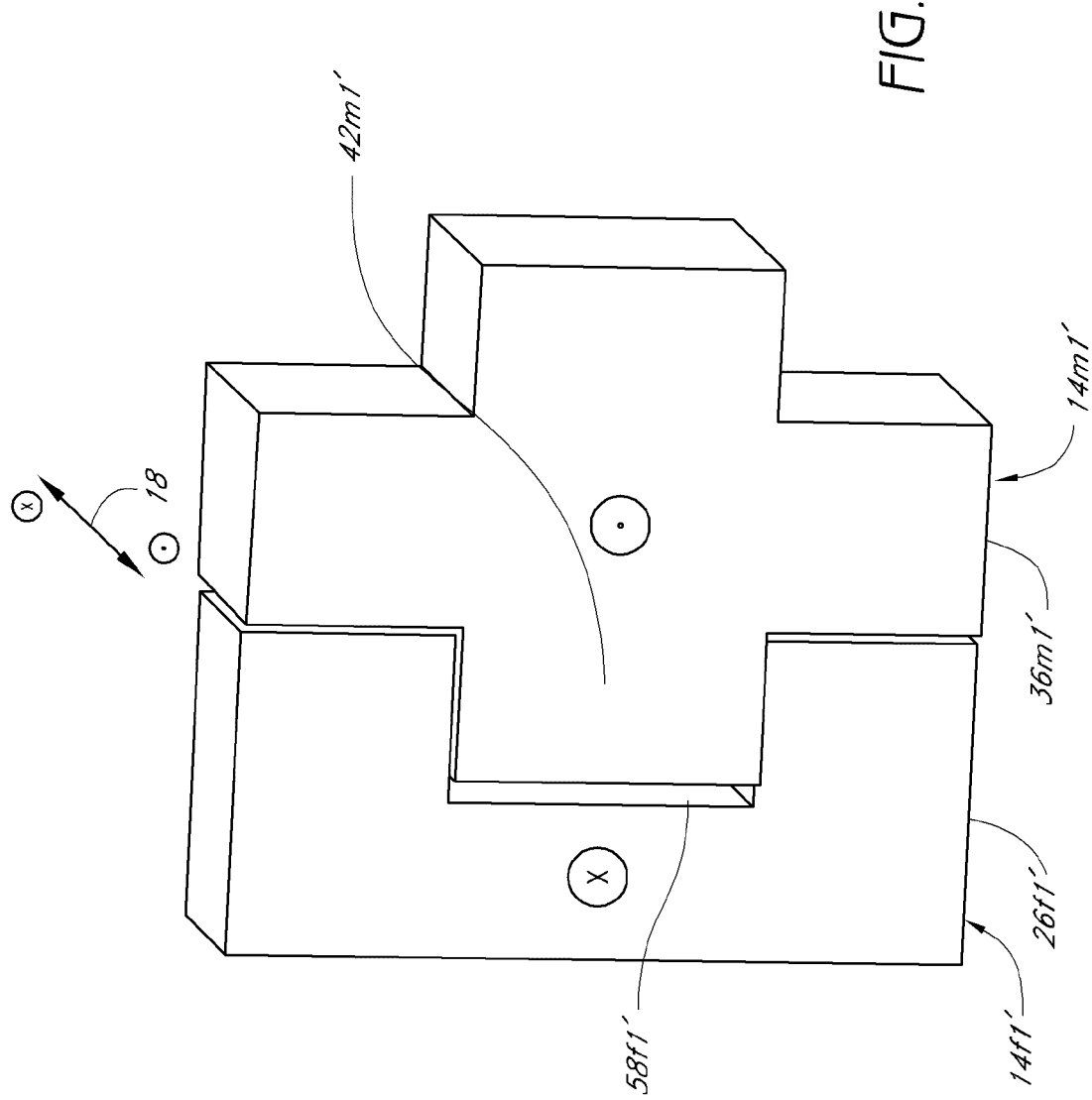
FIG. 9 is a simplified planar perspective view of a stent articulation geometry illustrating features and advantages in accordance with an embodiment of the inventions.

FIG. 9 shows an capture and/or articulation geometry between a male structural element 14m1' and a female structural element 14/1' that joins or links adjacent elements 14m1', 14/1' in accordance with one embodiment. Female rib 26/1' includes a groove, slot, recess or track 58/1' through which a portion, stops, teeth or tabs 42m1' of a male rib 36m1' slide during stent expansion. Advantageously, this prevents the male rib 36m1' from jumping out of its track and disturbing the stent profile. The slide or expansion direction is generally denoted by arrows 18. The groove 58/1' also keeps the male rib 36m1' in place in the stent collapsed state.

Figure 10:
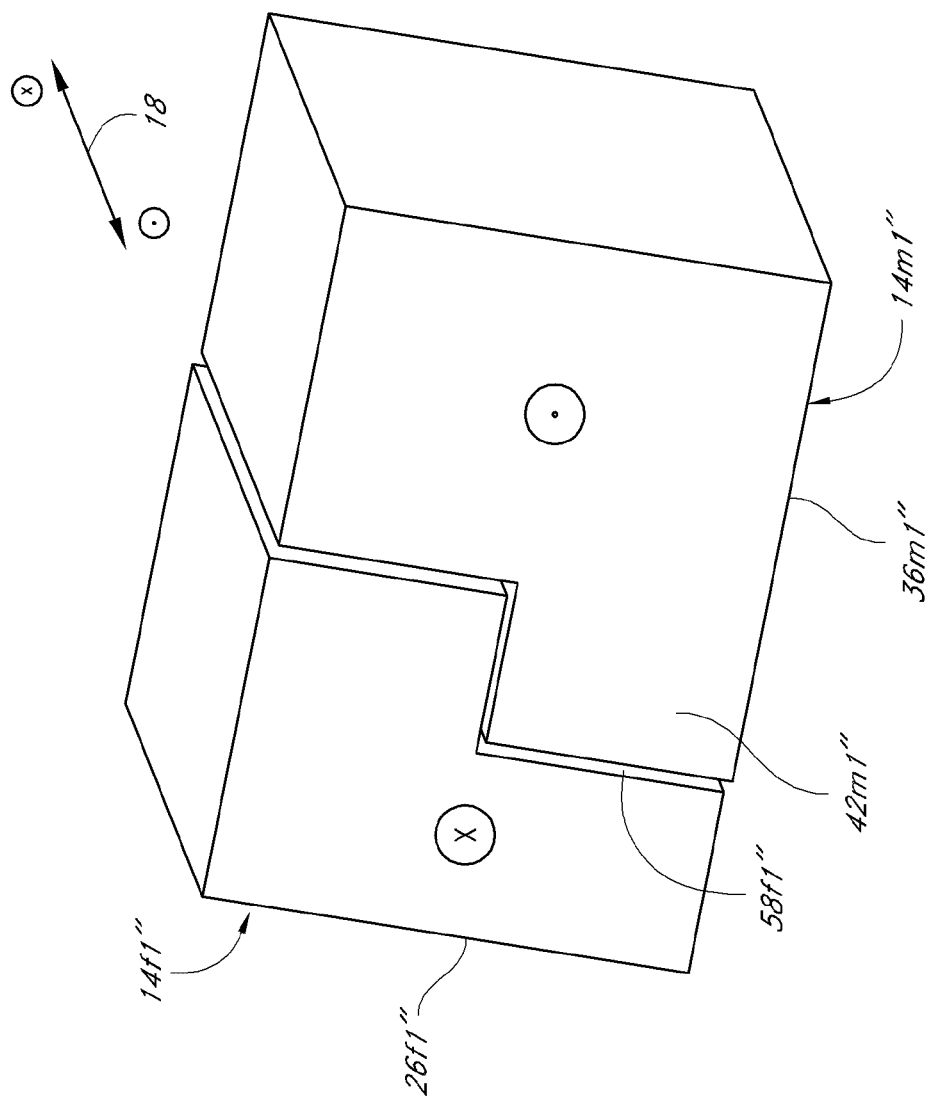
FIG. 10 is a simplified planar perspective view of a stent articulation geometry illustrating features and advantages in accordance with another embodiment of the inventions.

FIG. 10 shows an capture and/or articulation geometry between a male structural element 14m1" and a female structural element 14/1" that joins or links adjacent elements 14m1", 14/1" in accordance with another embodiment. Female rib 26/1" includes a groove, slot, recess or track 58/1" through which a portion, stops, teeth or tabs 42m1" of a male rib 36m1" slide during stent expansion. Advantageously, this prevents the male rib 36m1" from jumping out of its track and disturbing the stent profile. The slide or expansion direction is generally denoted by arrows 18. The groove 58/1" also keeps the male rib 36m1" in place in the stent collapsed state.

Figure 11:
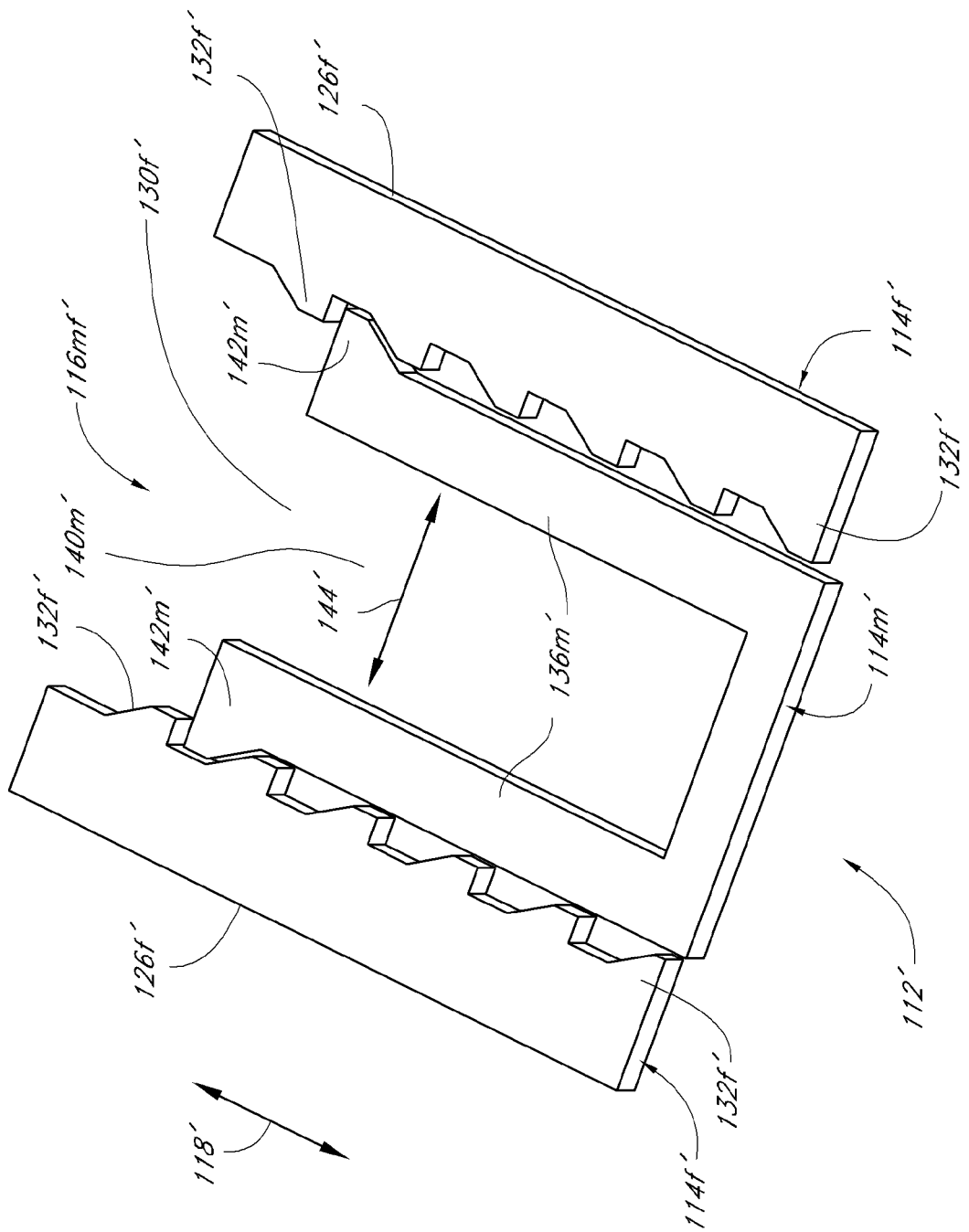
FIG. 11 is a simplified planar perspective partial view of an axially nested slide and lock stent section with an axially deflecting arm mechanism illustrating features and advantages in accordance with an embodiment of the inventions.

FIG. 11 shows a portion of an axially nested expandable stent section, segment or frame 112' in accordance with one embodiment. The section 112' generally comprises a male structural element 114m' and a female structural element 114f' radially or circumferentially coupled by a slide and lock articulating mechanism 116mf". During stent expansion, there is circumferential relative motion between the mating male structural element 114m' and female structural element 114f' as generally shown by arrows 118'. One or both of the mating male-female structural elements 114m' and 114f' may slidably move apart.

The female structural element 114f' generally comprises a pair of ribs or arms 126f' spaced by a gap 130f'. In the collapsed state, at least a portion of the male structural element 114m' extends within the gap 130f'. The male structural element 114m' generally comprises a pair of ribs or arms 136m' spaced by a gap 140m'.

In the embodiment of FIG. 11, each of the female ribs 126f' includes a plurality of inwardly extending spaced stops, teeth or tabs 132f' that engage the male structural element 114m' and each of the male ribs 136m' includes an outwardly extending end stop, tooth or tab 142m' that engage the female structural element 114f' and its stops 132f'. The stops 132f' and 142m' are configured to permit one-way slidable relative motion between the male and female structural elements 114m', 114f'.

During stent expansion, the stops 132f' and the stops 142m' cross one another. This is accomplished by utilizing an axially deflecting mechanism. Thus, during "cross-over" the female ribs 126f' and/or the male ribs 136m' are respectively deflected outwards and inwards and then resume their original undeflected position. This axial motion is generally denoted by arrows 144'. In one embodiment, spring elements facilitate this rib deflection by providing a resilient biasing mechanism to achieve substantially elastic rib deflection or deformation.

As indicated above, either the female ribs 126f', the male ribs 136m', both or any other suitable combination of ribs may axially deflect to achieve the desired expansion and other deployment characteristics. The axial deflection is caused by the generation of a generally axial or longitudinal force when the female stops 132f' and respective male stops 142m' slide over, engage or abut one another. As discussed herein, at full expansion, a hard stop or end capture mechanism is provided to limit further stent expansion.

Advantageously, there is substantially no or minimal overlap between nesting male structural elements 114m' and female structural elements 114f' in both the stent collapsed state and the stent expanded state, and more particularly in the expanded state. The female ribs 126f' and male ribs 136m' of a given section 112' are axially and/or radially displaced from one another and from the ribs or elements of adjacent sections. Thus, the structural elements 114' are referred to as being axially nested since their radial overlap is substantially reduced or minimal. Multiple slide and lock sections 112' may be connected axially by suitable linkage sections that may include spring elements, as described above and herein.

Figure 12:
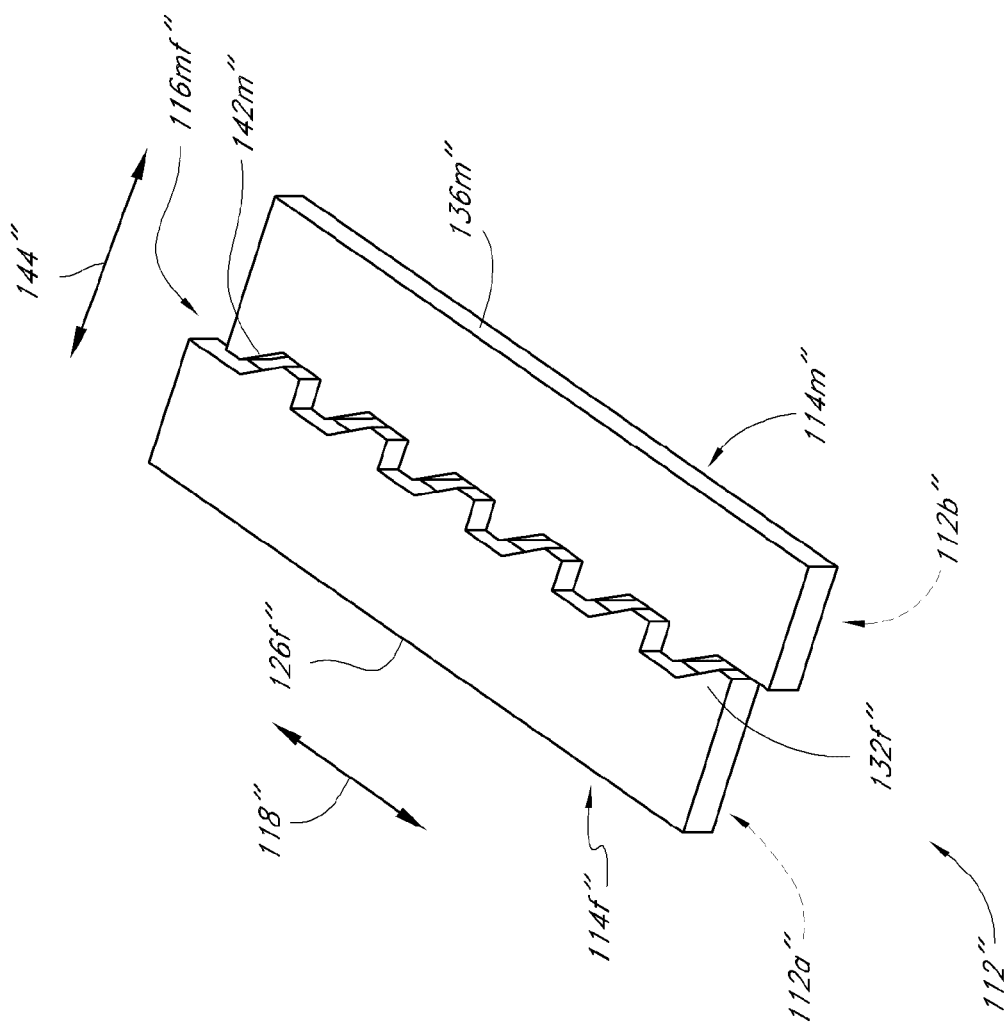
FIG. 12 is a simplified planar perspective partial view of at least one axially nested slide and lock stent section with an axially deflecting arm mechanism illustrating features and advantages in accordance with another embodiment of the inventions.

FIG. 12 shows a portion of an axially nested expandable stent section, segment or frame 112" in accordance with another embodiment. This embodiment illustrates the implementation of additional teeth and lockout points, as discussed further below.

In one embodiment, the drawing of FIG. 12 illustrates two side-by-side, axial or longitudinal stent sections 112a" and 112b" (shown in phantom lead lines). Thus, axially nested stent sections 112a", 112b" and structural elements 114f", 114m" are axially or longitudinally coupled.

The section 112" generally comprises a female structural element 114f" and a male structural element 114m" radially or circumferentially coupled by a slide and lock articulating mechanism 116mf". During stent expansion, there is circumferential relative motion between the mating male structural element 114m" and female structural element 114f" as generally shown by arrows 118". One or both of the mating male-female structural elements 114m" and 114f" may slidably move apart.

The female structural element 114f" generally comprises a pair of spaced ribs or arms 126f" (only one shown). At least a portion of the male structural element 114m" extends between the female ribs 126f". The male structural element 114m" generally comprises a pair of spaced ribs or arms 136m" (only one shown).

In the embodiment of FIG. 12, each of the female ribs 126f" includes a plurality of inwardly extending spaced stops, teeth or tabs 132f" that engage the male structural element 114m" and each of the male ribs 136m" includes a plurality of outwardly extending spaced stops, teeth or tabs 142m" that engage the female structural element 114f" and its stops 132f". The stops 132f" and 142m" are configured to permit one-way slidable relative motion between the male and female structural elements 114m", 114f".

During stent expansion, the stops 132f" and the stops 142m" cross one another. This is accomplished by utilizing an axially deflecting mechanism. Thus, during "cross-over" the female ribs 126f" and/or the male ribs 136m" are respectively deflected outwards and inwards and then resume their original undeflected position. This axial motion is generally denoted by arrows 144". In one embodiment, spring elements facilitate this rib deflection by providing a resilient biasing mechanism to achieve substantially elastic rib deflection or deformation.

As indicated above, either the female ribs 126f", the male ribs 136m", both or any other suitable combination of ribs may axially deflect to achieve the desired expansion and other deployment characteristics. The axial deflection is caused by the generation of a generally axial or longitudinal force when the female stops 132f" and respective male stops 142m" slide over, engage or abut one another. As discussed herein, at full expansion, a hard stop or end capture mechanism is provided to limit further stent expansion.

Advantageously, there is substantially no or minimal overlap between nesting male structural elements 114m" and female structural elements 114f" in both the stent collapsed state and the stent expanded state, and more particularly in the expanded state. The female ribs 126f" and male ribs 136m" of a given section 112" are axially and/or radially displaced from one another and from the ribs or elements of adjacent sections. Thus, the structural elements 114" are referred to as being axially nested since their radial overlap is substantially reduced or minimal. The slide and lock sections 112" may be connected axially by suitable linkage sections that may include spring elements, as described above and herein.

Figure 13A:
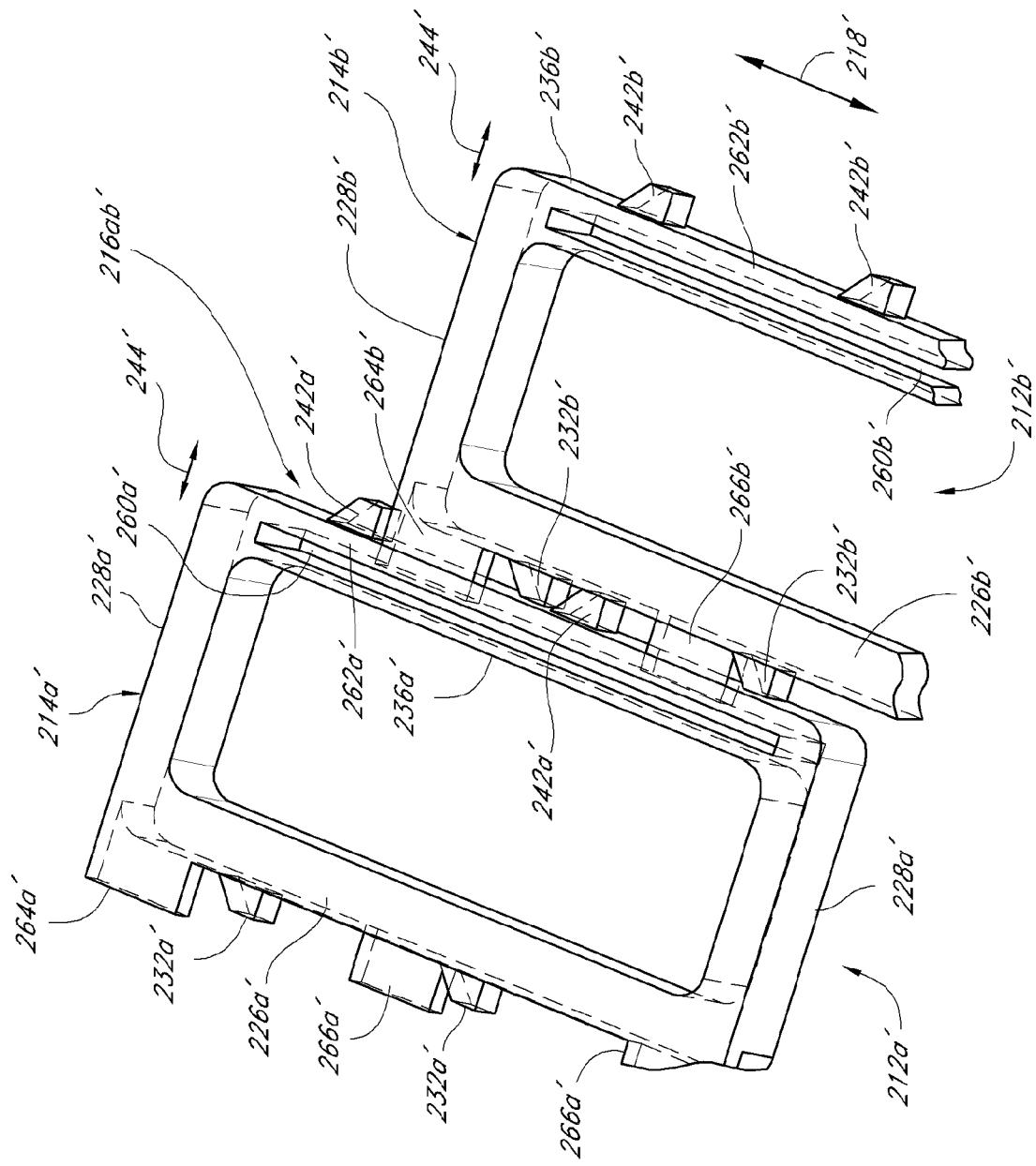
FIGS. 13A and 13B are simplified planar perspective partial views of axially nested slide and lock stent sections with an axially deflecting arm mechanism illustrating features and advantages in accordance with yet another embodiment of the inventions.
Figure 13B:
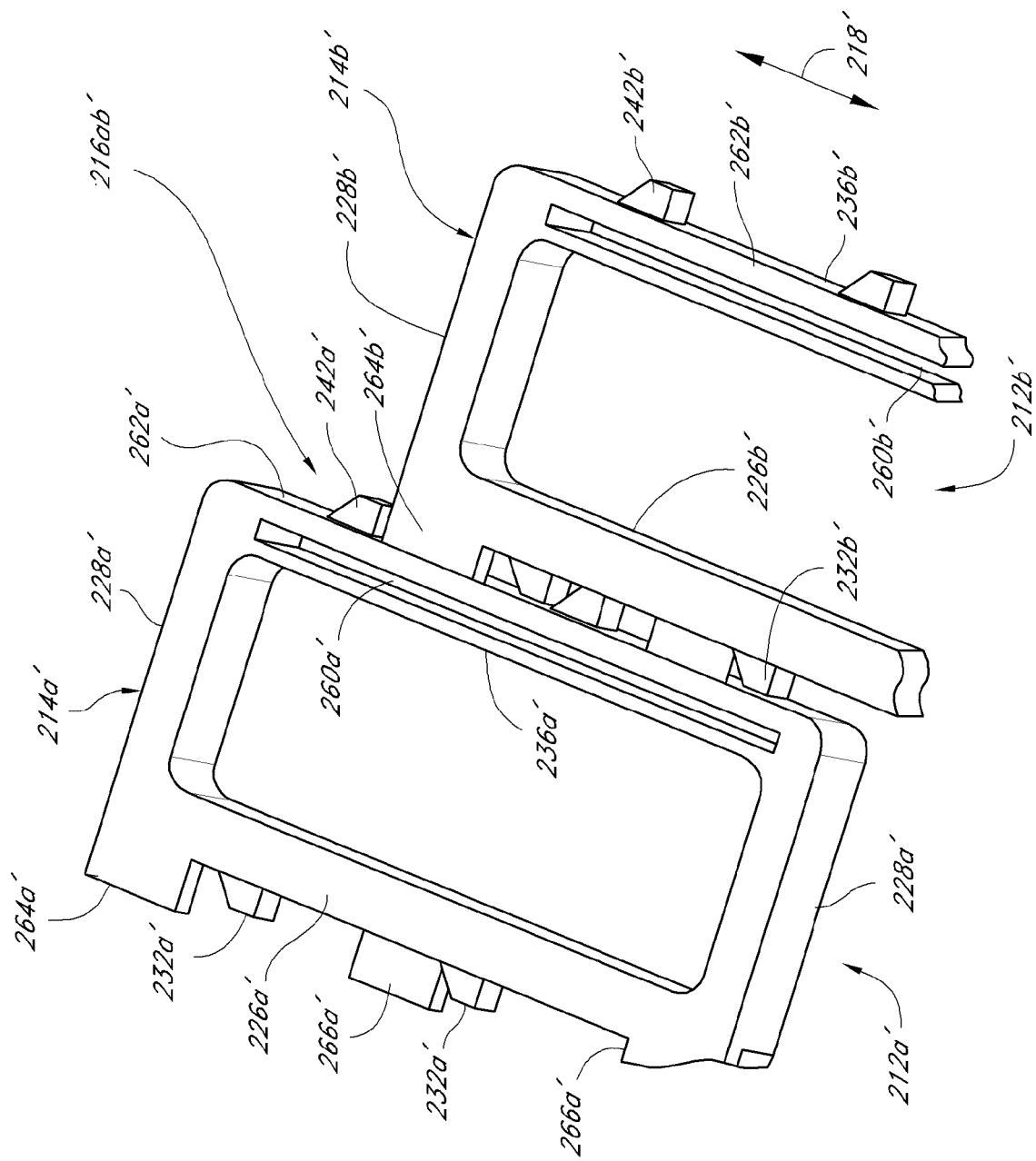

FIGS. 13A and 13B show a pair of longitudinally arranged and axially nested expandable stent sections, segments or frames 212a', 212b' in accordance with one embodiment. Each section 212a', 212b' comprises at least one structural element 214a', 214b' respectively. Structural elements 214a', 214b' of respective adjacent sections 212a', 212b' are axially or longitudinally coupled to one another by a one-way slide and lock articulating mechanism 216ab'. As discussed further below, one or more capture wings are provided that keeps the parts 214a', 214b' coupled and generally side by side.

During stent expansion, there is circumferential relative motion between the mating structural element 214a' and structural element 214b' as generally shown by arrows 218'. One or both of the mating structural elements 214a' and 214b' may slidably move apart.

The structural element 214a' generally comprises a pair of ribs or arms 226a', 236a' spaced by end portions 228a'. The structural element 214b' generally comprises a pair of ribs or arms 226b', 236b' spaced by end portions 228b'. The ribs 236a' and 226b' are axially or longitudinally coupled.

The rib 236a' includes a slot 260a' along substantially its entire length to create a deflectable member 262a'. The deflectable member 262a' has a plurality of spaced stops, teeth or tabs 242a' that engage the rib 226b' of the structural element 214b'. The rib 226b' has a plurality of spaced stops, teeth or tabs 232b' that engage the opposed stops 242a' during stent expansion. The stops 242a' and 232b' are configured to permit one-way slidable relative motion between the structural elements 214a', 214b'.

During stent expansion, the stops 242a' and the stops 232b' cross one another. This is accomplished by utilizing an axially deflecting mechanism. Thus, during "cross-over" the deflectable member 262a' is deflected and then resumes its original undeflected position. This axial motion is generally denoted by arrows 244'. The axial deflection is caused by the generation of a generally axial or longitudinal force when the stops 242a' and respective stops 232b' slide over, engage or abut one another. In a modified embodiment, spring elements may facilitate rib deflection by providing a resilient biasing mechanism to achieve substantially elastic rib deflection or deformation.

The rib 226b' further includes a overlapping capture wings or elements 264b' and 266b' that axially or longitudinally connect the ribs 226b' and 236a'. The capture wing 264b' is raised relative to the stops 242a', 232b' and extends over the deflectable member 262a'. The capture wing 266b' is lowered relative to the stops 242a', 232b' and extends below the deflectable member 262a'. Any number of capture wings may be utilized with efficacy, as needed or desired.

The capture wings 264b', 266b' maintain a coupling between the structural elements 214a', 214b' and keep them in a generally side by side plane in the collapsed state and as the stent expands. As discussed herein, at full expansion, a hard stop or end capture mechanism is provided to limit further stent expansion.

The rib 226a' is generally similar in structure to the rib 226b' and includes stops, teeth or tabs 232a', overlapping capture wings or elements 264a' and 266a'. The rib 236b' is generally similar in structure to the rib 236a' and includes stops, teeth or tabs 242b', a slot 260b' and a deflectable member 262b'.

Advantageously, there is substantially no or minimal overlap between axially nesting structural elements 214a' and 214b' in both the stent collapsed state and the stent expanded state, and more particularly in the expanded state. The articulating ribs 236a', 226b' of axially adjacent structural elements 214a', 214b' are axially displaced from one another. Also, the ribs and elements of a given section 212' are axially and/or radially displaced from one another and from the ribs or elements of adjacent sections. Thus, the structural elements 214' are referred to as being axially nested since their radial overlap is substantially reduced or minimal. The slide and lock sections 212' may also be connected axially by suitable linkage sections that may include spring elements, as described above and herein.

Figure 14A:
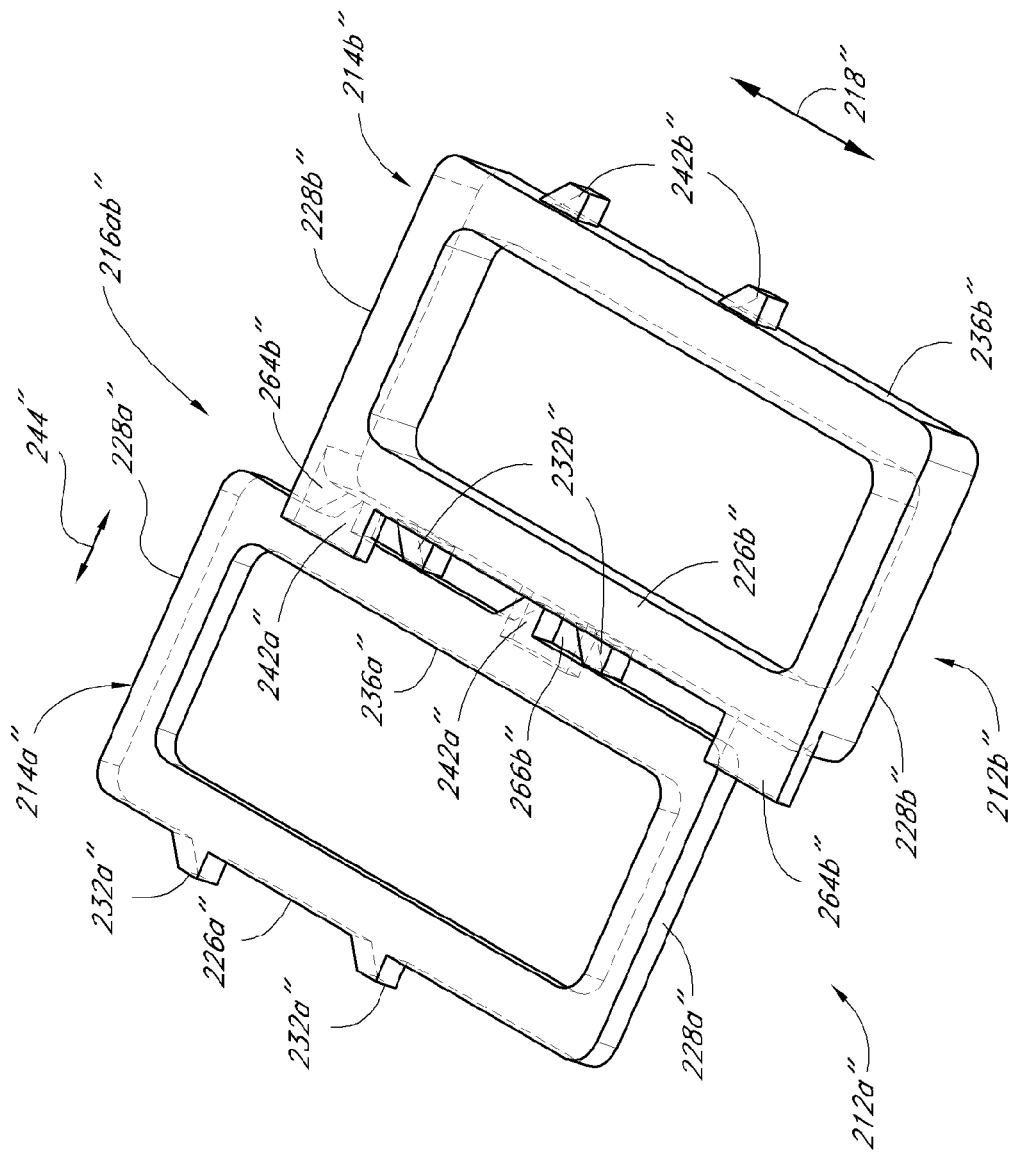
FIGS. 14A and 14B are simplified planar perspective partial views of axially nested slide and lock stent sections with an axially deflecting mechanism illustrating features and advantages in accordance with still another embodiment of the inventions.
Figure 14B:
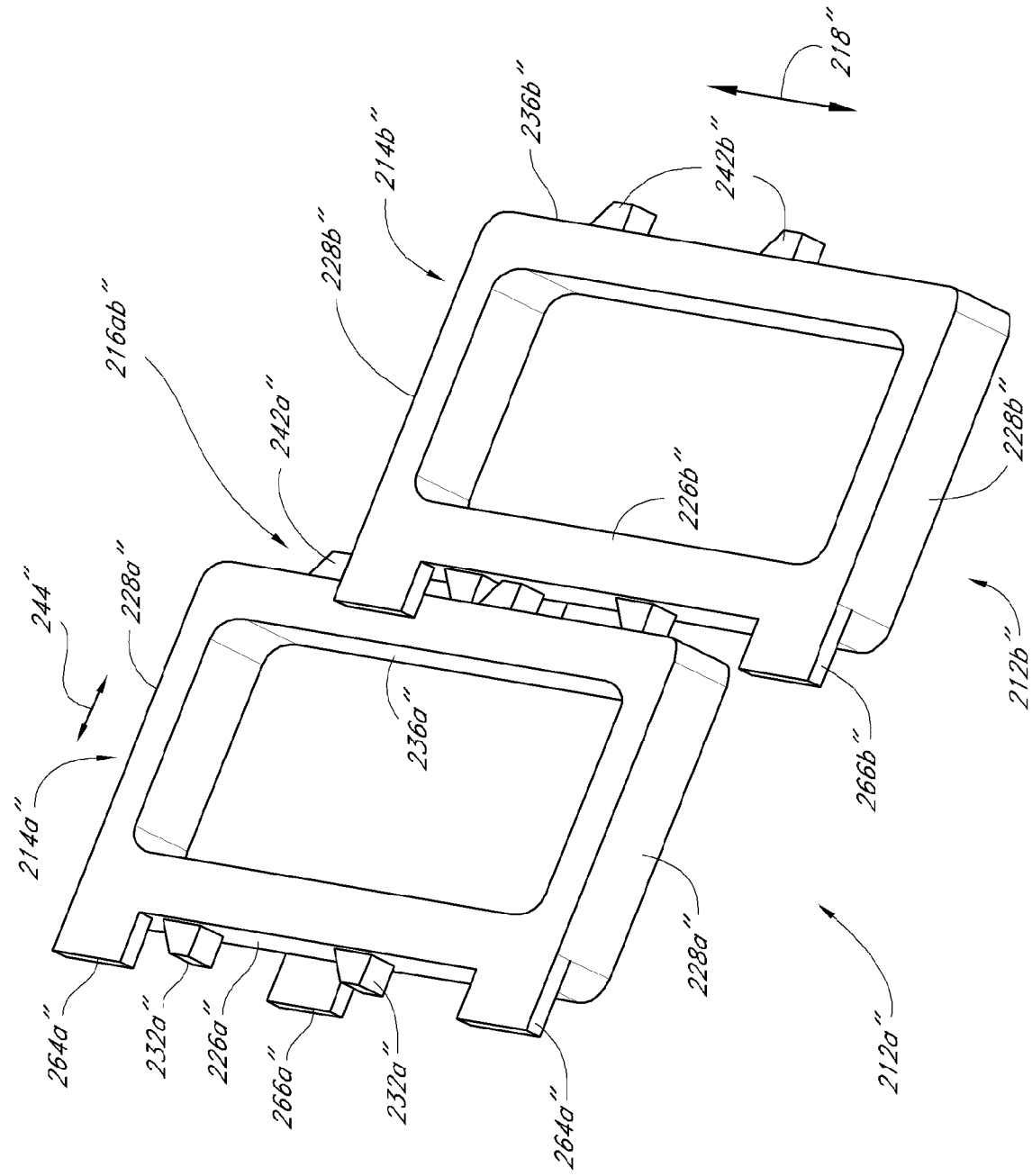

FIGS. 14A and 14B show a pair of longitudinally arranged and axially nested expandable stent sections, segments or frames 212a", 212b" in accordance with another embodiment. Each section 212a", 212b" comprises at least one structural element 214a", 214b" respectively. Structural elements 214a", 214b" of respective adjacent sections 212a", 212b" are axially or longitudinally coupled to one another by a one-way slide and lock articulating mechanism 216ab". As discussed further below, one or more capture wings are provided that keeps the parts 214a", 214b" coupled and generally side by side.

During stent expansion, there is circumferential relative motion between the mating structural element 214a" and structural element 214b" as generally shown by arrows 218". One or both of the mating structural elements 214a" and 214b" may slidably move apart.

The structural element 214a" generally comprises a pair of ribs or arms 226a", 236a" spaced by end portions 228a". The structural element 214b" generally comprises a pair of ribs or arms 226b", 236b" spaced by end portions 228b'. The ribs 236a" and 226b" are axially or longitudinally coupled.

The rib 236a" has a plurality of spaced stops, teeth or tabs 242a" that engage the rib 226b" of the structural element 214b". The rib 226b" has a plurality of spaced stops, teeth or tabs 232b" that engage the opposed stops 242a" during stent expansion. The stops 242a" and 232b" are configured to permit one-way slidable relative motion between the structural elements 214a", 214b".

The embodiment of FIGS. 14A and 14B utilizes a substantially axial deflecting mechanism during stent expansion in which the structural elements 214a", 214b" and/or the sections 212a", 212b" are deflectable in substantially their entirety. This may be accomplished by utilizing spring linkage elements or the like that facilitate element deflection by providing a resilient biasing mechanism to achieve substantially elastic deflection or deformation.

During stent expansion, the stops 242a" and the stops 232b" cross one another. This is accomplished by utilizing an axially deflecting mechanism. Thus, during "cross-over" the structural element 236a" is deflected and then resumes its original undeflected position. This axial motion is generally denoted by arrows 244". The axial deflection is caused by the generation of a generally axial or longitudinal force when the generally rigid stops 242a" and associated generally rigid stops 232b" slide over, engage or abut one another The rib 226b" further includes overlapping capture wings or elements 264b" and elements 266b" that axially or longitudinally connect the ribs 226b" and 236a". The capture wings 264b" are raised relative to the stops 242a", 232b" and extend over the rib 236a". The capture wing 266b" is lowered relative to the stops 242a", 232b" and extends below the rib 236a". Any number of capture wings may be utilized with efficacy, as needed or desired.

The capture wings 264b", 266b" maintain a coupling between the structural elements 214a", 214b" and keep them in a generally side by side plane in the collapsed state and as the stent expands. As discussed herein, at full expansion, a hard stop or end capture mechanism is provided to limit further stent expansion.

The rib 226a" is generally similar in structure to the rib 226b" and includes stops, teeth or tabs 232a", overlapping capture wings or elements 264a" and 266a". The rib 236b" is generally similar in structure to the rib 236a' and includes stops, teeth or tabs 242b".

Advantageously, there is substantially no or minimal overlap between axially nesting structural elements 214a" and 214b" in both the stent collapsed state and the stent expanded state, and more particularly in the expanded state. The articulating ribs 236a", 226b" of axially adjacent structural elements 214a", 214b" are axially displaced from one another. Also, the ribs and elements of a given section 212" are axially and/or radially displaced from one another and from the ribs or elements of adjacent sections. Thus, the structural elements 214" are referred to as being axially nested since their radial overlap is substantially reduced or minimal. The slide and lock sections 212" may also be connected axially by suitable linkage sections that may include spring elements, as described above and herein.

Figure 15:
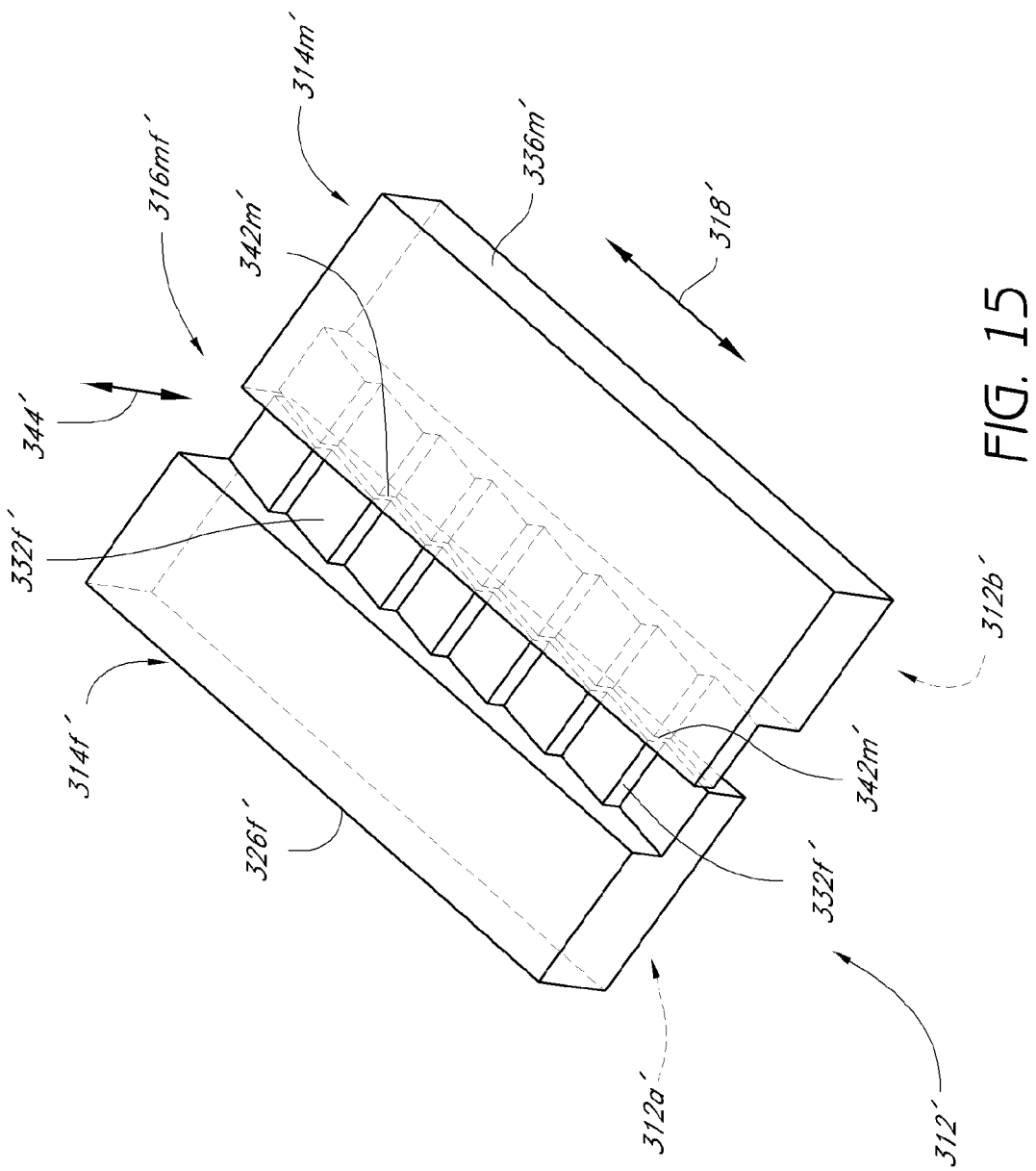
FIG. 15 is a simplified planar perspective partial view of an axially nested slide and lock stent section with a radially deflecting arm mechanism illustrating features and advantages in accordance with an embodiment of the inventions.

FIG. 15 shows a portion of an axially nested expandable stent section, segment or frame 312' in accordance with one embodiment. The section 312' generally comprises a male structural element 314m' and a female structural element 314f' radially or circumferentially coupled by a slide and lock articulating mechanism 316mf". During stent expansion, there is circumferential relative motion between the mating male structural element 314m' and female structural element 314f' as generally shown by arrows 318'. One or both of the mating male-female structural elements 314m' and 314f' may slidably move apart.

The female structural element 314f' generally comprises a pair of spaced ribs or arms 326f' (only one shown). At least a portion of the male structural element 314m' extends between the female ribs 326f'. The male structural element 314m' generally comprises a pair of spaced ribs or arms 336m' (only one shown).

In the embodiment of FIG. 15, each of the female ribs 326f' includes a plurality of spaced stops, teeth or tabs 332f' that engage the male structural element 314m' and each of the male ribs 336m' includes a plurality of spaced stops, teeth or tabs 342m' that engage the female structural element 314f' and its stops 332f'. The stops 332f' and 342m' are configured to permit one-way slidable relative motion between the male and female structural elements 314m', 314f'.

During stent expansion, the stops 332f' and the stops 342m' cross or slide over one another. This is accomplished by utilizing a radially deflecting mechanism. Thus, during "cross-over" the female ribs 326f' and/or the male ribs 336m' are deflected radially and then resume their original undeflected position. This radial motion is generally denoted by arrows 344'. In one embodiment, spring elements facilitate this rib deflection by providing a resilient biasing mechanism to achieve substantially elastic rib deflection or deformation.

As indicated above, either the female ribs 326f', the male ribs 336m', both or any other suitable combination of ribs may radially deflect to achieve the desired expansion and other deployment characteristics. The radial deflection is caused by the generation of a generally radial force when the female stops 332f' and respective male stops 342m' slide over, engage or abut one another. As discussed herein, at full expansion, a hard stop or end capture mechanism is provided to limit further stent expansion.

Advantageously, there is substantially minimal overlap between nesting male structural elements 314m' and female structural elements 314f' in both the stent collapsed state and the stent expanded state, and more particularly in the expanded state. The radial thickness of overlapping stops or elements 332f', 342m' is between about the same as the stent material nominal thickness and about two times the stent material nominal thickness. The female ribs 326f' and male ribs 336m' of a given section 312' are substantially axially and/or radially displaced from one another and from the ribs or elements of adjacent sections. Thus, the structural elements 314' are referred to as being axially nested since their radial overlap is substantially reduced or minimal. The slide and lock sections 312' may be connected axially by suitable linkage sections that may include spring elements, as described above and herein.

In one embodiment, the drawing of FIG. 15 illustrates two substantially side-by-side, axial or longitudinal stent sections 312a' and 312b' (shown in phantom lead lines). Thus, axially nested stent sections 312a', 312b' and structural elements 314f', 314m' are axially or longitudinally coupled with minimal radial overlap. The radial thickness of overlapping stops, teeth or elements 332f', 342m' is between about the same as the stent material nominal thickness and about two times the stent material nominal thickness.

Figure 16:
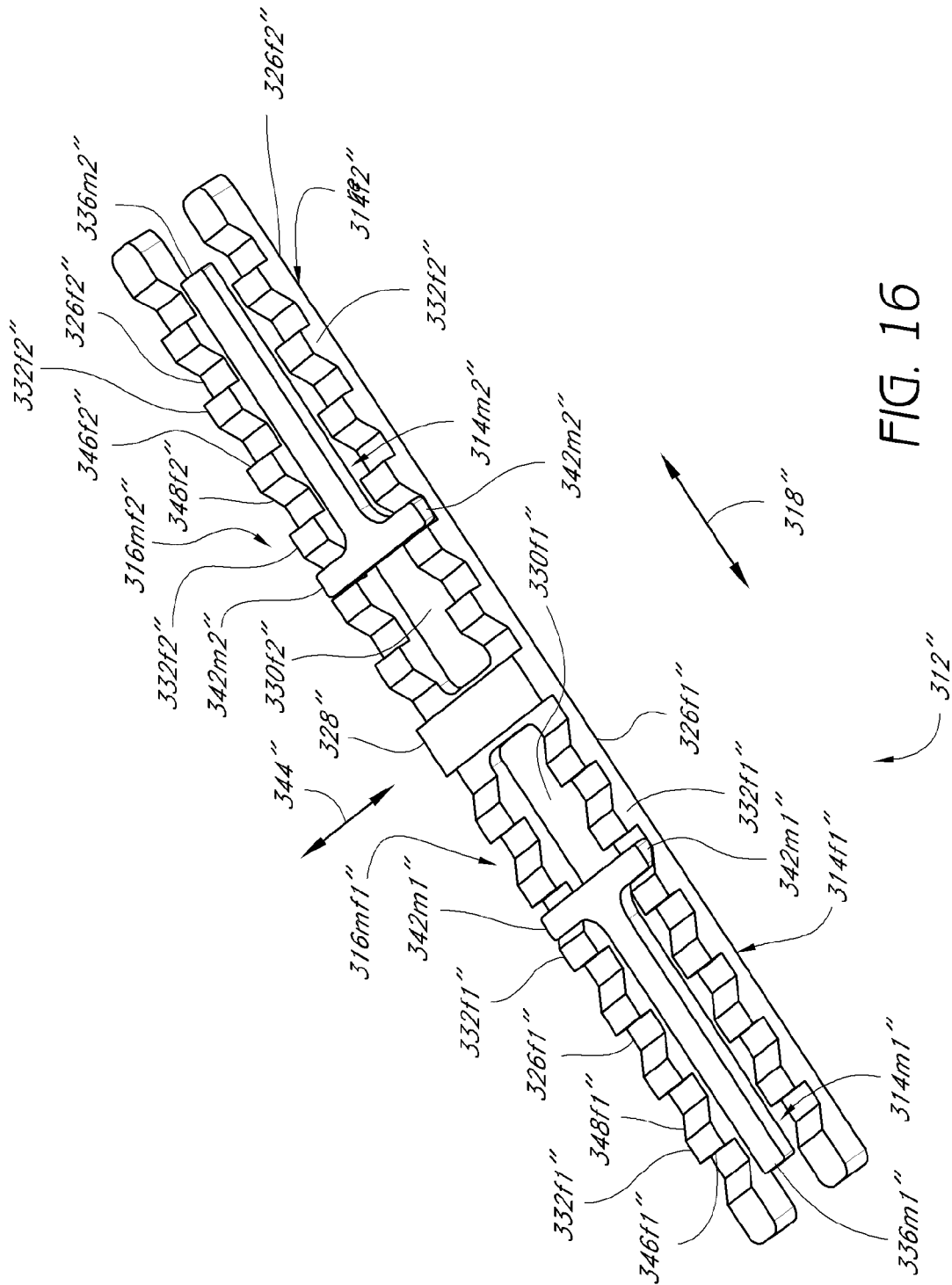
FIG. 16 is a simplified planar perspective view of an axially nested slide and lock stent section with a radially deflecting arm mechanism illustrating features and advantages in accordance with another embodiment of the inventions.
Figure 17:
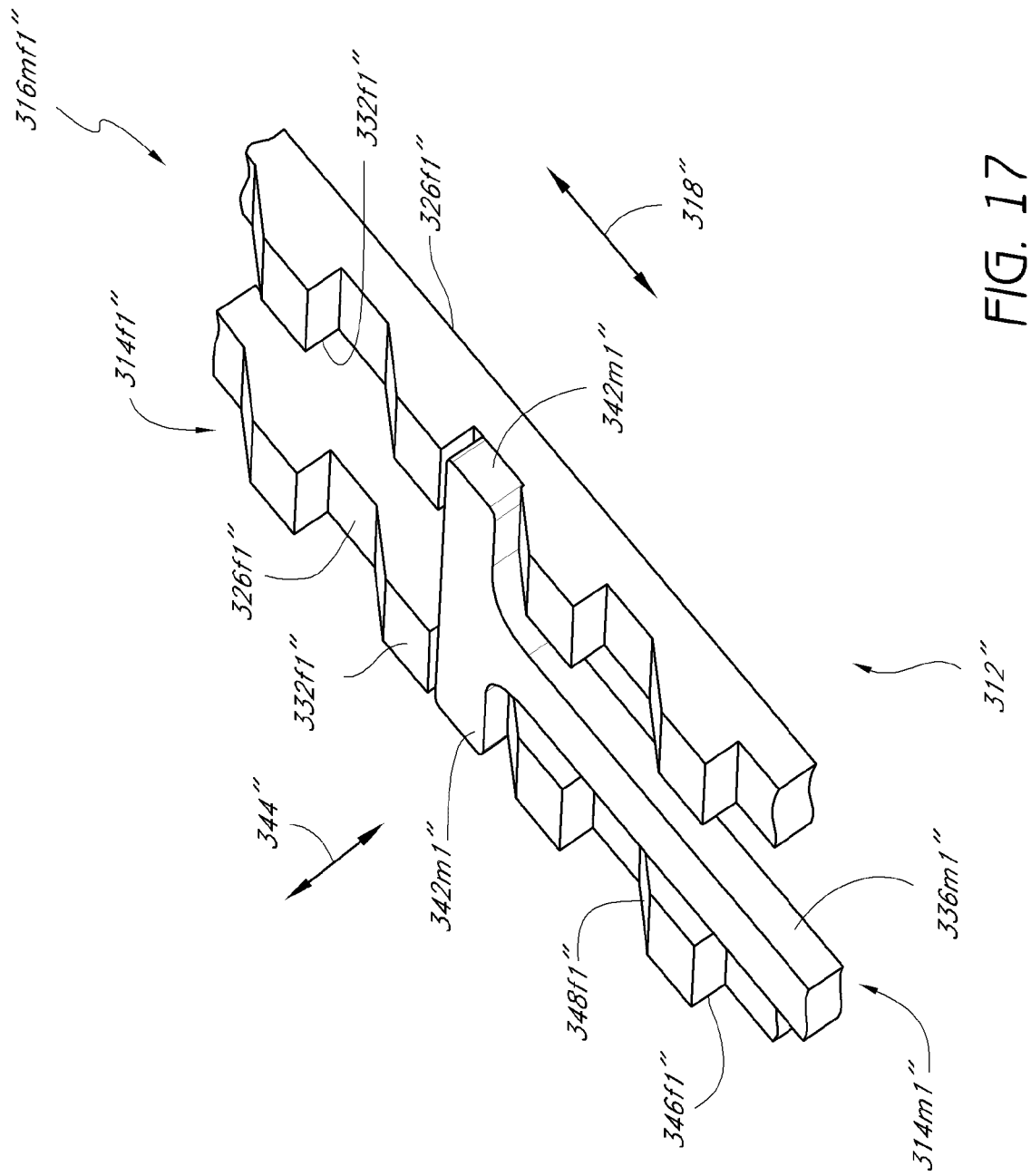
FIG. 17 is simplified planar perspective enlarged partial view of the stent section of FIG. 16 illustrating features and advantages in accordance with an embodiment of the inventions.
Figure 18:
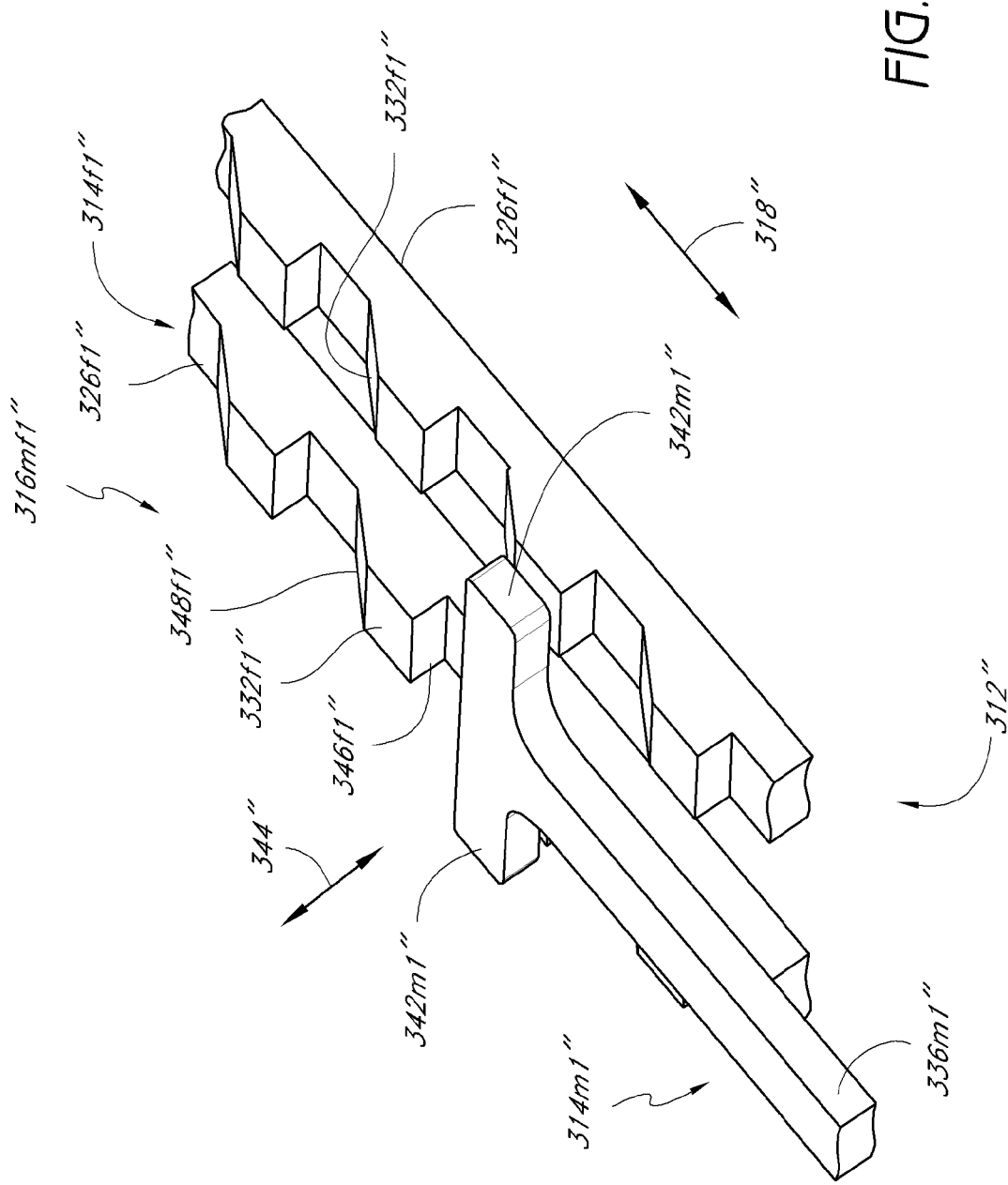
FIG. 18 is a simplified planar perspective enlarged partial view of the stent section of FIG. 16 showing radial rib deflection and illustrating features and advantages in accordance with an embodiment of the inventions.

FIG. 16 shows an axially nested expandable stent section, segment or frame 312" in accordance with another embodiment. FIG. 17 is an enlarged view of the axially, longitudinally or non-radially overlapping design mechanism in a locked position and FIG. 18 is an enlarged view showing radial rib deflection in a sliding position.

The section 312" includes a pair of male structural elements 314m1", 314m2" and a pair of female structural elements 314f1", 314f2" that respectively slidingly mate via respective interlocking articulating mechanisms 316mf1", 316mf2". In modified embodiments, fewer or more structural elements may be efficaciously utilized, as needed or desired.

During stent expansion, there is circumferential relative motion between the mating male structural elements 314m1", 314m2" and female structural elements 314f1", 314f2" as generally shown by arrows 318". One or both of the mating male-female structural elements 314m1", 314f1" and 314m2", 314f2" may slidably move apart.

The female structural element 314f1" generally comprises a pair of spaced ribs or arms 326f1" to form a gap 330f1" therebetween. Each of the ribs 326f1" includes a plurality of spaced radially extending stops, teeth or tabs 332f1" that engage the male structural element 314m1".

The female structural element 314f2" generally comprises a pair of spaced ribs or arms 326f2" to form a gap 330f2" therebetween. Each of the ribs 326f2" includes a plurality of spaced radially extending stops, teeth or tabs 332f2" that engage the male structural element 314m2".

The female structural elements 314f1", 314f2" share a common end portion 328" to which the ribs 326f1" and 326f2" are connected. In one embodiment, the female structural elements 314f1", 314f2" comprise an integral unit. In modified embodiments, the female structural elements 314f1", 314f2" can efficaciously be connected by other techniques, as needed or desired.

The male structural element 314m1" generally comprises a rib or arm 336m1" with a pair of axially extending stops, teeth, tabs or wings 342m1" that engage the female structural element 314f1" and its stops 332f1". In the collapsed and partially expanded states, the rib 336m1" extends into the gap 330f1" between the female ribs 326f1". The stops 332f1", 342m1" are configured to permit one-way slidable relative motion between the male and female structural elements 314m1", 314f1".

The male structural element 314m2" generally comprises a rib or arm 336m2" with a pair of axially extending stops, teeth, tabs or wings 342m2" that engage the female structural element 314f2" and its stops 332f2". In the collapsed and partially expanded states, the rib 336m2" extends into the gap 330f2" between the female ribs 326f2". The stops 332f2", 342m2" are configured to permit one-way slidable relative motion between the male and female structural elements 314m2", 314f2".

The male structural elements 314m1", 314m2" can share a common end portion to which the ribs 336m1" and 336m2" are connected. In one embodiment, the male structural elements 314m1", 314m2" comprise an integral unit. In modified embodiments, the male structural elements 314m1", 314m2" can efficaciously be connected by other techniques, as needed or desired.

During stent expansion, there is circumferential relative motion between the female ribs 326f1" and male rib 336m1" with one or both slidably moving apart. Similarly, there is circumferential relative motion between the female ribs 326f2" and male rib 336m2" with one or both slidably moving apart. The motion is generally denoted by arrows 318".

The female stops 332f1", 332f2" are configured so that they have generally flat respective end surfaces 346f1", 346f2" to substantially reduce or minimize recoil and generally tapered respective engaging surfaces 348f1", 348f2" to facilitate one-way sliding. The male stops 342m1", 342m2" may also be similarly configured to substantially reduce or minimize recoil and facilitate one-way sliding. Other suitable configurations that inhibit undesirable recoil and facilitate one-way expansion may be efficaciously utilized, as needed or desired.

During stent expansion, the stops 332f1" and the stops 342m1" cross or slide over one another. This is accomplished by utilizing a radially deflecting mechanism. Thus, and as illustrated by FIGS. 17 and 18, during "cross-over" the female ribs 326f1" and/or the male rib 336m1" are deflected radially and then resume their original undeflected position. This radial motion is generally denoted by arrows 344".

Similarly, during stent expansion, the stops 332f2" and the stops 342m2" cross or slide over one another. This is accomplished by utilizing a radially deflecting mechanism. Thus, during "cross-over" the female ribs 326f2" and/or the male rib 336m2" are deflected radially and then resume their original undeflected position. This radial motion is generally denoted by arrows 344". In one embodiment, spring elements facilitate the rib deflection by providing a resilient biasing mechanism to achieve substantially elastic rib deflection or deformation.

As indicated above, either the female ribs 326f1", 326f2", the male ribs 336m1", 336m2", both or any other suitable combination of ribs may radially deflect to achieve the desired expansion and other deployment characteristics. The radial deflection is caused by the generation of a generally radial force when the female stops 332f1", 332f2" and respective male stops 342m1", 342m2" slide over, engage or abut one another. As discussed herein, at full expansion, a hard stop or end capture mechanism is provided to limit further stent expansion.

Advantageously, there is substantially minimal overlap between nesting male structural elements 314m1", 314m2" and respective female structural elements 314f1", 314f2" in both the stent collapsed state and the stent expanded state, and more particularly in the expanded state. The radial thickness of overlapping elements 314m1", 314f1" and 314m2", 314f2" is between about the same as the stent material nominal thickness and about two times the stent material nominal thickness. The female ribs 326f" and male rib(s) 336m" of a given section 312" are substantially axially and/or radially displaced from one another and from the ribs or elements of adjacent sections. Thus, the structural elements 314" are referred to as being axially nested since their radial overlap is substantially reduced or minimal. The slide and lock sections 312" may be connected axially by suitable linkage sections that may include spring elements, as described above and herein.

Figure 19:
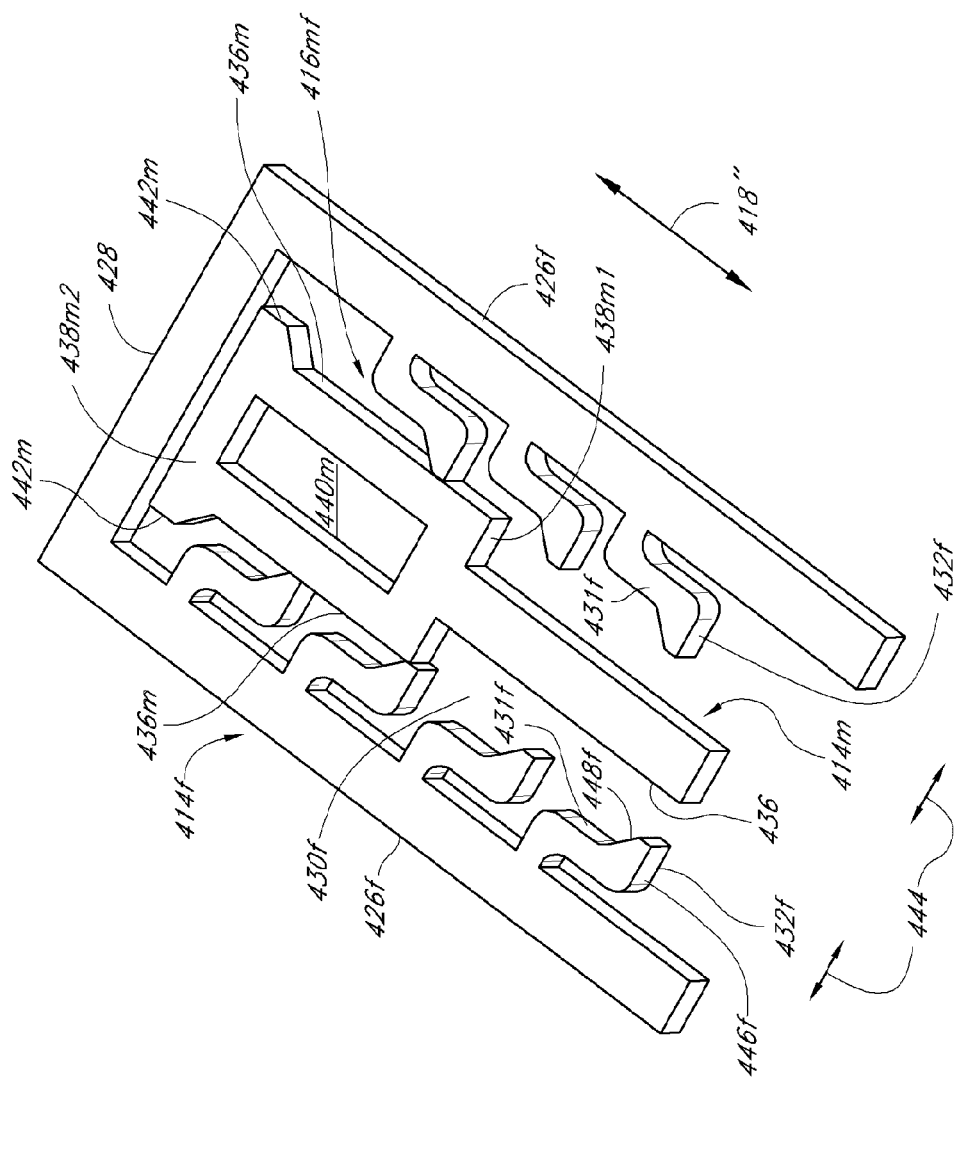
FIG. 19 is a simplified planar perspective partial view of an axially nested slide and lock stent section with an axially deflecting mechanism in a collapsed state illustrating features and advantages in accordance with an embodiment of the inventions.
Figure 20:
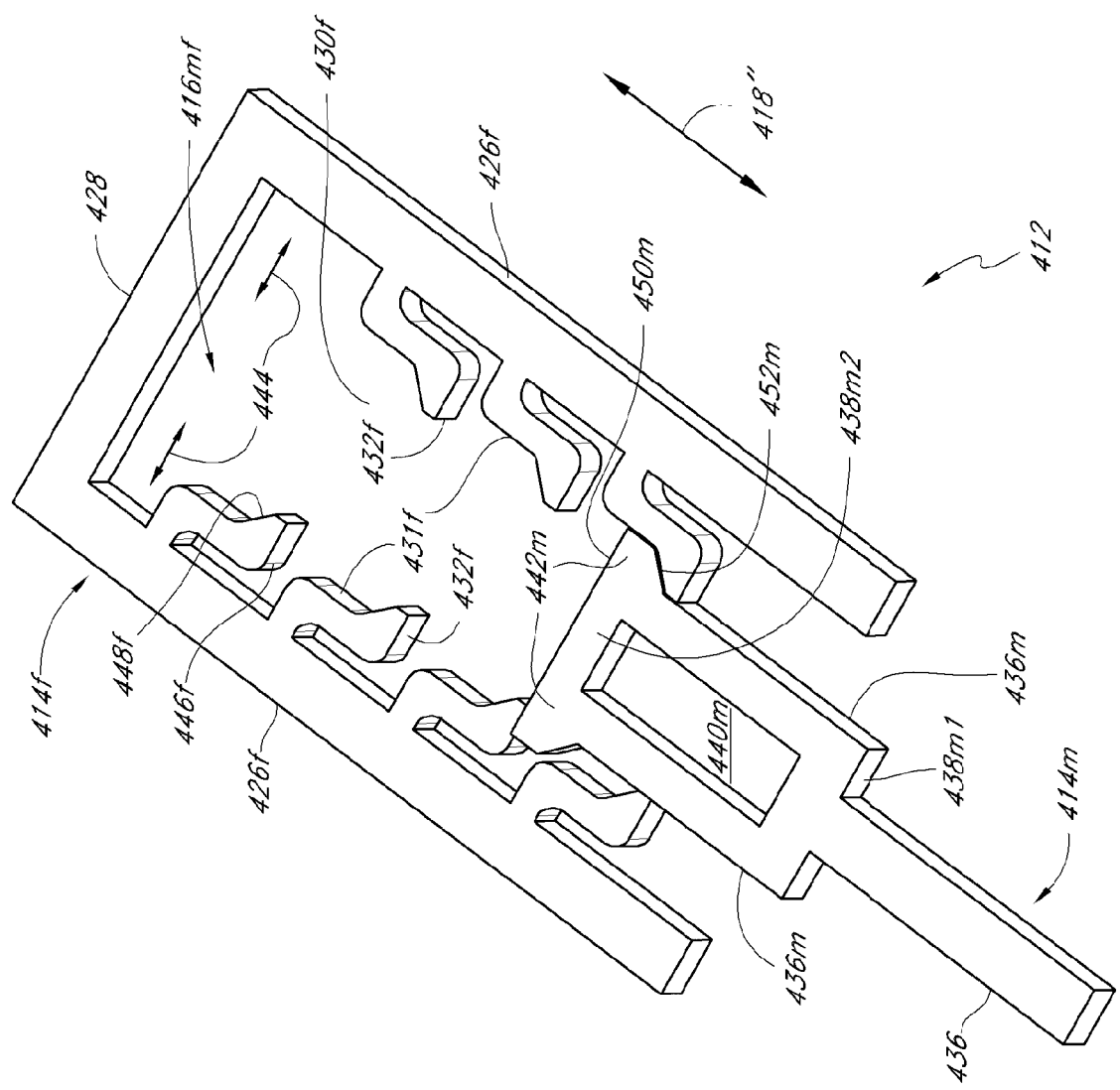
FIG. 20 is a simplified planar perspective partial view of the axially nested slide and lock stent section of FIG. 19 in an expanded state illustrating features and advantages in accordance with an embodiment of the inventions.

FIGS. 19 and 20 show a portion of an axially nested expandable stent section, segment or frame 412 in accordance with one embodiment. FIG. 19 illustrates a stent collapsed state and FIG. 20 illustrates a stent expanded state.

The section 412 generally comprises a male structural element 414m and a female structural element 414f radially or circumferentially coupled by a slide and lock articulating mechanism 416mf. During stent expansion, there is circumferential relative motion between the mating male structural element 414m and female structural element 414f as generally shown by arrows 418. One or both of the mating male-female structural elements 414m and 414f may slidably move apart.

The female structural element 414f generally comprises a pair of ribs or arms 426f spaced by an end portion 428 to from a gap 430f therebetween. In the collapsed state, at least a portion of the male structural element 414m extends within the gap 430f.

The male structural element 414m generally comprises a main rib or arm 436 that bifurcates or divides into two ribs or arms 436m. The ribs 436m are spaced by a proximal end portion 438m1 and distal end portion 438m2 to form a gap 440m therebetween.

In the embodiment of FIGS. 19 and 20, each of the female ribs 426f includes a plurality of inwardly extending spaced deflectable fingers or elements 431f that extend into the gap 430f. The fingers 431f terminate in stops, teeth or tabs 432f that engage the male structural element 414m.

Each of the male ribs 436m includes an outwardly extending end stop, tooth or tab 442m that engage the female structural element 414f and its stops 432f. The stops 432f and 442m are configured to permit one-way slidable relative motion between the male and female structural elements 414m, 414f. The stops 432f are arranged in an alternating repetitive or staggered pattern for enhanced resolution and greater selection and adaptability in expansion size.

The female stops 432f are configured so that they have generally flat respective end surfaces 446f to substantially reduce or minimize recoil and generally tapered respective engaging surfaces 448f to facilitate one-way sliding. Similarly, the male stops 442m are configured so that they have generally flat respective end surfaces 450m to substantially reduce or minimize recoil and generally tapered respective engaging surfaces 452m to facilitate one-way sliding. Other suitable configurations that inhibit undesirable recoil and facilitate one-way expansion may be efficaciously utilized, as needed or desired.

During stent expansion, the stops 432f and the stops 442m cross one another. This is accomplished by utilizing an axially deflecting mechanism. Thus, during "cross-over" the male stop engaging fingers 431f deflected generally axially outwards and then resume their original undeflected position. This axial motion is generally denoted by arrows 444. Alternatively, or in addition, deflectable fingers or elements may be provided on the male structural element 414m.

The axial deflection is caused by the generation of a generally axial or longitudinal force when the female stops 432f and respective male stops 442m slide over, engage or abut one another. As discussed herein, at full expansion, a hard stop or end capture mechanism is provided to limit further stent expansion.

Advantageously, there is substantially no or minimal overlap between nesting male structural elements 414m and female structural elements 414f in both the stent collapsed state and the stent expanded state, and more particularly in the expanded state. The female ribs 426f and male ribs 436, 436m of a given section 412 are axially and/or radially displaced from one another and from the ribs or elements of adjacent sections. Thus, the structural elements 414 are referred to as being axially nested since their radial overlap is substantially reduced or minimal. Multiple slide and lock sections 412 may be connected axially by suitable linkage sections that may include spring elements, as described above and herein.

Some Stent Embodiments

FIGS. 21-27 show conceptual views of embodiments of expandable axially nested slide and lock vascular devices, prostheses or stents 510 in deployed and undeployed states. The stent 510 has a tubular form with a wall comprising a plurality of generally longitudinally arranged linked circumferential sections, segments or frames 512a, 512s. The stent 510 has a through lumen 520 which is expandable from a first diameter to a second diameter. The stent 510 and/or the lumen 520 have a generally longitudinal axis 524.

Advantageously, the axially nested embodiments of the stent 510 allow suitable crossing profiles (e.g. luminal size) while maintaining desirable radial strength and luminal patency. In the non-expanded state, there is also minimal or reduced overlap between structural elements, so that the luminal size facilitates insertion of a guiding catheter balloon or the like to expand the vascular device.

The stent 510 comprises alternatingly arranged slide and lock sections 512a and linkage sections 512s. Each section 512a includes a pair of male structural elements 514m1, 514m2 and a pair of female structural elements 514f1, 514f2 that each slidingly mate with the male structural elements 514m1, 514m2 via respective interlocking articulating mechanisms 516mf1, 516mf2. (Each of the structural elements 514 may also be described as comprising two structural elements since each mates at two circumferential locations.)

Figure 21:
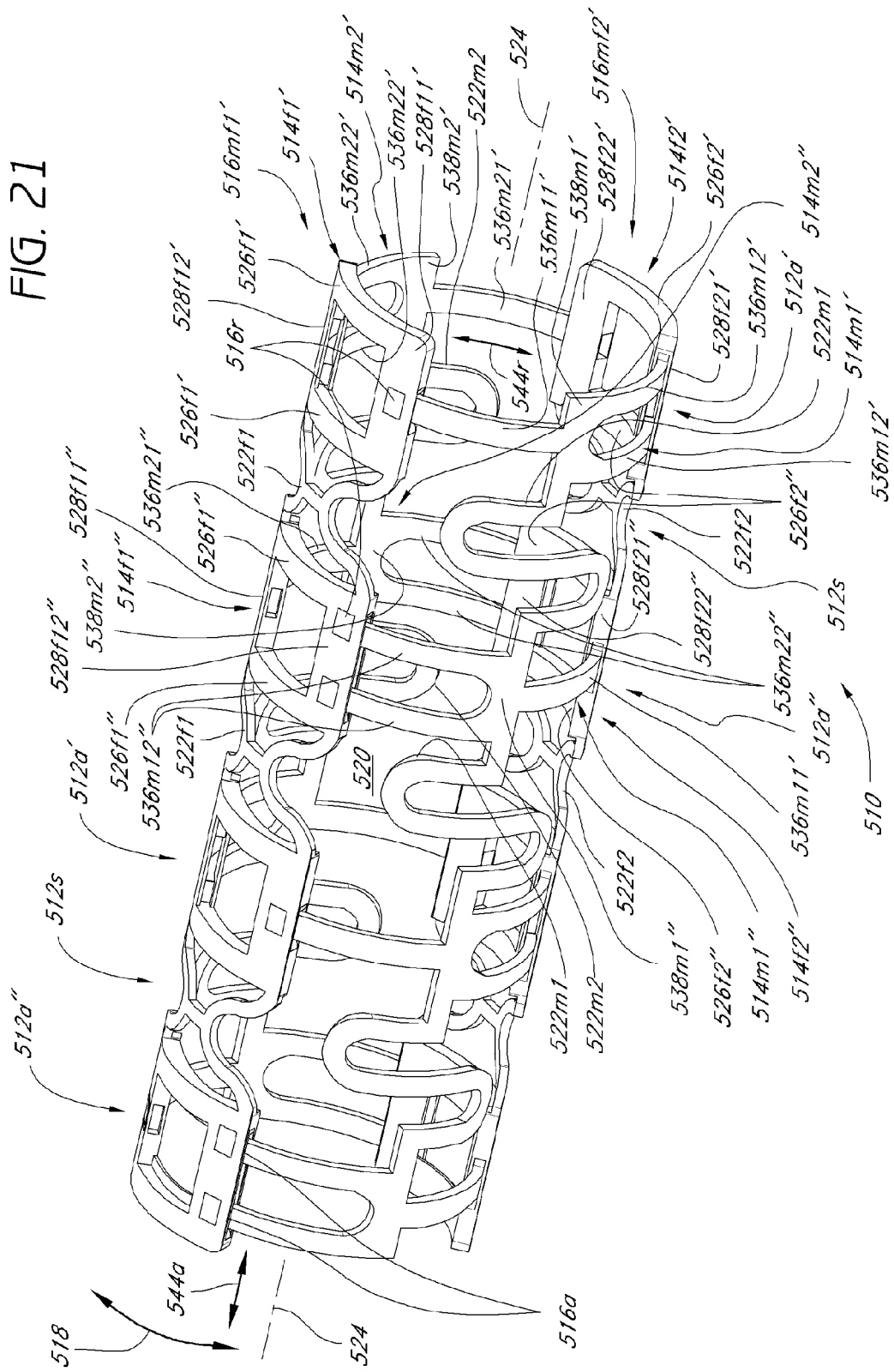
FIG. 21 is a conceptual simplified perspective view of an axially nested slide and lock stent in a deployed state illustrating features and advantages in accordance with an embodiment of the inventions.
Figure 22:
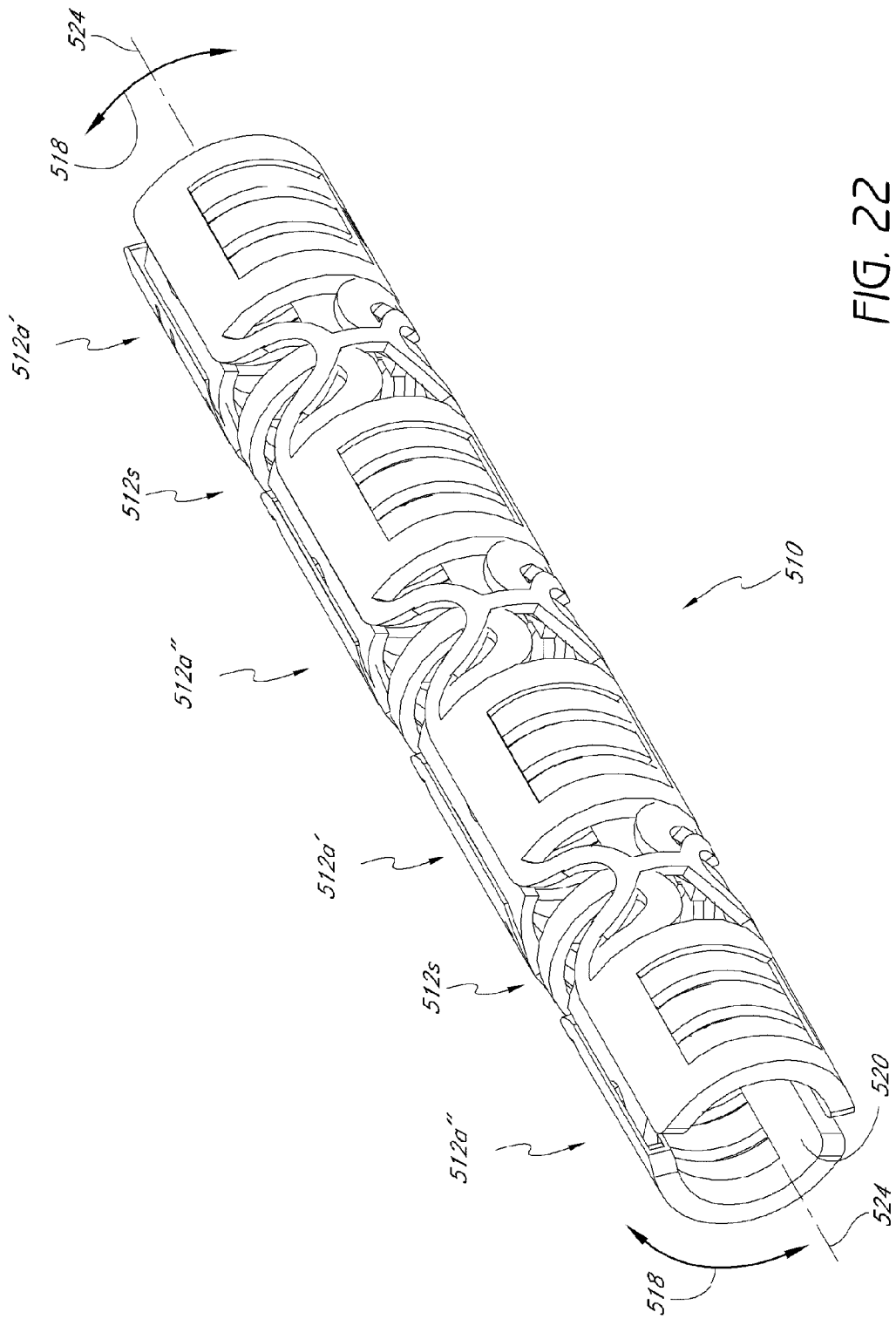
FIG. 22 is a conceptual simplified perspective view of an axially nested slide and lock stent in an undeployed state illustrating features and advantages in accordance with an embodiment of the inventions.
Figure 23A:
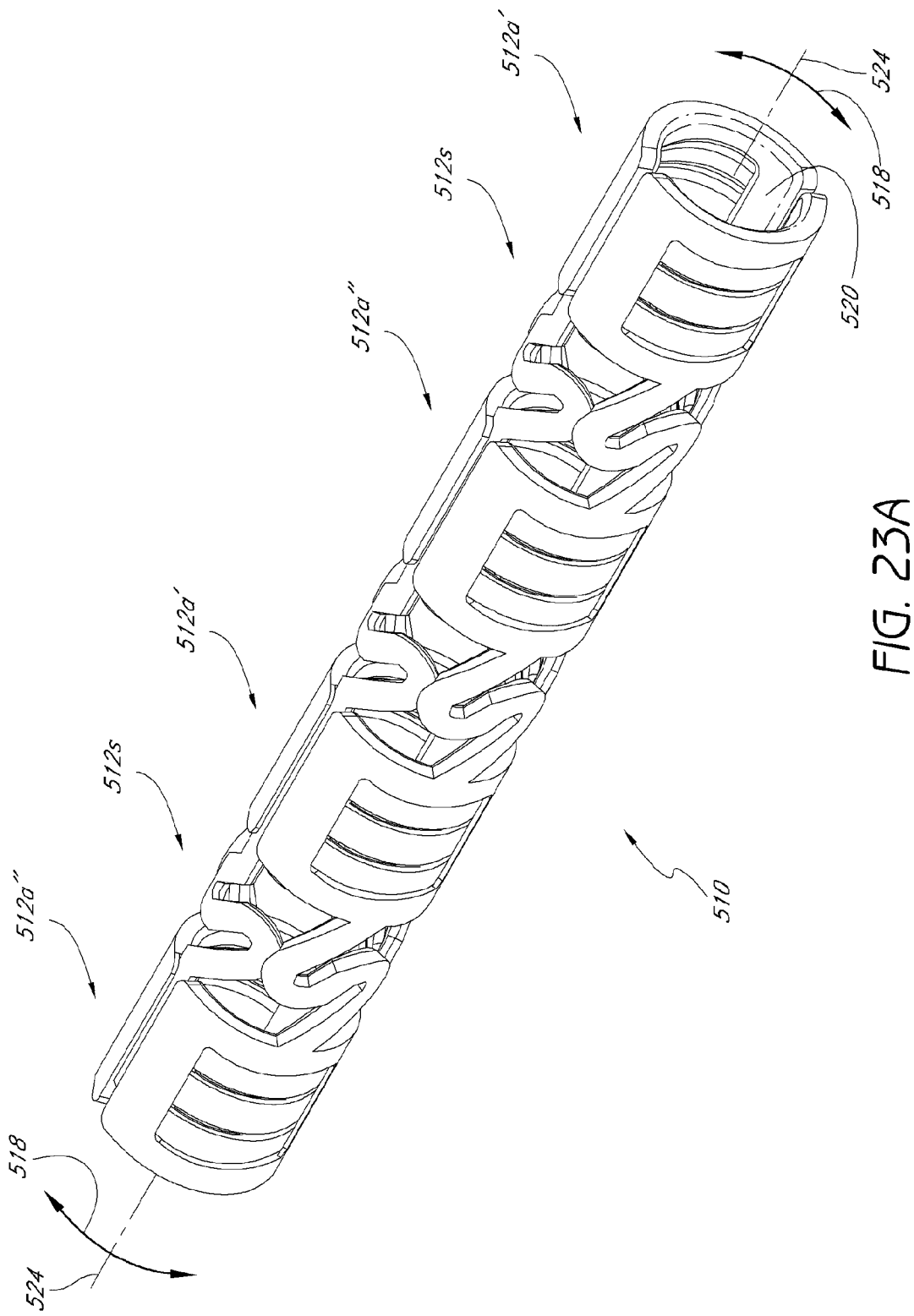
FIGS. 23A and 23B are conceptual simplified perspective views of an axially nested slide and lock stent in an undeployed state illustrating features and advantages in accordance with an embodiment of the inventions.
Figure 23B:
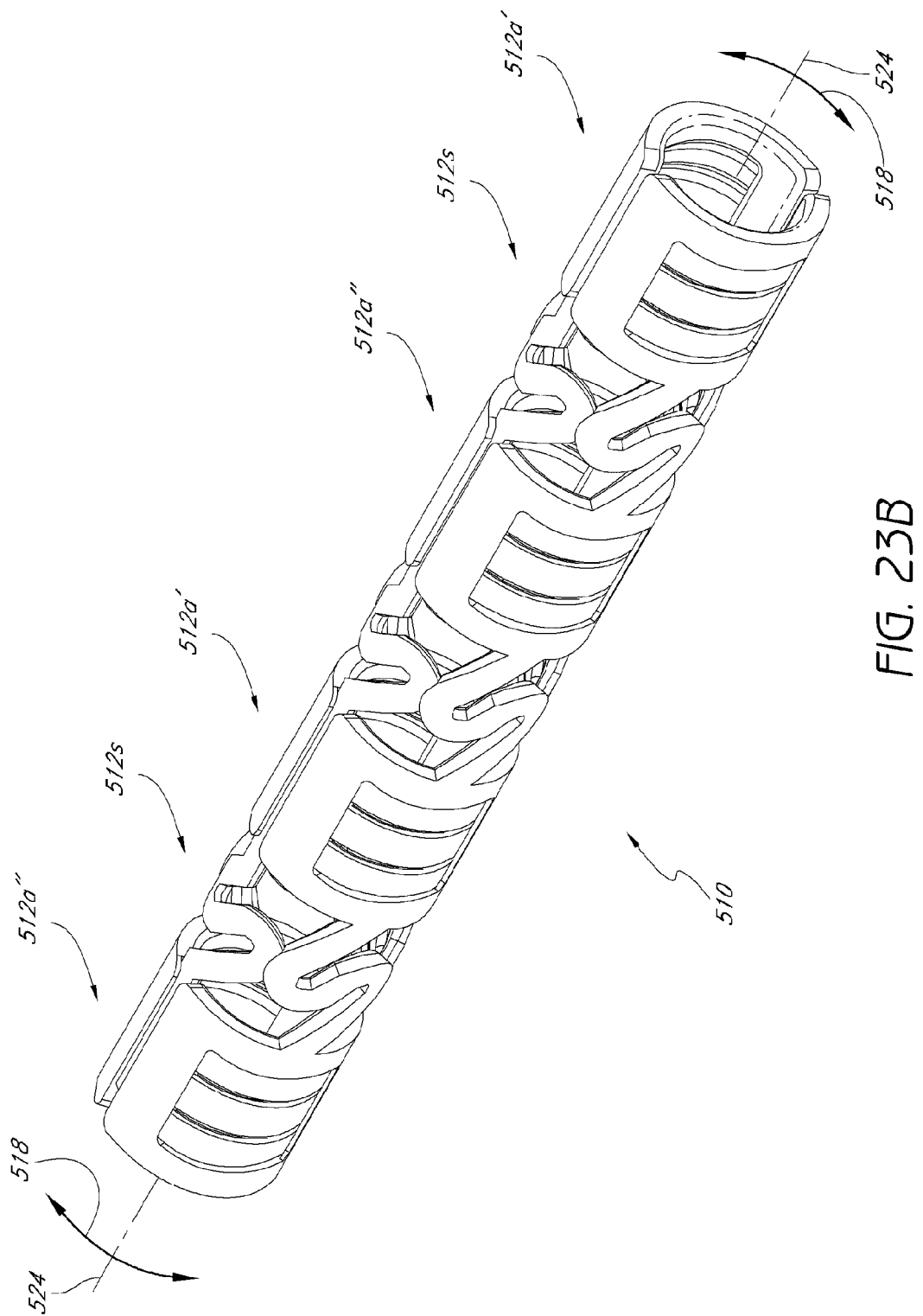

As conceptually illustrated in FIG. 21, the articulating mechanisms may comprises radially deflecting locking mechanisms 516r (arrows 544r) or axially (laterally) deflecting locking mechanisms 516a (arrows 544a). The number of structural elements in a section and/or the number of sections in a stent may be efficaciously varied and selected, as needed or desired.

The axial or longitudinal coupling between the structural elements 514 of adjacent sections 512a, the radial coupling between structural elements 514 of the same section 512a, and the design and configuration of the sections 512 and structural elements 514 are such that there is minimal or reduced overlapping in the radial or circumferential direction between the structural elements 514 in both the non-expanded and expanded states. Thus, the structural elements 514, sections 512 and/or stent 510 are referred to as being axially, longitudinally or non-radially nested. (There is also minimal or reduced radial overlap between linkage elements 522 of the same and adjacent sections 512s in both the undeployed and deployed states.)

One of the stent sections 512a' generally comprises male structural elements 514m1', 514m2' and female structural elements 514f1', 514f2'. The proximate stent section 512a" generally includes male structural elements 514m1", 514m2" and female structural elements 514f1", 514f2". (The sections 512a', 512a" are generally similar in structure except for being angularly offset and this nomenclature is used in some instances to provide a more clear description—the use of 512a encompasses one or both of 512a' and 512a" as does other similar use of 'prime' and "double-prime".)

The female structural element 514f1' generally comprises a pair of ribs or arms 526f1' spaced by end portions 528f11, 528f12'. As discussed above and below herein, the end portions 528f11', 528f12' have slide and lock articulating mechanisms such as tongue-groove configuration stops, tabs or teeth that engage respective male structural elements 514m1', 514m2' to provide radially and/or axially deflecting mechanisms for stent expansion and lock-out.

The female structural element 514f2' generally comprises a pair of ribs or arms 526f2' spaced by end portions 528f21', 528f22'. As discussed above and below herein, the end portions 528f21', 528f22' have slide and lock articulating mechanisms such as tongue-groove configuration stops, tabs or teeth that engage respective female structural elements 514m2', 514m1' to provide radially and/or axially deflecting mechanisms for stent expansion and lock-out.

The male structural element 514m1' generally comprises a rib or arm 536m11' and a pair of spaced ribs or arms 536m12' extending in a direction opposite to the rib 536m11'. The ribs 536m11', 536m12' share a common end portion 538m1'. In the stent collapsed state, the male rib 536m11' extends in the gap between the female ribs 526f1' and the male ribs 536m12' extend in the gap between the female ribs 526f2'.

As discussed above and below herein, the ribs 536m11', 536m12' have slide and lock articulating mechanisms such as tongue-groove configuration stops, tabs or teeth that engage respective female structural elements 514f1', 514f2' to provide radially and/or axially deflecting mechanisms for stent expansion and lock-out. More specifically, the ribs 536m11', 536m12' engage respective female end portions 528f11', 528f22'.

The male structural element 514m2' generally comprises a rib or arm 536m21' and a pair of spaced ribs or arms 536m22' extending in a direction opposite to the rib 536m21'. The ribs 536m21', 536m22' share a common end portion 538m2'. In the stent collapsed state, the male rib 536m21' extends in the gap between the female ribs 526f2' and the male ribs 536m22' extend in the gap between the female ribs 526f1'.

As discussed above and below herein, the ribs 536m21', 536m22' have slide and lock articulating mechanisms such as tongue-groove configuration stops, tabs or teeth that engage respective female structural elements 514f2', 514f1' to provide radially and/or axially deflecting mechanisms for stent expansion and lock-out. More specifically, the ribs 536m21', 536m22' engage respective female end portions 528f21', 528f12'.

The female structural element 514f1" generally comprises a pair of ribs or arms 526f1" spaced by end portions 528f11", 528f12". As discussed above and below herein, the end portions 528f11", 528f12" have slide and lock articulating mechanisms such as tongue-groove configuration stops, tabs or teeth that engage respective male structural elements 514m2", 514m1" to provide radially and/or axially deflecting mechanisms for stent expansion and lock-out.

The female structural element 514f2" generally comprises a pair of ribs or arms 526f2" spaced by end portions 528f21", 528f22". As discussed above and below herein, the end portions 528f21", 528f22" have slide and lock articulating mechanisms such as tongue-groove configuration stops, tabs or teeth that engage respective male structural elements 514m1", 514m2" to provide radially and/or axially deflecting mechanisms for stent expansion and lock-out.

The male structural element 514m1" generally comprises a rib or arm 536m11" and a pair of spaced ribs or arms 536m12" extending in a direction opposite to the rib 536m11". The ribs 536m11", 536m12" share a common end portion 538m1". In the stent collapsed state, the male rib 536m11" extends in the gap between the female ribs 526f2" and the male ribs 536m12" extend in the gap between the female ribs 526f1".

As discussed above and below herein, the ribs 536m11", 536m12" have slide and lock articulating mechanisms such as tongue-groove configuration stops, tabs or teeth that engage respective female structural elements 514f2", 514f1" to provide radially and/or axially deflecting mechanisms for stent expansion and lock-out. More specifically, the ribs 536m11", 536m12" engage respective female end portions 528f21", 528f12".

The male structural element 514m2" generally comprises a rib or arm 536m21" and a pair of spaced ribs or arms 536m22" extending in a direction opposite to the rib 536m21". The ribs 536m21", 536m22" share a common end portion 538m2". In the stent collapsed state, the male rib 536m21" extends in the gap between the female ribs 526f1" and the male ribs 536m22" extend in the gap between the female ribs 526f2".

As discussed above and below herein, the ribs 536m21", 536m22" have slide and lock articulating mechanisms such as tongue-groove configuration stops, tabs or teeth that engage respective female structural elements 514f1", 514f2" to provide radially and/or axially deflecting mechanisms for stent expansion and lock-out. More specifically, the ribs 536m21", 536m22" engage respective female end portions 528f11", 528f22".

Each linkage section 512s includes a plurality of elements 522 and connects adjacent stent sections 512a' and 512a". One or more of the linkage elements 522 may comprise spring elements. The spring elements 522 provide flexibility and allow expansion of the linkage sections 512s along with stent expansion. The spring elements 522 also allow for radial and/or axial rib deflection during stent expansion to a deployed state. The spring elements 522 facilitate this rib deflection by providing a resilient biasing mechanism to achieve substantially elastic rib deflection or deformation.

In one embodiment, each linkage section 512s generally comprises four linkage elements 522m1, 522m2, 522f1, 522f2. In modified embodiments, fewer or more linkage elements may be efficaciously utilized, as needed or desired.

The linkage elements 522m1 axially or longitudinally connect the male structural elements 514m1 (514m1', 514m1"). In one embodiment, the linkage elements 522m1 and the male structural elements 514m1 comprise an integral unit. In modified embodiments, the linkage elements 522m1 and the male structural elements 514m1 can efficaciously be connected by other techniques, as needed or desired.

The linkage elements 522f2 axially or longitudinally connect the male structural elements 514m2 (514m2', 514m2"). In one embodiment, the linkage elements 522m2 and the male structural elements 514m2 comprise an integral unit. In modified embodiments, the linkage elements 522f2 and the male structural elements 514m2 can efficaciously be connected by other techniques, as needed or desired.

The linkage elements 522f1 axially or longitudinally connect the female structural elements 514f1 (514f1', 514f1"). In one embodiment, the linkage elements 522f1 and the female structural elements 514f1 comprise an integral unit. In modified embodiments, the linkage elements 522f1 and the female structural elements 514f1 can efficaciously be connected by other techniques, as needed or desired.

The linkage elements 522f2 axially or longitudinally connect the female structural elements 514f2 (514f2', 514f2"). In one embodiment, the linkage elements 522f2 and the female structural elements 514f2 comprise an integral unit. In modified embodiments, the linkage elements 522f2 and the female structural elements 514f2 can efficaciously be connected by other techniques, as needed or desired.

During stent expansion, there is circumferential relative motion between the mating male structural elements 514m1, 514m2 and female structural elements 514f1, 514f2 as generally shown by arrows 518. One or both of the male structural elements 514m1, 514m2, one or both of the female structural elements 514f1, 514f2, both the male and female structural elements 514m1, 514m2, 514f1, 514f2, or any suitable combination thereof may slidably move apart.

More specifically, during expansion, there is circumferential relative motion between: the female ribs 526f1' and the male rib 536m11' with one or both slidably moving apart; the female ribs 526f1' and the male ribs 536m22' with one or both slidably moving apart; the female ribs 526f2' and the male rib 536m21' with one or both slidably moving apart; and the female ribs 526f2' and the male ribs 536m12' with one or both slidably moving apart. The motion is generally denoted by arrows 518.

Similarly, during stent expansion, there is circumferential relative motion between: the female ribs 526f1" and the male rib 536m21" with one or both slidably moving apart; the female ribs 526f1" and the male ribs 536m12" with one or both slidably moving apart; the female ribs 526f2" and the male rib 536m11" with one or both slidably moving apart; and the female ribs 526f2" and the male ribs 536m22" with one or both slidably moving apart. The motion is generally denoted by arrows 518.

As discussed herein, at full expansion, a hard stop or end capture mechanism is provided to limit further stent expansion. Each section 512a can comprise one or more end capture mechanisms such as hard stops, straps or other suitable devices that prevent further expansion between mating male and female structural elements 514m and 514f.

Advantageously, there is substantially no or minimal overlap between nesting male structural elements 514m and associated female structural elements 514f in both the collapsed state and the expanded state, and more particularly in the expanded state. For example, for a given stent section 512a', in the collapsed state the female ribs 526f1' and the male ribs 536m11', 536m22' are substantially axially or longitudinally displaced or offset while in the expanded state the same are substantially radially or circumferentially displaced or offset, thereby minimizing radial overlap in both the collapsed and expanded states.

Also, for axially displaced stent sections 512a' and 512a", for example, the female ribs 526f1' and the male rib 536m1" are substantially axially or longitudinally displaced or offset from the female ribs 526f1" and male ribs 536m12". Thus, the stent 510, its sections 512a and/or structural elements 514 are referred to as being axially nested since their radial overlap is substantially reduced or minimal in both the collapsed and expanded sates.

Figure 24:
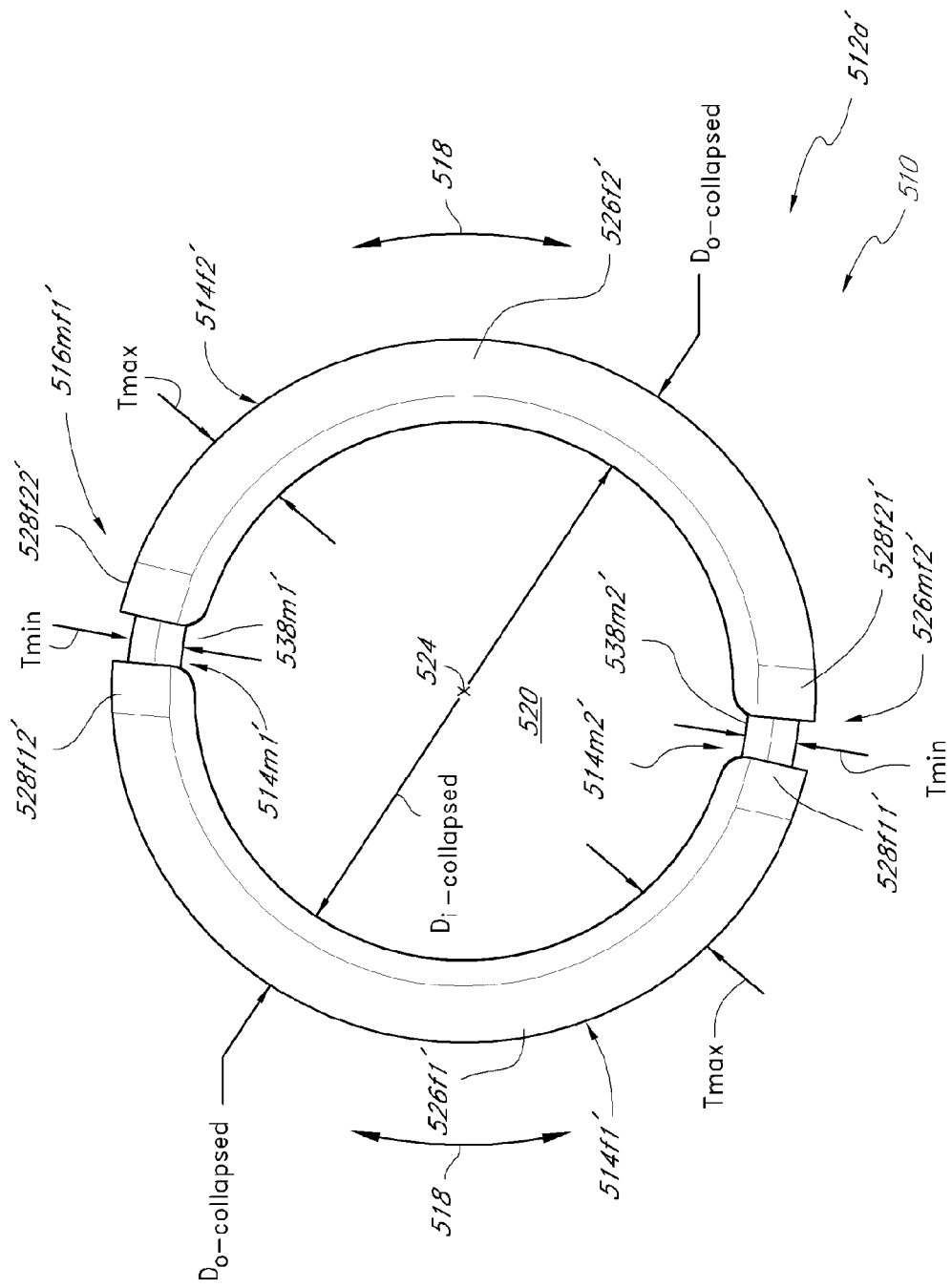
FIG. 24 is a simplified end view of the stent of FIG. 23B illustrating features and advantages in accordance with an embodiment of the inventions.
Figure 25:
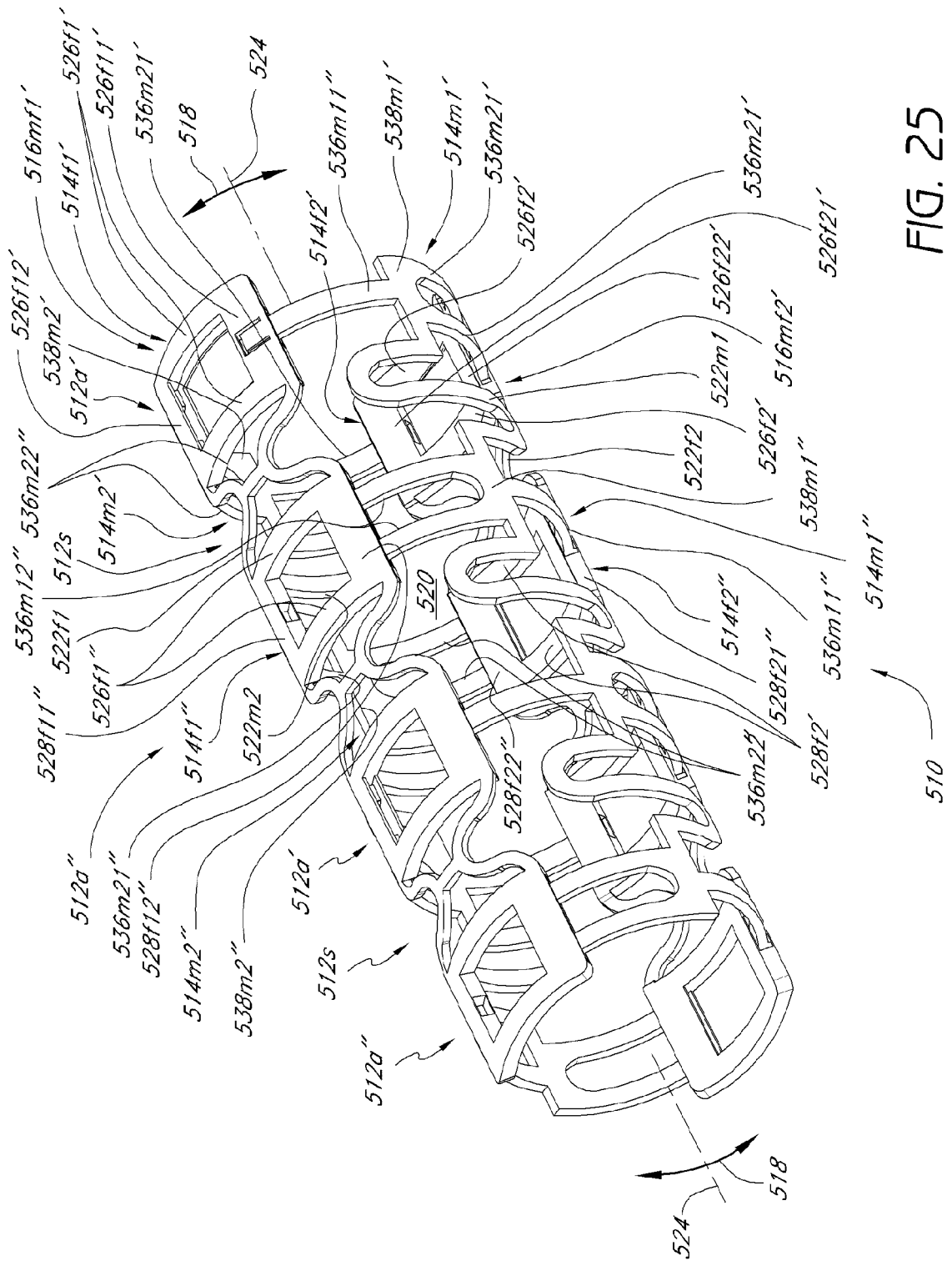
FIG. 25 is a conceptual simplified perspective view of the stent of FIG. 22 in a deployed state illustrating features and advantages in accordance with an embodiment of the inventions.
Figure 26A:
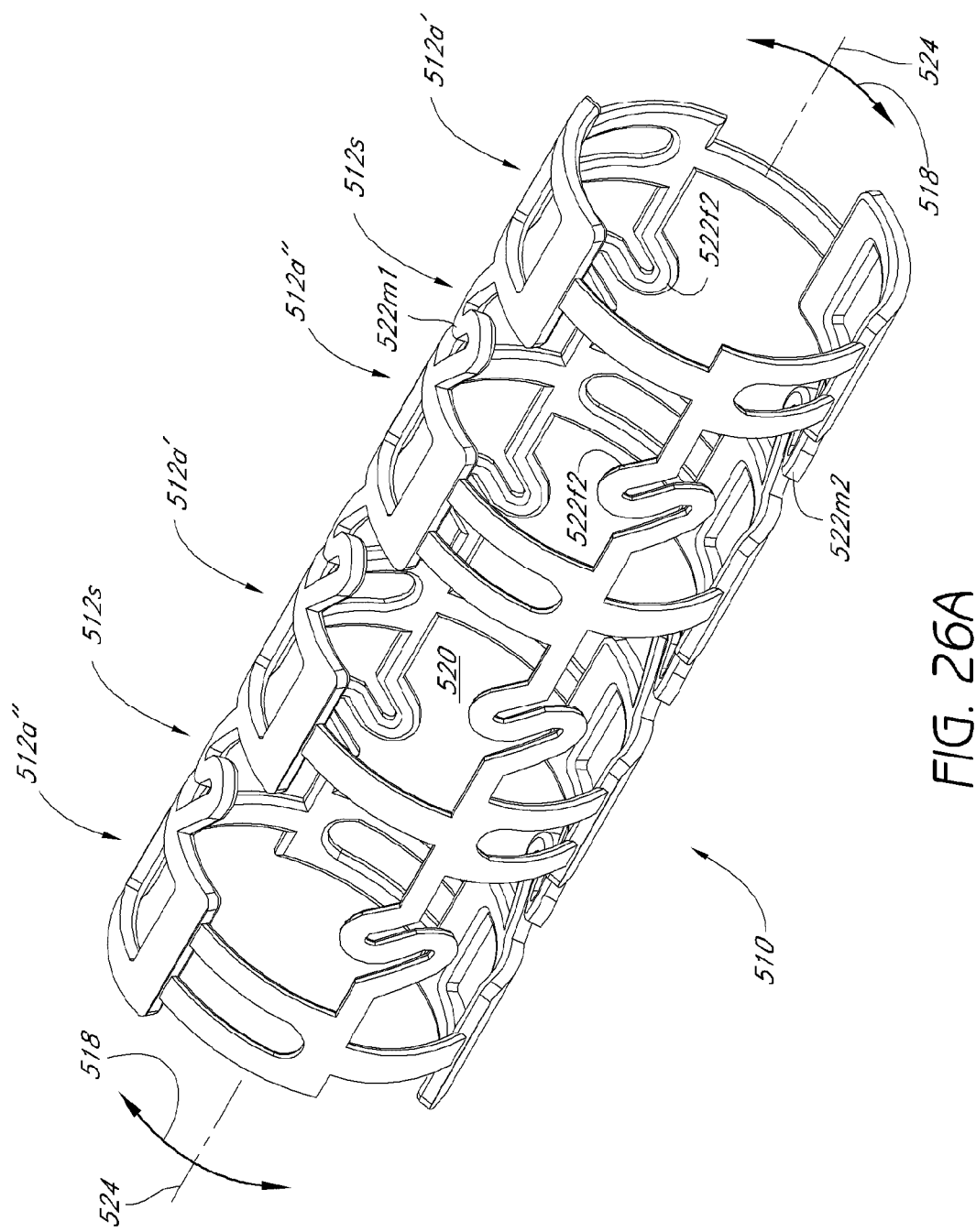
FIGS. 26A and 26B are conceptual simplified perspective views of the respective stents of FIGS. 23A and 23B in a deployed state illustrating features and advantages in accordance with an embodiment of the inventions.
Figure 26B:
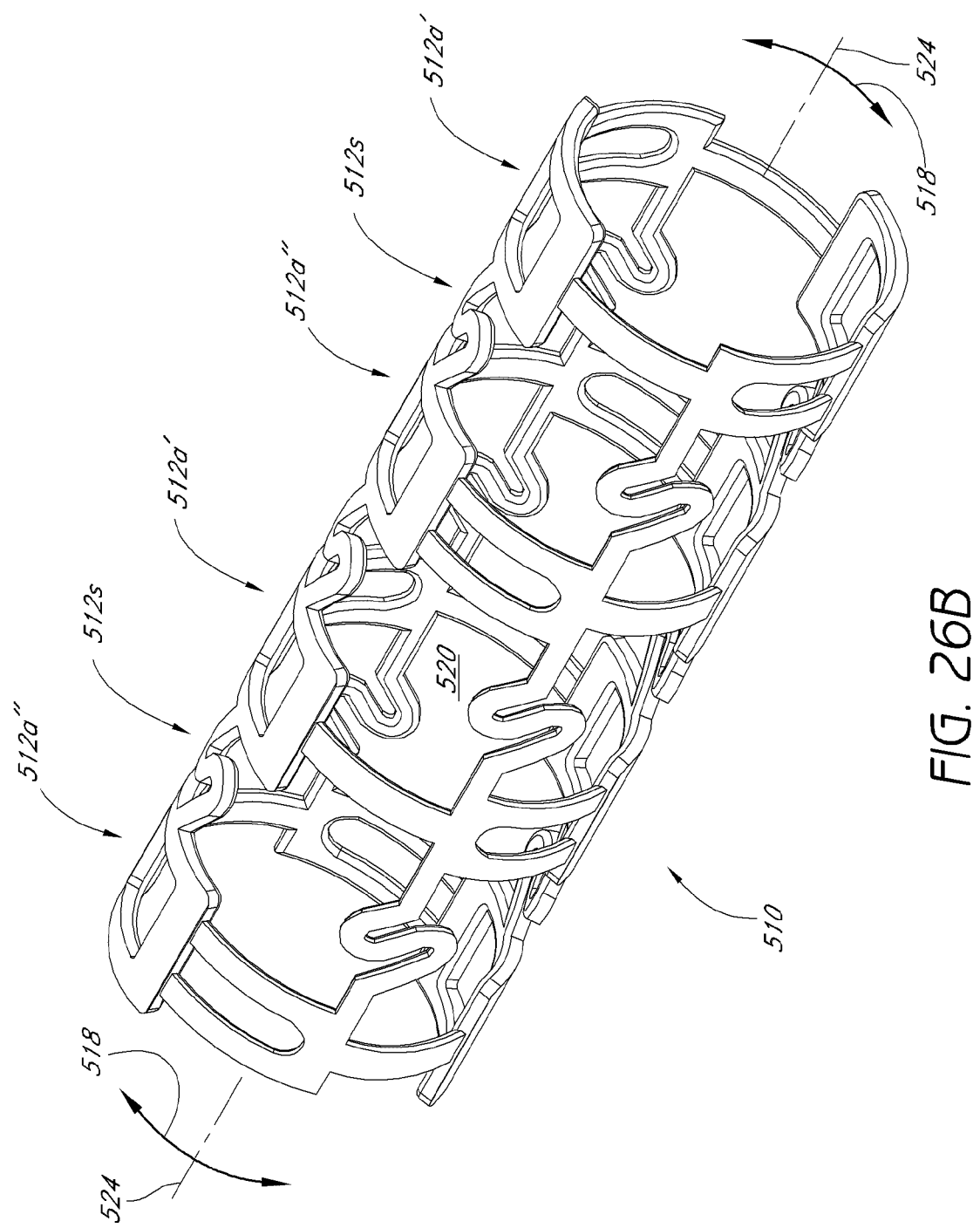
Figure 27:
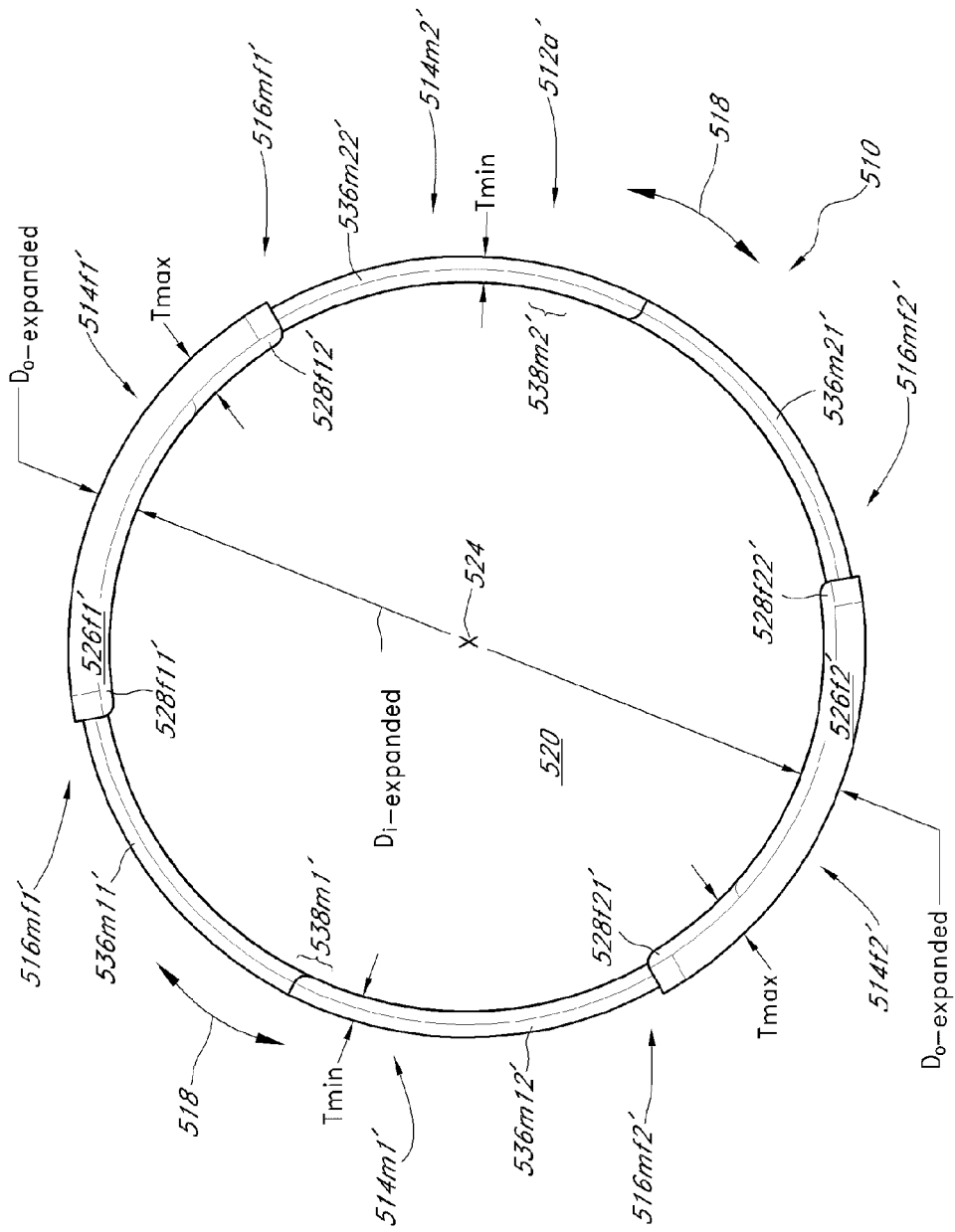
FIG. 27 is a simplified end view of the stent of FIG. 26B illustrating features and advantages in accordance with an embodiment of the inventions.
Figure 28:
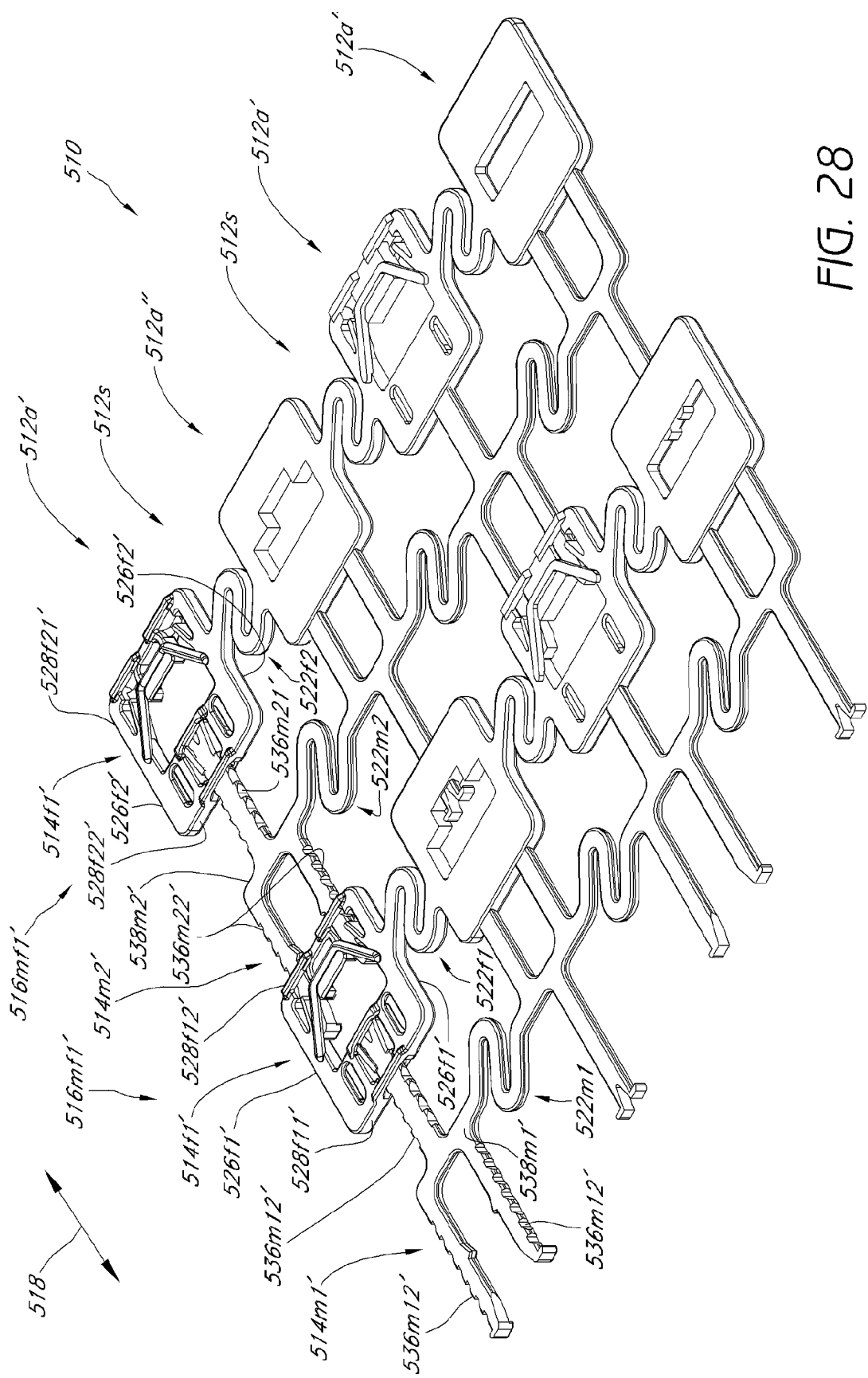
FIG. 28 is a simplified planar perspective view of an axially nested slide and lock stent in a partially expanded state illustrating features and advantages in accordance with an embodiment of the inventions.
Figure 29:
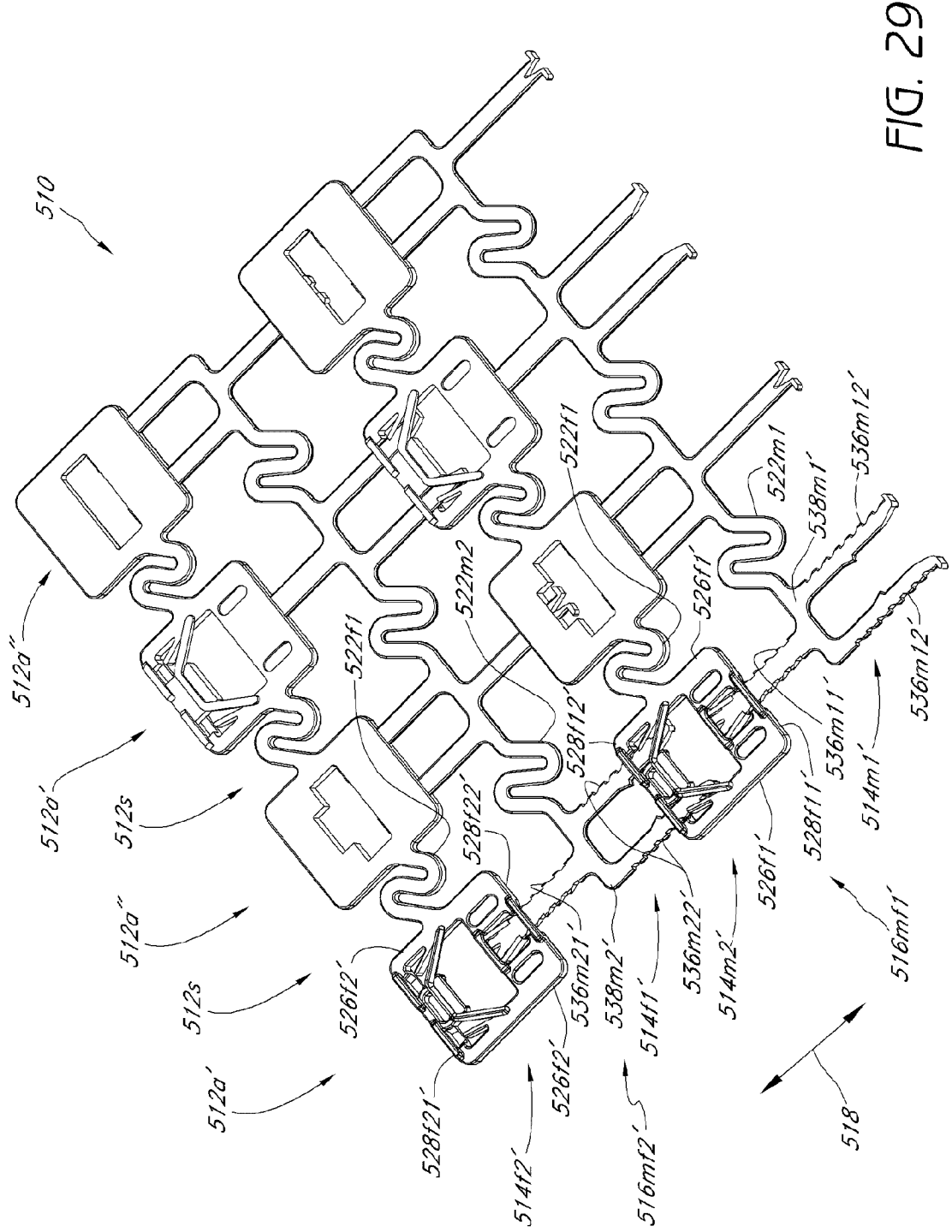
FIG. 29 is a simplified planar perspective view of an axially nested slide and lock stent in an almost fully expanded state illustrating features and advantages in accordance with an embodiment of the inventions.

Referring in particular to FIGS. 24 and 27, the stent 510 has a minor inner collapsed diameter $D_{i\text{-}collapsed}$, a major outer collapsed diameter $D_{o\text{-}collapsed}$, a minor inner expanded diameter $D_{i\text{-}expanded}$ and a major outer expanded diameter $D_{o\text{-}expanded}$. The stent wall curvature decreases as the stent 510 expands, but its radius of curvature increases.

The stent wall has a minimum thickness $T_{min}$ and a maximum thickness $T_{max}$. The thicknesses $T_{min}$ and thickness $T_{max}$ remain substantially unchanged in the collapsed and expanded states. In one embodiment, the minimum thickness $T_{min}$ is the thickness of the male structural elements 514m and the maximum $T_{max}$ is the thickness of the female structural elements 514f. If the thickness $T_{min}$ is considered to be the nominal material thickness then, in one embodiment, the maximum wall thickness is given by, where k is embodiment dependent:

$$T_{min} < T_{max} \leq kT_{min}$$

In one embodiment k is about two (2). In another embodiment, k is in the range from about 1.5 to about 3, including all values and sub-ranges therebetween. In yet another embodiment, k is in the range from about 1.25 to about 5, including all values and sub-ranges therebetween. In modified embodiments, other suitable values and/or ranges of k may be efficaciously utilized, as needed or desired.

Embodiments of the inventions provide an axially nested vascular device 510 to achieve both competitive crossing profiles (e.g. luminal size) while maintaining other key features, such as, for example, radial strength and luminal patency. Advantageously, an axially nested device design allows for use of thicker materials to maintain radial strength, as needed or desired.

The maximum thickness $T_{max}$ is substantially the same in both the collapsed and expanded states. Thus, in the collapsed state, there is also minimal or reduced overlap between structural elements (e.g., 514m, 514f), so that the luminal size facilitates insertion of a guiding catheter balloon or the like to expand the vascular device.

During manufacture and assembly of the axially nested embodiments, the device structural elements (e.g., 514m, 514f) and/or ribs (e.g. the female ribs 526f1' and the male ribs 536m11', 536m22') are positioned side by side (axially) in the predilated or non-expanded state to substantially reduce or minimize the device crossing profile and bulk in both the undeployed (non-expanded, predilated) and deployed (expanded, dilated) states. Advantageously, by substantially reducing or eliminating the excess bulk typically encountered with a radially nesting device design, embodiments of the inventions can be used to achieve competitive devices and crossing profiles with a wide variety of materials at a wide variety of thicknesses, thereby desirably allowing for optimum device design and performance.

FIGS. 28-37 show different views of the axially nested slide and lock vascular device, prosthesis or stent 510. These drawings illustrate, among other things, features of the articulating slide and lock mechanisms, deflecting arm mechanisms and capture mechanisms at full expansion in accordance with some embodiments of the stent 510.

The male rib 536m11' includes a plurality of outwardly extending stops, tabs or teeth 542m11' that extend on both sides of the rib 536m11'. The stops 542m11' engage the female structural element 514f1 in a one-way slide and lock articulating motion.

Figure 31:
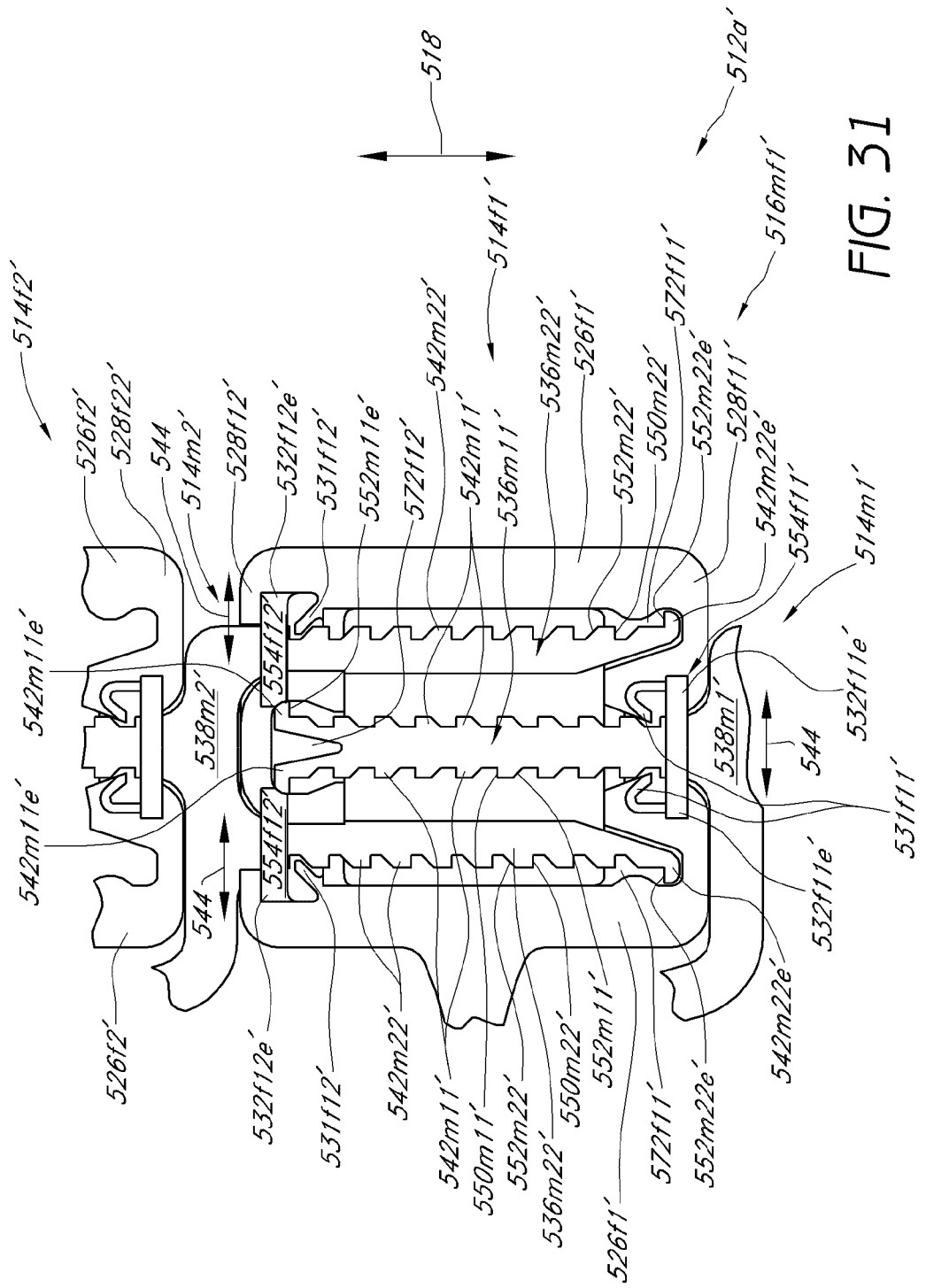
FIG. 31 is a simplified planar partial view of an axially nested slide and lock stent section in a collapsed state illustrating features and advantages in accordance with an embodiment of the inventions.
Figure 33:
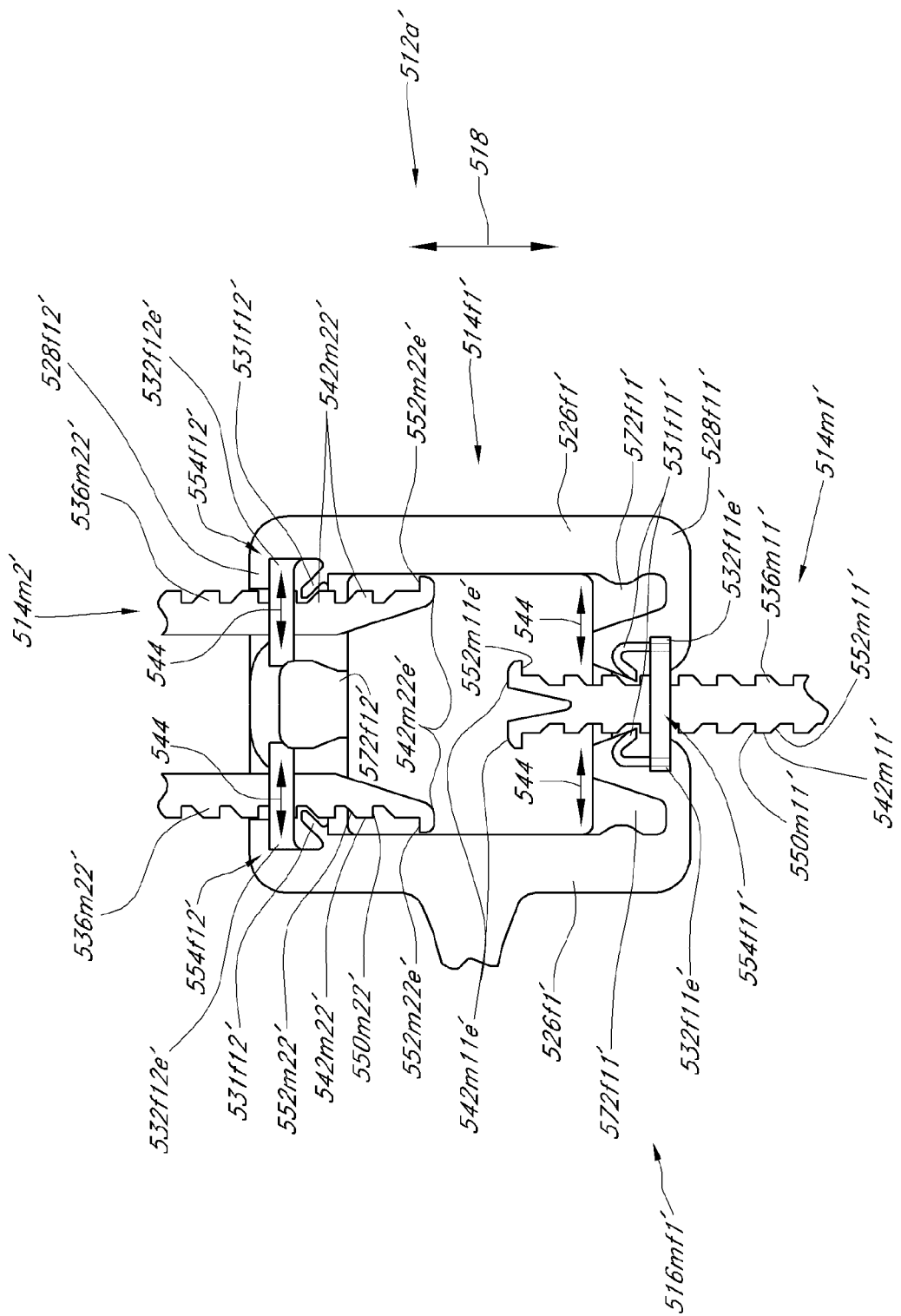
FIG. 33 is a simplified planar partial view of an axially nested slide and lock stent section a partially expanded state illustrating features and advantages in accordance with an embodiment of the inventions.

The male stops 542m11' are configured so that they have generally flat end surfaces 550m11' to substantially reduce or minimize recoil and generally tapered engaging surfaces 552m11' to facilitate one-way sliding (see, for example, FIGS. 31 and 33). Other suitable configurations that inhibit undesirable recoil and facilitate one-way expansion may be efficaciously utilized, as needed or desired.

The male rib 536m11' also includes a pair of outwardly extending end stops, tabs, wings or teeth 542m11e' with one each extending on each sides of the rib 536m11'. The end stops 542m11e' engage a capture mechanism of the female structural element 514f1' to control and limit the maximum stent expansion.

The end stops 542m11e' have generally flat engaging surfaces 552m11e' that facilitate lock-out and capture at full expansion (see, for example, FIGS. 31 and 33). Other suitable lock-out and capture configurations may be efficaciously utilized, as needed or desired.

Each of the male ribs 536m12' includes a plurality of outwardly extending stops, tabs or teeth 542m12'. The stops 542m12' engage the female structural element 514f2' in a one-way slide and lock articulating motion.

Figure 34:
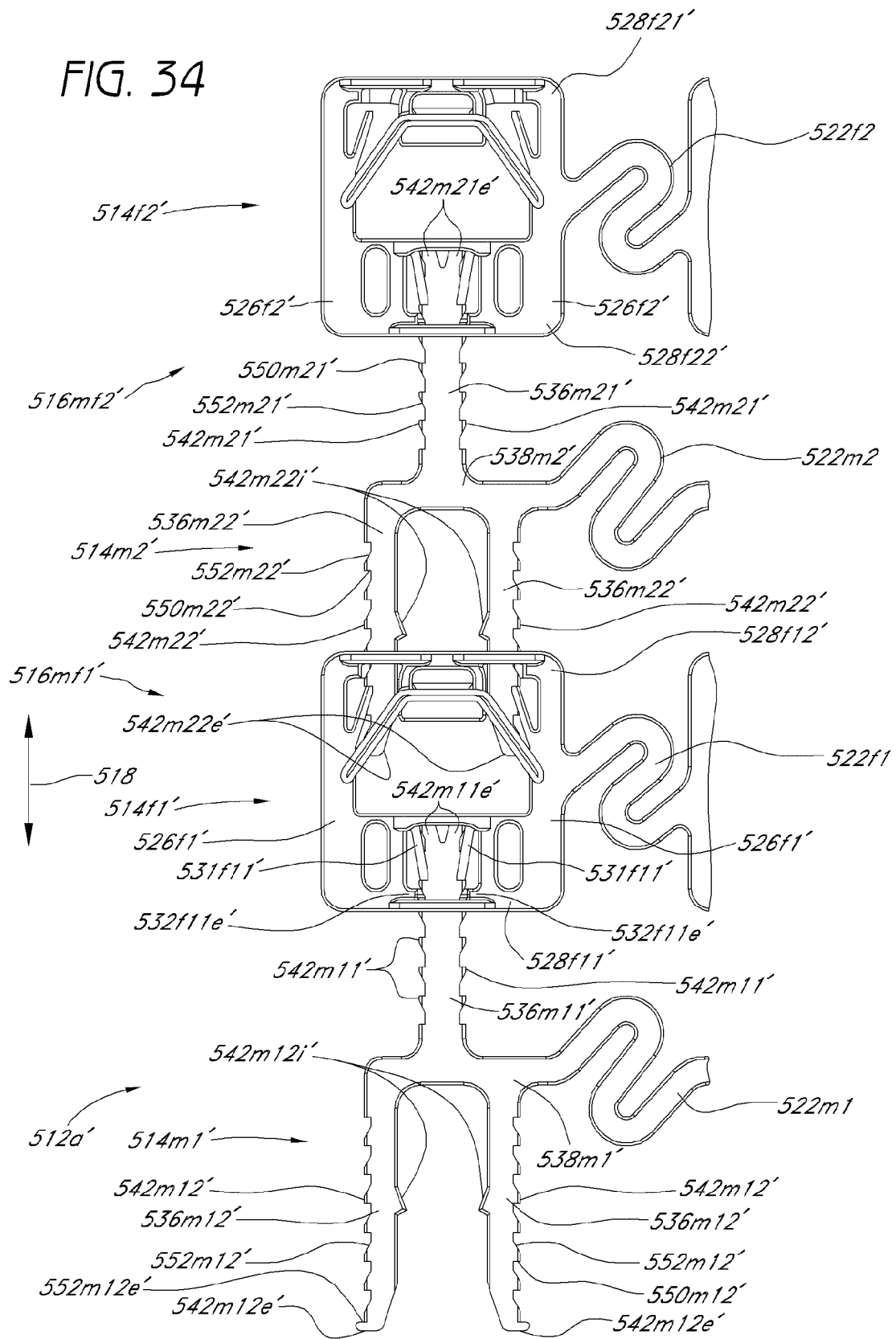
FIG. 34 is a simplified planar view of an axially nested slide and lock stent section in an almost fully expanded state illustrating features and advantages in accordance with an embodiment of the inventions.

The male stops 542m12' are configured so that they have generally flat end surfaces 550m21' to substantially reduce or minimize recoil and generally tapered engaging surfaces 552m21' to facilitate one-way sliding (see, for example, FIG. 34). Other suitable configurations that inhibit undesirable recoil and facilitate one-way expansion may be efficaciously utilized, as needed or desired.

In one embodiment, one or both of the male ribs 536m12' include one or more inwardly extending stops, tabs or teeth 542m12i' (see, for example, FIG. 34). These stops 542m12i' are configured to allow only one-way sliding and provide a mechanism to substantially reduce or minimize recoil.

Each of the male ribs 536m12' also includes an outwardly extending end stop, tab, wing or tooth 542m12e'. The end stops 542m12e' engage a capture mechanism of the female structural element 514f2' to control and limit the maximum stent expansion.

The end stops 542m12e' have generally flat engaging surfaces 552m12e' that facilitate lock-out and capture at full expansion (see, for example, FIG. 34). Other suitable lock-out and capture configurations may be efficaciously utilized, as needed or desired.

The male rib 536m21' includes a plurality of outwardly extending stops, tabs or teeth 542m21' that extend on both sides of the rib 536m21'. The stops 542m21' engage the female structural element 514f2' in a one-way slide and lock articulating motion.

The male stops 542m21' are configured so that they have generally flat end surfaces 550m21' to substantially reduce or minimize recoil and generally tapered engaging surfaces 552m21' to facilitate one-way sliding (see, for example, FIG. 34). Other suitable configurations that inhibit undesirable recoil and facilitate one-way expansion may be efficaciously utilized, as needed or desired.

The male rib 536m21' also includes a pair of outwardly extending end stops, tabs, wings or teeth 542m21e' with one each extending on each sides of the rib 536m21'. The end stops 542m21e' engage a capture mechanism of the female structural element 514f2' to control and limit the maximum stent expansion.

Figure 32:
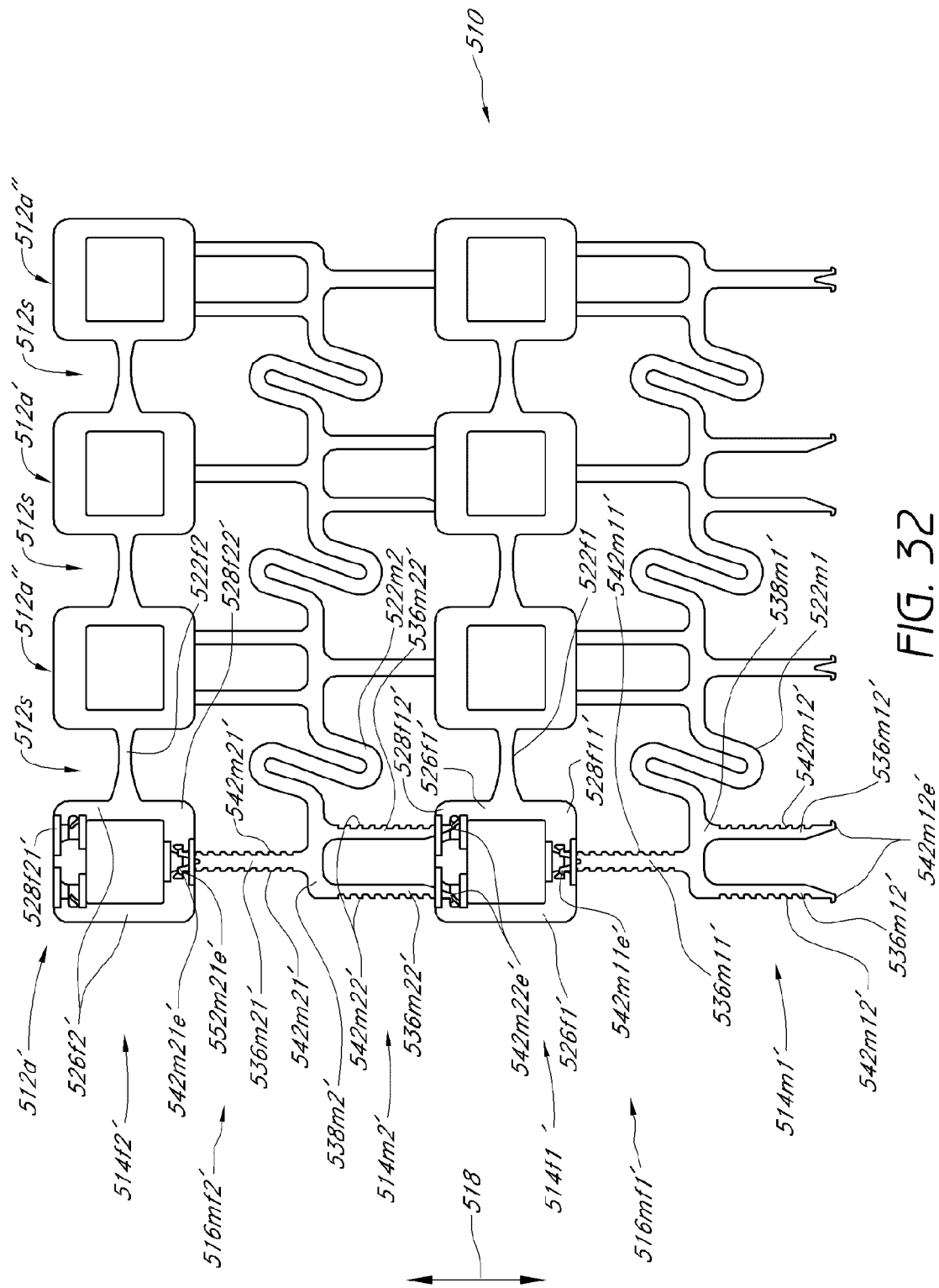
FIG. 32 is a simplified planar view of an axially nested slide and lock stent in a fully expanded state illustrating features and advantages in accordance with an embodiment of the inventions.

The end stops 542m21e' have generally flat engaging surfaces 552m21e' that facilitate lock-out and capture at full expansion (see, for example, FIG. 32). Other suitable lock-out and capture configurations may be efficaciously utilized, as needed or desired.

Each of the male ribs 536m22' includes a plurality of outwardly extending stops, tabs or teeth 542m22'. The stops 542m22' engage the female structural element 514f1' in a one-way slide and lock articulating motion.

The male stops 542m12' are configured so that they have generally flat end surfaces 550m22' to substantially reduce or minimize recoil and generally tapered engaging surfaces 552m22' to facilitate one-way sliding (see, for example, FIGS. 31 and 33). Other suitable configurations that inhibit undesirable recoil and facilitate one-way expansion may be efficaciously utilized, as needed or desired.

In one embodiment, one or both of the male ribs 536m22' include one or more inwardly extending stops, tabs or teeth 542m22i' (see, for example, FIG. 34). These stops 542m22i' are configured to allow only one-way sliding and provide a mechanism to substantially reduce or minimize recoil.

Each of the male ribs 536m22' also includes an outwardly extending end stop, tab, wing or tooth 542m22e'. The end stops 542m22e' engage a capture mechanism of the female structural element 514f1' to control and limit the maximum stent expansion.

The end stops 542m22e' have generally flat engaging surfaces 552m22e' that facilitate lock-out and capture at full expansion (see, for example, FIGS. 31 and 33). Other suitable lock-out and capture configurations may be efficaciously utilized, as needed or desired.

The female structural elements 514f1' and 514f2' are of generally similar construction as are the other female structural elements of the stent 510. Thus, for brevity, the female structural element 514m1' is discussed in greater detail below with respect to articulation, lock-out and capture features. It is to be understood that a generally similar arrangement is encompassed by the other male structural elements 514m of the stent 510.

The end portion 528f11' of the female structural element 514f1' slidingly articulates with the male rib 536m11' as generally denoted by arrows 518. The end portion 528f11' also advantageously provides an internal protected locking mechanism for rib articulation and capture of the rib 536m11' at full stent expansion.

The end portion 528f11' includes a pair of spaced deflectable elements, fingers, stops or tabs 531f11'. During expansion, the deflectable elements 531f11' and the respective stops 542m11' cross one another. This is accomplished by utilizing an axially deflecting mechanism.

Thus, during "cross-over" the deflectable elements 531f11' are deflected outwards and then resume their original undeflected position. This axial, longitudinal or lateral motion is generally denoted by arrows 544. The axial deflection is caused by the generation of a generally axial or longitudinal force when the deflectable elements 531f11' and respective male stops 542m11' slide over, engage or abut one another.

A lock-out and capture mechanism includes one or more spaced end stops, tabs or teeth 532f11e' that engage respective end hard stops 542m11e' of the male rib 536m11' at full stent expansion, and prevent further expansion. This provides to control and limit stent expansion to a predetermined deployment diameter.

A raised capture strap or device 554f11' and an associated slot, gap or recess 556f11' can be provided proximate to the hard stops 532f11e'. The capture strap 554f11' can serve to protect and/or align the male rib 536m11' and the articulating and lock-out mechanisms, and also prevent the male rib 536m11' from jumping out of its track. The internal protected articulating and locking mechanisms advantageously allow clearance space at the outer stent periphery which shields and protects the mechanisms from external surface interferences.

The slot 556f11' extends between the end hard stops 532f11e' and allows passage of the male rib articulating stops 542m11' but prevents the male rib end hard stops 542m11e' to pass through, thereby desirably providing a lock-out and capture mechanism. The slot 556f11' can also provide protection, clearance space and/or alignment of the male rib 536m11' and its engaging mechanisms, and also prevent the male rib 536m11' from jumping out of its track.

Figure 35:
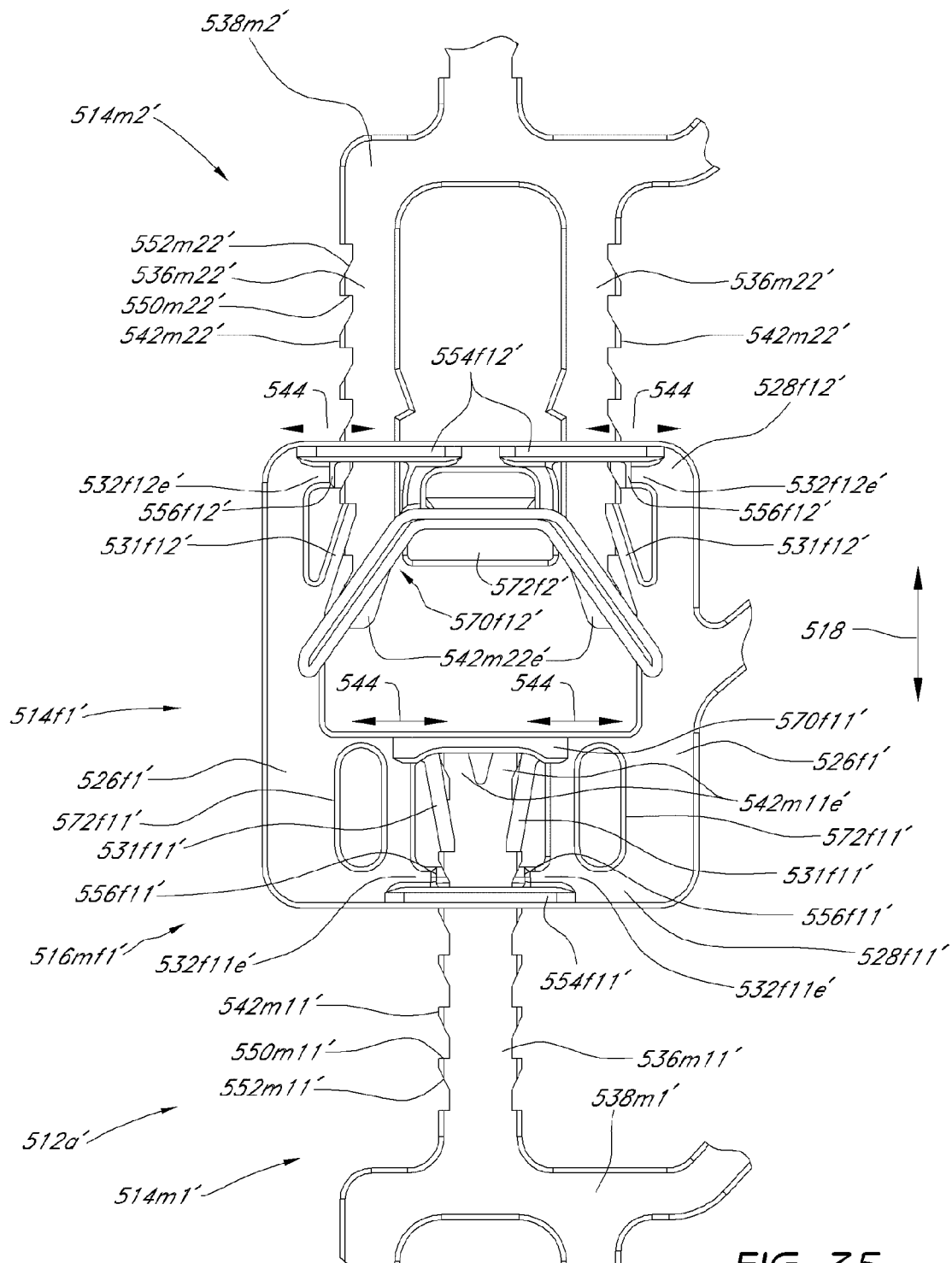
FIG. 35 is a simplified planar partial view of an axially nested slide and lock stent section in an almost fully expanded state illustrating features and advantages in accordance with an embodiment of the inventions.
Figure 36:
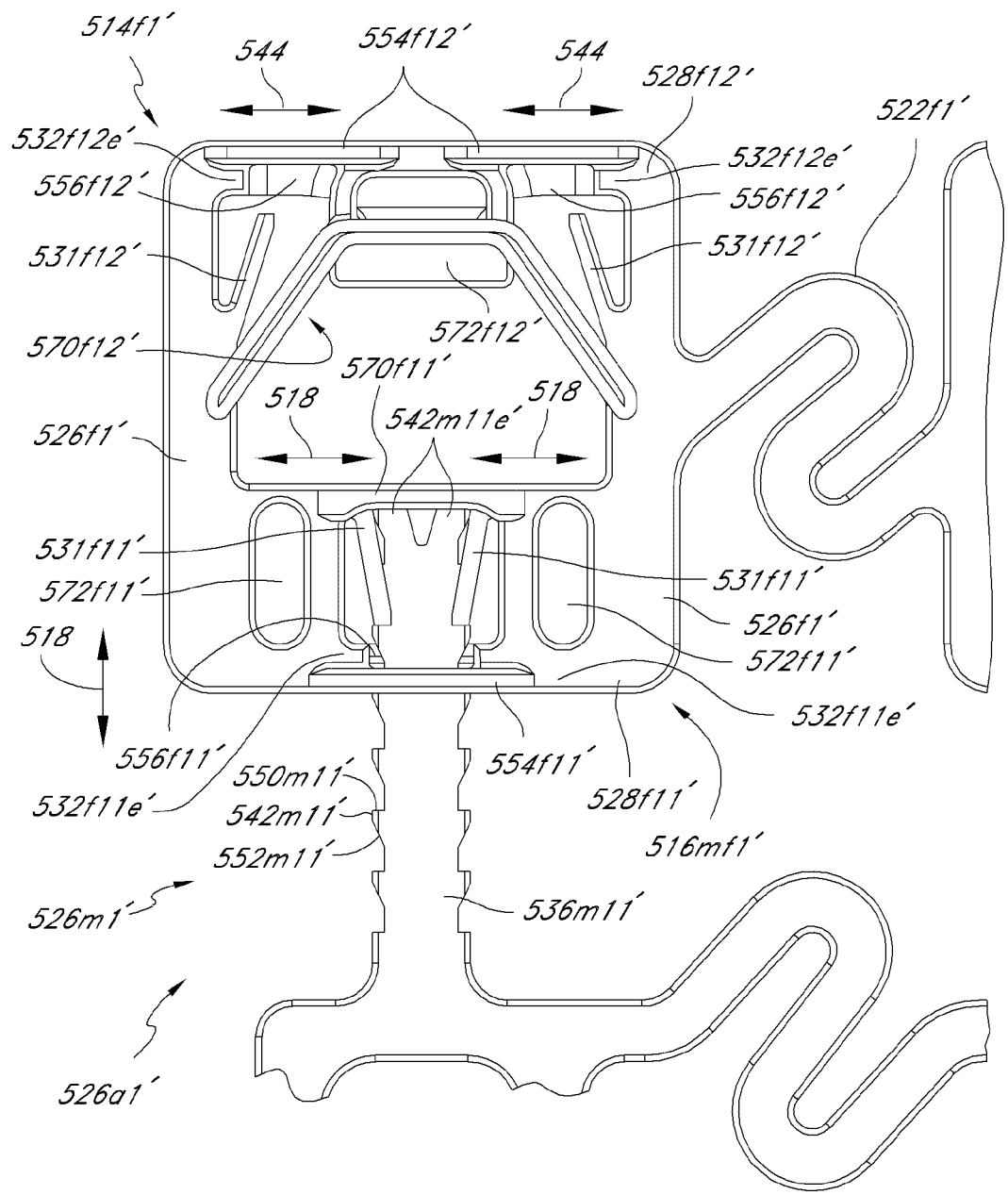
FIG. 36 is another simplified planar partial view of an axially nested slide and lock stent section in an almost fully expanded state illustrating features and advantages in accordance with an embodiment of the inventions.
Figure 37:
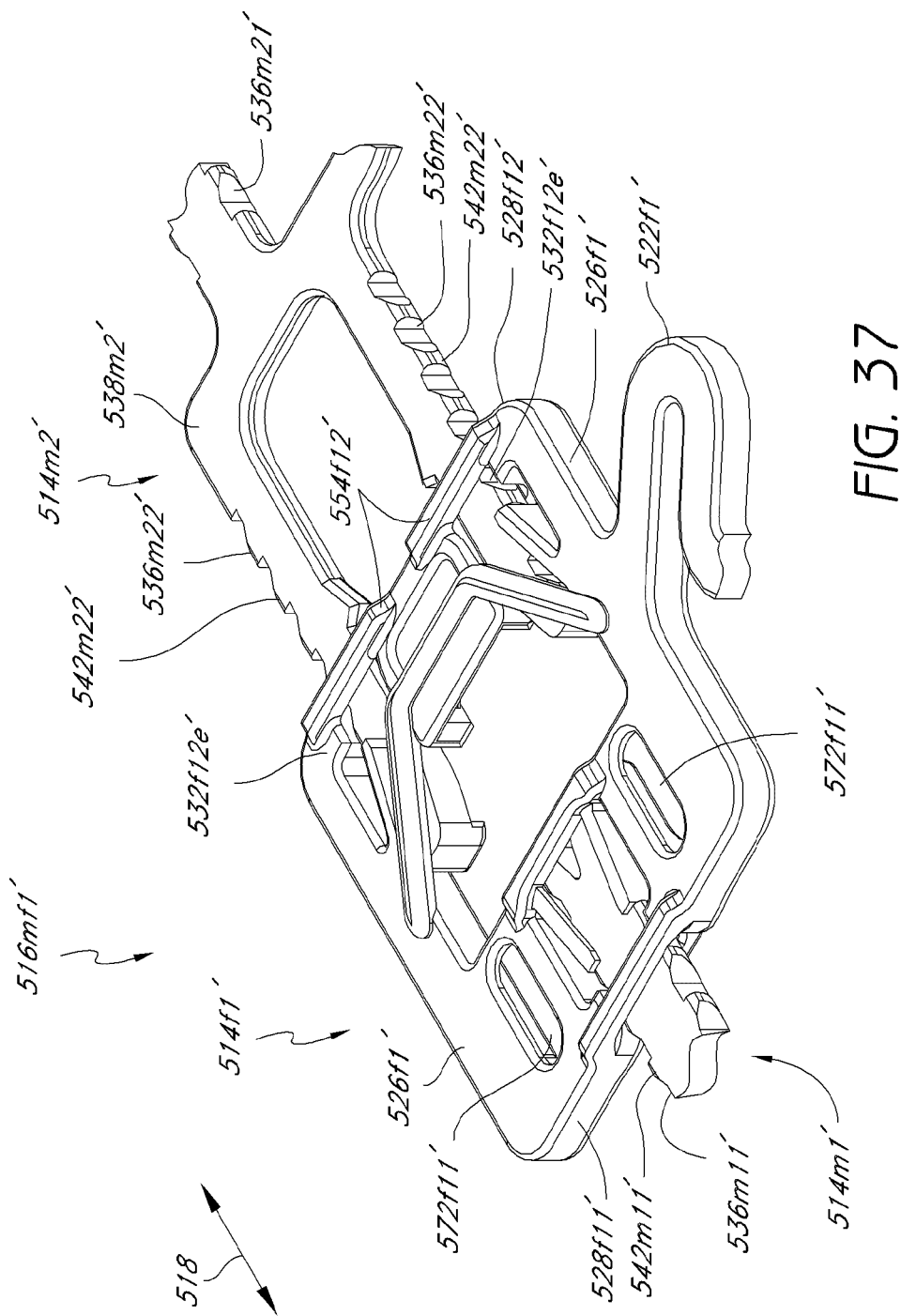
FIG. 37 is a simplified planar perspective partial view of an axially nested slide and lock stent section in an almost fully expanded state illustrating features and advantages in accordance with an embodiment of the inventions.

In some embodiments, the end portion 528f11' includes a shielding and alignment strap, device or element 570f11' (see, for example, FIGS. 35 and 36). The raised element 570f11' provides protection, clearance space and/or alignment of the male rib 536m11' and its engaging mechanisms, and also prevents the male rib 536m11' from jumping out of its track.

The end portion 528/11' can also include one or more spaced clearance elements, spaces, gaps or recesses 572/11'. Advantageously, the raised portions of the elements 572/11' provide protection, clearance space and/or alignment of the male ribs 536m22' in particular during the collapsed and initial stages of stent expansion.

The end portion 528/12' of the female structural element 514/1' slidingly articulates with the male ribs 536m22' as generally denoted by arrows 518. The end portion 528/12' also advantageously provides an internal protected locking mechanism for rib articulation and capture of the ribs 536m22' at full stent expansion.

The end portion 528/12' includes a pair of spaced deflectable elements, fingers, stops or tabs 531/12'. During expansion, the deflectable elements 531/12' and the respective stops 542m22' cross one another. This is accomplished by utilizing an axially deflecting mechanism.

Thus, during "cross-over" the deflectable elements 531/12' are deflected outwards and then resume their original undeflected position. This axial, longitudinal or lateral motion is generally denoted by arrows 544. The axial deflection is caused by the generation of a generally axial or longitudinal force when the deflectable elements 531/12' and respective male stops 542m22' slide over, engage or abut one another.

A lock-out and capture mechanism includes one or more spaced end stops, tabs or teeth 532/12e' that engage respective end hard stops 542m22e' of the male ribs 536m22' at full stent expansion, and prevent further expansion. This provides to control and limit stent expansion to a predetermined deployment diameter.

A pair of raised capture straps or devices 554/12' and associated slots, gaps or recesses 556/12' can be provided proximate to respective hard stops 532/12e'. The capture straps 554/12' can serve to protect and/or align respective male ribs 536m22' and the articulating and lock-out mechanisms, and also prevent the male ribs 536m22' from jumping out of their track. The internal protected articulating and locking mechanisms advantageously allow clearance space at the outer stent periphery which shields and protects the mechanisms from external surface interferences.

The slots 556/12' extend between the end hard stops 532/12e' and allow passage of respective male rib articulating stops 542m22' but prevent the male rib end hard stops 542m22e' to pass through, thereby desirably providing a lock-out and capture mechanism. The slots 556/12' can also provide protection, clearance space and/or alignment of respective female ribs 536f22' and their engaging mechanisms, and also prevent the male ribs 536m22' from jumping out of their track.

In some embodiments, the end portion 528/12' includes a shielding and alignment strap, device or element 570/12' (see, for example, FIGS. 35 and 36). The raised element 570/12' is configured to provide protection, clearance space and/or alignment of the female ribs 536f22' and their engaging mechanisms. The raised element 57/12' is also shaped to provide additional stent strength and facilitate a curved structure when the stent 510 is coiled or rolled down. The shape logic of the device 570/12' is to provide a capture element configuration and structural support for the "box" shape and/or to provide stiffness and support to the center section.

The end portion 528/12' can also include a clearance element, space, gap or recess 572/12'. Advantageously, the raised portion of the element 572/12' provides protection, clearance space and/or alignment of the male rib 536m11' in particular during the collapsed and initial stages of stent expansion.

Figure 30:
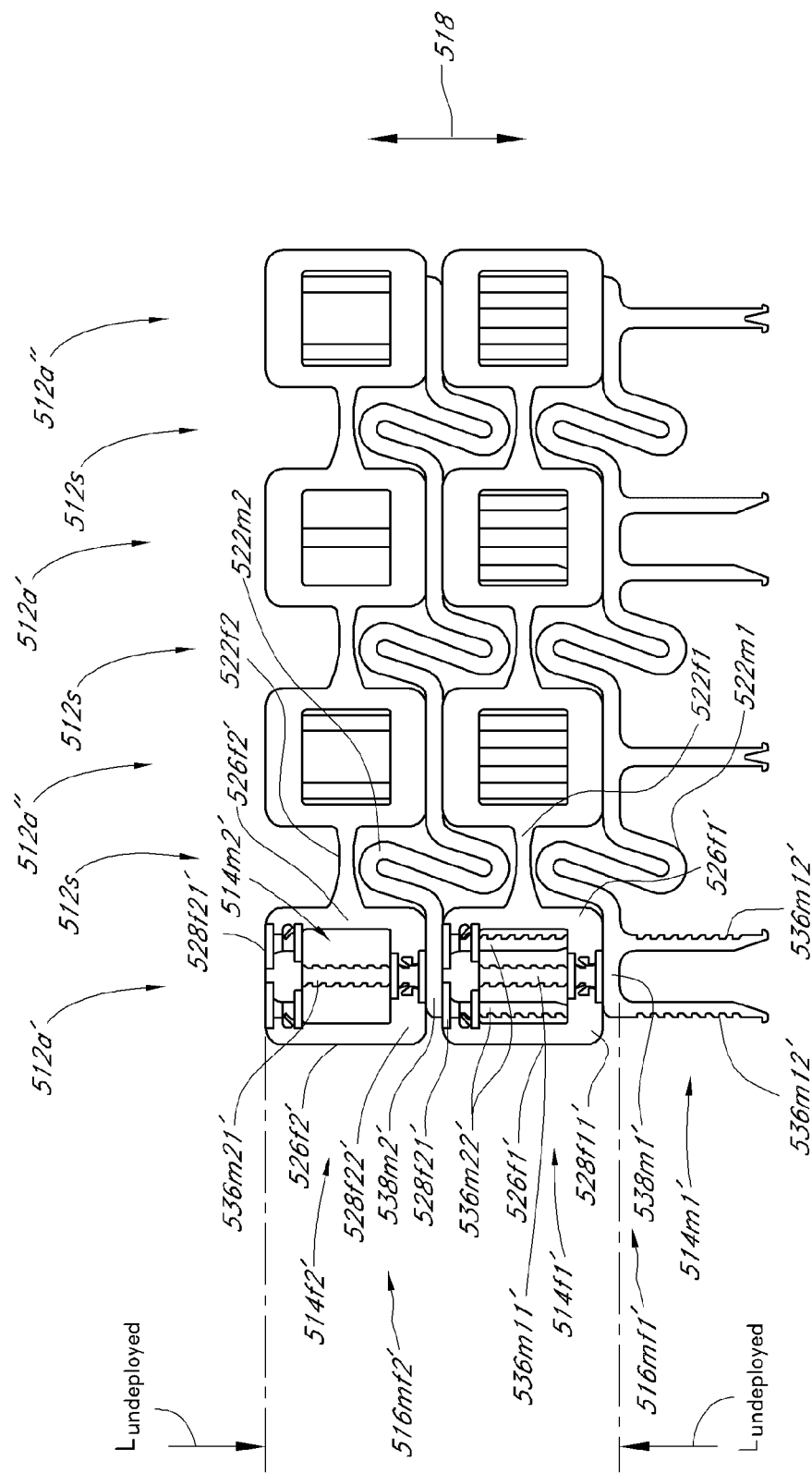
FIG. 30 is a simplified planar view of an axially nested slide and lock stent in a collapsed state illustrating features and advantages in accordance with an embodiment of the inventions.

Referring in particular to FIG. 30, in one embodiment, the undeployed length $L_{undeployed}$ is about 5.1 mm (0.2 inches) and the undeployed stent diameter is about 1.6 mm (0.064 inches). In other embodiments, the undeployed lengths and undeployed diameters may efficaciously be higher or lower, as needed or desired.

Referring in particular to FIG. 32, in one embodiment, the deployed length $L_{deployed}$ is about 10.6 mm (0.419 inches) and the deployed stent diameter is about 3.4 mm (0.133 inches). In other embodiments, the deployed lengths and deployed diameters may efficaciously be higher or lower, as needed or desired.

Figure 38:
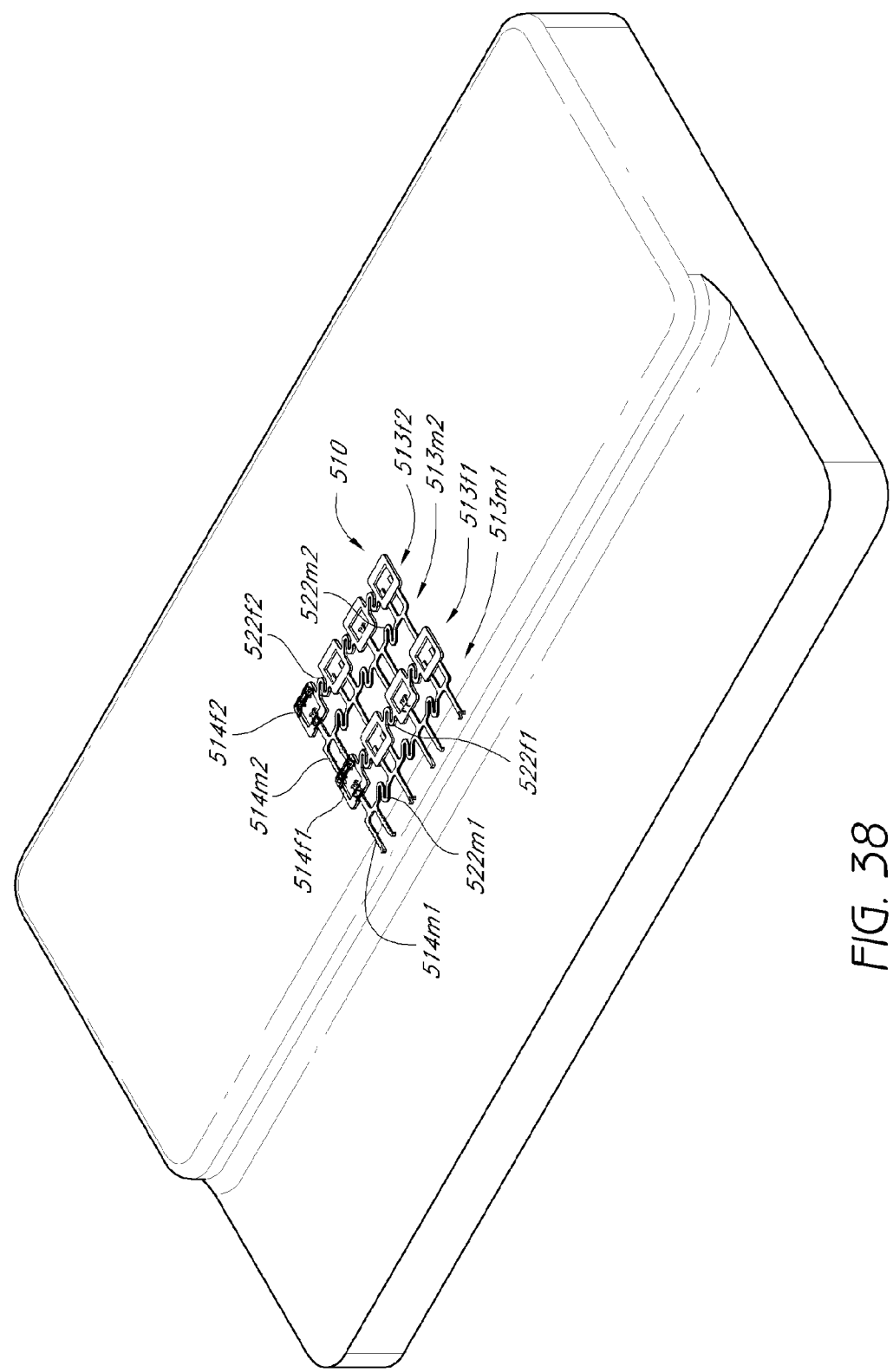
FIG. 38 is a simplified planar perspective view of an axially nested slide and lock stent during its manufacture and assembly illustrating features and advantages in accordance with an embodiment of the inventions.
Figure 39:
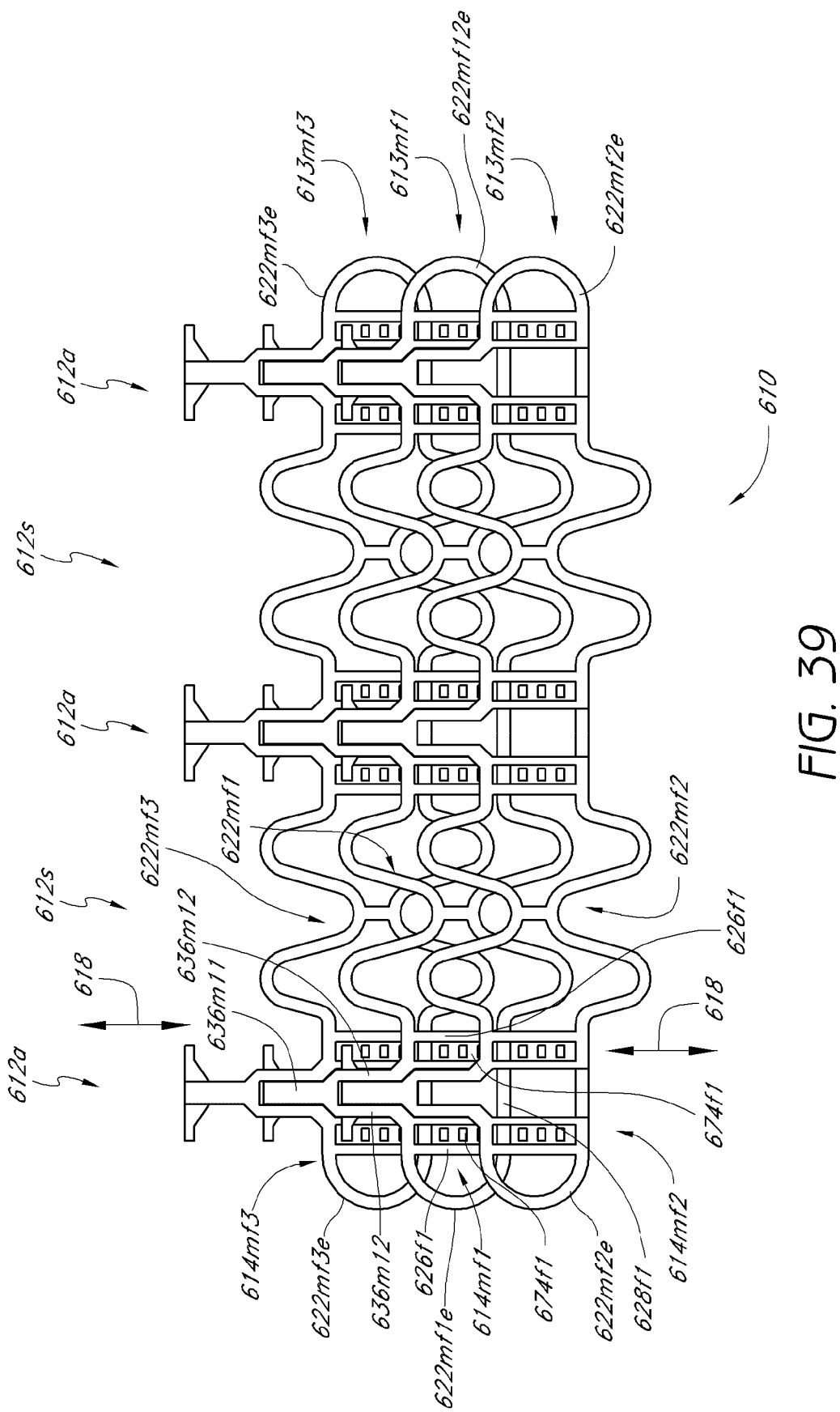
FIG. 39 is a simplified planar view of an axially nested slide and lock stent in a compacted state illustrating features and advantages in accordance with an embodiment of the inventions.
Figure 40:
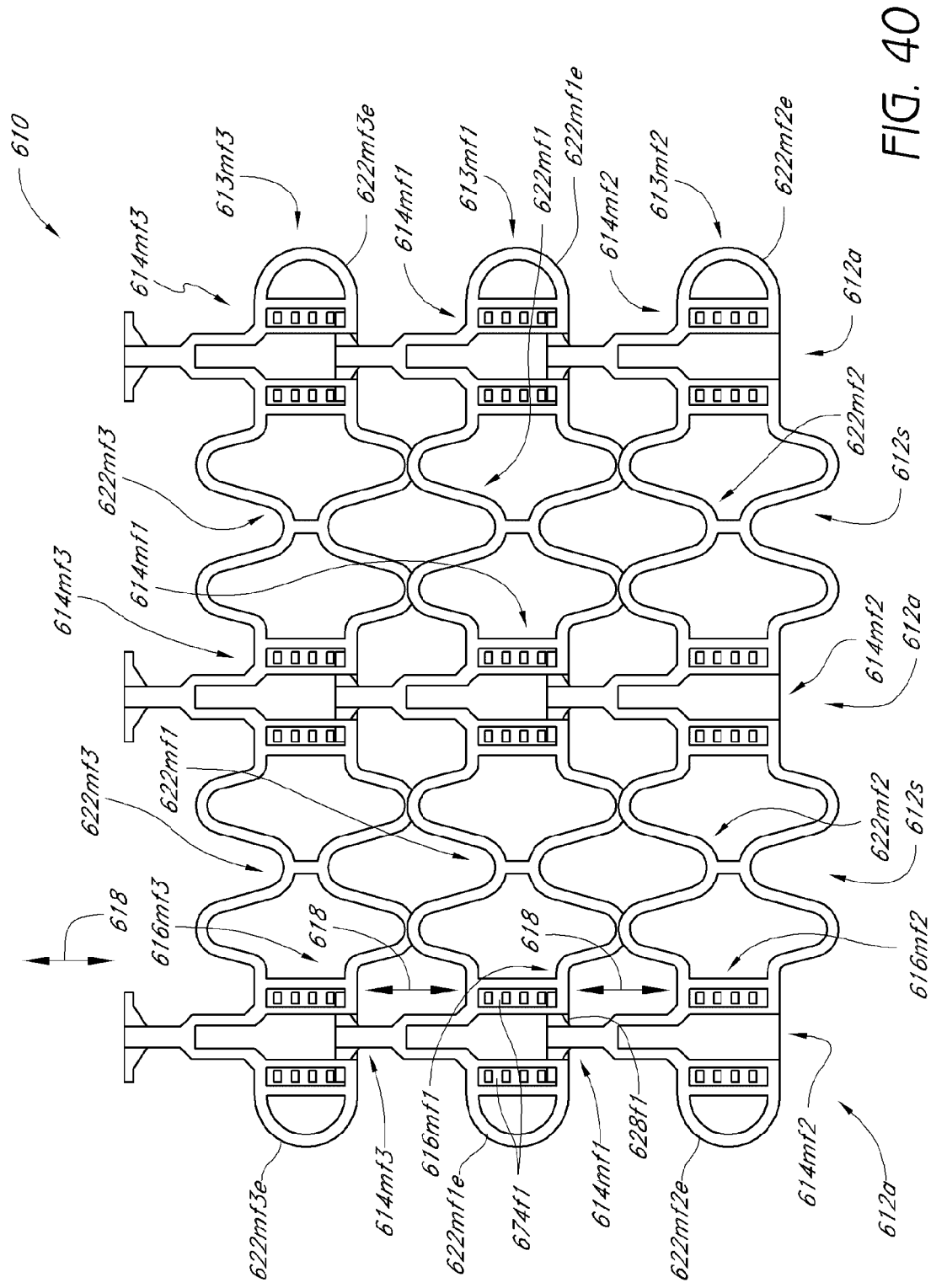
FIG. 40 is a simplified planar view of the stent of FIG. 39 in an expanded state illustrating features and advantages in accordance with an embodiment of the inventions.
Figure 41:
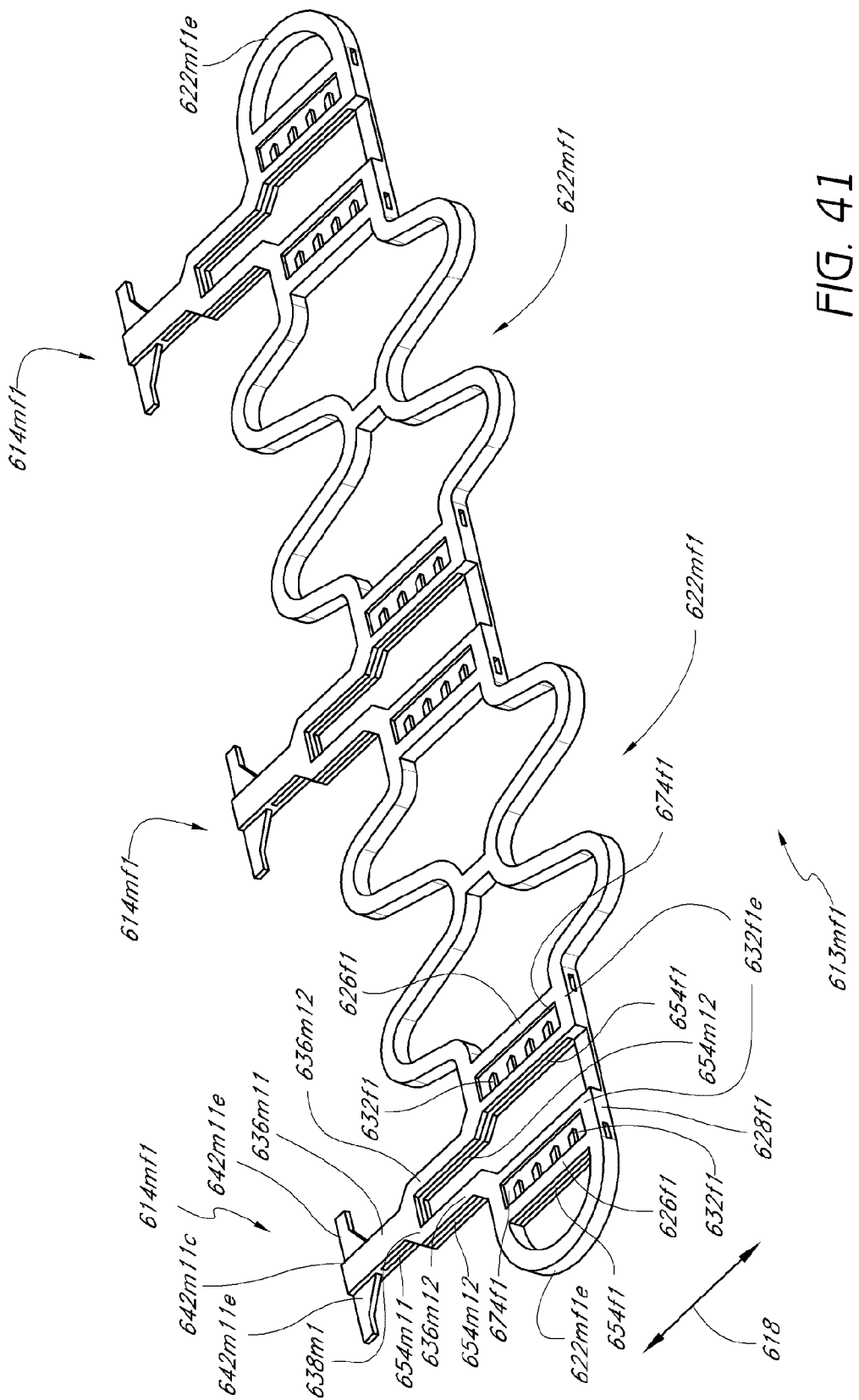
FIG. 41 is a simplified planar perspective partial view of the stent of FIG. 39 illustrating features and advantages in accordance with an embodiment of the inventions.

FIG. 38 shows the expandable stent 510 during a phase of its fabrication and assembly. In some embodiments, the stent 510 is formed using a lamination and laser cutting process to yield the structure as shown in FIG. 38. The stent 510 is then rolled into a tubular shape in the collapsed state.

In some embodiments, axially extending rows 513f1, 513m1, 513f2, 513m2 can each be formed as an integral unit and then connected and rolled into a tubular form in the collapsed state. This may be accomplished by using an injection molding technique or the like, among others. The row 513f1 comprises female structural elements 514f1 connected by linkage elements 522f1, the row 513m1 comprises male structural elements 514m1 connected by linkage elements 522m1, the row 513f2 comprises female structural elements 514f2 connected by linkage elements 522f2 and the row 513m2 comprises male structural elements 514m2 connected by linkage elements 522m2.

Some Further Stent Embodiments

FIGS. 39-42 show views of an expandable axially nested slide and lock vascular device, prosthesis or stent 610 including deployed and undeployed states. In a rolled configuration, the stent 610 has a tubular form with a wall comprising a plurality of generally longitudinally arranged linked circumferential sections, segments or frames 612a, 612s. The stent 610 is expandable from a first diameter to a second diameter.

Advantageously, the axially nested embodiments of the stent 610 allow suitable crossing profiles (e.g. luminal size) while maintaining desirable radial strength and luminal patency. In the non-expanded state, there is also minimal or reduced overlap between structural elements, so that the luminal size facilitates insertion of a guiding catheter balloon or the like to expand the vascular device.

The stent 610 comprises alternatingly arranged slide and lock sections 612a and linkage sections 612s. Each section 612a includes three structural elements 614mf1, 614mf2, 614mf3 that each slidingly mate with one another via respective interlocking articulating mechanisms 616mf1, 616mf2, 616mf3. (Each of the structural elements 614 may also be described as comprising two structural elements—one male and one female—since each mates at two circumferential locations.)

Each linkage section 612s includes three elements 622mf1, 622mf2, 622mf3. The linkage elements 622mf1 connect structural elements 614mf1 to form a stent element row 613mf1. The linkage elements 622mf2 connect structural elements 614mf2 to form a stent element row 613mf2. The linkage elements 622mf3 connect structural elements 614mf3 to form a stent element row 613mf3. The number of elements in a section or row and the number of sections and rows in a stent may be efficaciously varied and selected, as needed or desired.

One or more of the linkage elements 622 may comprise spring elements. The spring elements 622 provide flexibility and allow expansion of the linkage sections 612s along with stent expansion. The spring elements 622 also allow for radial and/or axial element or member deflection during stent expansion to a deployed state. The spring elements 622 facilitate this deflection by providing a resilient biasing mechanism to achieve substantially elastic deflection or deformation.

The linkage elements 622$mf$1 axially or longitudinally connect the structural elements 614$mf$1. In one embodiment, the linkage elements 622$mf$1 and the structural elements 614$mf$1 comprise an integral unit, that is, the stent row 613$mf$1 comprises an integral unit. In modified embodiments, the linkage elements 622$mf$1 and the structural elements 614$mf$1 can efficaciously be connected by other techniques, as needed or desired.

The linkage elements 622$mf$2 axially or longitudinally connect the structural elements 614$mf$2. In one embodiment, the linkage elements 622$mf$2 and the structural elements 614$mf$2 comprise an integral unit, that is, the stent row 613$mf$2 comprises an integral unit. In modified embodiments, the linkage elements 622$mf$2 and the structural elements 614$mf$2 can efficaciously be connected by other techniques, as needed or desired.

The linkage elements 622$mf$3 axially or longitudinally connect the structural elements 614$mf$3. In one embodiment, the linkage elements 622$mf$3 and the structural elements 614$mf$3 comprise an integral unit, that is, the stent row 613$mf$3 comprises an integral unit. In modified embodiments, the linkage elements 622$mf$3 and the structural elements 614$mf$3 can efficaciously be connected by other techniques, as needed or desired.

In some embodiments, each of the axially extending rows 613$mf$1, 613$mf$2, 613$mf$3 are first formed as independent units that may be independent integral units. The stent rows 613$mf$1, 613$mf$2, 613$mf$3 are then connected and rolled into a tubular form in the collapsed state.

The axial or longitudinal coupling between the structural elements 614 of adjacent sections 612$a$, the radial coupling between structural elements 614 of the same section 612$a$, and the design and configuration of the sections 612 and structural elements 614 are such that there is minimal or reduced overlapping in the radial or circumferential direction between the structural elements 614 in both the non-expanded and expanded states. Thus, the structural elements 614, sections 612 and/or stent 610 are referred to as being axially, longitudinally or non-radially nested. (There is also minimal or reduced radial overlap between linkage elements 622 of the same and adjacent sections 612$s$ in both the undeployed and deployed states.)

During stent expansion, there is circumferential relative motion between the mating structural elements 614$mf$1, 614$mf$2, 614$mf$3 as generally shown by arrows 518. One or more or all of structural elements 614$mf$1, 614$mf$2, 614$mf$3 in any suitable combination may slidably move apart.

The structural element 614$mf$1 generally comprises female portion with a pair spaced of ribs or arms 626/1 and a male portion with a pair of spaced ribs or arms 636$m$12 terminating in a single rib or arm 636$m$11. The end structural elements 614$mf$1 may comprises side extensions or supports 622$mf$1$e$. As discussed above and below herein, the structural element 614$mf$1 has one or more slide and lock articulating mechanisms such as tongue-groove configuration stops, tabs or teeth that engage respective coupled structural elements 614$mf$2, 614$mf$3 to provide radially deflecting mechanisms for stent expansion and lock-out.

The female ribs 626/1 are spaced by an end portion 628/1. Each of the ribs 626/1 includes a cavity 674/1 in which a plurality of radially deflectable elements, stops, tabs or teeth 632/1 extend. Each of the ribs 626/1 further includes slots 654/1 that receive a mating portion from the adjacent structural element 614$mf$2. Each of the slots 654/1 terminates at the end portion 628/1 at a respective one of end hard stops 632/1$e$ that control and limit the maximum stent expansion to a predetermined diameter.

The deflectable elements 632/1 engage the male portion of the radially coupled structural element 614$mf$2 in a one-way slide and lock articulating motion. The deflectable elements 632/1 are configured so that they have generally flat end surfaces 646/1 to substantially reduce or minimize recoil and generally tapered engaging surfaces 648/1 to facilitate one-way sliding (see, for example, FIG. 42). Other suitable configurations that inhibit undesirable recoil and facilitate one-way expansion may be efficaciously utilized, as needed or desired.

The male portion of the structural element 614$mf$1 has a generally central portion 638$m$1 that connects the ribs 636$m$12 and the rib 636$m$11. As discussed further below, the central portion 638$m$1 serves as a hard stop in the stent collapsed state.

Each of the ribs 636$m$12 includes a slot 654$m$12 that receives a mating portion from the adjacent structural element 614$mf$2. Each of the slots 654$m$12 is connected to or is in communication with at least one of the respective female portion slots 654/1. The male rib 636$m$11 may also include a slot 654$m$11 that is connected to or is in communication with the slots 654$m$12.

The male rib 636$m$11 includes a pair of outwardly extending end stops, tabs, wings or teeth 642$m$11$e$ with one each extending on each sides of the rib 636$m$11. The stops 642$m$11$e$ engage the female portion of the adjacent structural element 614$mf$3 in a one-way slide and lock articulating motion. The stops 642$m$11$e$ are configured so that they have generally flat end surfaces 650$m$11$e$ to substantially reduce or minimize recoil. Other suitable configurations that inhibit undesirable recoil may be efficaciously utilized, as needed or desired.

As discussed further below, the end stops 642$m$11$e$ engage a capture mechanism of a mating structural element to control and limit the maximum stent expansion. The end stops 642$m$11$e$ are configured to have generally flat engaging surfaces 652$m$11$e$ that facilitate lock-out and capture at full expansion while allowing one-way slide and lock motion during expansion. Other suitable lock-out and capture configurations may be efficaciously utilized, as needed or desired.

The end wings 642$m$11$e$ are spaced by a generally central raised portion 642$m$11$c$. As discussed further below, the central portion 642$m$11$c$ serves as a hard stop in the stent collapsed state.

Figure 42:
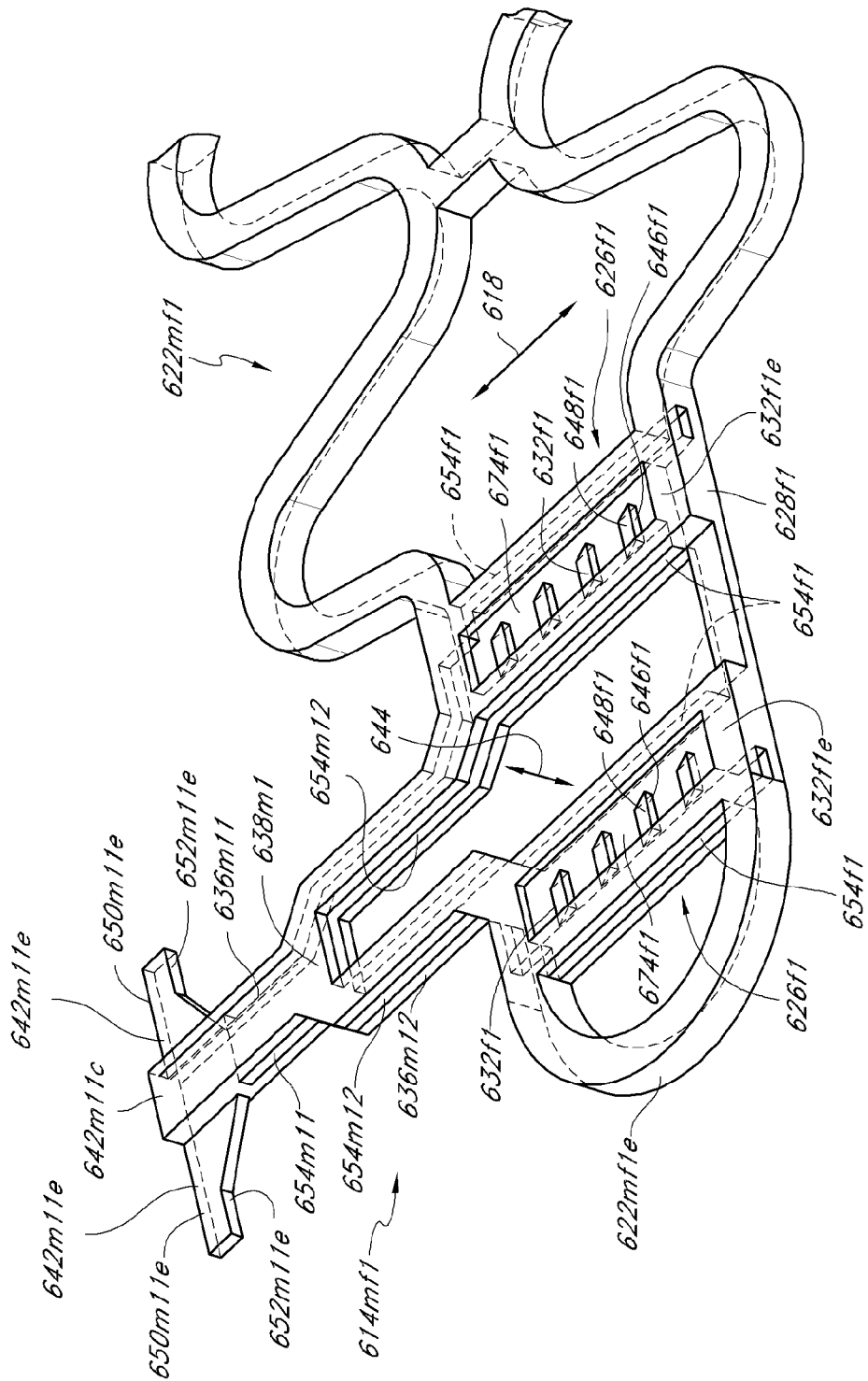
FIG. 42 is a simplified planar perspective enlarged view of structural element of the stent of FIG. 39 illustrating features and advantages in accordance with an embodiment of the inventions.

The end stops 642$m$11$e$ have generally flat engaging surfaces 652$m$11$e$ that facilitate lock-out and capture at full expansion (see, for example, FIG. 42). Other suitable lock-out and capture configurations may be efficaciously utilized, as needed or desired.

The structural elements 614$mf$1, 614$mf$2, 614$mf$3 are of generally similar construction. Thus, for brevity, the features of the structural element 614$mf$1 have been discussed in greater detail with respect to articulation, lock-out and capture features. It is to be understood that a generally similar arrangement is encompassed by the other structural elements 614$mf$2 and 614$mf$3 of the stent 610, and similar reference numerals are used herein.

Thus, for example, if the female ribs of the structural element 614$mf$1 are denoted by 626/1, then the female ribs of the structural elements 614$mf$2 and 614$mf$3 are respectively denoted by 626/2 and 626/3, and so on. Similarly, if the male rib of the structural element 614*mf*1 is denoted by 636*m*11, then the male ribs of the structural elements 614*mf*2 and 614*mf*3 are respectively denoted by 636*m*21 and 636*m*31, and so on.

Advantageously, there is substantially no or minimal overlap between nesting structural elements 614*mf*1, 614*mf*2 and 614*mf*3 in both the collapsed state and the expanded state, and more particularly in the expanded state. Thus, the stent 610, its sections 612*a* and/or structural elements 614 are referred to as being axially nested.

Embodiments of the inventions provide an axially nested vascular device 610 to achieve both competitive crossing profiles (e.g. luminal size) while maintaining other key features, such as, for example, radial strength and luminal patency. Advantageously, an axially nested device design allows for use of thicker materials to maintain radial strength, as needed or desired.

During manufacture and assembly of the axially nested embodiments, the device structural elements (e.g., 614*mf*1, 614*mf*2) and/or ribs (e.g. the female ribs 626*m*1 and the male ribs 636*m*12) are positioned side by side (axially) in the predilated or non-expanded state to substantially reduce or minimize the device crossing profile and bulk in both the undeployed (non-expanded, predilated) and deployed (expanded, dilated) states. Advantageously, by substantially reducing or eliminating the excess bulk typically encountered with a radially nesting device design, embodiments of the inventions can be used to achieve competitive devices and crossing profiles with a wide variety of materials at a wide variety of thicknesses, thereby desirably allowing for optimum device design and performance.

The articulation between the structural elements 614*mf*1 and 614*mf*2 of a given stent section 612*a* is discussed below. As the skilled artisan will recognize, a similar articulation is applicable to other mating structural elements of the stent 610. Thus, for brevity it is not repeated herein.

In the collapsed state (FIG. 39), the male portion of the structural element 614*mf*2 mates with the structural element 614*mf*1. More specifically, the male rib 636*m*21 extends into the gap between the ribs 636*m*12, the wings 642*m*21*e* extend into respective slots 654*m*12 and the raised hard stop 642*m*21*c* abuts against the raised portion 638*m*1. Advantageously, in the collapsed state, there is axial nesting between the mating structural elements 614*mf*1 and 614*mf*2 at least in part because the respective ribs 636*m*12 and 636*m*21 are axially or longitudinally displaced or offset from one another.

In the collapsed state, the male ribs 636*m*22 extend into the gap between the female ribs 626*f*1. Again advantageously, in the collapsed state, there is axial nesting between the mating structural elements 614*mf*1 and 614*mf*2 at least in part because the female ribs 626*f*1 and male ribs 636*m*22 are axially or longitudinally displaced or offset from one another.

During stent expansion, there is circumferential relative motion between male ribs 636*m*21, 636*m*22 of the structural element 614*mf*2 and the ribs 636*m*12, 626*f*1 of the structural element 614*mf*1 as generally indicated by arrows 618. The male ribs 636*m*21 withdraw from the gap between the ribs 636*m*12 and the male ribs 636*m*22 withdraw from the gap between the ribs 626*f*1. The wings 642*m*21*e* slide within respective slots 654*m*11 such that their relative motion is towards the female ribs 626*f*1.

As the rib 636*m*21 begins to extend out of the gap between the ribs 636*m*12 and into the gap between the ribs 626*f*1, and the ribs 636*m*22 begin to extend out of the gap between the ribs 626*f*1, the wings 642*m*21*e* slide into respective slots 654*f*1 and cavities 674*f*1. The wings 642*m*21*e* engage the respective deflectable elements, fingers, stops or tabs 632*f*1.

Thus, during expansion, the deflectable elements 632*f*1 and the respective wings 642*m*21*e* cross one another. This is accomplished by utilizing a generally radially deflecting mechanism.

Thus, during "cross-over" the deflectable elements 632*f*1 are deflected radially inwards and then resume their original undeflected position. This radial motion is generally denoted by arrows 644. The radial deflection is caused by the generation of a generally radial force when the deflectable elements 632*f*1 and respective wings 642*m*21*e* slide over, engage or abut one another.

The tapered surfaces 648*f*1 of the deflectable elements 632*f*1 facilitate sliding in one direction. The generally flat end surfaces 646*f*1 of the deflectable elements 632*f*1 and the generally flat end surfaces of the wings 650*m*21*e* desirably substantially reduce or minimize recoil.

At full expansion, the hard stops 652*m*21*e* of the wings 642*m*21*e* and the respective end hard stops 632*f*1*e* of the structural element portion 628*f*1 contact, engage or abut against one other, and prevent further stent expansion. This lock-out and capture mechanism provides to control and limit stent expansion to a predetermined deployment diameter.

The internal protected articulating and locking mechanisms of the stent 610 advantageously allow clearance space at the outer stent periphery which shields and protects the mechanisms from external surface interferences. Raised and recessed portions of the structural elements 614*mf* provide this shielding, for example, the top portions of the female ribs 626*f*1. The structural elements 614*mf* are also configured to facilitate alignment between the mating elements.

Still Further Stent Embodiments

Figure 43:
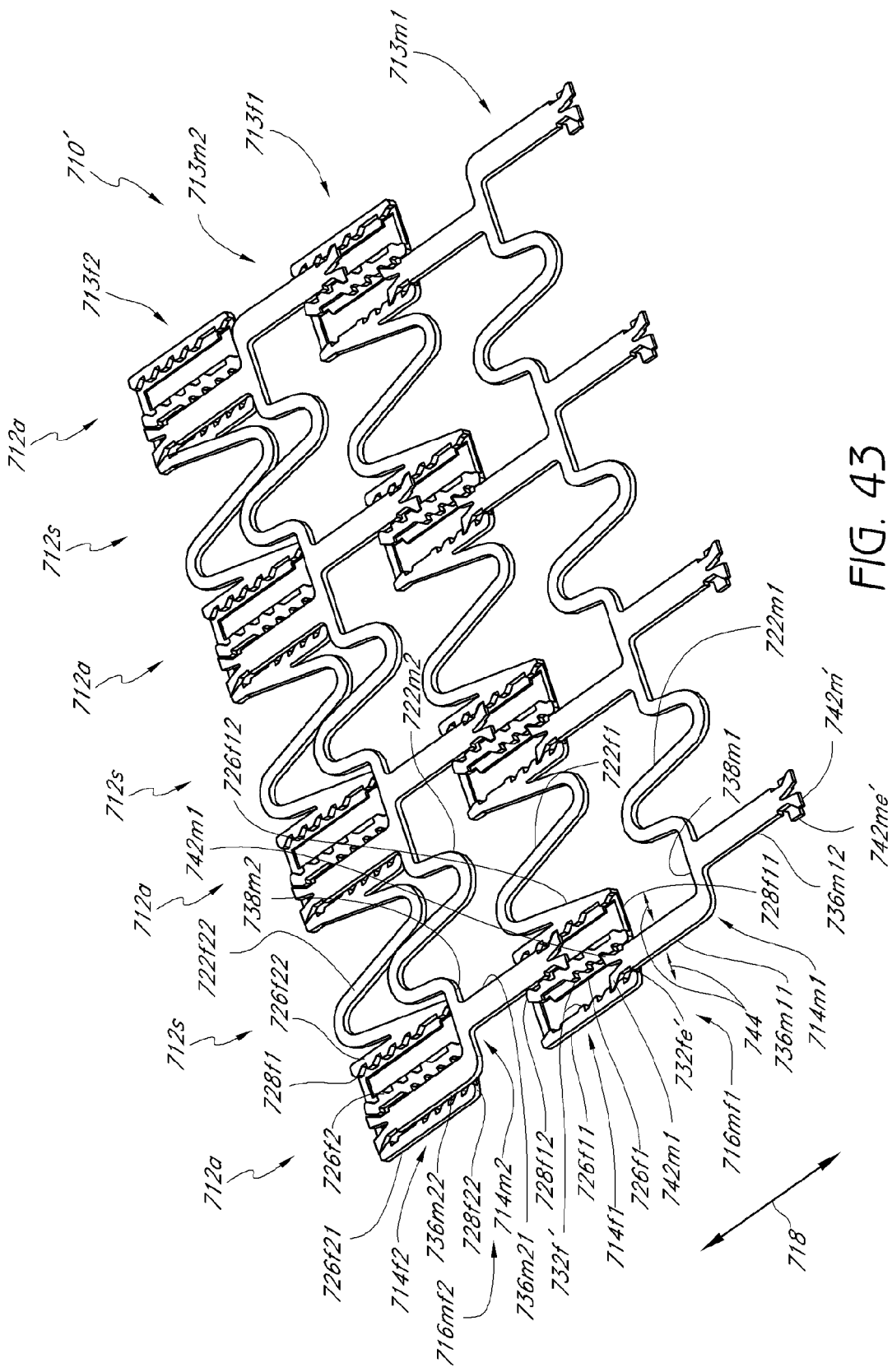
FIG. 43 is a simplified planar perspective view of an axially nested slide and lock stent in a partially expanded state illustrating features and advantages in accordance with an embodiment of the inventions.
Figure 44:
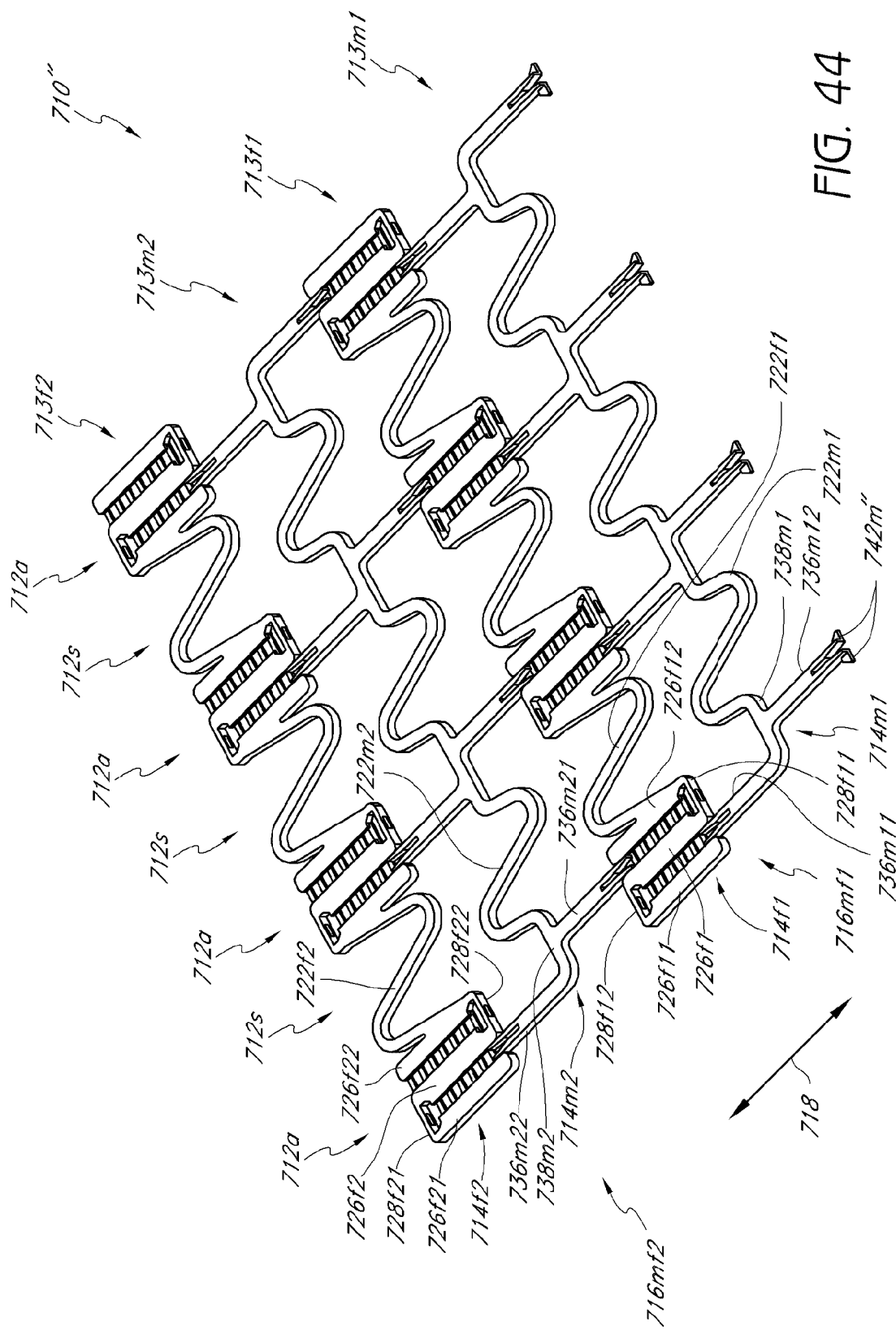
FIG. 44 is a simplified planar perspective view of an axially nested slide and lock stent in an expanded state illustrating features and advantages in accordance with another embodiment of the inventions.
Figure 45:
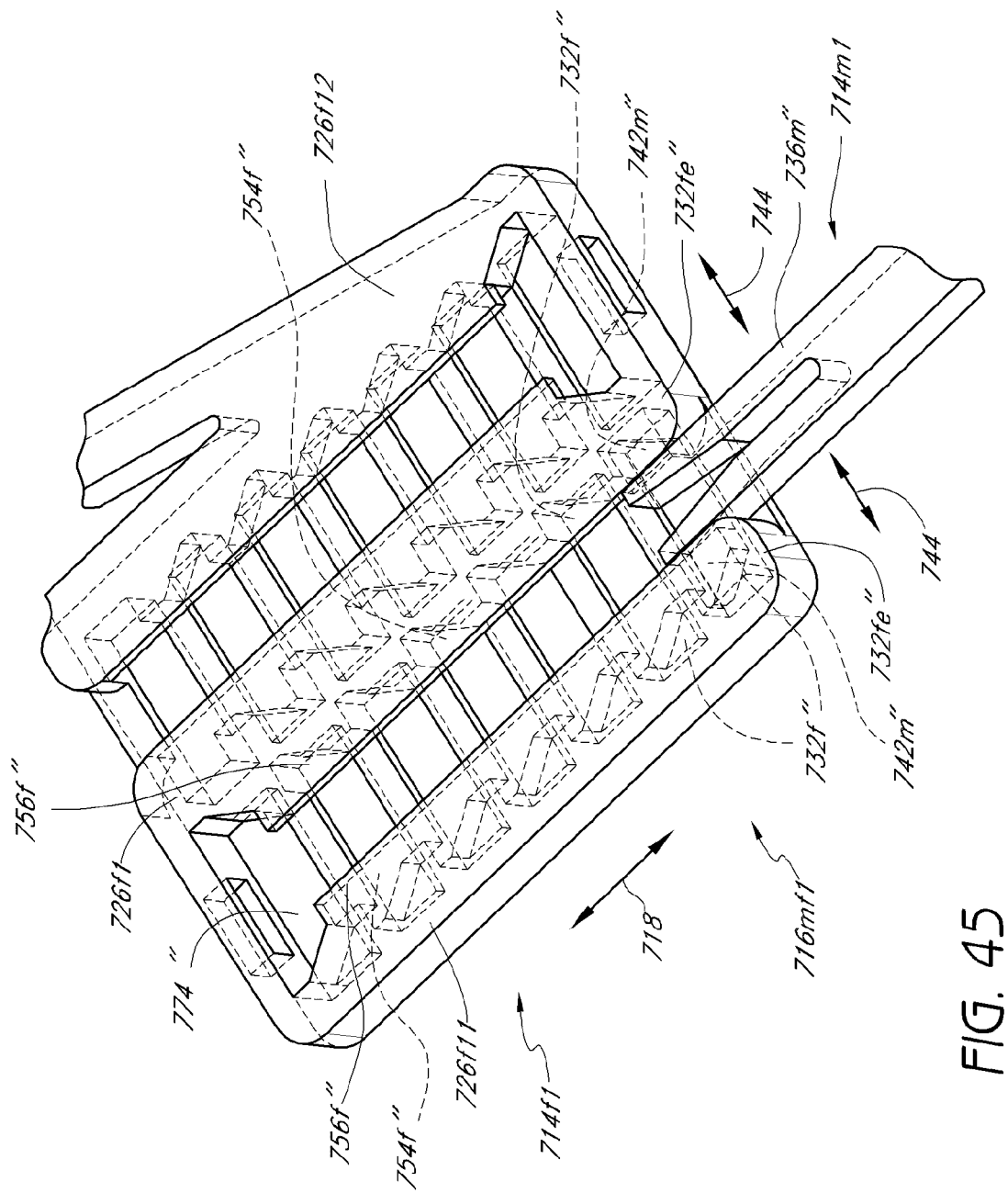
FIG. 45 is a simplified planar enlarged perspective view of a slide and lock articulation mechanism of the stent of FIG. 44 illustrating features and advantages in accordance with another embodiment of the inventions.

FIGS. 43 and 44 show views of expandable axially nested slide and lock vascular devices, prostheses or stents 710 (710' and 710"). FIG. 45 shows an enlarged view of an articulating and lock-out mechanism 716*mf*1 of the stent 710".

In a rolled configuration, the stent 710 has a tubular form with a wall comprising a plurality of generally longitudinally arranged linked circumferential sections, segments or frames 712*a*, 712*s*. The stent 710 is expandable from a first diameter to a second diameter. (The axially nested stents 710' and 710" are generally similar in overall design but their articulating and lock-out mechanisms have different constructions, as discussed further below, in accordance with embodiments of the inventions.)

Advantageously, the axially nested embodiments of the stent 710 allow suitable crossing profiles (e.g. luminal size) while maintaining desirable radial strength and luminal patency. In the non-expanded state, there is also minimal or reduced overlap between structural elements, so that the luminal size facilitates insertion of a guiding catheter balloon or the like to expand the vascular device.

The stent 710 comprises alternatingly arranged slide and lock sections 712*a* and linkage sections 712*s*. Each section 712*a* includes a pair of female structural elements 714*f*1, 714*f*2 and a pair of male structural elements 714*m*1, 714*m*2 that each slidingly mate with the female structural elements 714*f*1, 714*f*2 via respective interlocking articulating mechanisms 716*mf*1, 716*mf*2. (Each of the structural elements 714 may also be described as comprising two structural elements since each mates at two circumferential locations.)

As described further below, the articulating mechanisms 716 comprise substantially axially (laterally) deflecting locking mechanisms. The number of structural elements in a section and/or the number of sections in a stent may be efficaciously varied and selected, as needed or desired.

The axial or longitudinal coupling between the structural elements 714 of adjacent sections 712*a*, the radial coupling between structural elements 714 of the same section 712a, and the design and configuration of the sections 712 and structural elements 714 are such that there is minimal or reduced overlapping in the radial or circumferential direction between the structural elements 714 in both the non-expanded and expanded states. Thus, the structural elements 714, sections 712 and/or stent 710 are referred to as being axially, longitudinally or non-radially nested. (There is also minimal or reduced radial overlap between linkage elements 722 of the same and adjacent sections 712s in both the undeployed and deployed states.)

Each of the stent linkage sections 712s generally comprises linkage elements 722m1, 722f1, 722m2, 722f2 which are connected to respective structural elements 714m1, 714f1, 714m2, 714f2. Stent row 713m1 generally comprises the elements 714m and 722m1, row 713f1 generally comprises the elements 714f1 and 722f1, row 713m2 generally comprises the elements 714m2 and 722m2, and row 713f2 generally comprises the elements 714f2 and 722f2.

The female structural element 714f1 generally comprises a generally central rib, arm or portion 726f1 spaced from a pair of side ribs or arms 726f11, 726f12. End portions 728f11, 728f12 connect the ribs 726f1, 726f11, 726f22. As discussed above and below herein, the female structural element 714f1 and one or more of its ribs 726f1, 726f11, 726f22 have slide and lock articulating mechanisms such as tongue-groove configuration stops, tabs, wings or teeth that engage male structural elements 714m1, 714m2 to provide axially deflecting mechanisms for stent expansion and lock-out.

The female structural element 714f2 generally comprises a generally central rib, arm or portion 726f2 spaced from a pair of side ribs or arms 726f21, 726f22. End portions 728f21, 728f22 connect the ribs 726f2, 726f21, 726f22. As discussed above and below herein, the female structural element 714f2 and one or more of its ribs 726f2, 726f21, 726f22 have slide and lock articulating mechanisms such as tongue-groove configuration stops, tabs, wings or teeth that engage female structural elements 714f1, 714f2 to provide axially deflecting mechanisms for stent expansion and lock-out.

The male structural element 714m1 generally comprises a first rib or arm 736m11 and a second rib or arm 736m12 extending in opposite directions. The ribs 736m11, 736m12 share a share a common end portion 738m1. In the stent collapsed state, the male rib 736m11 extends in the gap between and/or is engaged with the female ribs 726f1, 726f11 and the male rib 736m12 extends in the gap between and/or is engaged with the female ribs 726f2, 726f22. As discussed above and below herein, the ribs 736m11, 736m12 have slide and lock articulating mechanisms such as tongue-groove configuration stops, tabs, wings or teeth that engage respective female structural elements 714f1, 714f2 to provide axially deflecting mechanisms for stent expansion and lock-out.

The male structural element 714m2 generally comprises a first rib or arm 736m21 and a second rib or arm 736m22 extending in opposite directions. The ribs 736m21, 736m22 share a share a common end portion 738m2. In the stent collapsed state, the male rib 736m21 extends in the gap between and/or is engaged with the female ribs 726f1, 726f12 and the male rib 736m22 extends in the gap between and/or is engaged with the female ribs 726f2, 726f21. As discussed above and below herein, the ribs 736m21, 736m22 have slide and lock articulating mechanisms such as tongue-groove configuration stops, tabs, wings or teeth that engage respective female structural elements 714f1, 714f2 to provide axially deflecting mechanisms for stent expansion and lock-out.

Each linkage section 712s includes a plurality of the elements 722 (722m1, 722f1, 722m2, 722f2) and connects adjacent stent sections 712a. One or more of the linkage elements 722 may comprise spring elements. In the embodiment of FIGS. 43 and 44, the spring elements 722 provide device flexibility and can allow expansion of the linkage sections 712s along with stent expansion.

The linkage elements 722m1 axially or longitudinally connect the male structural elements 714m1. In one embodiment, the linkage elements 722m1 and the male structural elements 714m1 comprise an integral unit, that is, the stent row 713m1 comprises an integral unit. In modified embodiments, the linkage elements 722m1 and the male structural elements 714m1 can efficaciously be connected by other techniques, as needed or desired.

The linkage elements 722m2 axially or longitudinally connect the male structural elements 714m2. In one embodiment, the linkage elements 722m2 and the male structural elements 714m2 comprise an integral unit, that is, the stent row 713m2 comprises an integral unit. In modified embodiments, the linkage elements 722m2 and the male structural elements 714m2 can efficaciously be connected by other techniques, as needed or desired.

The linkage elements 722f1 axially or longitudinally connect the female structural elements 714f1. In one embodiment, the linkage elements 722f1 and the female structural elements 714f1 comprise an integral unit, that is, the stent row 713f1 comprises an integral unit. In modified embodiments, the linkage elements 722f1 and the female structural elements 714f1 can efficaciously be connected by other techniques, as needed or desired.

The linkage elements 722f2 axially or longitudinally connect the female structural elements 714f2. In one embodiment, the linkage elements 722f2 and the female structural elements 714f2 comprise an integral unit, that is, the stent row 713f2 comprises an integral unit. In modified embodiments, the linkage elements 722f2 and the female structural elements 714f2 can efficaciously be connected by other techniques, as needed or desired.

During stent expansion, there is circumferential relative motion between the mating male structural elements 714m1, 714m2 and female structural elements 714f1, 714f2 as generally shown by arrows 718. One or both of the male structural elements 714m1, 714m2, one or both of the female structural elements 714f1, 714f2, both the male and female structural elements 714m1, 714m2, 714f1, 714f2, or any suitable combination thereof may slidably move apart to achieve the desired or predetermined expansion.

More specifically, during expansion, there is circumferential relative motion between: the female ribs 726f1, 726f11 and the male rib 736m11 with one or both slidably moving apart; the female ribs 726f1, 726f12 and the male rib 736m21 with one or both slidably moving apart; the female ribs 726f2, 726f21 and the male rib 736m22 with one or both slidably moving apart; and the female ribs 726f2, 726f22 and the male rib 736m12 with one or both slidably moving apart. The motion is generally denoted by arrows 718.

As discussed herein, at full expansion, a capture mechanism is provided to limit further stent expansion to a predetermined deployment diameter. Each section 712a and/or structural element 714 can comprise one or more capture mechanisms such as straps, hard stops, and the like among other suitable devices that prevent further expansion between mating male and female structural elements 714m and 714f and control the maximum expansion. Any of the capture mechanisms as disclosed, taught or suggested herein may efficaciously be used in conjunction with the stent 710 and any of the other stent embodiments, as needed or desired.

Advantageously, there is substantially no or minimal overlap between nesting male structural elements 714m and associated female structural elements 714f in both the collapsed state and the expanded state, and more particularly in the expanded state. For example, for a given stent section 712a, in the collapsed state the female ribs 726f/1, 726f/11, 726f/12 and the male ribs 736m11, 736m21 are substantially axially or longitudinally displaced or offset while in the expanded state the same are substantially radially or circumferentially displaced or offset, thereby minimizing radial overlap in both the collapsed and expanded states. Thus, the stent 710, its sections 712 and/or structural elements 714 are referred to as being axially nested since their radial overlap is substantially reduced or minimal in both the collapsed and expanded states.

Embodiments of the inventions provide an axially nested vascular device 710 to achieve both competitive crossing profiles (e.g. luminal size) while maintaining other key features, such as, for example, radial strength and luminal patency. Advantageously, an axially nested device design allows for use of thicker materials to maintain radial strength, as needed or desired.

During manufacture and assembly of the axially nested embodiments, the device structural elements (e.g., 714m, 714f) and/or ribs (e.g. the female ribs 726f/1, 726f/11, 726f/12 and the male ribs 736m11, 736m21) are positioned side by side (axially) in the predilated or non-expanded state to substantially reduce or minimize the device crossing profile and bulk in both the undeployed (non-expanded, predilated) and deployed (expanded, dilated) states. Advantageously, by substantially reducing or eliminating the excess bulk typically encountered with a radially nesting device design, embodiments of the inventions can be used to achieve competitive devices and crossing profiles with a wide variety of materials at a wide variety of thicknesses, thereby desirably allowing for optimum device design and performance.

The articulation between the structural elements 714m1 and 714f/1 of a given stent section 712a is discussed below. As the skilled artisan will recognize, a similar articulation is applicable to other mating structural elements and/or ribs of the stent 710. Thus, for brevity it is not repeated herein.

Referring in particular to FIG. 43, that is the stent 710', the male rib 736m11 includes a pair of outwardly extending deflectable elements, stops, tabs, wings or teeth 742m' with one each extending on each side of the rib 736m11. The stops 742m' engage respective stops, tabs or teeth 732f' of the female ribs 726f/1, 726f/11 in a one-way slide and lock articulating motion. This is accomplished by utilizing a generally axial deflecting mechanism.

Thus, during "cross-over" the deflectable wings 742m' are deflected axially inwards and then resume their original undeflected position. This axial motion is generally denoted by arrows 744. The axial deflection is caused by the generation of a generally axial force when the deflectable wings 742m' and respective teeth 732f' slide over, engage or abut one another.

The stops 742m', 732f' are configured to facilitate one-way sliding relative motion as generally shown by arrows 718. The stops 742m', 732f' are also configured to substantially reduce or minimize recoil. Other suitable configurations that inhibit facilitate one-way motion and undesirable recoil may be efficaciously utilized, as needed or desired.

At full expansion, a hard stop 742me' of the male rib 736m11 and a safety hard stop 732fe' of the structural element portion 728f/11 contact, engage or abut against one other, and prevent further stent expansion. This lock-out and capture mechanism provides to control and limit stent expansion to a predetermined deployment diameter. The safety stop 742me' also prevents the male rib 736m11 from jumping off the female ribs 726f/1, 726f/11 during deployment and keeps the rib 736m11 in its appropriate track.

Referring in particular to FIGS. 44 and 45, that is the stent 710", the male rib 736m11 includes a pair of outwardly extending deflectable elements, stops, tabs, wings or teeth 742m" with one each extending on each side of the rib 736m11. In the collapsed state, the wings 742m" are positioned in a cavity 774f" between the female ribs 726f/1, 726f/11.

During stent expansion, the wings 742m" engage respective internal stops, tabs or teeth 732f" of the female ribs 726f/1, 726f/11 in a one-way slide and lock articulating motion. This is accomplished by utilizing a generally axial deflecting mechanism.

Thus, during "cross-over" the deflectable wings 742m" are deflected axially inwards and then resume their original undeflected position. This axial motion is generally denoted by arrows 744. The axial deflection is caused by the generation of a generally axial force when the deflectable wings 742m" and respective teeth 732f" slide over, engage or abut one another.

The stops 742m", 732f" are configured to facilitate one-way sliding relative motion as generally shown by arrows 718. The stops 742m", 732f" are also configured to substantially reduce or minimize recoil. Other suitable configurations that inhibit facilitate one-way motion and undesirable recoil may be efficaciously utilized, as needed or desired.

The teeth 732f" are positioned within respective slots 754f" and under respective raised or top portions 756f" of respective female ribs 726f/1, 726f/11. Thus, the wings 742m" also extend into the slots 754f". Advantageously, the top portions 756f" prevents the male rib 736m11 from jumping off the female ribs 726f/1, 726f/11 during deployment and keeps the rib 736m11 in its appropriate track.

At full expansion, one or more hard stops 732fe" of the structural element portion 728f/11 contact, engage or abut against the wings 742m", and prevent further stent expansion. This lock-out and capture mechanism provides to control and limit stent expansion to a predetermined deployment diameter.

Figure 46:
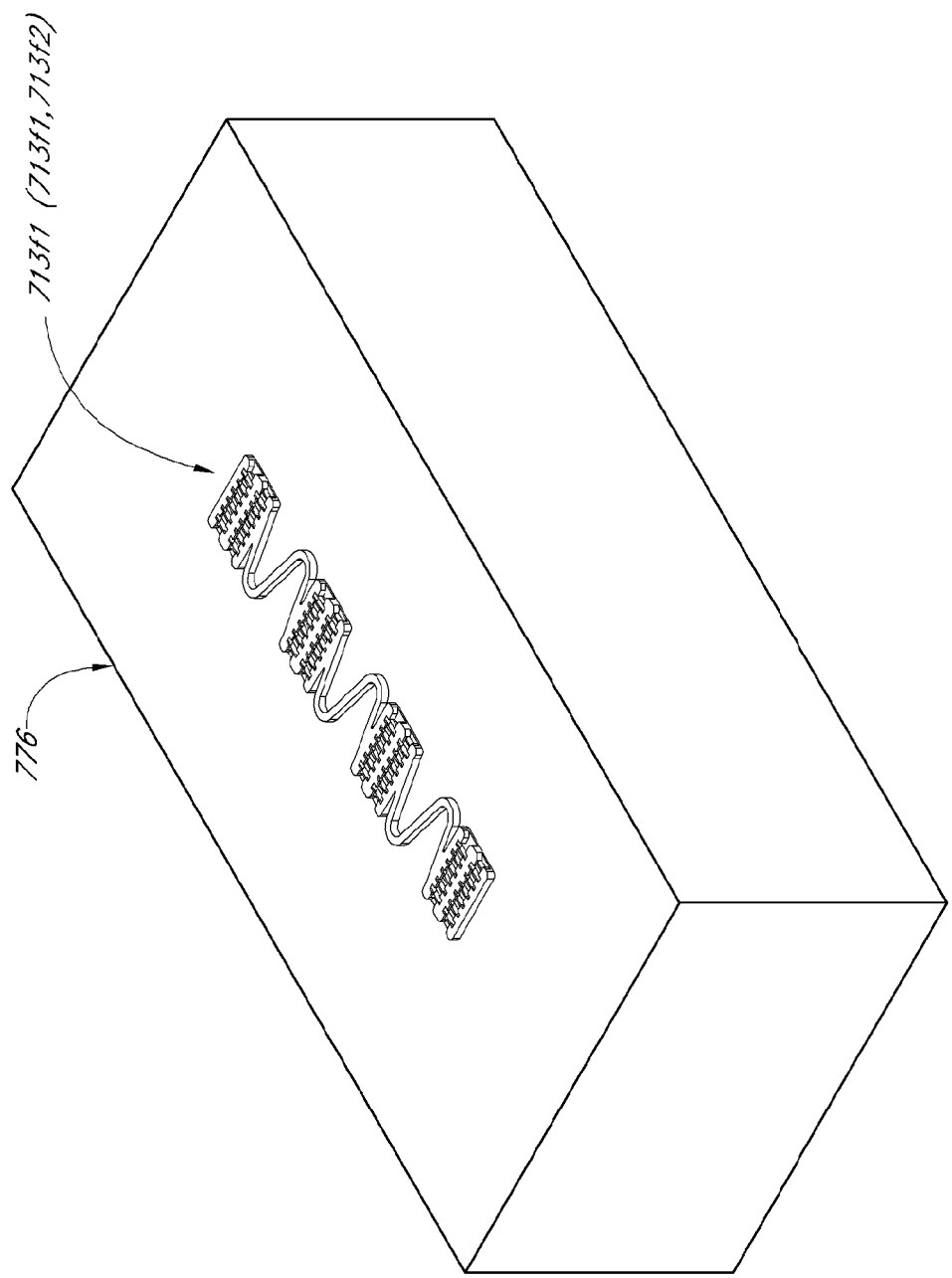
FIG. 46 is a simplified planar perspective partial view of the stent of FIG. 43 or FIG. 44 during its manufacture and assembly illustrating features and advantages in accordance with an embodiment of the inventions.

FIG. 46 shows a die 776 that is used to fabricate the stent rows 713f/1, 713f/2 in accordance with one embodiment. An injection molding process or the like, among others, may be used to form stent rows 713f/1, 713f/2 as integral units. The stent rows 713m1, 713m2 can also be similarly formed as integral units. The axially extending rows 713f/1, 713m1, 713f/2, 713m2 can then be connected and rolled into a tubular form in the collapsed state.

Yet Further Stent Embodiments

Figure 47:
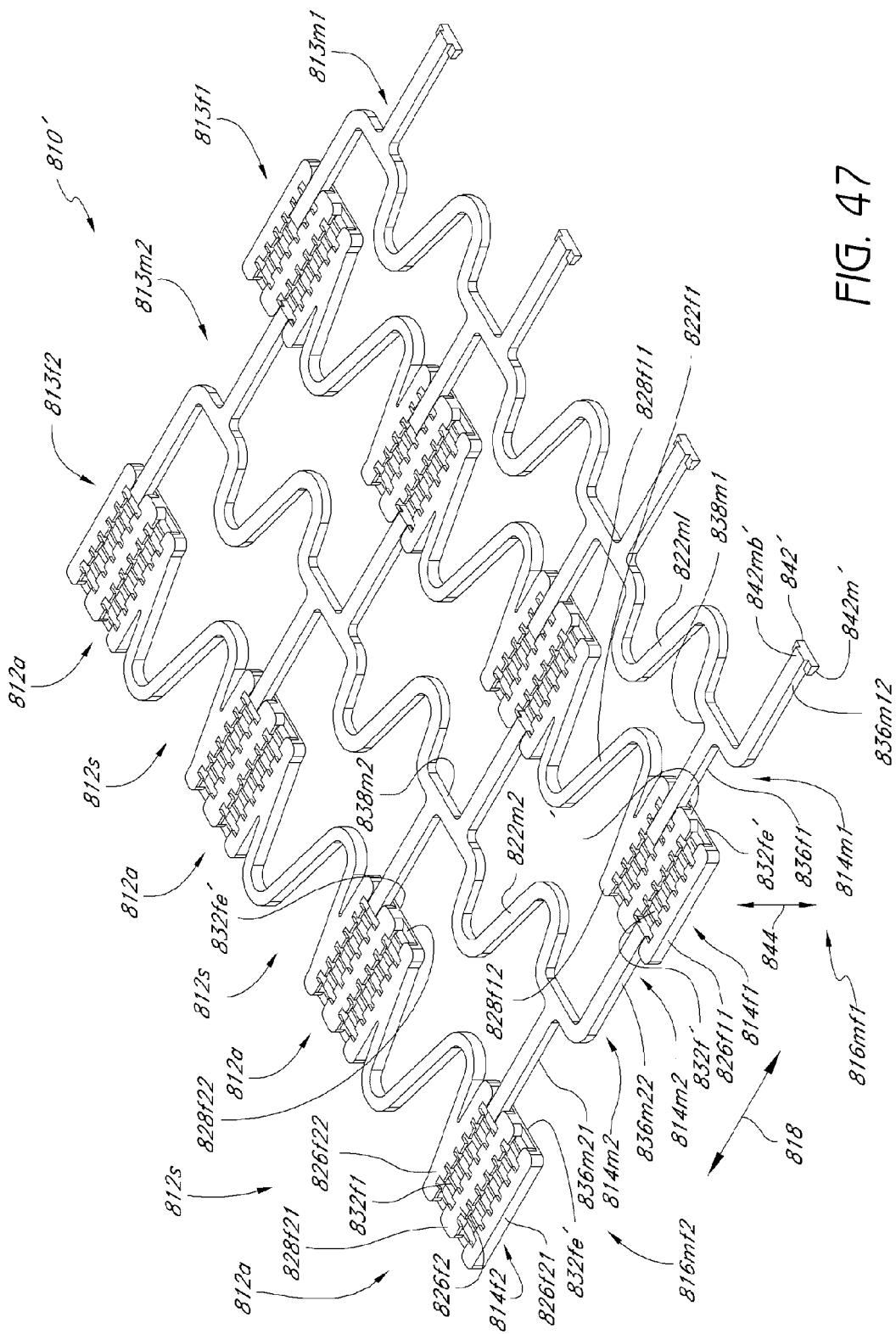
FIG. 47 is a simplified planar perspective view of an axially nested slide and lock stent in a partially expanded state illustrating features and advantages in accordance with an embodiment of the inventions.
Figure 48:
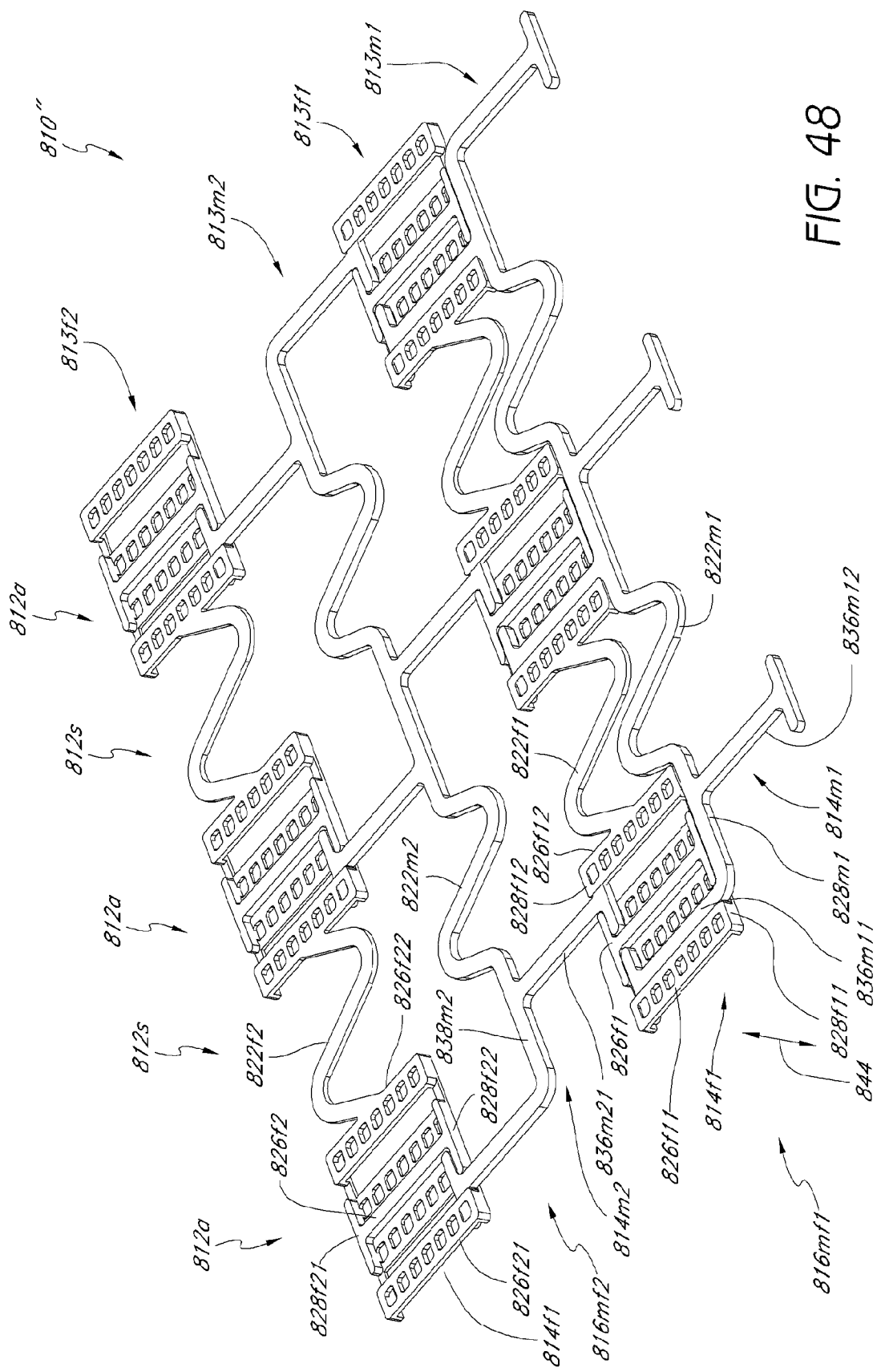
FIG. 48 is a simplified planar perspective view of an axially nested slide and lock stent in a partially expanded state illustrating features and advantages in accordance with another embodiment of the inventions.

FIGS. 47 and 48 show views of expandable axially nested slide and lock vascular devices, prostheses or stents 810 (810' and 810"). In a rolled configuration, the stent 810 has a tubular form with a wall comprising a plurality of generally longitudinally arranged linked circumferential sections, segments or frames 812a, 812s. The stent 810 is expandable from a first diameter to a second diameter. (The axially nested stents 810' and 810" are generally similar in overall design but their articulating and lock-out mechanisms may have slightly different constructions, as shown in the drawings, in accordance with embodiments of the inventions.)

Advantageously, the axially nested embodiments of the stent 810 allow suitable crossing profiles (e.g. luminal size) while maintaining desirable radial strength and luminal patency. In the non-expanded state, there is also minimal or reduced overlap between structural elements, so that the luminal size facilitates insertion of a guiding catheter balloon or the like to expand the vascular device.

The stent 810 comprises alternatingly arranged slide and lock sections 812a and linkage sections 812s. Each section 812a includes a pair of male structural elements 814m1, 814m2 and a pair of female structural elements 814f1, 814f2 that each slidingly mate with the male structural elements 814m1, 814m2 via respective interlocking articulating mechanisms 816mf1, 816mf2. (Each of the structural elements 814 may also be described as comprising two structural elements since each mates at two circumferential locations.)

As described further below, the articulating mechanisms 816 comprise substantially radially deflecting locking mechanisms. The number of structural elements in a section and/or the number of sections in a stent may be efficaciously varied and selected, as needed or desired.

The axial or longitudinal coupling between the structural elements 814 of adjacent sections 812a, the radial coupling between structural elements 814 of the same section 812a, and the design and configuration of the sections 812 and structural elements 814 are such that there is minimal or reduced overlapping in the radial or circumferential direction between the structural elements 814 in both the non-expanded and expanded states. Thus, the structural elements 814, sections 812 and/or stent 810 are referred to as being axially, longitudinally or non-radially nested. (There is also minimal or reduced radial overlap between linkage elements 822 of the same and adjacent sections 812s in both the undeployed and deployed states.)

Each of the stent linkage sections 812s generally comprises linkage elements 822m1, 822f1, 822m2, 822f2 which are connected to respective structural elements 814m1, 814f1, 814m2, 814f2. Stent row 813m2 generally comprises the elements 814m1 and 822m1, row 813f1 generally comprises the elements 814f1 and 822f1, row 813m2 generally comprises the elements 814m2 and 822m2, and row 813f2 generally comprises the elements 814f2 and 822f2.

The female structural element 814f1 generally comprises a generally central rib, arm or portion 826f1 spaced from a pair of side ribs or arms 826f11, 826f12. End portions 828f11, 828f12 connect the ribs 826f1, 826f11, 826f22. As discussed above and below herein, the female structural element 814f1 and one or more of its ribs 826m1, 826m11, 826m22 have slide and lock articulating mechanisms such as tongue-groove configuration stops, tabs, wings or teeth that engage male structural elements 814m1, 814m2 to provide radially deflecting mechanisms for stent expansion and lock-out.

The female structural element 814f2 generally comprises a generally central rib, arm or portion 826f2 spaced from a pair of side ribs or arms 826f21, 826f22. End portions 828f21, 828f22 connect the ribs 826f2, 826f21, 826f22. As discussed above and below herein, the female structural element 814f2 and one or more of its ribs 826f2, 826f21, 826f22 have slide and lock articulating mechanisms such as tongue-groove configuration stops, tabs, wings or teeth that engage male structural elements 814m1, 814m2 to provide radially deflecting mechanisms for stent expansion and lock-out.

The male structural element 814m1 generally comprises a first rib or arm 836m11 and a second rib or arm 836m12 extending in opposite directions. The ribs 836m11, 836m12 share a share a common end portion 838m1. In the stent collapsed state, the male rib 836m11 extends in the gap between and/or is engaged with the female ribs 826f1, 826f11 and the male rib 836m12 extends in the gap between and/or is engaged with the female ribs 826f2, 826f22. As discussed above and below herein, the ribs 836f11, 836f12 have slide and lock articulating mechanisms such as tongue-groove configuration stops, tabs, wings or teeth that engage respective female structural elements 814f1, 814f2 to provide radially deflecting mechanisms for stent expansion and lock-out.

The male structural element 814m2 generally comprises a first rib or arm 836m21 and a second rib or arm 836m22 extending in opposite directions. The ribs 836m21, 836m22 share a share a common end portion 838m2. In the stent collapsed state, the male rib 836m21 extends in the gap between and/or is engaged with the female ribs 826f1, 826f12 and the male rib 836m22 extends in the gap between and/or is engaged with the female ribs 826f2, 826f21. As discussed above and below herein, the ribs 836m21, 836m22 have slide and lock articulating mechanisms such as tongue-groove configuration stops, tabs, wings or teeth that engage respective female structural elements 814f1, 814f2 to provide radially deflecting mechanisms for stent expansion and lock-out.

Each linkage section 812s includes a plurality of the elements 822 (822m1, 822f1, 822m2, 822f2) and connects adjacent stent sections 812a. One or more of the linkage elements 822 may comprise spring elements. In the embodiments of FIGS. 47 and 48, the spring elements 822 provide device flexibility and can allow expansion of the linkage sections 812s along with stent expansion.

The linkage elements 822m1 axially or longitudinally connect the male structural elements 814m1. In one embodiment, the linkage elements 822m1 and the male structural elements 814m1 comprise an integral unit, that is, the stent row 813m1 comprises an integral unit. In modified embodiments, the linkage elements 822m1 and the male structural elements 814m1 can efficaciously be connected by other techniques, as needed or desired.

The linkage elements 822m2 axially or longitudinally connect the male structural elements 814m2. In one embodiment, the linkage elements 822m2 and the male structural elements 814m2 comprise an integral unit, that is, the stent row 813m2 comprises an integral unit. In modified embodiments, the linkage elements 822m2 and the male structural elements 814m2 can efficaciously be connected by other techniques, as needed or desired.

The linkage elements 822f1 axially or longitudinally connect the female structural elements 814f1. In one embodiment, the linkage elements 822f1 and the female structural elements 814f1 comprise an integral unit, that is, the stent row 813f1 comprises an integral unit. In modified embodiments, the linkage elements 822f1 and the female structural elements 814f1 can efficaciously be connected by other techniques, as needed or desired.

The linkage elements 822f2 axially or longitudinally connect the female structural elements 814f2. In one embodiment, the linkage elements 822f2 and the female structural elements 814f2 comprise an integral unit, that is, the stent row 813f2 comprises an integral unit. In modified embodiments, the linkage elements 822f2 and the female structural elements 814f2 can efficaciously be connected by other techniques, as needed or desired.

During stent expansion, there is circumferential relative motion between the mating male structural elements 814m1, 814m2 and female structural elements 814f1, 814f2 as generally shown by arrows 818. One or both of the male structural elements 814m1, 814m2, one or both of the female structural elements 814f1, 814f2, both the male and female structural elements 714m1, 714m2, 714f1, 714f2, or any suitable combination thereof may slidably move apart to achieve the desired or predetermined expansion.

More specifically, during expansion, there is circumferential relative motion between: the female ribs 826f1, 826f11 and the male rib 836m11 with one or both slidably moving apart; the female ribs 826f1, 826f12 and the male rib 836m21 with one or both slidably moving apart; the female ribs 826f2, 826f21 and the male rib 836m22 with one or both slidably moving apart; and the female ribs 826f2, 826f22 and the male rib 836m12 with one or both slidably moving apart. The motion is generally denoted by arrows 818.

As discussed herein, at full expansion, a capture mechanism is provided to limit further stent expansion to a predetermined deployment diameter. Each section 812a and/or structural element 814 can comprise one or more capture mechanisms such as straps, hard stops, and the like among other suitable devices that prevent further expansion between mating male and female structural elements 814m and 814f and control the maximum expansion. Any of the capture mechanisms as disclosed, taught or suggested herein may efficaciously be used in conjunction with the stent 810 and any of the other stent embodiments, as needed or desired.

Advantageously, there is substantially no or minimal overlap between nesting male structural elements 814m and associated female structural elements 814f in both the collapsed state and the expanded state, and more particularly in the expanded state. For example, for a given stent section 812a, in the collapsed state the female ribs 826f1, 826f11, 826f12 and the male ribs 836m11, 836m21 are substantially axially or longitudinally displaced or offset while in the expanded state the same are substantially radially or circumferentially displaced or offset, thereby minimizing radial overlap in both the collapsed and expanded states. Thus, the stent 810, its sections 812 and/or structural elements 814 are referred to as being axially nested since their radial overlap is substantially reduced or minimal in both the collapsed and expanded states.

Embodiments of the inventions provide an axially nested vascular device 810 to achieve both competitive crossing profiles (e.g. luminal size) while maintaining other key features, such as, for example, radial strength and luminal patency. Advantageously, an axially nested device design allows for use of thicker materials to maintain radial strength, as needed or desired.

During manufacture and assembly of the axially nested embodiments, the device structural elements (e.g., 814m, 814f) and/or ribs (e.g. the female ribs 826f1, 826f11, 826f12 and the male ribs 836m11, 836m21) are positioned side by side (axially) in the predilated or non-expanded state to substantially reduce or minimize the device crossing profile and bulk in both the undeployed (non-expanded, predilated) and deployed (expanded, dilated) states. Advantageously, by substantially reducing or eliminating the excess bulk typically encountered with a radially nesting device design, embodiments of the inventions can be used to achieve competitive devices and crossing profiles with a wide variety of materials at a wide variety of thicknesses, thereby desirably allowing for optimum device design and performance.

The articulation between the structural elements 814m1 and 814f1 of a given stent section 812a is discussed below. As the skilled artisan will recognize, a similar articulation is applicable to other mating structural elements and/or ribs of the stent 810. Thus, for brevity it is not repeated herein.

Referring in particular to FIG. 47, that is the stent 810', the male rib 836m11 includes a pair of outwardly extending stops, tabs, wings or teeth 842m' with one each extending on each side of the rib 836m11. The male rib 836m11 also has a radially inwardly pointing bump, stop, tab or tooth 842mb'.

During stent expansion, the bump 842mb' engages respective stops, tabs or teeth 832f of the female ribs 826f1, 826f11 in a one-way slide and lock articulating motion. This is accomplished by utilizing a generally radial deflecting mechanism.

Thus, during "cross-over" the male rib 836m11 is radially outwardly deflected and then resumes its original undeflected position. This radial motion is generally denoted by arrows 844. The radial deflection is caused by the generation of a generally radial force when the bump 842m' and respective teeth 832f slide over, engage or abut one another.

The stops 842m', 832f are configured to facilitate one-way sliding relative motion as generally shown by arrows 818. The stops 842m', 732f are also configured to substantially reduce or minimize recoil. Other suitable configurations that inhibit facilitate one-way motion and undesirable recoil may be efficaciously utilized, as needed or desired.

The wings 842m" extend into side slots of one or both of the female ribs 826f1, 826f11. Advantageously, this prevents the male rib 836m11 from jumping off the female ribs 826f1, 826f11 during deployment and keeps the rib 836m11 in its appropriate track.

At full expansion, one or more hard stops 832fe' of the structural element portion 828f11 contact, engage or abut against the wings 842m', and prevent further stent expansion. This lock-out and capture mechanism provides to control and limit stent expansion to a predetermined deployment diameter.

Referring in particular to FIG. 48, that is the stent 810", the articulating between male and female structural elements 814m, 814f is generally similar to that described herein with respect to the stent 810'. Thus, as the skilled artisan will appreciate, it is not repeated herein.

Figure 49:
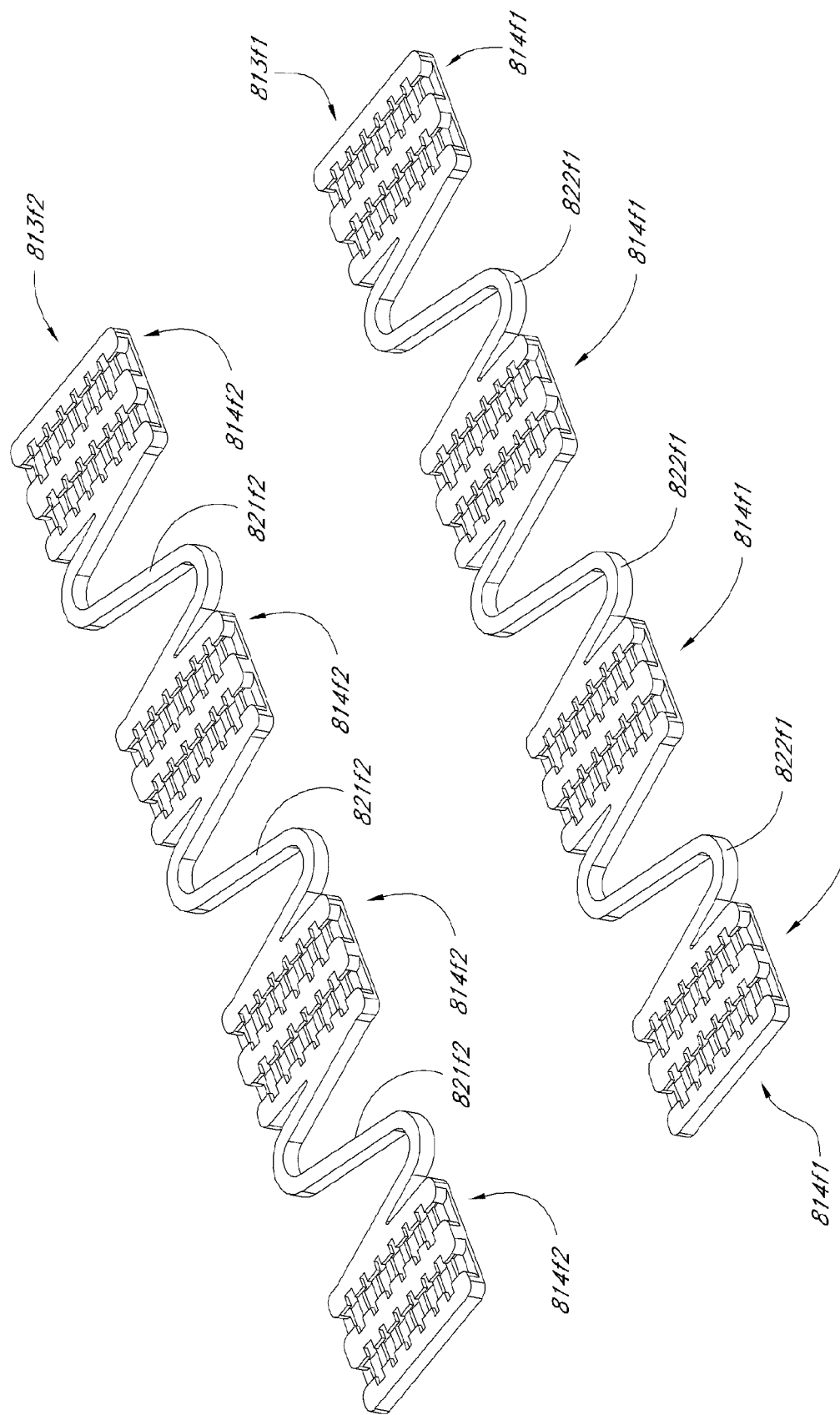
FIG. 49 is a simplified planar perspective partial view of the stent of FIG. 47 during its manufacture and assembly illustrating features and advantages in accordance with an embodiment of the inventions.

FIG. 49 shows two of the stent rows 813f1, 813f2 in accordance with one embodiment. An injection molding process or the like, among others, may be used to form stent rows 813f1, 813f2 as integral units. The stent rows 813m1, 813m2 can also be similarly formed as integral units. The axially extending rows 813f1, 813m1, 813f2, 813m2 can then be connected and rolled into a tubular form in the collapsed state.

Figure 50:
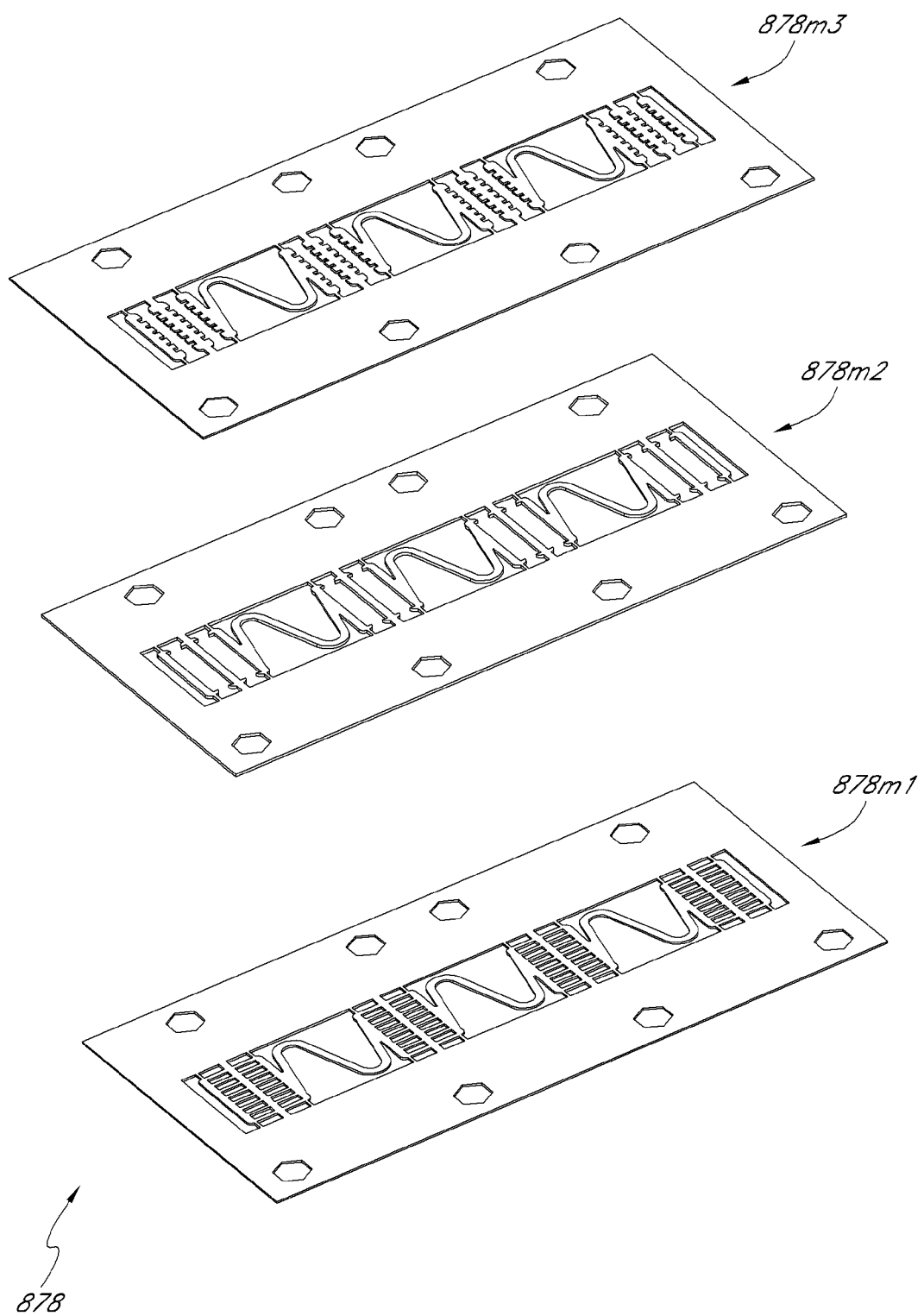
FIG. 50 is a simplified planar perspective partial view of the stent of FIG. 47 during its manufacture and assembly illustrating features and advantages in accordance with another embodiment of the inventions.
Figure 51:
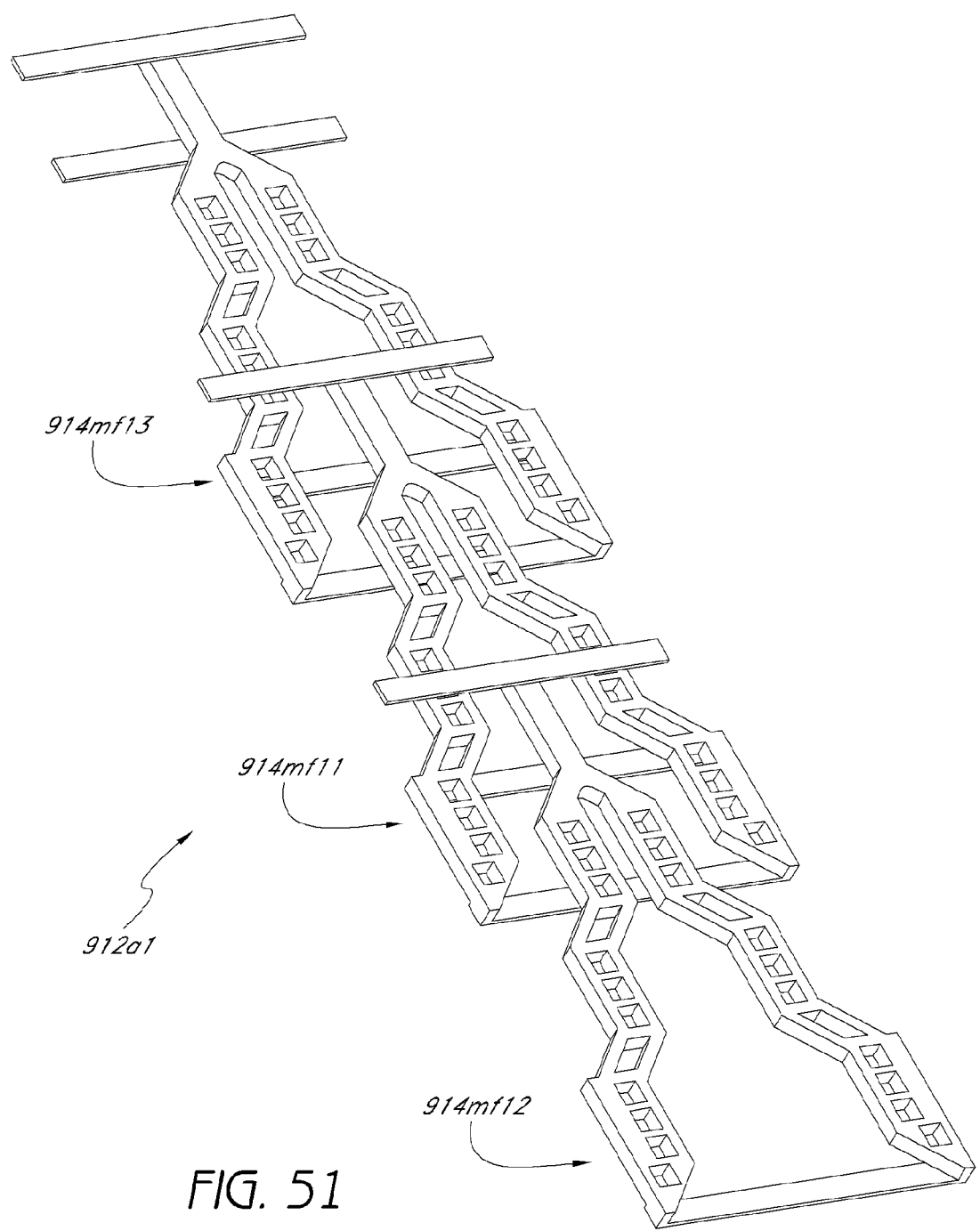
FIG. 51 is a conceptual planar perspective view of structural elements of an axially nested slide and lock stent in a partially expanded state illustrating features and advantages in accordance with an embodiment of the inventions.
Figure 52:
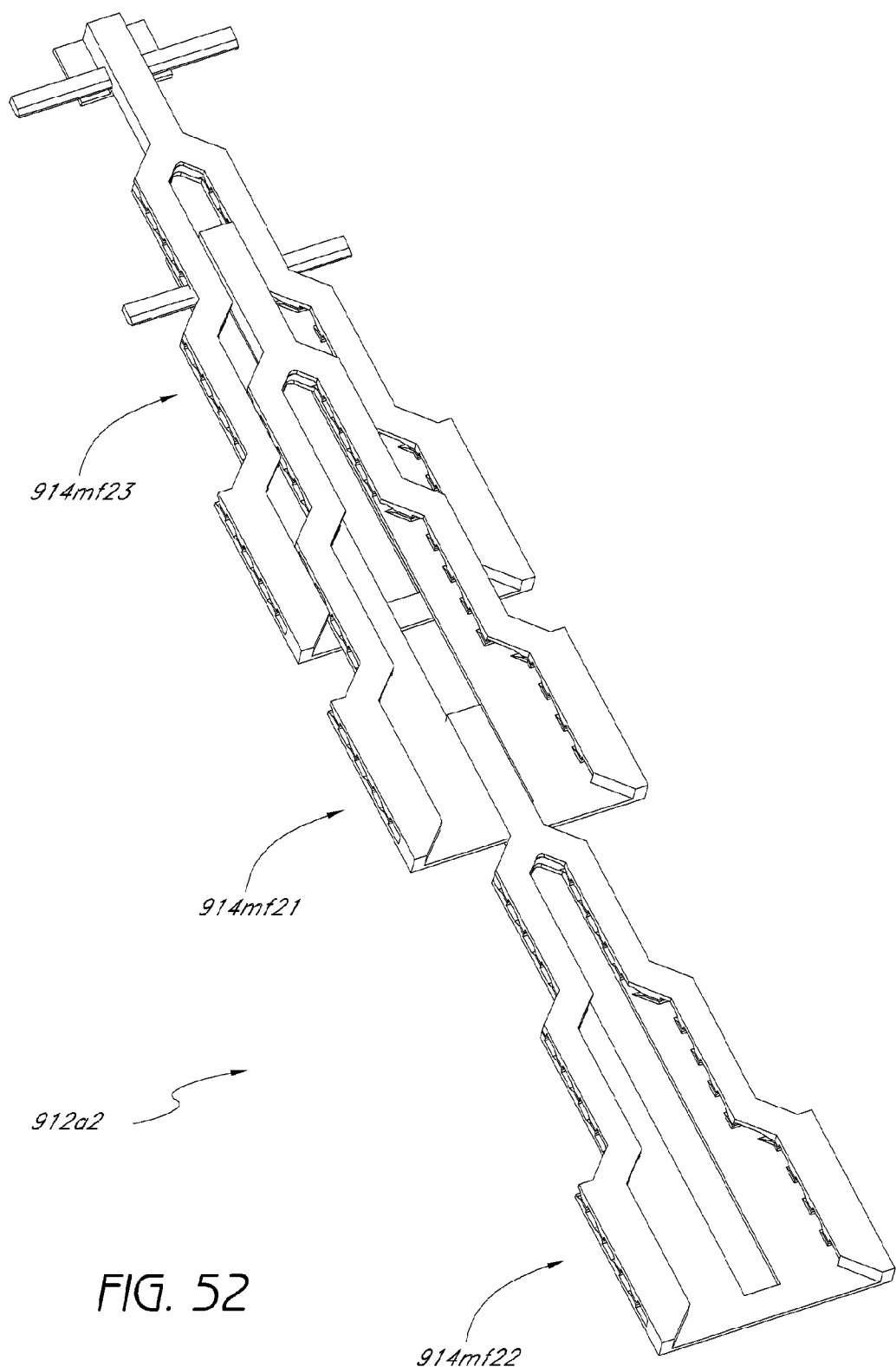
FIG. 52 is a conceptual planar perspective view of structural elements of an axially nested slide and lock stent in a partially expanded state illustrating features and advantages in accordance with another embodiment of the inventions.
Figure 53:
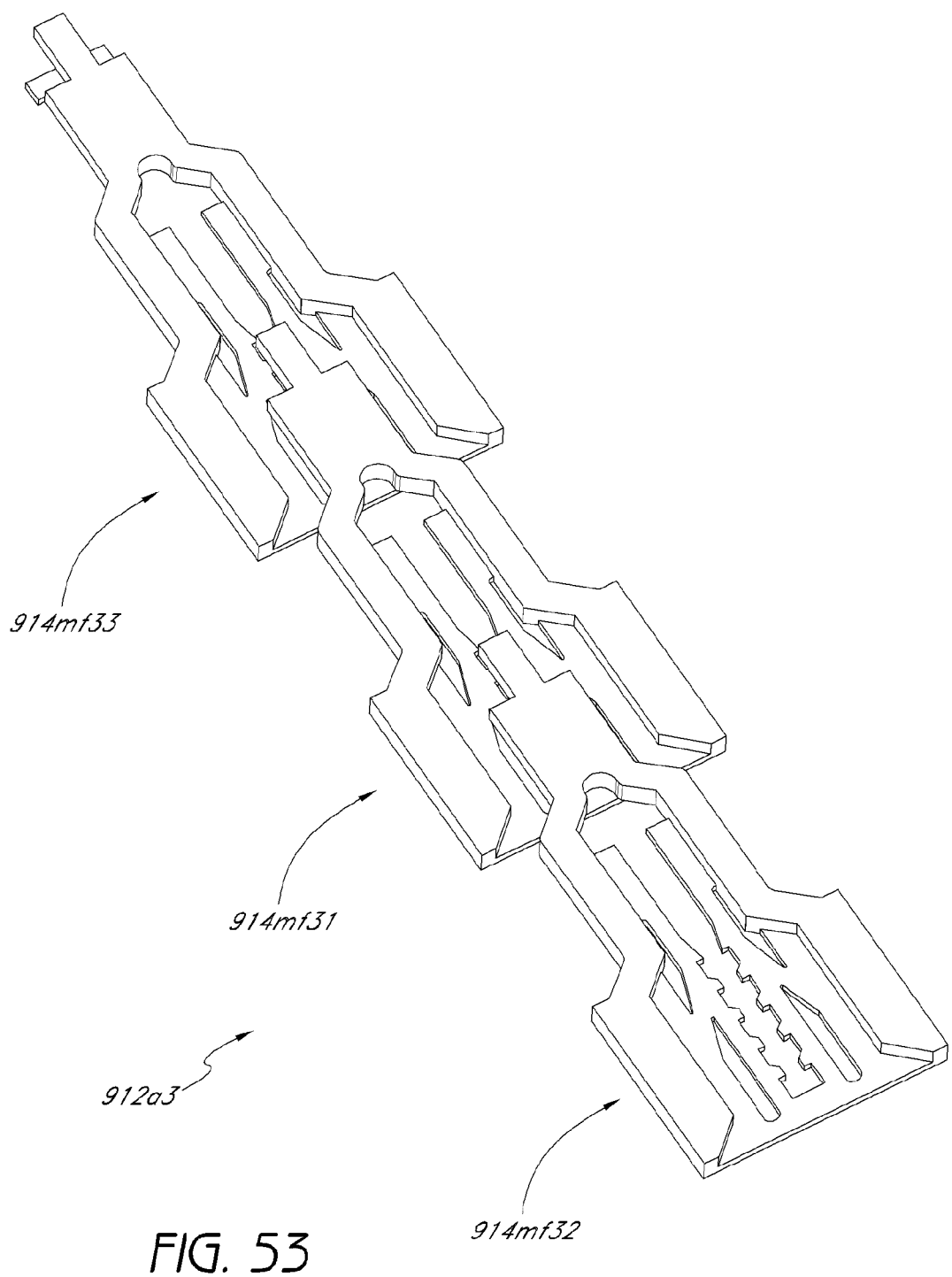
FIG. 53 is a conceptual planar perspective view of structural elements of an axially nested slide and lock stent in a partially expanded state illustrating features and advantages in accordance with yet another embodiment of the inventions.
Figure 54:
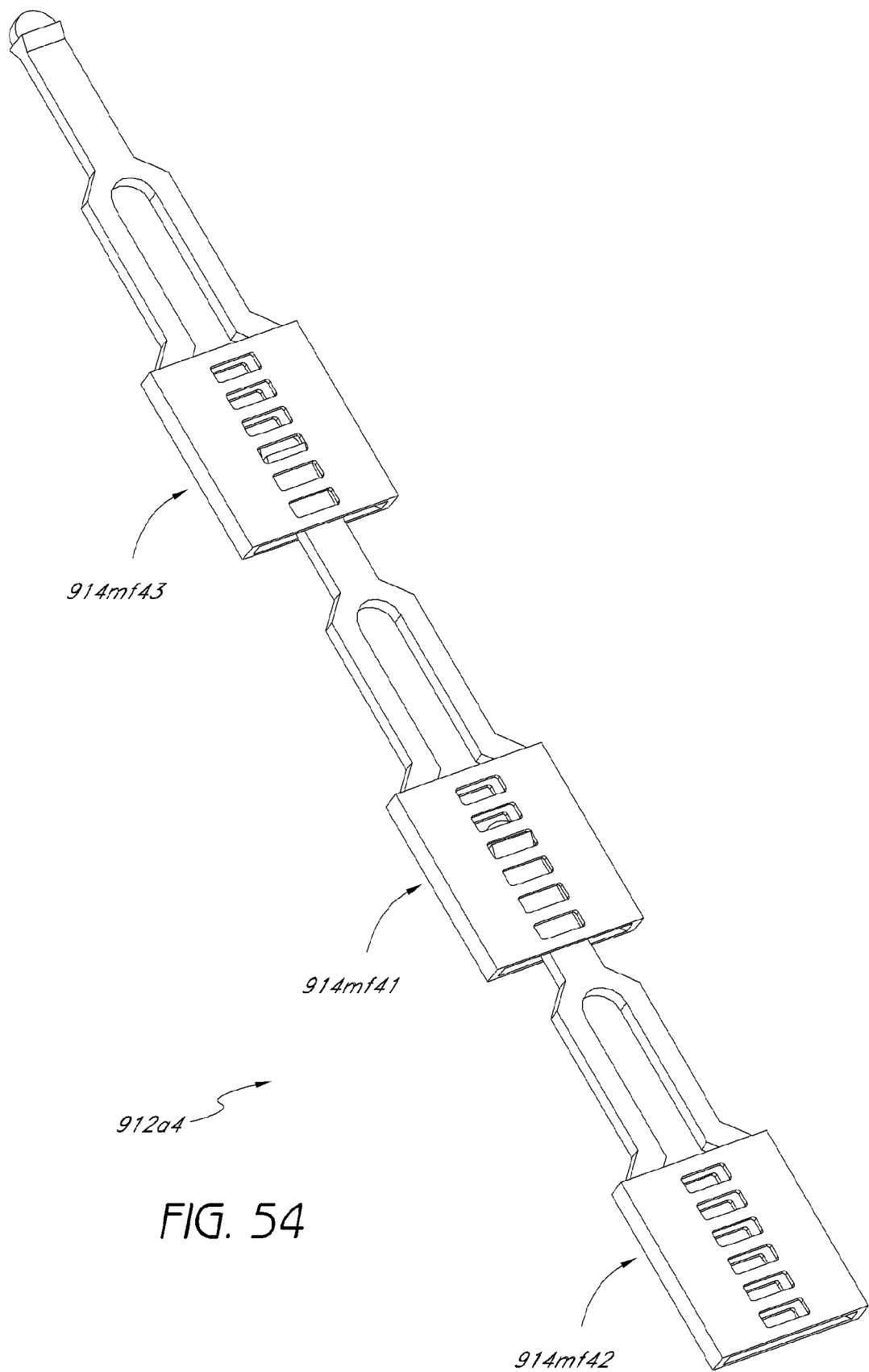
FIG. 54 is a conceptual planar perspective view of structural elements of an axially nested slide and lock stent in a partially expanded state illustrating features and advantages in accordance with still another embodiment of the inventions.
Figure 55:
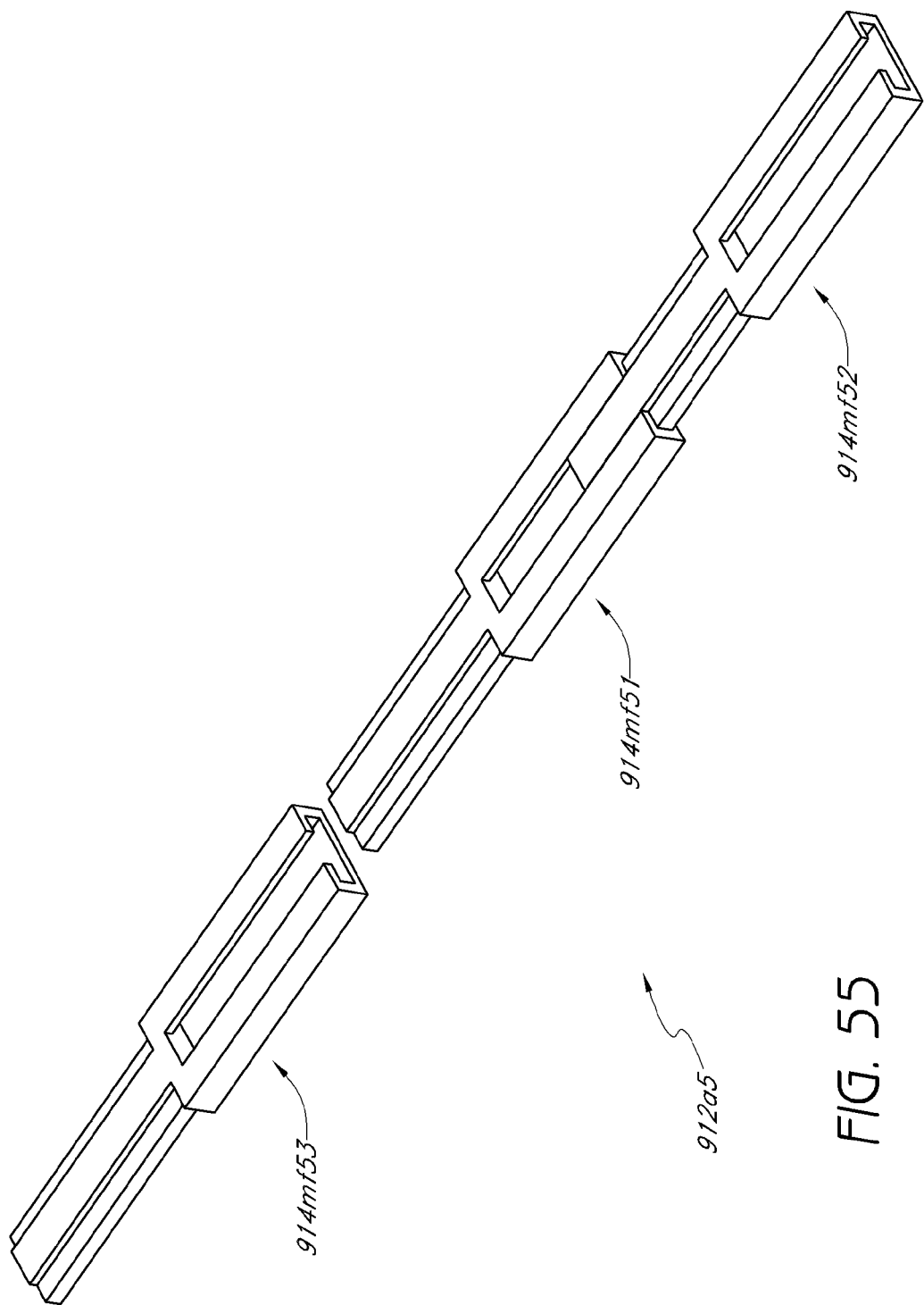
FIG. 55 is a conceptual planar perspective view of structural elements of an axially nested slide and lock stent in a partially expanded state illustrating features and advantages in accordance with a further embodiment of the inventions.
Figure 56:
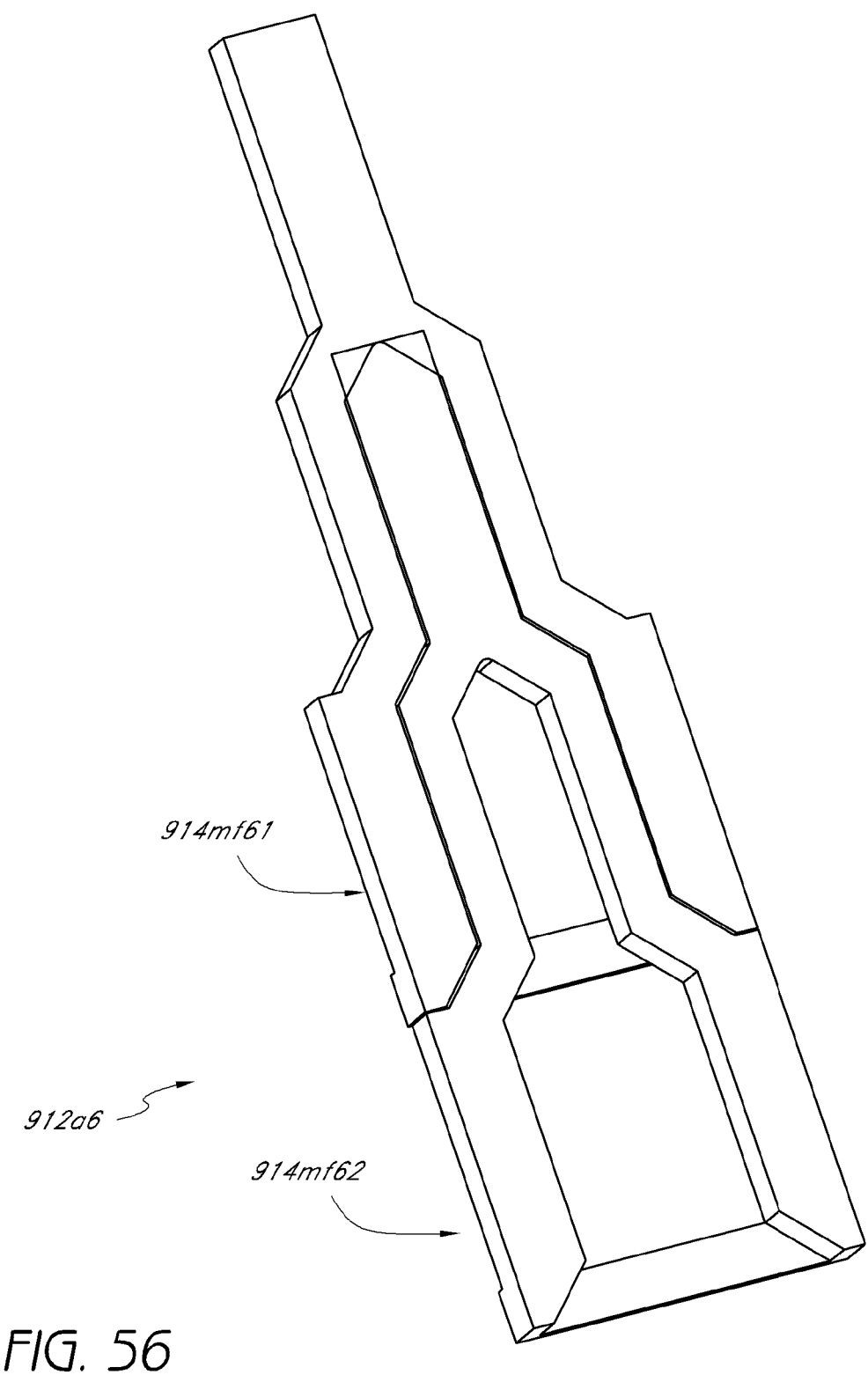
FIG. 56 is a conceptual planar perspective view of structural elements of an axially nested slide and lock stent in a partially expanded state illustrating features and advantages in accordance with a another further embodiment of the inventions.
Figure 57:
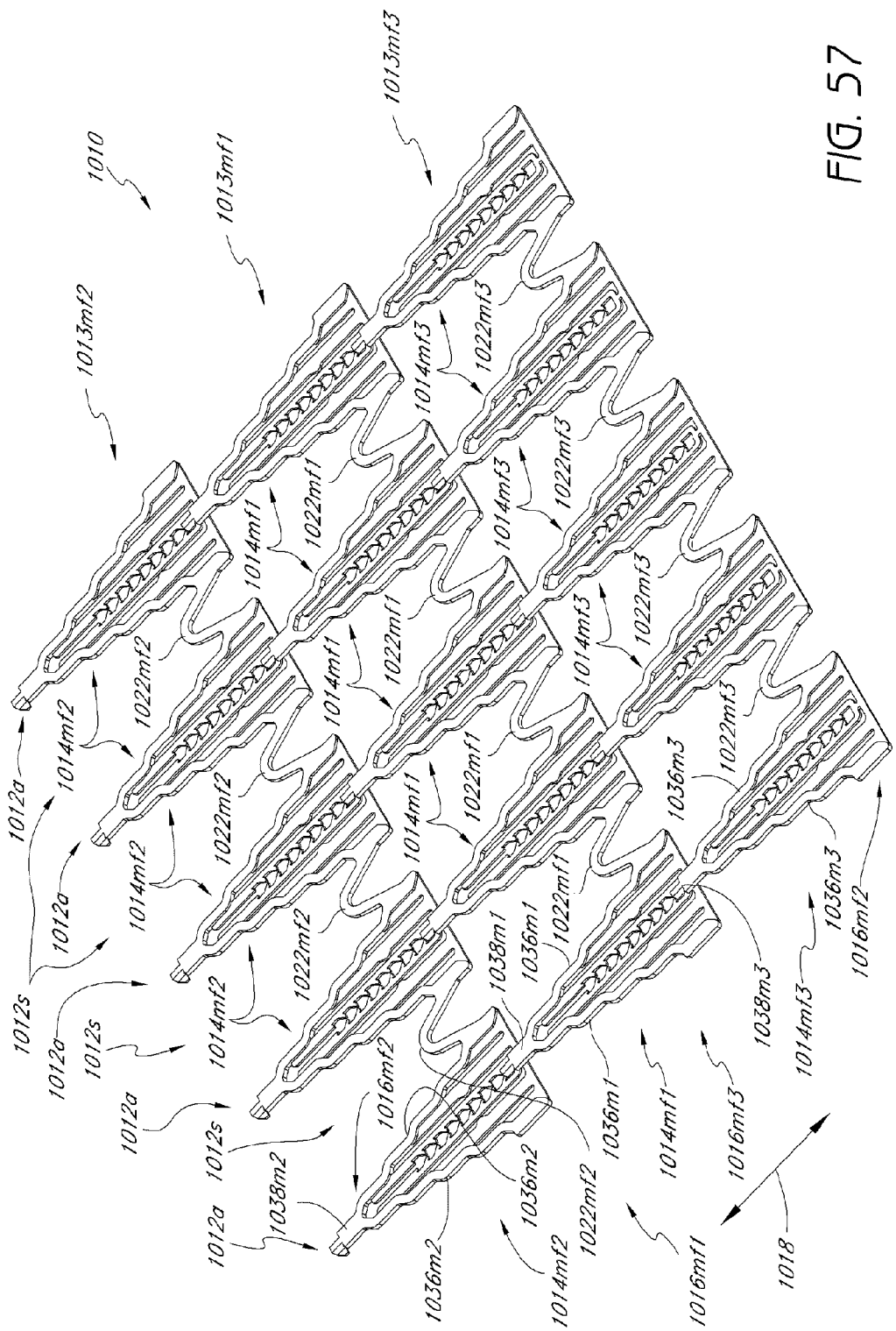
FIG. 57 is a simplified planar perspective view of an axially nested slide and lock stent illustrating features and advantages in accordance with an embodiment of the inventions.
Figure 58:
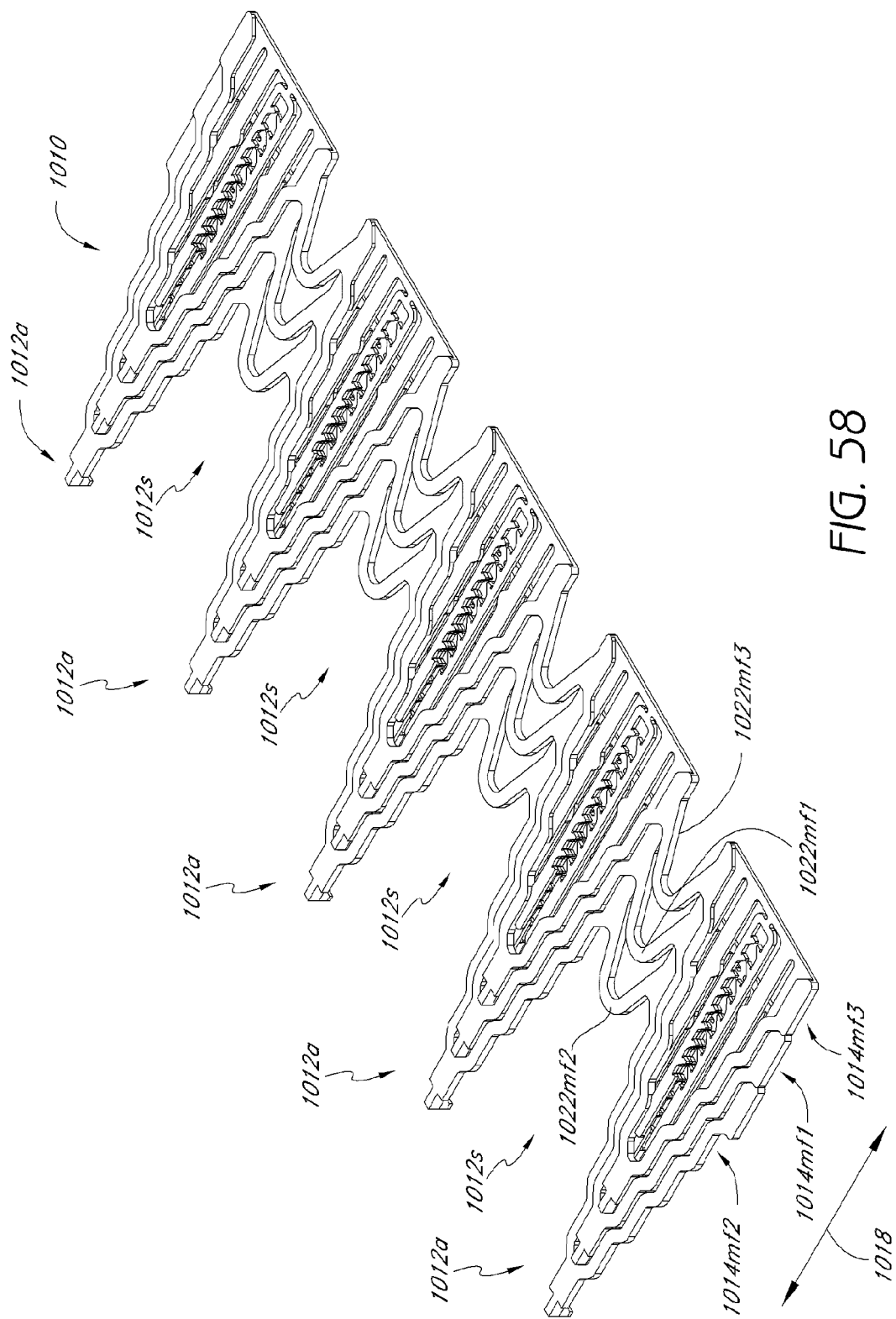
FIG. 58 is a simplified planar perspective view of the stent of FIG. 57 in a collapsed state illustrating features and advantages in accordance with an embodiment of the inventions.
Figure 59:
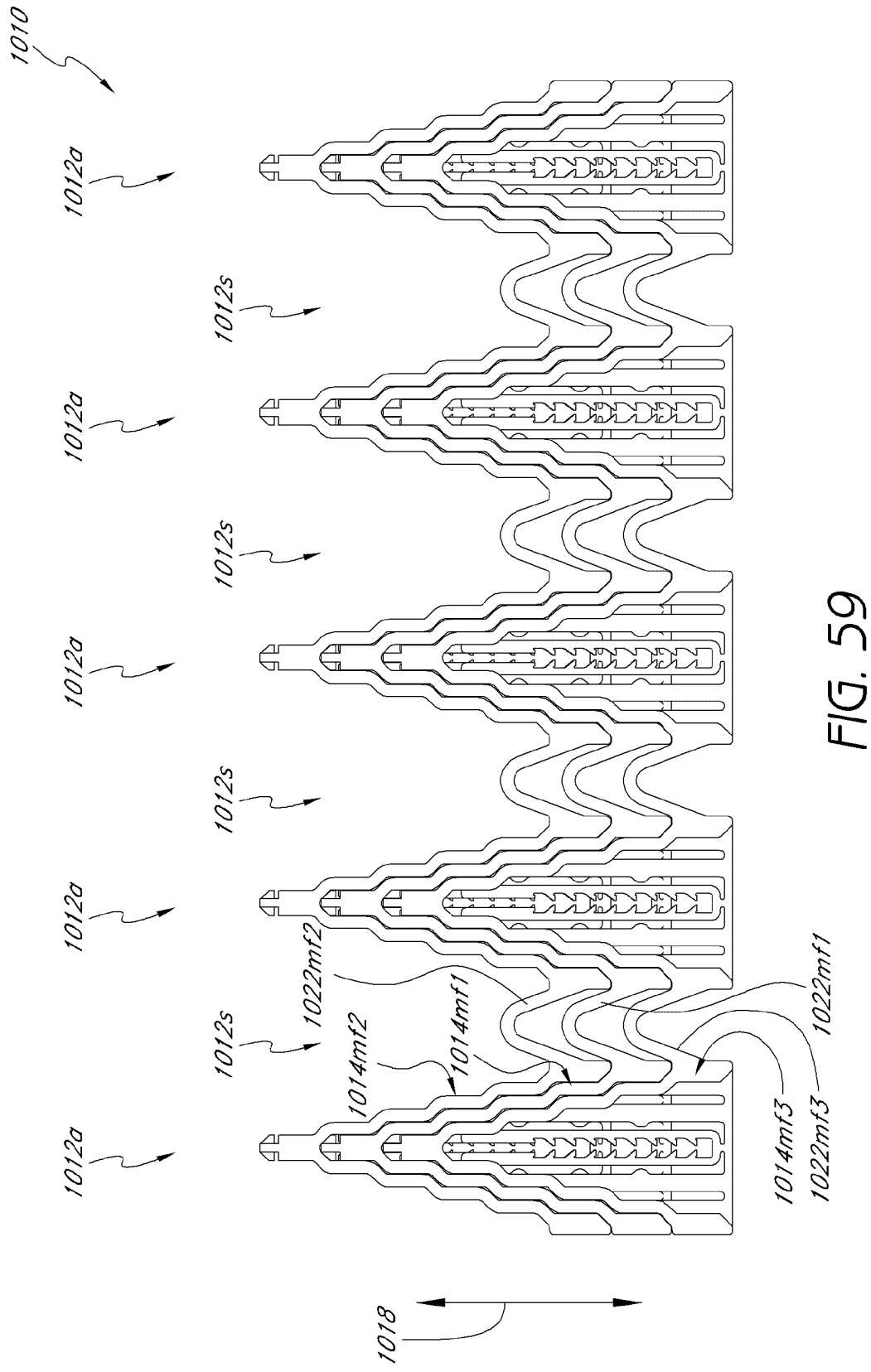
FIG. 59 is a simplified planar view of the stent of FIG. 57 in a collapsed state illustrating features and advantages in accordance with an embodiment of the inventions.
Figure 60:
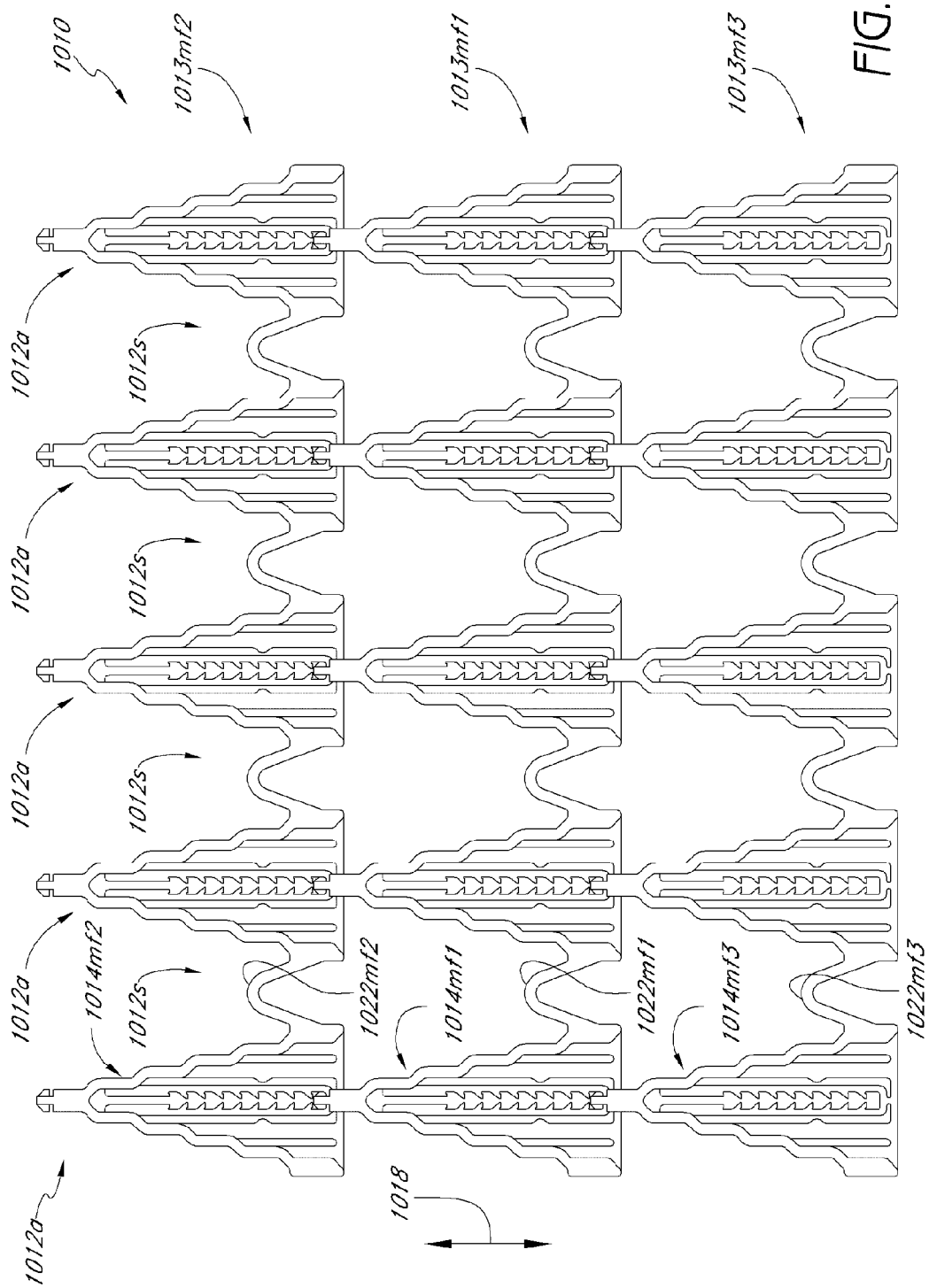
FIG. 60 is a simplified planar view of the stent of FIG. 57 in an expanded state illustrating features and advantages in accordance with an embodiment of the inventions.

FIG. 50 shows an exploded view of a lamination stack 878 used to fabricate the stent rows 813 (813f1, 813f2) by a lamination process in accordance with one embodiment. The stent rows 813m1, 81mf2 can also be similarly formed. The axially extending rows 813f1, 813m1, 813f2, 813m2 can then be connected and rolled into a tubular form in the collapsed state.

The lamination stack 878 generally comprises three sheets or pallets 878f1, 878f2, 878f3 which have the desired features formed thereon, for example, by laser cutting, etching and the like. The pallets 878f1, 878f2, 878f3 are aligned and joined, for example, by bonding, welding and the like to form a unit. The excess material (e.g., side and end rails) is removed to form the rows 813 (813f1, 813f2).

The pallet 878f1 includes features that correspond to stops engaged by an articulating female rib. The pallet 878f2 includes features that correspond to hard stops that control and limit the diameter in collapsed and fully deployed states. The pallet 878f3 includes features that correspond to teeth that align and hold the articulating rib in place.

FIGS. 51-56 show various conceptual views of axially nested one-way slide and lock stent geometries and configurations in accordance with embodiments of the inventions. The nesting utilizes a "telescope" concept. The drawings show embodiments of stent sections, segments or frames 912a with structural elements 914mf. The stent sections include articulating mechanisms that may comprises radially deflecting locking mechanisms or axially (laterally) deflecting locking mechanisms. These slide and lock articulating mechanisms may include tongue-groove configurations stops, tabs, wings or teeth that provide radially and/or axially deflecting mechanisms for stent expansion and lock-out. Any of the articulating mechanism as disclosed, taught or suggested herein including any disclosed, taught or suggested by the embodiments of FIGS. 51-56 may efficaciously be used, as needed or desired.

The embodiments of FIGS. 51-56 can include capture mechanisms that serve to control and limit stent expansion to a predetermined deployment diameter. Each section 912 and/or structural element 914 can comprise one or more capture mechanisms such as straps, hard stops, and the like among other suitable devices that prevent further expansion between mating structural elements 914 and control the maximum expansion. Any of the capture mechanisms as disclosed, taught or suggested herein may efficaciously be used in conjunction with the embodiments of FIGS. 51-56, as needed or desired.

Some Additional Stent Embodiments

FIGS. 57-62 show views of an expandable axially nested slide and lock vascular device, prosthesis or stent 1010 including deployed and undeployed states. In a rolled configuration, the stent 1010 has a tubular form with a wall comprising a plurality of generally longitudinally arranged linked circumferential sections, segments or frames 1012a, 1012s. The stent 1010 is expandable from a first diameter to a second diameter. The general design of the stent 1010 may be conceptually characterized as a one-way sliding "telescope-like" configuration.

Advantageously, the axially nested embodiments of the stent 1010 allow suitable crossing profiles (e.g. luminal size) while maintaining desirable radial strength and luminal patency. In the non-expanded state, there is also minimal or reduced overlap between structural elements, so that the luminal size facilitates insertion of a guiding catheter balloon or the like to expand the vascular device.

The stent 1010 comprises alternatingly arranged slide and lock sections 1012a and linkage sections 1012s. Each section 1012a includes three structural elements 1014mf1, 1014mf2, 1014mf3 that each slidingly mate with one another via respective interlocking articulating mechanisms 1016mf1, 1016mf2, 1016mf3. (Each of the structural elements 1014 may also be described as comprising two structural elements—one male and one female—since each mates at two circumferential locations.)

Each linkage section 1012s includes three elements 1022mf1, 1022mf2, 1022mf3. The linkage elements 1022mf1 connect structural elements 1014mf1 to form a stent element row 1013mf1. The linkage elements 1022mf2 connect structural elements 1014mf2 to form a stent element row 1013mf2. The linkage elements 1022mf3 connect structural elements 1014mf3 to form a stent element row 1013mf3. The number of elements in a section or row and the number of sections and rows in a stent may be efficaciously varied and selected, as needed or desired.

One or more of the linkage elements 1022 may comprise spring elements. The spring elements 1022 provide device flexibility and allow expansion of the linkage sections 1012s along with stent expansion. The spring elements 1022 can also allow for radial and/or axial element or member deflection during stent expansion to a deployed state. The spring elements 1022 facilitate this deflection by providing a resilient biasing mechanism to achieve substantially elastic deflection or deformation.

The linkage elements 1022mf1 axially or longitudinally connect the structural elements 1014mf1. In one embodiment, the linkage elements 1022mf1 and the structural elements 1014mf1 comprise an integral unit, that is, the stent row 1013mf1 comprises an integral unit. In modified embodiments, the linkage elements 1022mf1 and the structural elements 1014mf1 can efficaciously be connected by other techniques, as needed or desired.

The linkage elements 1022mf2 axially or longitudinally connect the structural elements 1014mf2. In one embodiment, the linkage elements 1022mf2 and the structural elements 1014mf2 comprise an integral unit, that is, the stent row 1013mf2 comprises an integral unit. In modified embodiments, the linkage elements 1022mf2 and the structural elements 1014mf2 can efficaciously be connected by other techniques, as needed or desired.

The linkage elements 1022mf3 axially or longitudinally connect the structural elements 1014mf3. In one embodiment, the linkage elements 1022mf3 and the structural elements 1014mf3 comprise an integral unit, that is, the stent row 1013mf3 comprises an integral unit. In modified embodiments, the linkage elements 1022mf3 and the structural elements 1014mf3 can efficaciously be connected by other techniques, as needed or desired.

In some embodiments, each of the axially extending rows 1013mf1, 1013mf2, 1013mf3 are first formed as independent units that may be independent integral units. The stent rows 1013mf1, 1013mf2, 1013mf3 are then connected and rolled into a tubular form in the collapsed state.

The axial or longitudinal coupling between the structural elements 1014 of adjacent sections 1012a, the radial coupling between structural elements 1014 of the same section 1012a, and the design and configuration of the sections 1012 and structural elements 1014 are such that there is minimal or reduced overlapping in the radial or circumferential direction between the structural elements 1014, in particular in the expanded or deployed state. Thus, the structural elements 1014, sections 1012 and/or stent 1010 are referred to as being axially, longitudinally or non-radially nested. (There is also minimal or reduced radial overlap between linkage elements 1022 of the same and adjacent sections 1012s in both the undeployed and deployed states, and more particularly in the deployed state.)

During stent expansion, there is circumferential relative motion between the mating structural elements 1014mf1, 1014mf2, 1014mf3 as generally shown by arrows 1018. One or more or all of structural elements 1014mf1, 1014mf2, 1014mf3 in any suitable combination may slidably move apart.

Each of the structural elements 1014mf1, 1014mf2, 1014mf3 has a generally similar structure and each comprises a male portion and a female portion. Thus, for brevity, only the male portion of the structural element 1014mf1 and the female portion of the structural element 1014mf2 and their articulation, lock-out and capture features are described in detail below.

It is to be understood that a generally similar arrangement is encompassed by the other structural elements 1014 of the stent 1010, and similar reference numerals are used herein. Thus, for example, if the male ribs of the structural element 1014mf1 are denoted by 1036m1, then the male ribs of the structural elements 1014mf2 and 1014mf3 are respectively denoted by 1036m2 and 1026m3, and so on.

The male portion of the structural element 1014mf1 mates or articulates with the female portion of the structural element 1014mf2 in a one-way sliding manner. Similarly, the male portion of the structural element 1014mf2 mates or articulates with the female portion of the structural element 1014mf3 in a one-way sliding manner. Also similarly, the male portion of the structural element 1014mf3 mates or articulates with the female portion of the structural element 1014mf1 in a one-way sliding manner. As discussed above and below herein, the slide and lock articulating mechanisms of the structural elements 1014 include features such as deflectable elements or members, tongue-groove configuration stops, tabs or teeth that provide axially deflecting mechanisms for stent expansion and lock-out.

The male portion of the structural element 1014*mf*1 generally includes a pair of spaced ribs or arms 1036*m*1 with a gap therebetween. The male ribs 1036*m*1 converge towards one another to terminate and join at a common end portion 1038*m*1.

Figure 61:
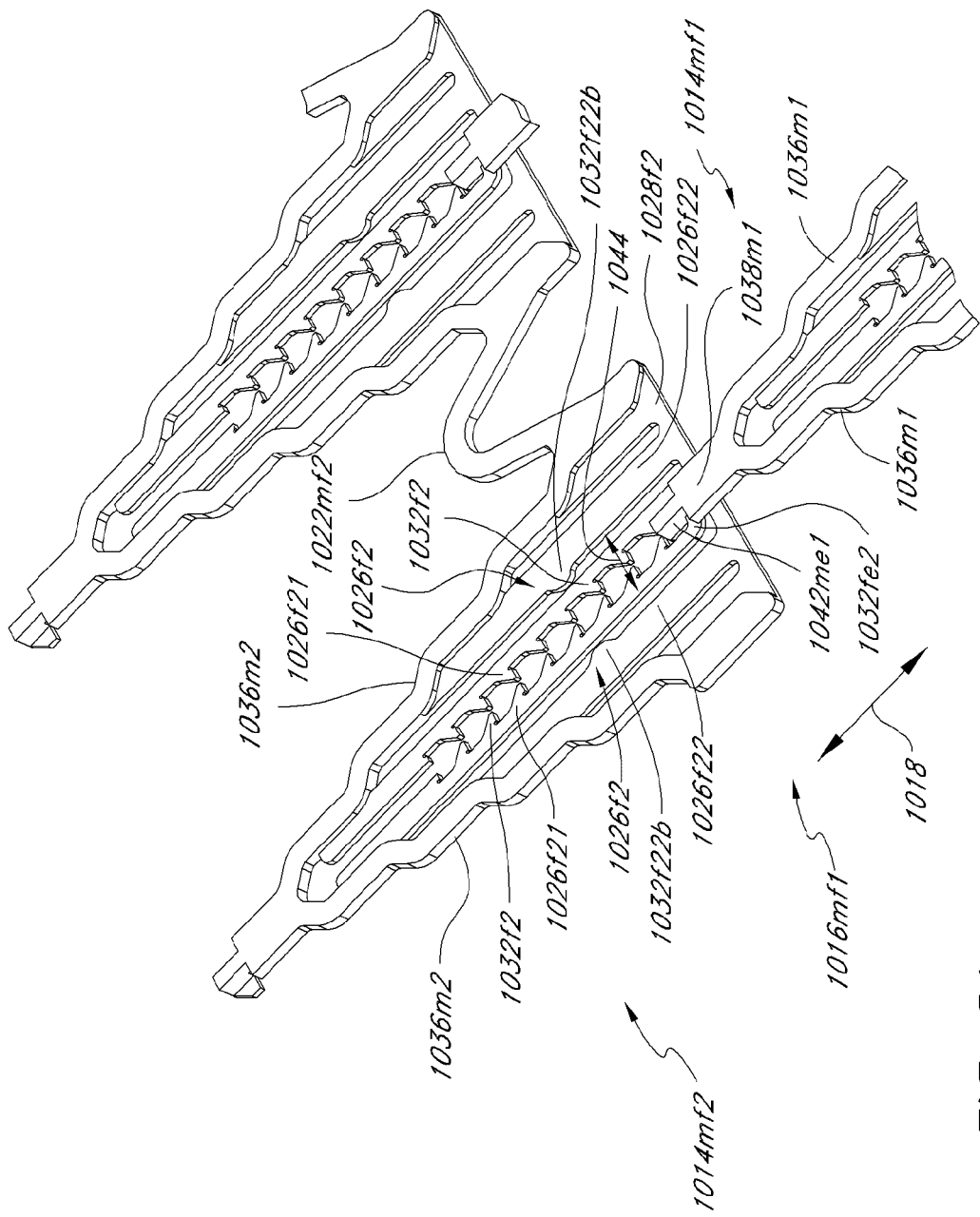
FIG. 61 is a simplified planar perspective top view of a slide and lock articulation mechanism of the stent of FIG. 57 illustrating features and advantages in accordance with an embodiment of the inventions.
Figure 62:
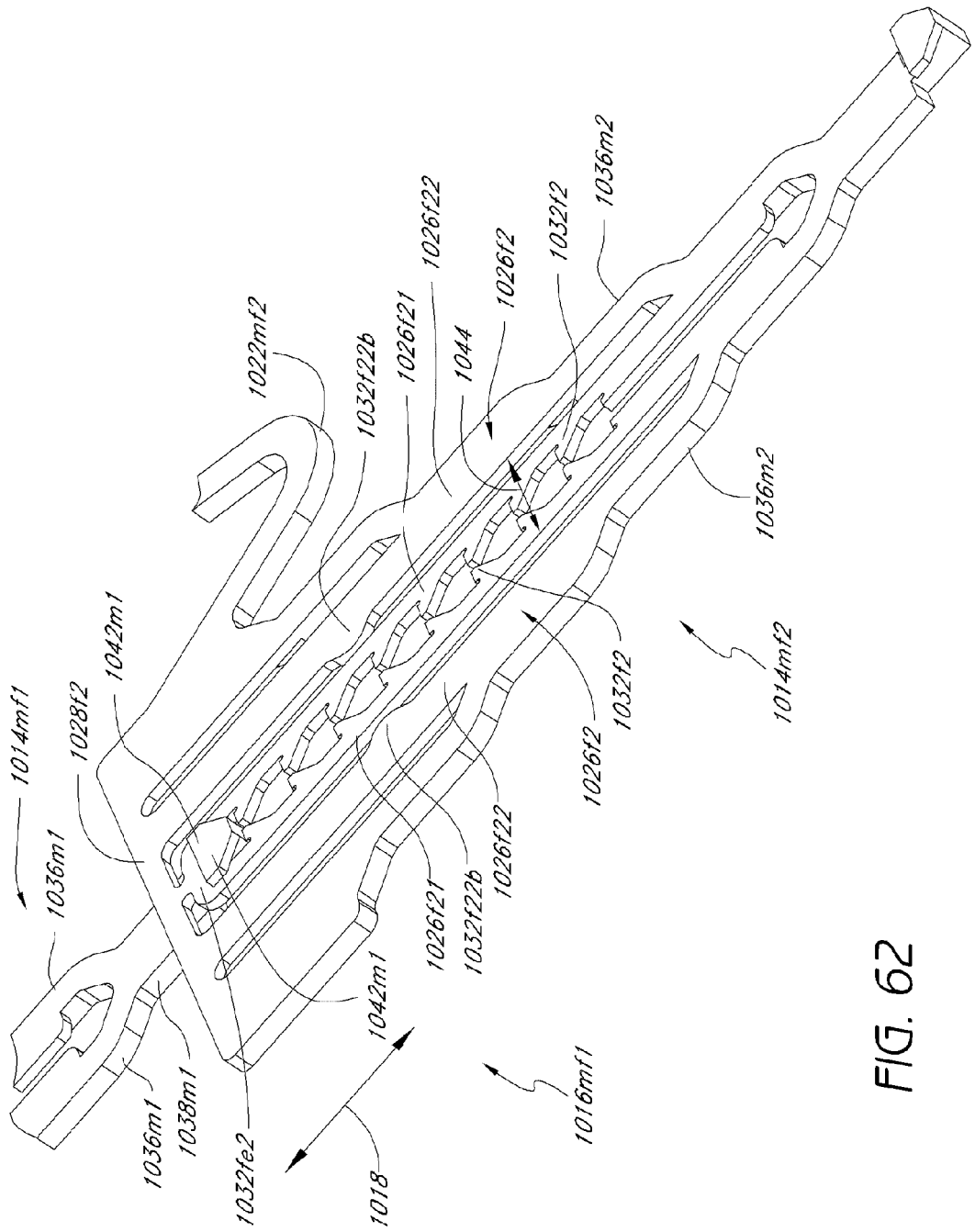
FIG. 62 is a simplified planar perspective bottom view of a slide and lock articulation mechanism of the stent of FIG. 57 illustrating features and advantages in accordance with an embodiment of the inventions.

As best seen in FIGS. 61 and 62, the end portion 1038*m*1 includes a radially inwards extending end tab, tooth or stop 1042*me*1 that terminates in a pair of outwardly and axially extending tabs, teeth, stops or wings 1042*m*1. As discussed further below, the end stop 1042*me*1 engages the female portion of the adjacent structural element 614*mf*2 in a one-way slide and lock articulating motion. The end stop 1014*me*1 is configured to substantially reduce or minimize recoil.

As discussed further below, the end stop 1042*me*1 also serves as a safety hard stop in the collapsed state and at full stent expansion. At full expansion, the end stop 1042*me*1 engages a capture mechanism of the mating structural element 1014*mf*2 to control and limit the maximum stent expansion to a predetermined deployment diameter. Other suitable lock-out and capture configurations may be efficaciously utilized, as needed or desired.

Referring in particular to FIGS. 61 and 62, the female portion of the structural element 1014*mf*2 generally comprises a pair of spaced ribs or arms 1026*f*2 within the gap between the male ribs 1036*m*2. The female ribs 1026*f*2 are radially inwardly recessed relative to the male ribs 1036*m*2 to provide clearance space for the mating male ribs 1036*m*1 in the collapsed state and during stent expansion. The female ribs 1026*f*1 are connected by an end portion 1028*f*1 that has one or more hard stops 1032*fe*2 that control and limit the maximum stent expansion to a predetermined diameter.

Each of the ribs 1026*f*2 includes a pair of spaced sub-ribs, -arms or rails 1026*f*21, 1026*f*22. The rails 1026*f*21 are axially deflectable and have a plurality of inwardly axially extending stops, tabs or teeth 1032*f*2. As discussed further below, the teeth 1032*f*2 engage the male portion of the radially coupled structural element 1014*mf*1 in a one-way slide and lock articulating motion, and in one embodiment, are not deflectable.

The teeth 1032*f*2 are configured so that they have generally flat end surfaces to substantially reduce or minimize recoil and generally tapered engaging surfaces to facilitate one-way sliding. Other suitable configurations that inhibit undesirable recoil and facilitate one-way expansion may be efficaciously utilized, as needed or desired.

Each of the ribs 1026*f*22 includes an axial deflection control device, bump or protrusion 1032*f*22*b* that is spaced by a predetermined amount from a respective one of the deflectable rails or ribs 1026*f*21. Advantageously, the bumps 1032*f*22*b* serve to control the maximum deflection of the rails or ribs 1026*f*21 so that they do not deform or bend beyond a prescribed range. The bumps 1032*f*22*b* also desirably act as "speed bumps" to control deployment and maintain uniformity of deployment.

Advantageously, there is substantially no or minimal overlap between nesting structural elements 1014*mf*1, 1014*mf*2 and 1014*mf*3 in both the collapsed state and the expanded state, and more particularly in the expanded state. Thus, the stent 1010, its sections 1012*a* and/or structural elements 1014 are referred to as being axially nested. Any overlap in the collapsed state is such that a suitable crossing profile is still achieved.

Embodiments of the inventions provide an axially nested vascular device 1010 to achieve both competitive crossing profiles (e.g. luminal size) while maintaining other key features, such as, for example, radial strength and luminal patency. Advantageously, an axially nested device design allows for use of thicker materials to maintain radial strength, as needed or desired.

During manufacture and assembly of the axially nested embodiments, at least some of the device ribs (e.g. the male ribs 1036*m*1 and the male ribs 1036*m*1) are positioned side by side (axially) in the predilated or non-expanded state to substantially reduce or minimize the device crossing profile and bulk in both the undeployed (non-expanded, predilated) and deployed (expanded, dilated) states. Advantageously, by substantially reducing or eliminating the excess bulk typically encountered with a radially nesting device design, embodiments of the inventions can be used to achieve competitive devices and crossing profiles with a wide variety of materials at a wide variety of thicknesses, thereby desirably allowing for optimum device design and performance.

The articulation between the structural elements 1014*mf*1 and 1014*mf*2 of a given stent section 1012*a* is discussed below. As the skilled artisan will recognize, a similar articulation is applicable to other mating structural elements of the stent 1010. Thus, for brevity it is not repeated herein.

During stent expansion, there is circumferential relative motion between the ribs of the structural element 1014*mf*1 and the ribs of the structural element 1014*mf*1 as generally indicated by arrows 1018. The male ribs 1036*m*1 withdraw from the gap between the ribs 1036*m*2.

The end stop 1042*me*1 slides within the gap between the female ribs 1026*f*21 and the wings 1042*m*1 slide along the lower or radially inwards surface of the female toothed ribs 1026*f*21. Advantageously, the ribs 1026*f*21 and/or wings 1042*m*1 prevent the male ribs 1036*m*1 from jumping out of their track and keep them in position.

The stop 1042*me*1 engages the teeth 1032*f*2 of the female ribs 1026*f*21. Thus, during expansion, the teeth 1032*f*2 of the deflectable female ribs 1026*f*21 and the stop 1042*me*1 cross one another. This is accomplished by utilizing a generally axially deflecting mechanism.

Thus, during "cross-over" the deflectable female ribs 1026*f*21 are deflected axially outwards and then resume their original undeflected position. This axial motion is generally denoted by arrows 1044. The axial deflection is caused by the generation of a generally axial force when the teeth 1032*f*2 and the stop 1042*me*1 slide over, engage or abut one another. Advantageously, the axial deflection control bumps 1032*f*22*b* substantially prevent undesirable or excessive deflection and control deployment to maintain uniformity of deployed stent.

At full expansion, the safety hard stop 1042*me*1 and the respective end hard stops 1032*fe*2 of the structural element portion 1028*f*2 contact, engage or abut against one other, and prevent further stent expansion. This lock-out and capture mechanism provides to control and limit stent expansion to a predetermined deployment diameter.

The internal protected articulating and locking mechanisms of the stent 1010 advantageously allow clearance space at the outer stent periphery which shields and protects the mechanisms from external surface interferences. Raised and recessed portions of the structural elements 1014*mf* can provide this shielding and the structural elements 1014*mf* are also configured to facilitate alignment between the mating elements.

Figure 63:
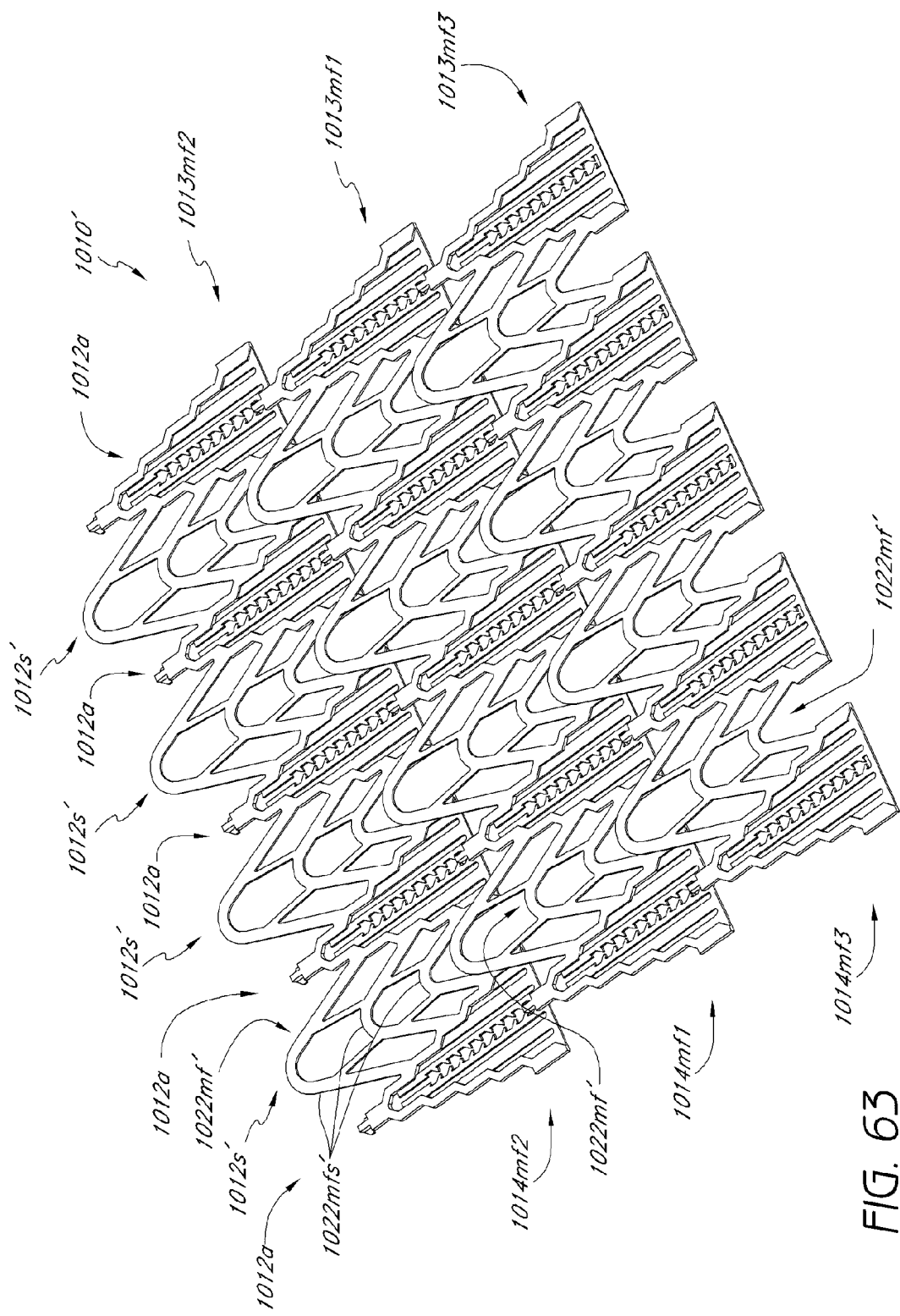
FIG. 63 is a simplified planar perspective view of an axially nested slide and lock stent in an expanded state illustrating features and advantages in accordance with another embodiment of the inventions.

FIG. 63 shows an expandable axially nested slide and lock vascular device, prosthesis or stent 1010' in accordance with another embodiment. The stent 1010' is generally similar to the stent 1010 except that it has linkage sections 1012s' that have a modified construction.

Each linkage section 1012s' includes three elements 1022mf" that are generally similar to one another. Each linkage element 1022mf" generally comprises a plurality of interconnected sub-elements 1022mfs'. One or more of the linkage elements 1022mf" and/or the sub-elements 1022mfs' may comprise spring elements, as needed or desired.

Yet Additional Stent Embodiments

Figure 64:
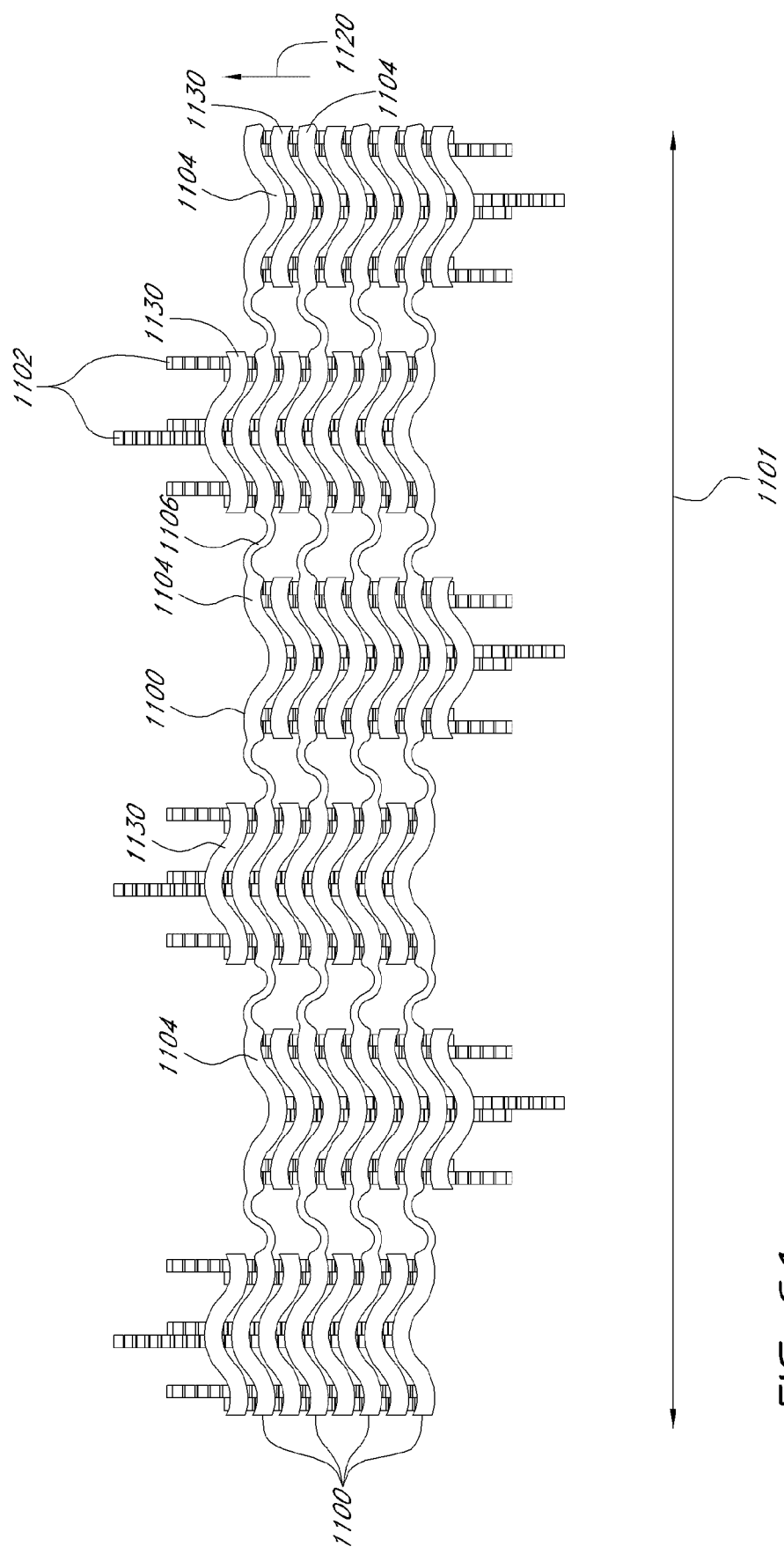
FIG. 64 is a planar view of an axially nested slide and lock stent in a nested state illustrating features and advantages in accordance with another embodiment of the inventions.

Referring now to FIGS. 64-69, an embodiment of an axially nested stent is shown. The stent can comprise a tubular member having longitudinal and circumferential axes and that is expandable from a collapsed or axially nested unexpanded state to an expanded state. As shown in FIG. 64, in an embodiment, the tubular member can comprise a plurality of elongate linkage sections 1100 and at least one interconnection member 1102 that can be used to interconnect the linkage sections 1100. The linkage sections 1100 can be oriented to be substantially parallel with a longitudinal axis 1101; thus, when in an assembled state, the linkage sections 1100 can be circumferentially disposed about the longitudinal axis 1101, and can thereby form the tubular member. Nevertheless, it is also noted that the linkage sections 1100 need not be oriented substantially parallel about the longitudinal axis 1101, but that other configurations can be developed that enable the linkage sections 1100 to be oriented substantially skew with respect to the longitudinal axis 1101 of the tubular member.

Figure 65:
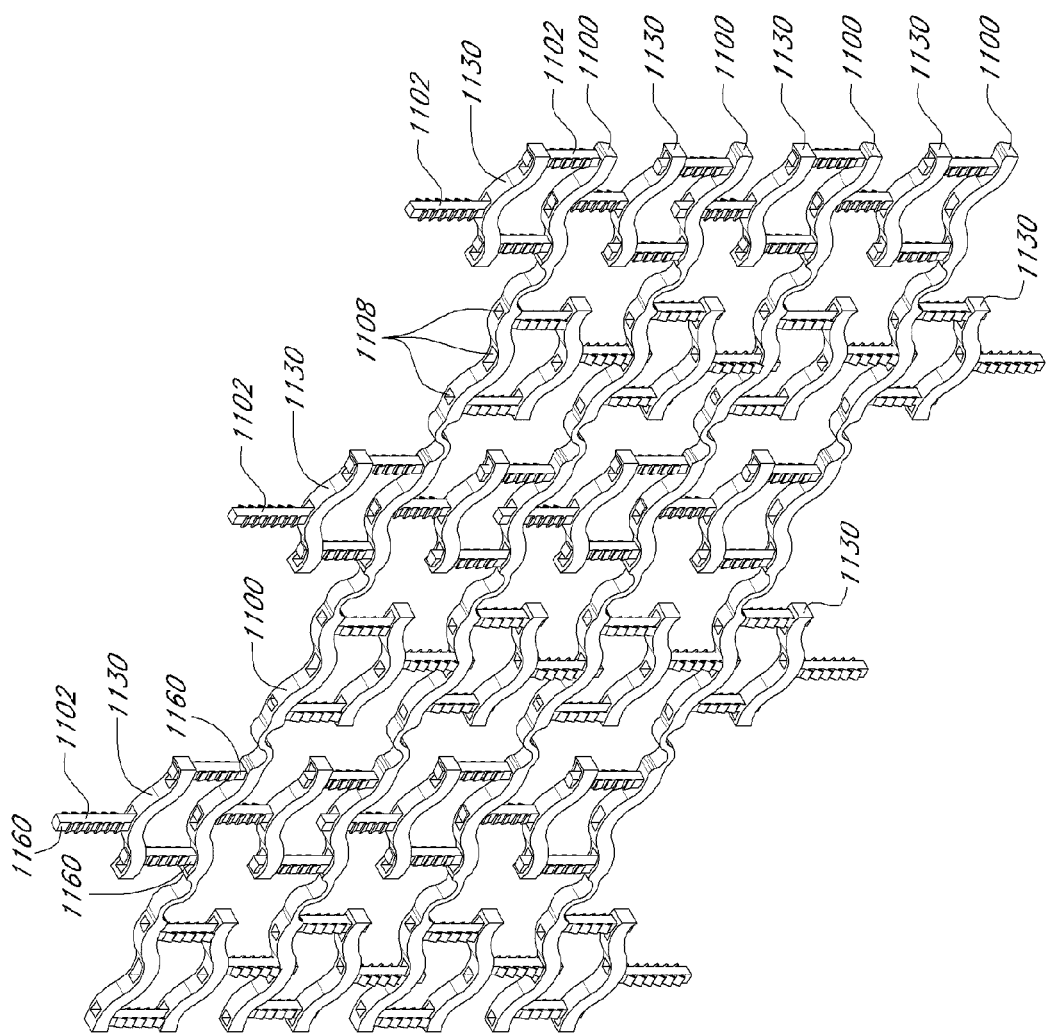
FIG. 65 is a perspective view of the axially nested slide and lock stent of FIG. 64 in an expanded state.

FIG. 64 illustrates a portion of the stent showing the linkage sections 1100 in the axially nested unexpanded or collapsed state. As such, the linkage sections 1100 can be disposed substantially adjacent to one another. However, it is also contemplated that the linkage sections 1100 can be separated from each other in the unexpanded state. As shown in FIG. 65, the stent can achieve the expanded state when the linkage sections 1100 are radially separated from each other.

In some embodiments, the linkage sections 1100 can be separated at a maximum distance generally defined by the length and configuration of the interconnection member 1102. For example, the interconnection member 1102 can be configured to include stop members at a distal end thereof or other features that limit the total expansion of the stent by limiting the relative movement of the interconnection member 1102 relative to the linkage section 1100. Stop members in some embodiments are discussed further below.

Thus, in some embodiments, the linkage sections 1100 can be separated at a distance just less than the length of an interconnection member 1102. In other embodiments, as shown in FIG. 65, the stent can be configured such that the linkage sections 1100 are separated from one another at a maximum distance that is greater than the length of an individual interconnection member 1102. For example, the stent can comprise an intermediate member having a plurality of interconnection members 1102 extending therefrom to provide greater expansion for the stent. Such embodiments will be described in greater detail below with reference to FIG. 65.

In accordance with an aspect of some embodiments, the linkage sections 1100 can comprise a plurality of link elements 1104, a flexible section 1106 extending intermediate the link elements 1104, and at least one engagement aperture 1108 (shown in FIGS. 65-66B). The link elements 1104 can be generally elongate. The link elements 1104 can also be generally straight; however, the link elements 1104 can be arcuately shaped, zig-zag, or can define multifarious geometrical shapes.

Further, the link elements 1104 can define an overall length that is substantially greater than its overall width. However, it is also contemplated that the overall width can be approximately equal to or greater than the overall length. The link elements 1104 can define a first end 1110 and a second end 1112. In some embodiments, the flexible section 1106 can be configured to extend intermediate a first end 1110' of a given link element 1104' and the second end 1112 of the link element 1104. Thus, the link elements 1104, 1104' can be interconnected in an end-to-end manner.

In some embodiments, such as those shown in FIGS. 64-66B, the linkage section 1100 can be configured in a curvilinear design and the linkage sections 1100 can be at least partially axially nestable when positioned adjacent to each other in the unexpanded state. Further, the flexible sections 1106 can also be configured to be curvilinear, which may facilitate flexibility of the stent with respect to the longitudinal axis thereof. Thus, the stent can flex so as to conform to the shape of a body lumen into which it is implanted. Accordingly then, the linkage sections 1100 can allow the stent to assume configurations other than that of a right circular cylinder.

Referring to FIGS. 66A-66B, the engagement apertures 1108 of the linkage sections 1100 can be disposed through at least one link element 1104 in a circumferential direction 1120. In some embodiments, the engagement aperture 1108 can be a through-hole that passes from a first side 1122 of the link element 1104 to a second side 1124 of the link element 1104. However, it is also contemplated that the engagement aperture 1108 can be configured as a slot or groove into which at least a portion of the interconnection member 1102 can be received.

As shown in FIGS. 64-66B, some embodiments of the stent can be configured such that the link elements 1104 each include a plurality of engagement apertures 1108. Although the link elements 1104 are shown as including three engagements apertures 1108, it is contemplated that a pair of engagement apertures 1108 or even a single engagement aperture 1108 can be used. Such design modifications can be performed in response to the overall configuration and design requirements of the stent.

The interconnection member 1102 can be configured to be received into the engagement aperture 1108 of the linkage section 1104. In some embodiments, the interconnection member 1102 can extend from one link element toward the engagement aperture 1108 of another link element 1104. In yet other embodiments, the stent can be configured to include an intermediate or interlink member 1130 to which the interconnection member 1102 can be attached. Thus, as will be described in greater detail below, the interlink member 1130 can be positioned intermediate adjacent linkage sections 1100 and be configured such that a plurality of interconnection members 1102 extend from the interlink members 1130 into the engagement apertures 1108 of the linkage elements 1104 of the linkage sections 1100.

Referring now to FIGS. 67A-67B, an embodiment of the interlink member 1130 is shown. The interlink member 1130 can include an interlink body 1132 having first and second sides 1134, 1136. The interlink body 1132 can be configured to define a shape that complements the shape or configuration of the link element 1104 of the linkage section 1100. The interlink member 1130 can be configured to be nestable intermediate adjacent linkage sections 1100. In some embodiments, the interlink member 1130 can be positioned intermediate adjacent link elements 1104 of adjacent linkage sections 1100. However, it is also contemplated that the interlink member 1130 can span between multiple link elements 1104 of linkage sections 1100. Thus, although FIGS. 64-65 illustrate a single interlink member 1130 disposed intermediate adjacent interlink elements 1104, it is contemplated that the interlink element 1130 can extend along the longitudinal axis 1101 so as to be interposed between pairs of linkage elements 1104 of adjacent linkage sections 1100.

FIG. 67A also illustrates that at least one interconnection member 1102 can extend from the interlink member 1130. As such, one or more interconnection members 1102 can extend from either of the first and second sides 1134, 1136, to facilitate the interconnection of adjacent linkage sections 1100.

In the embodiment shown in FIG. 67A, the interlink body 1132 can be configured to conform substantially to the shape of a sinusoidal curve with an engagement member 1102 extending from a central crest 1140 of the interlink body and a pair of interconnection members 1102 extending from the respective end troughs 1142 of the interlink body. Such a configuration can be advantageous in an embodiment such as that illustrated in FIGS. 64-65 due to the unique configuration of the linkage sections 1100 which utilize link elements 1104 that are alternately configured to conform to the shape of a sinusoidal curve and a co-sinusoidal curve. Thus, as shown in FIG. 65, along the longitudinal axis, the interlink member 1130 can similarly be alternately positioned to conform to the shape of the linkage sections 1100.

In some embodiments, the stent can achieve a uniform longitudinal spacing of the interconnection members 1102. Nevertheless, other configurations can be employed that likewise achieve uniform spacing of the linkage sections 1100 and the interconnection members 1102. In this regard, it is contemplated that the linkage sections 1100, the interlink members 1130 and the interconnection members 1102 can be configured to provide a substantially symmetrical design that can distribute forces and stresses evenly throughout the stent.

Referring again to FIGS. 67A-67B, the interconnection member can include a ratcheting means 1150. The ratcheting means 1150 can be configured to engage the engagement apertures 1108 of the link elements 1104 to allow one-way movement of the interconnection member 1102 relative to the link element 1104. In this manner, the interconnection member 1102 can therefore facilitate the expansion of the stent, but nevertheless prevent the stent from collapsing from the expanded state.

In some embodiments, such as that illustrated in FIG. 67B, the ratcheting means 1150 can include a plurality of teeth 1152 disposed along at least one of a top surface 1154 and a bottom surface 1156 of the interconnection member 1102. Preferably, the teeth 1152 are disposed along both the top and bottom surfaces 1154, 1156 of the interconnection member 1102. Additionally, it is contemplated that the shape of the teeth 1152 can be configured to facilitate expansion of the stent using very minimal expansive force, while being configured to withstand substantial compressive forces to prevent collapse of the stent. In this regard, each of the teeth 1152 can be configured as a projection extending from the interconnection member 1102 that tapers towards its distal end either in the widthwise or lengthwise dimension.

In some embodiments, each of the teeth 1152 can be shaped substantially as a right triangle or an oblique triangle, when seen from a side view such as the view in FIG. 67B. Further, as illustrated in FIG. 67B, each of the teeth 1152 can be configured as an oblique projection shaped as a paddle that has a distal free end and a proximal fixed end that is coupled to the interconnection member 1102. In this regard, the distal free end of the paddles can be configured to deflect in a substantially radial direction as the interconnection member 1102 passes through the engagement aperture 1108 during expansion of the stent. However, after the paddle exits the engagement aperture 1108 the paddle can be configured to be resilient to thereby return to an engaged position and thereby prevent the interconnection member 1102 from reversing its movement. Thus, the interconnection member 1108 can provide one-way movement of the interconnection member 1102 relative to the engagement aperture 1108. In such an embodiment, it is contemplated that the paddle or tooth 1152 can easily radially deflect to allow the expansion of the stent while engaging the engagement aperture 1108 to prevent collapsing of the stent.

Referring again to FIG. 65, it is contemplated that when the stent achieves a fully expanded state, a distal end 1160 of the interconnection member 1102 can be configured to be received into and become substantially fixed relative to the respective engagement aperture 1108. Thus, the movement of the interconnection member 1102 relative to the engagement aperture 1108 can be limited such as by the stop element mentioned above, thus preventing the interconnection member 1102 from exiting the engagement aperture 1108 after the stent becomes fully expanded. The stop members can optionally be configured as those shown in FIG. 69.

Figure 68A:
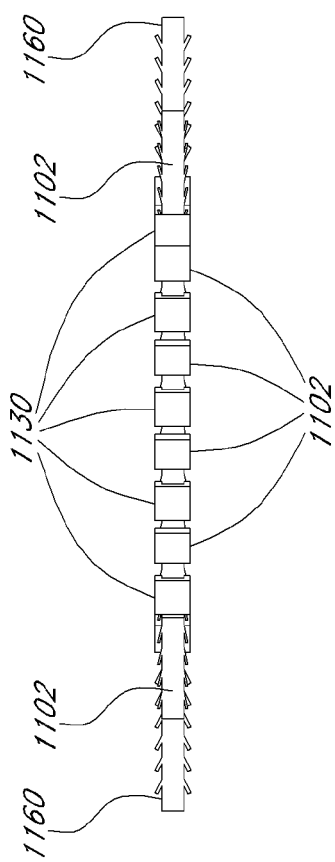
FIG. 68A is a side view of the stent shown in a nested state as in FIG. 64.
Figure 68B:
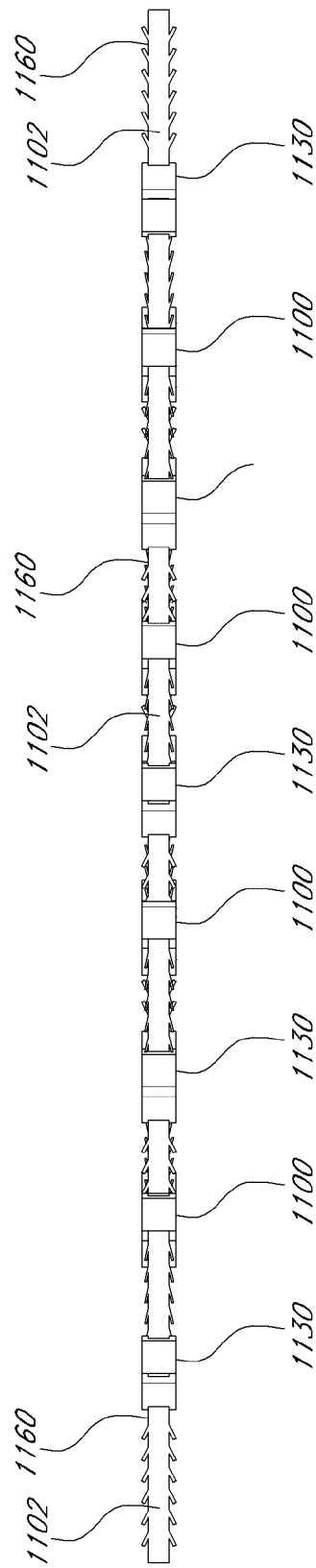
FIG. 68B is a side view of the stent shown in an expanded state as in FIG. 65.

FIGS. 68A-68B illustrate side views of the stent in an axially nested unexpanded or collapsed state and expanded state, respectively. FIG. 68A shows a linkage section 1100 and an adjacent linkage section 1100' as well as an interlink member 1130 interposed between the linkage sections 1100, 1100'. As also shown in FIG. 68A, another interlink member 1130' is disposed adjacent linkage section 1100'. In this regard, as shown in FIG. 65, adjacent interlink members 1130 can be configured such that the interconnection members 1102 are offset from each other. The interconnection members 1102 each extend in opposing circumferential directions and are received into engagement apertures (not shown) of the linkage sections 1100, 1100'. In such an embodiment, the interconnection members 1102 and linkage sections 1100 can move relative to each other in a common circumferential layer (which is illustrated as planar in FIGS. 68A-B). Thus, these components can be axially nested within each other.

Additionally, with reference to FIGS. 65, 67A, and 68A-68B, the interconnection member 1102 extending from the central crest 1140 of interlink member 1130 in FIG. 68A can be longitudinally offset from the interconnection member 1102 of interlink member 1130 in FIG. 68A can be longitudinally offset from the interconnection member 1102' extending from the central crest of the interlink member 1130'. The offset configuration of the interconnection members of adjacent interlink members can allow the interconnection member to be of a greater length so as to increase the ratio of the circumference of the stent in the expanded state to the circumference of the stent in the unexpanded state. Further, the offset configuration also provides for more uniform and stable structural properties in the stent.

In this regard, it is contemplated that the interlink member can also include apertures corresponding to each interconnection member of the interlink member and that are configured to receive at least a portion of respective interconnection members of adjacent interlink members. Such an embodiment is illustrated generally in FIGS. 64 and 65. Thus, the length of the interconnection member 1102 can be maximized by including corresponding apertures in adjacent interlink members such that when the stent is in the collapsed or unexpanded state, the interconnection members can be received into such apertures.

Furthermore, FIGS. 68A-68B also illustrate an aspect of various embodiments disclosed herein, which is that the linkage sections 1100, 1100' and the interlink members 1130, 1130' as well as the interconnection members 1102, 1102' can be configured such that in the unexpanded state, all of the elements of the stent are substantially axially nested. In some embodiments, this feature can generally eliminate any radially protruding elements that would otherwise disrupt fluid flow through the interior of the stent or cause the stent to snag as it is placed into the body lumen.

Figure 69:
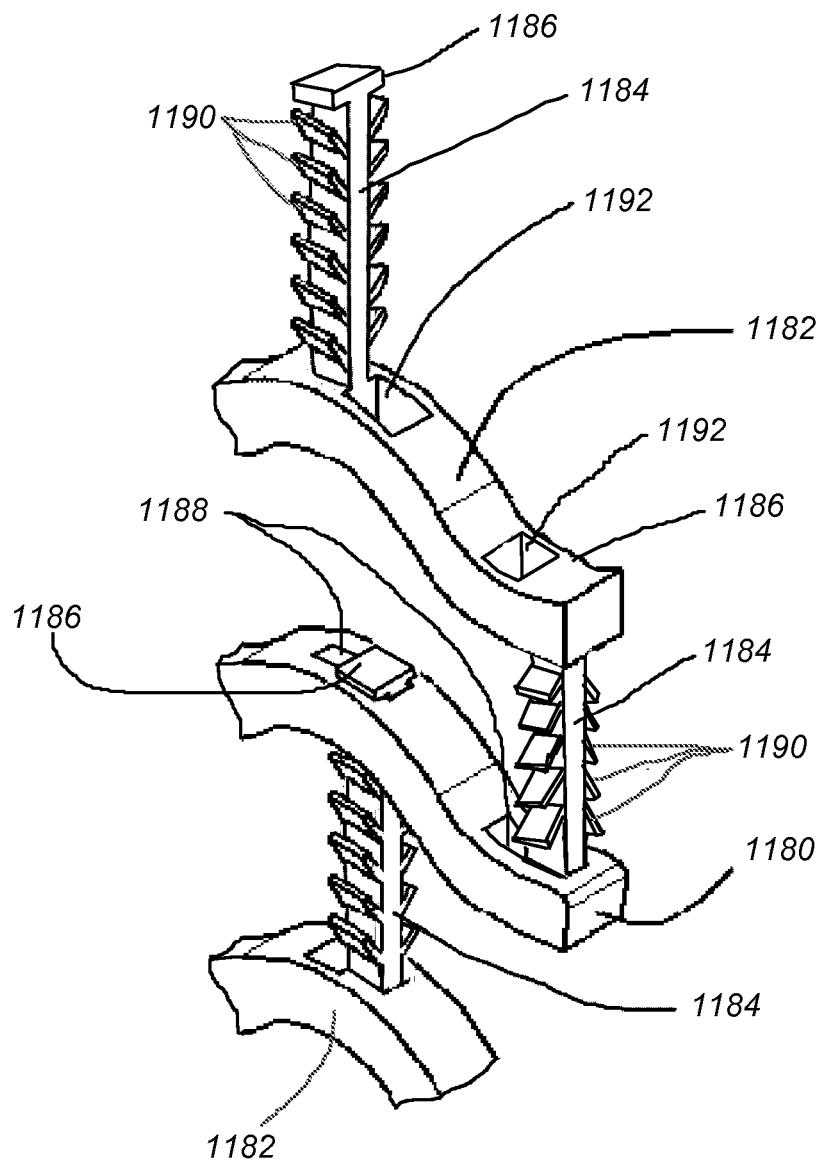
FIG. 69 is a partial perspective view of an embodiment of the stent illustrating stop members for limiting expansion of the stent.

As mentioned above, some embodiments of the stent can comprise stop members in order to limit expansion of the stent. For example, as shown in the embodiment of FIG. 69, shown in an expanded state, the stent can comprise a linkage section 1180 and an interlink member 1182. The interlink member 1182 can comprise one or more interconnection members 1184 having stop members 1186 disposed at distal ends thereof. Further, the linkage section 1180 can comprise one or more engagement apertures 1188. Further, the interlink member 1182 can comprise one or more alignment apertures 1192.

The interconnection member 1184 can comprise an elongate body with a cross-sectional dimension or passing profile that is different from the passing profile of the stop member 1186. The passing profile of the body of the interconnection member 1184, including in some embodiments, teeth 1190, can be smaller than passing profiles of the engagement aperture 1188 and the alignment aperture 1192. In this manner, the body of the interconnection member 1184 can freely move through both of the engagement aperture 1188 and the alignment aperture 1192. The stop member 1186 of the interconnection member 1184 can define a passing profile that is smaller in size that the passing profile of the alignment aperture 1192. However, the passing profile of the stop member 1186 can be larger than the passing profile of the engagement aperture 1188. Thus, the interconnection member 1184 can slide through the engagement aperture 1188 and the alignment aperture 1192 until the movement of the interconnection member 1184 is impeded due to the larger profile of the stop member 1186 than the engagement aperture 1188. In this manner, the engagement aperture 1188 can prevent further movement of the interconnection member 1184 relative to the linkage section 1180.

Thus, in some embodiments, it is contemplated that motion of the interconnection member can also be limited by the use of an enlarged distal end that interacts with the engagement aperture of the linkage section. Although FIG. 69 illustrates that only the linkage section has engagement apertures and that only the interlink member has alignment apertures and interconnection members, it is contemplated that the interconnection member and the linkage section can both comprise one or more alignment apertures, one or more engagement apertures, and one or more interconnection members. In some embodiments, the stent can comprise a series of common, repeating elements that comprise one or more alignment apertures, one or more engagement apertures, and one or more interconnection members. In other words, it is contemplated that instead of have both interlink members and linkage sections, the stent could comprise a single linkage member that repeats and is interconnected to adjacent linkage members to form the circumference of the stent.

Figure 70:
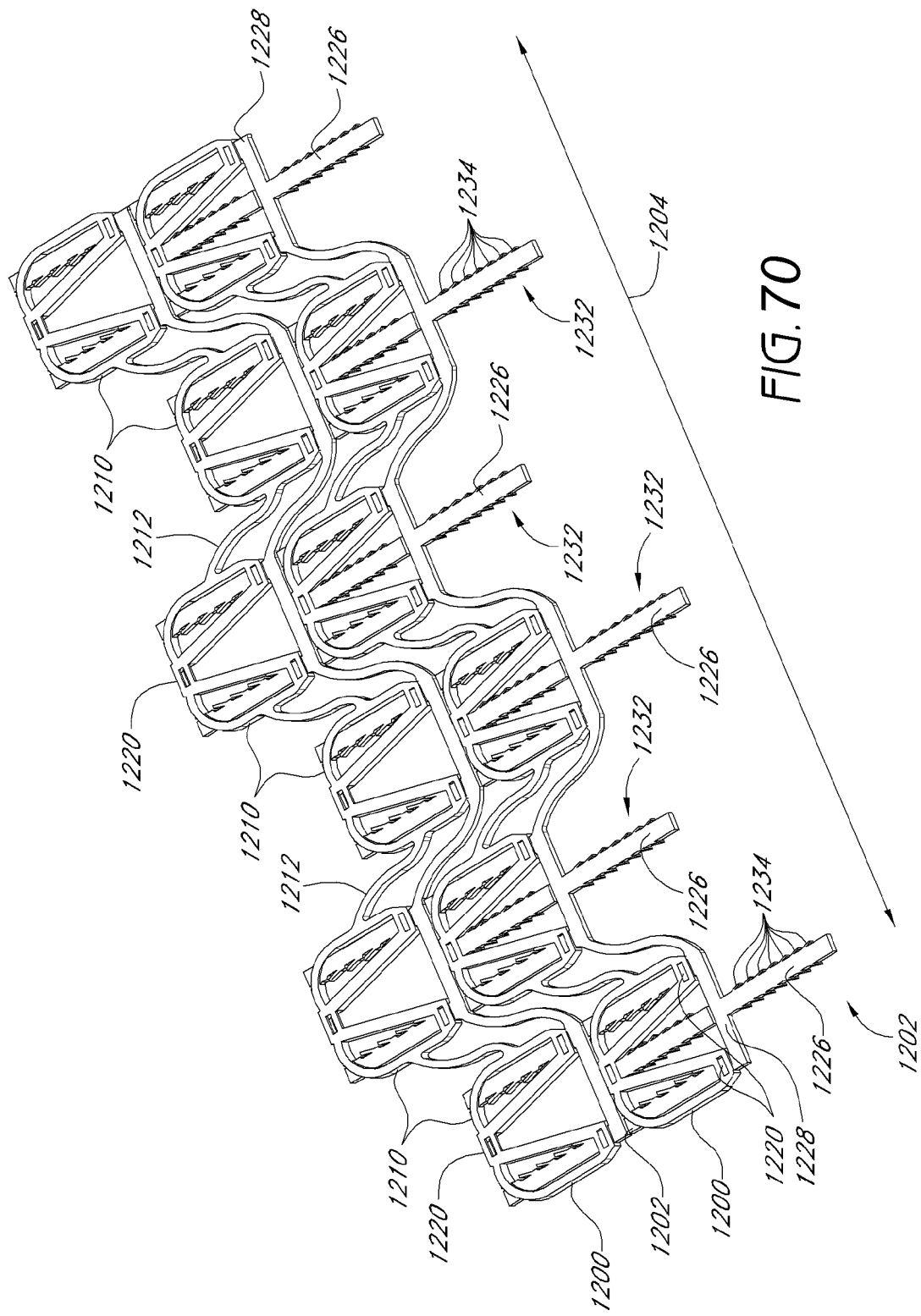
FIG. 70 is a perspective view of another axially nested slide and lock stent in a nested state illustrating features and advantages in accordance with another embodiment of the inventions.
Figure 71:
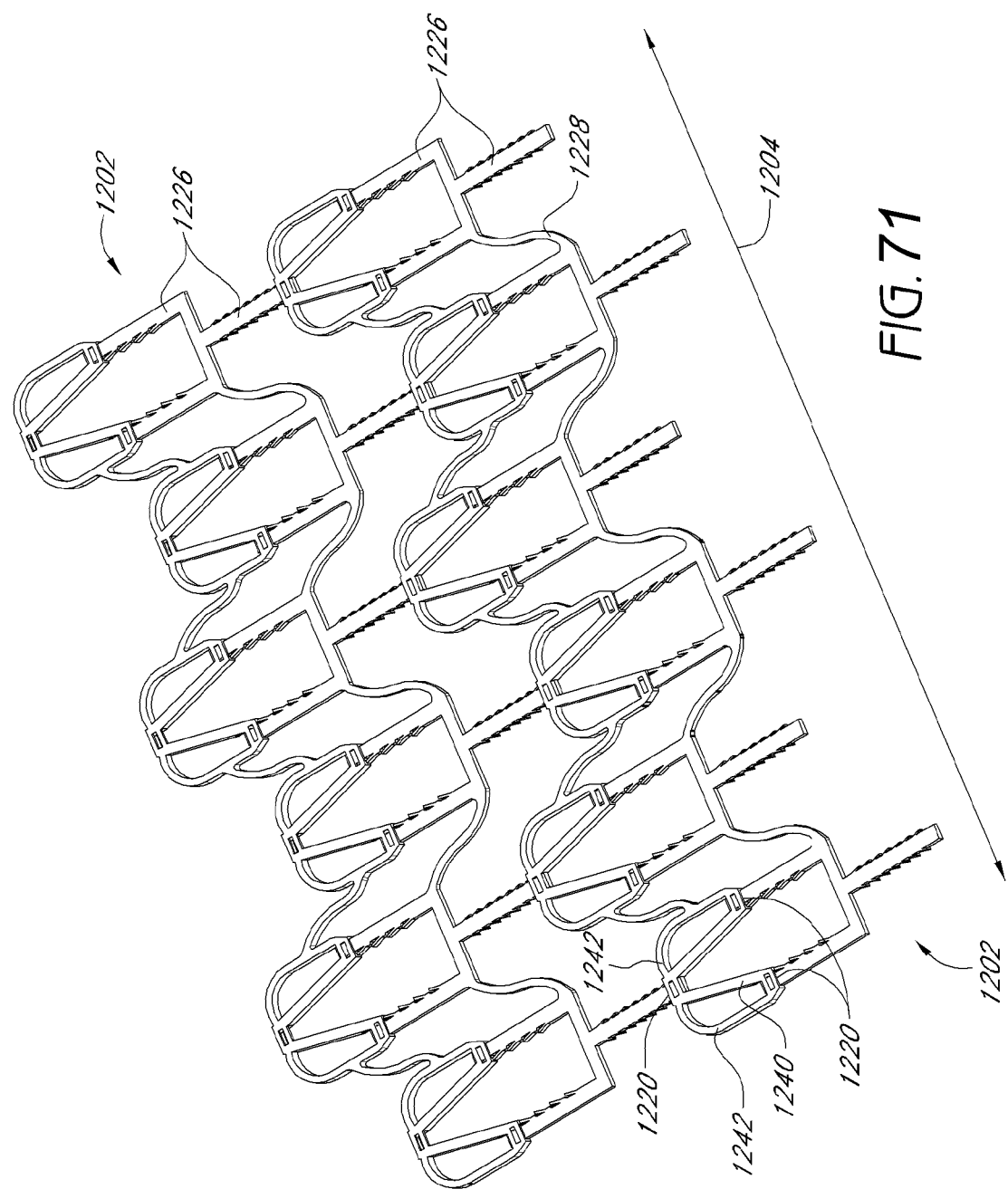
FIG. 71 is a perspective view of the axially nested slide and lock stent of FIG. 70 in an expanded state.

Referring now to FIGS. 70-71, another embodiment of an axially nested stent is shown. As with the embodiment illustrated in FIGS. 64-68B, the embodiment of the stent shown in FIGS. 70-71 illustrates only a portion of the stent which can be formed to comprise a tubular member having longitudinal and circumferential axes. Similarly, the stent can be expandable from a collapsed or axially nested unexpanded state to an expanded state. As shown in FIG. 70, in an embodiment, the tubular member can comprise a plurality of elongate linkage sections 1200 and at least one interconnector module 1202 that can be used to interconnect the linkage sections 1200.

The linkage sections 1200 can be arranged to be substantially parallel with a longitudinal axis 1204; thus, when in an assembled state, the linkage sections 1200 can be circumferentially disposed about the longitudinal axis 1204, and can thereby form the tubular member. Nevertheless, it is also noted that the linkage sections 1200 need not be oriented substantially parallel about the longitudinal axis 1204, but that other configurations can be developed that enable the linkage sections 1200 to be oriented substantially skew with respect to the longitudinal axis 1204 of the tubular member.

The embodiment of the stent illustrated in FIGS. 70-71 provides for a narrow profile and modular construction. As shown, the linkage sections 1200 can comprise a plurality of link modules 1210 that are interconnected via a plurality of respective flexible sections 1212. The flexible sections 1212 can extend intermediate side portions of adjacent link modules 1210. The flexible sections 1212 are preferably curvilinear to facilitate conformance of the shape of the stent and movement of the modules 1210 thereof during placement and expansion of the stent. Nevertheless, the flexible sections 1212 can be linear or have any variety of bends or angles along their length. Furthermore, in some embodiments, the flexible sections 1212 can extend intermediate other portions of the modules 1210, such as corners thereof.

The linkage section 1200 can be configured to include a plurality of engagement apertures 1220. The engagement apertures 1220 of the linkage section 1200 can be disposed through at least one link module 1210 in a circumferential direction (which is generally oriented orthogonally relative to the longitudinal direction 1204). In some embodiments, the engagement aperture 1220 can be a through-hole that passes from a first side of the link module 1210 to a second side of the link module 1210. However, it is also contemplated that the engagement aperture 1220 can be configured as a slot or groove into which at least a portion of the interconnector module 1202 can be received.

The embodiment of the linkage sections 1200 illustrated in FIGS. 70-71 are depicted as including three engagement apertures 1220, with a single engagement aperture 1220 on a first end of the linkage section 1200 and two engagement apertures 1220 on a second end of the linkage section 1200. However, the linkage section 1200 can be configured to include two, four, or any number of engagement apertures 1220. Further, the number of engagement apertures 1220 can correspond to the configuration of the interconnector module 1202; however, other embodiments are contemplated wherein the number of engagement apertures 1220 for a given end of the linkage section does not correspond to the configuration of the interconnector module 1202.

The interconnector module 1202 can be configured to interconnect adjacent linkage sections 1200. The interconnector module 1202 can comprise a plurality of interconnection members 1226 extending from an interconnector body 1228 thereof. As such, the interconnector module 1202 can extend from one link module 1210 toward the engagement aperture 1220 of another link module 1210. It is contemplated that the interconnection members 1226 and the interconnector body 1228 can be integrally formed from a continuous piece of material. The interconnector module 1202 can be a flexible element generally configured to circumferentially nest with respective adjacent linkage sections 1200. Further, it is contemplated that the interconnector body 1228 can be used to distribute forces throughout the structure of the stent in order to reduce localized stresses and forces.

Similar to the embodiments described above, the interconnector module 1202 can also be configured with the interconnection members 1226 of the interconnector module 1202 being offset from each other in the longitudinal direction 1204. Further, as illustrated in FIGS. 70-71, the interconnection member 1226 can comprise a ratcheting means 1232, which can comprise a plurality of teeth 1234 disposed along at least one side surface of the interconnector module 1202. Preferably, the teeth 1234 are disposed along both of the side surfaces of the interconnection member 1226.

Additionally, it is contemplated that the shape of the teeth 1234 can be configured to facilitate expansion of the stent using very minimal expansive force, while being configured to withstand substantial compressive forces to prevent collapse of the stent. In this regard, each of the teeth 1234 can be configured as a projection extending from the interconnection member 1226 that tapers towards its distal end either in the widthwise or lengthwise dimension. The teeth 1234 can also be configured as noted above, as a right triangle or an oblique triangle, when seen from a top view. Further, as illustrated in FIGS. 70-71, each of the teeth 1234 can be configured as an oblique projection shaped as a paddle that has a distal free end and a proximal fixed end that is coupled to the interconnection member 1226. The features and configuration of the paddle can be as similarly described above to prevent collapsing of the stent.

Referring again to FIG. 71, the link modules 1210 can be configured with a central A-frame 1240 and opposing lateral wings 1242. As discussed above, the engagement apertures 1220 can be disposed in the link module 1210 in a generally circumferential direction. The engagement apertures 1220 can be disposed at an apex and bases of the A-frame 1240, as shown in FIG. 71. Further, the lateral wings 1242 can comprise elongate connectors that extend from the respective bases of the A-frame 1240 to the apex thereof. The flexible sections 1212 can interconnect with the link modules 1210 along the length of the lateral wings 1242. It is contemplated that the lateral wings 1242 can allow flexibility of the stent construction and can tend to mitigate and/or reduce stresses in the stent resulting from distorting forces exerted on the stent. As a result, the unique configuration of the link module 1210 can tend to improve the structural stability of the stent and reduce localized stresses and forces.

Metal Stents and Methods of Manufacturing

Preferred materials for making the stents in accordance with some embodiments of the inventions include cobalt chrome, 316 stainless steel, tantalum, titanium, tungsten, gold, platinum, iridium, rhodium and alloys thereof or pyrolytic carbon. In still other alternative embodiments, the stents may be formed of a corrodible material, for instance, a magnesium alloy. Although preferred stent embodiments have been described as being conventional balloon expandable stents, those skilled in the art will appreciate that stent constructions according to the present inventions may also be formed from a variety of other materials to make a stent crush-recoverable. For example, in alternative embodiments, such as self expandable stents, shape memory alloys that allow for such as Nitinol and Elastinite® may be used in accordance with embodiments of the inventions.

Preferably, sheets are work-hardened prior to forming of the individual stent elements to increase strength. Methods of work hardening are well known in the art. Sheets are rolled under tension, annealed under heat and then re-worked. This may be continued until the desired modulus of hardness is obtained. Most stents in commercial use today employ 0% to 10% work hardened material in order to allow for "softer" material to deform to a larger diameter. In contrast, because expansion of the sliding and locking radial elements in accordance with embodiments of the inventions depends on sliding rather than material deformation, it is preferred to use harder materials, preferably in the range of about 25-95% work hardened material to allow for thinner stent thickness. More preferably, the stent materials are 50-90% work hardened and most preferably, the materials are 80-85% work hardened.

Preferred methods of forming the individual elements from the metal sheets may be laser cutting, laser ablation, die-cutting, chemical etching, plasma etching and stamping and water jet cutting of either tube or flat sheet material or other methods known in the art which are capable of producing high-resolution components. The method of manufacture, in some embodiments, depends on the material used to form the stent. Chemical etching provides high-resolution components at relatively low price, particularly in comparison to high cost of competitive product laser cutting. Some methods allow for different front and back etch artwork, which could result in chamfered edges, which may be desirable to help improve engagements of lockouts. Further one may use plasma etching or other methods known in the art which are capable of producing high-resolution and polished components. The current inventions is not limited to the means by which stent or stent elements can be fabricated.

Once the base geometry is achieved, the elements can be assembled numerous ways. Tack-welding, adhesives, mechanical attachment (snap-together and/or weave together), and other art-recognized methods of attachment, may be used to fasten the individual elements. Some methods allow for different front and back etch artwork, which could result in chamfered edges, which may be desirable to help improve engagements of lockouts. In one preferred method of manufacture, the components of the stent may be heat set at various desired curvatures. For example, the stent may be set to have a diameter equal to that of the deflated balloon, as deployed, at a maximum diameter, or greater than the maximum diameter. In yet another example, elements can be electropolished and then assembled, or electropolished, coated, and then assembled, or assembled and then electropolished.

In another embodiment, in particular with shape memory alloys, the stent is heat set at beyond the maximum diameter then built mid diameter than placed over catheter and reverse ratcheted and locked into smaller diameter and onto catheter with positive catch hold down mechanism to achieve a small profile and excellent retention.

Polymeric Stents

While metal stents possess certain desirable characteristics, the useful lifespan of a stent is estimated to be in the range of about 6 to 9 months, the time at which in-stent restenosis stabilizes and healing plateaus. In contrast to a metal stent, a bioresorbable stent may not outlive its usefulness within the vessel. Moreover, a bioresorbable stent may be used to deliver a greater dose of a therapeutic agent, deliver multiple therapeutic agents at the same time or at various times of its life cycle, to treat specific aspects or events of vascular disease. Additionally, a bioresorbable stent may also allow for repeat treatment of the same approximate region of the blood vessel. Accordingly, there remains an important unmet need to develop temporary (i.e., bioresorbable and/or radiopaque) stents, wherein the polymeric materials used to fabricate these stents have the desirable qualities of metal (e.g., sufficient radial strength and radiopacity, etc.), while circumventing or alleviating the many disadvantages or limitations associated with the use of permanent metal stents.

In one preferred embodiment, the stent may be formed from biocompatible polymers that are bio-resorbable (e.g., bio-erodible or bio-degradable). Bio-resorbable materials are preferably selected from the group consisting of any hydrolytically degradable and/or enzymatically degradable biomaterial. Examples of suitable degradable polymers include, but are not limited to, polyhydroxybutyrate/polyhydroxyvalerate copolymers (PHV/PHB), polyesteramides, polylactic acid, hydroxy acids (i.e. lactide, glycolide, hydroxybutyrate), polyglycolic acid, lactone based polymers, polycaprolactone, poly(propylene fumarate-co-ethylene glycol) copolymer (aka fumarate anhydrides), polyamides, polyanhydride esters, polyanhydrides, polylactic acid/polyglycolic acid with a calcium phosphate glass, polyorthesters, silk-elastin polymers, polyphosphazenes, copolymers of polylactic acid and polyglycolic acid and polycaprolactone, aliphatic polyurethanes, polyhydroxy acids, polyether esters, polyesters, polydepsidpetides, polysaccharides, polyhydroxyalkanoates, and copolymers thereof.

In one mode, the degradable materials are selected from the group consisting of poly(glycolide-trimethylene carbonate), poly(alkylene oxalates), polyaspartimic acid, polyglutarunic acid polymer, poly-p-dioxanone, poly-.beta.-dioxanone, asymmetrically 3,6-substituted poly-1,4-dioxane-2,5-diones, polyalkyl-2-cyanoacrylates, polydepsipeptides (glycine-DL-lactide copolymer), polydihydropyranes, polyalkyl-2-cyanoacrylates, poly-.beta.-maleic acid (PMLA), polyalkanotes and poly-.beta.-alkanoic acids. There are many other degradable materials known in the art. (See e.g., Biomaterials Science: An Introduction to Materials in Medicine (29 Jul., 2004) Ratner, Hoffman, Schoen, and Lemons; and Atala, A., Mooney, D. Synthetic Biodegradable Polymer Scaffolds. 1997 Birkhauser, Boston; incorporated herein by reference).

Further still, in a more preferred embodiment, the stents may be formed of a polycarbonate material, such as, for example, tyrosine-derived polycarbonates, tyrosine-derived polyarylates, iodinated and/or brominated tyrosine-derived polycarbonates, iodinated and/or brominated tyrosine-derived polyarylates. For additional information, see U.S. Pat. Nos. 5,099,060, 5,198,507, 5,587,507, 5,658,995, 6,048,521, 6,120,491, 6,319,492, 6,475,477, 5,317,077, and 5,216,115, each of which is incorporated by reference herein. In another preferred embodiment, the polymer is any of the biocompatible, bioabsorbable, radiopaque polymers disclosed in U.S. patent application Nos. 60/601,526; 60/586,796; and Ser. No. 10/952,202 the entire disclosures of which are incorporated herein by reference thereto.

Natural polymers (biopolymers) include any protein or peptide. Preferred biopolymers may be selected from the group consisting of alginate, cellulose and ester, chitosan, collagen, dextran, elastin, fibrin, gelatin, hyaluronic acid, hydroxyapatite, spider silk, cotton, other polypeptides and proteins, and any combinations thereof.

In yet another alternative embodiment, shape-shifting polymers may be used to fabricate stents constructed according to the present inventions. Suitable shape-shifting polymers may be selected from the group consisting of polyhydroxy acids, polyorthoesters, polyether esters, polyesters, polyamides, polyesteramides, polydepsidpetides, aliphatic polyurethanes, polysaccharides, polyhydroxyalkanoates, and copolymers thereof. For addition disclosure on bio-degradable shape-shifting polymers, see U.S. Pat. No. 6,160,084, which is incorporated by reference herein. For additional disclosure on shape memory polymers, see U.S. Pat. Nos. 6,388,043 and 6,720,402, each of which are incorporated by reference herein. Further the transition temperature may be set such that the stent is in a collapsed condition at a normal body temperature. However, with the application of heat during stent placement and delivery, such as via a hot balloon catheter or a hot liquid (e.g., saline) perfusion system, the stent expands to assume its final diameter in the body lumen. When a thermal memory material is used, it may provide a crush-recoverable structure.

Further still, stents may be formed from biocompatible polymers that are biostable (e.g., non-degrading and non-erodible). Examples of suitable non-degrading materials include, but are not limited to, polyurethane, Delrin, high density polyethylene, polypropylene, and poly(dimethyl siloxane).

In some embodiments, the layers may comprise or contain any example of thermoplastics, such as the following, among others: fluorinated ethylene-propylene, poly(2-hydroxyethlmethacrylate (aka pHEMA), poly(ethylene terephthalate) fiber (aka Dacron®) or film (Mylar®), poly(methyl methacrylate (aka PMMA), Poly(tetrafluoroethylene) (aka PTFE and ePTFE and Gore-Tex®), poly(vinylchloride), polyacrylates and polyacrylonitrile (PAN), polyamides (aka Nylon), polycarbonates and polycarbonate urethanes, polyethylene and poly(ethylene-co-vinyl acetate), polypropylene, polypropylene, polystyrene, polysulphone, polyurethane and polyetherurethane elastomers such as Pellethane® and Estane®, Silicone rubbers, Siloxane, polydimethylsiloxane (aka PDMS), Silastic®, Siliconized Polyurethane.

Methods of Manufacturing and Assembling Polymeric Stents

Where plastic and/or degradable materials are used, the elements may be made using laser ablation with a screen, stencil or mask; solvent casting; forming by stamping, embossing, compression molding, centripetal spin casting and molding; extrusion and cutting, three-dimensional rapid prototyping using solid free-form fabrication technology, stereolithography, selective laser sintering, or the like; etching techniques comprising plasma etching; textile manufacturing methods comprising felting, knitting, or weaving; molding techniques comprising fused deposition modeling, injection molding, room temperature vulcanized molding, or silicone rubber molding; casting techniques comprising casting with solvents, direct shell production casting, investment casting, pressure die casting, resin injection, resin processing electroforming, or injection molding or reaction injection molding. Certain preferred embodiments with the present polymers may be shaped into stents via combinations of two or more thereof, and the like.

Such processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. For additional information, see U.S. patent application Ser. No. 10/655,338, which is incorporated by reference herein.

Stents of the preferred embodiment are manufactured with elements prepared in full stent lengths or in partial lengths of which two or more are then connected or attached. If using partial lengths, two or more may be connected or attached to comprise a full length stent. In this arrangement the parts are assembled to give rise to a central opening. The assembled full or partial length parts and/or modules may be assembled by inter-weaving them in various states, from a collapsed state, to a partially expanded state, to an expanded state.

Further, elements may be connected or attached by solvent or thermal bonding, or by mechanical attachment. If bonding, preferred methods of bonding comprise the use of ultrasonic radiofrequency or other thermal methods, and by solvents or adhesives or ultraviolet curing processes or photoreactive processes. The elements may be rolled by thermal forming, cold forming, solvent weakening forming and evaporation, or by preforming parts before linking.

Another method of manufacture allows for assembly of the stent components that have been cut out and assembled into flat series of radial elements. The linkage elements between longitudinally adjacent series of radial elements may be connected (e.g., by welding, inter-weaving frame elements, etc.), the flat sheets of material are rolled to form a tubular member. Coupling arms from floating coupling elements and end portions may be joined (e.g., by welding) to maintain the tubular shape. In embodiments that do not include coupling elements, the end portions of the top and bottom radial elements in a series may be joined. Alternatively, where sliding is desired throughout the entire circumference, a sliding and locking articulation can be made between the end portion of the top radial element and the rib(s)/rails of the bottom radial element (e.g., by tack-welding, heat-staking or snap-together). Similarly, a corresponding articulation can be made between the end portion of the bottom radial element and the rib(s)/rails of the top radial element.

Rolling of the flat series of module(s) to form a tubular member can be accomplished by any means known in the art, including rolling between two plates, which are each padded on the side in contact with the stent elements. One plate is held immobile and the other can move laterally with respect to the other. Thus, the stent elements sandwiched between the plates may be rolled about a mandrel by the movement of the plates relative to one another. Alternatively, 3-way spindle methods known in the art may also be used to roll the tubular member. Other rolling methods that may be used in accordance with the present inventions include those used for "jelly-roll" designs, as disclosed for example, in U.S. Pat. Nos. 5,421,955, 5,441,515, 5,618,299, 5,443,500, 5,649,977, 5,643,314 and 5,735,872; the disclosures of which are incorporated herein in their entireties by reference thereto.

The construction of the slide-and-lock stents in these fashions provides a great deal of benefit over the prior art. The construction of the locking mechanism is largely material-independent. This allows the structure of the stent to comprise high strength materials, not possible with designs that require deformation of the material to complete the locking mechanism. The incorporation of these materials will allow the thickness required of the material to decrease, while retaining the strength characteristics of thicker stents. In preferred embodiments, the frequency of catches, stops or teeth present on selected circumferential elements prevents unnecessary recoil of the stent subsequent to expansion.

Radiopacity

Traditional methods for adding radiopacity to a medical product include the use of metal bands, inserts and/or markers, electrochemical deposition (i.e., electroplating), or coatings. The addition of radiopacifiers (i.e., radiopaque materials) to facilitate tracking and positioning of the stent could be accommodated by adding such an element in any fabrication method, by absorbing into or spraying onto the surface of part or all of the device. The degree of radiopacity contrast can be altered by element content.

For plastics and coatings, radiopacity may be imparted by use of monomers or polymers comprising iodine or other radiopaque elements, i.e., inherently radiopaque materials. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, a halogen such as iodine and/or bromine may be employed for its radiopacity and antimicrobial properties.

Multi-Material Vascular Prosthesis

In still other alternative embodiments, various materials (e.g., metals, polymers, ceramics, and therapeutic agents) may be used to fabricate stent embodiments. The embodiments may comprise: 1) differentially layered materials (through the vertical or radial axis) to create a stack of materials (materials may be stacked in any configuration, e.g., parallel, staggered, etc.); 2) spatially localized materials which may vary along the long axis and/or thickness of the stent body; 3) materials that are mixed or fused to create a composite stent body; 4) embodiments whereby a material is laminated (or coated) on the surface of the stent body (see Stent Surface Coatings with Functional Properties as well as see Therapeutic Agents Delivered by Stents); and, 5) stents comprised of 2 or more parts where at least one part is materially distinct from a second part, or any combination thereof.

The fashioning of a slide-and-lock multi-material stent can have between two or more materials. Thickness of each material may vary relative to other materials. This approach as needed or desired allows an overall structural member to be built with each material having one or more functions contributing towards enabling prosthesis function which includes, but is not limited to: 1) enabling mechanical properties for stent performance as defined by ultimate tensile strength, yield strength, Young's modulus, elongation at yield, elongation at break, and Poisson's ratio; 2) enabling the thickness of the substrate, geometrical shape (e.g., bifurcated, variable surface coverage); 3) enabling chemical properties of the material that bear relevance to the materials performance and physical state such as rate of degradation and resorption (which may impact therapeutic delivery), glass transition temperature, melting temperature, molecular weight; 4) enabling radiopacity or other forms of visibility and detection; 5) enabling radiation emission; 6) enabling delivery of a therapeutic agent (see Therapeutic Agents Delivered by Stents); and 7) enabling stent retention and/or other functional properties (see Stent Surface Coatings with Functional Properties).

In some embodiments, the materials may comprise load-bearing properties, elastomeric properties, mechanical strength that is specific to a direction or orientation e.g., parallel to another material and/or to the long axis of the stent, or perpendicular or uniform strength to another material and/or stent. The materials may comprise stiffeners, such as the following, boron or carbon fibers, pyrolytic carbon. Further, stents may be comprised of at least one re-enforcement such a fibers, nanoparticles or the like.

In another preferred mode of the inventions, the stent is made, at least in part, from a polymeric material, which may be degradable. The motivation for using a degradable stent is that the mechanical support of a stent may only be necessary for several weeks. In some embodiments, bioresorbable materials with varying rates of resorption may be employed. For additional information, see U.S. patent application Ser. No. 10/952,202 and No. 60/601,526, which are incorporated by reference herein. Degradable polymeric stent materials may be particularly useful if it also controls restenosis and thrombosis by delivering pharmacologic agents. Degradable materials are well suited for therapeutic delivery (see Therapeutic Agents Delivered by Stents).

In some embodiments, the materials may comprise or contain any class of degradable polymer as previously defined. Along with variation in the time of degradation and/or resorption the degradable polymer may have other qualities that are desirable. For example, in some embodiments the materials may comprise or contain any example of natural polymers (biopolymers) and/or those that degrade by hydrolytic and/or enzymatic action. In some embodiments, the material may comprise or contain any example of hydrogels that may or may not be thermally reversible hydrogels, or any example of a light or energy curable material, or magnetically stimulateable (responding) material. Each of these responses may provide for a specific functionality.

In some embodiments, the materials may comprise or be made from or with constituents which has some radiopaque material alternatively, a clinically visible material which is visible by x-ray, fluoroscopy, ultrasound, MRI, or Imatron Electron Beam Tomography (EBT).

In some embodiments, one or more of the materials may emit predetermined or prescribed levels of therapeutic radiation. In one embodiment, the material can be charged with beta radiation. In another embodiment, the material can be charged with Gamma radiation. In yet another embodiment, the material can be charged with a combination of both Beta and Gamma radiation. Stent radioisotopes that may be used include, but are not limited to, 103Pd and 32P (phosphorus-32) and two neutron-activated examples, 65Cu and 87Rb2O, (90)Sr, tungsten-188 (188).

In some embodiments, one or more of the materials may comprise or contain a therapeutic agent. The therapeutic agents may have unique, delivery kinetics, mode of action, dose, half-life, purpose, et cetera. In some embodiments, one or more of the materials comprise an agent which provides a mode and site of action for therapy for example by a mode of action in the extracellular space, cell membrane, cytoplasm, nucleus and/or other intracellular organelle. Additionally an agent that serves as a chemoattractant for specific cell types to influence tissue formation and cellular responses for example host-biomaterial interactions, including anti-cancer effects. In some embodiments, one or more of the materials deliver cells in any form or state of development or origin. These could for example be encapsulated in a degradable microsphere, or mixed directly with polymer, or hydrogel and serve as vehicle for pharmaceutical delivery. Living cells could be used to continuously deliver pharmaceutical type molecules, for instance, cytokines and growth factors. Nonliving cells may serve as a limited release system. For additional concepts of therapeutic delivery, see the section entitled: Therapeutic Agents Delivered by Stents.

Therapeutic Agents Delivered by Stents

In another preferred variation, the stent further comprises an amount of a therapeutic agent (as previously defined for a pharmaceutical agent and/or a biologic agent) sufficient to exert a selected therapeutic effect. In some preferred embodiments of the stent (e.g., polymer stents and multi-material stents) the therapeutic agent is contained within the stent as the agent is blended with the polymer or admixed by other means known to those skilled in the art. In other preferred embodiments of the stent, the therapeutic agent is delivered from a polymer coating on the stent surface. In some preferred embodiments of the stent a therapeutic agent is localized in or around a specific structural aspect of the device.

In another preferred variation the therapeutic agent is delivered by means of a non-polymer coating. In other preferred embodiments of the stent, the therapeutic agent is delivered from at least one region or one surface of the stent. The therapeutic can be chemically bonded to the polymer or carrier used for delivery of the therapeutic from at least one portion of the stent and/or the therapeutic can be chemically bonded to the polymer that comprises at least one portion of the stent body. In one preferred embodiment, more than one therapeutic agent may be delivered.

The amount of the therapeutic agent is preferably sufficient to inhibit restenosis or thrombosis or to affect some other state of the stented tissue, for instance, heal a vulnerable plaque, and/or prevent rupture or stimulate endothelialization or limit other cell types from proliferating and from producing and depositing extracellular matrix molecules. The agent(s) may be selected from the group consisting of antiproliferative agents, anti-inflammatory, anti-matrix metalloproteinase, and lipid lowering, cholesterol modifying, anti-thrombotic and antiplatelet agents, in accordance with preferred embodiments of the present inventions. Some of these preferred anti-proliferative agents that improve vascular patency include without limitation paclitaxel, Rapamycin, ABT-578, everolimus, dexamethasone, nitric oxide modulating molecules for endothelial function, tacrolimus, estradiol, mycophenolic acid, C6-ceramide, actinomycin-D and epothilones, and derivatives and analogs of each.

Some of these preferred agents act as an antiplatelet agent, antithrombin agent, compounds to address other pathologic events and/or vascular diseases. Various therapeutic agents may be classified in terms of their sites of action in the host: agents that exert their actions extracellularly or at specific membrane receptor sites, those that act on the plasma membrane, within the cytoplasm, and/or the nucleus.

In addition to the aforementioned, therapeutic agents may include other pharmaceutical and/or biologic agents intended for purposes of treating body lumens other than arteries and/or veins). Therapeutic agents may be specific for treating nonvascular body lumens such as digestive lumens (e.g., gastrointestinal, duodenum and esophagus, biliary ducts), respiratory lumens (e.g., tracheal and bronchial), and urinary lumens (e.g., urethra). Additionally such embodiments may be useful in lumens of other body systems such as the reproductive, endocrine, hematopoietic and/or the integumentary, musculoskeletal/orthopedic and nervous systems (including auditory and ophthalmic applications); and finally, stent embodiments with therapeutic agents may be useful for expanding an obstructed lumen and for inducing an obstruction (e.g., as in the case of aneurysms).

Therapeutic release may occur by controlled release mechanisms, diffusion, interaction with another agent(s) delivered by intravenous injection, aerosolization, or orally. Release may also occur by application of a magnetic field, an electrical field, or use of ultrasound.

Stent Surface Coatings with Functional Properties

In addition to stents that may deliver a therapeutic agent, for instance delivery of a biological polymer on the stent such as a repellant phosphorylcholine, the stent may be coated with other bioresorbable polymers predetermined to promote biological responses in the body lumen desired for certain clinical effectiveness. Further the coating may be used to mask (temporarily or permanently) the surface properties of the polymer used to comprise the stent embodiment. The coating may be selected from the broad class of any biocompatible bioresorbable polymer which may include any one or combination of halogenated and/or non-halogenated which may or may not comprise any poly(alkylene glycol). These polymers may include compositional variations including homopolymers and heteropolymers, stereoisomers and/or a blend of such polymers. These polymers may include for example, but are not limited to, polycarbonates, polyarylates, poly(ester amides), poly(amide carbonates), trimethylene carbonate, polycaprolactone, polydioxane, polyhydroxybutyrate, poly-hydroxyvalerate, polyglycolide, polylactides and stereoisomers and copolymers thereof, such as glycolide/lactide copolymers. In a preferred embodiment, the stent is coated with a polymer that exhibits a negative charge that repels the negatively charged red blood cells' outer membranes thereby reducing the risk of clot formation. In another preferred embodiment, the stent is coated with a polymer that exhibits an affinity for cells, (e.g., endothelial cells) to promote healing. In yet another preferred embodiment, the stent is coated with a polymer that repels the attachment and/or proliferation of specific cells, for instance arterial fibroblasts and/or smooth muscle cells in order to lessen restenosis and/or inflammatory cells such as macrophages.

Described above are the stents of the present inventions that may be modified with a coating to achieve functional properties that support biological responses. Such coatings or compositions of material with a therapeutic agent may be formed on stents or applied in the process of making a stent body via techniques such as dipping, spray coating, crosslinking combinations thereof, and the like. Such coatings or compositions of material may also serve purpose other than delivering a therapeutic, such as to enhance stent retention on a balloon when the coating is placed intraluminally on the stent body and/or placed over the entire device after the stent is mounted on the balloon system to keep the stent in a collapsed formation. Other purposes can be envisioned by those skilled in the art when using any polymer material.

In one aspect of the inventions, a stent would have a coating applied that has specific mechanical properties. The properties may include inter alia thickness, tensile strength, glass transition temperature, and surface finish. The coating is preferably applied prior to final crimping or application of the stent to the catheter. The stent may then be applied to the catheter and the system may have either heat or pressure or both applied in a compressive manner. In the process, the coating may form frangible bonds with both the catheter and the other stent surfaces. The bonds would enable a reliable method of creating stent retention and of holding the stent crossing profile over time. The bonds would break upon the balloon deployment pressures. The coating would be a lower Tg than the substrate to ensure no changes in the substrate.

Stent Deployment

First, a catheter is provided wherein an expandable member, preferably an inflatable balloon, such as an angioplasty balloon, is provided along a distal end portion. One example of a balloon catheter for use with a stent is described in U.S. Pat. No. 4,733,665 to Palmaz, which is incorporated by reference herein. A stent on a catheter is commonly collectively referred to as a stent system. Catheters include but are not limited to over-the-wire catheters, coaxial rapid-exchange designs and the Medtronic Zipper Technology that is a new delivery platform. Such catheters may include for instance those described in Bonzel U.S. Pat. Nos. 4,762,129 and 5,232,445 and by Yock U.S. Pat. Nos. 4,748,982; 5,496,346; 5,626,600; 5,040,548; 5,061,273; 5,350,395; 5,451,233 and 5,749,888. Additionally, catheters may include for instance those as described in U.S. Pat. Nos. 4,762,129; 5,092,877; 5,108,416; 5,197,978; 5,232,445; 5,300,085; 5,445,646; 5,496,275; 5,545,135; 5,545,138; 5,549,556; 5,755,708; 5,769,868; 5,800,393; 5,836,965; 5,989,280; 6,019,785; 6,036,715; 5,242,399; 5,158,548; and 6,007,545. The disclosures of the above-cited patents are incorporated herein in their entirety by reference thereto.

Catheters may be specialized with highly compliant polymers and for various purposes such as to produce an ultrasound effect, electric field, magnetic field, light and/or temperature effect. Heating catheters may include for example those described in U.S. Pat. Nos. 5,151,100, 5,230,349; 6,447,508; and 6,562,021 as well as WO9014046A1. Infrared light emitting catheters may include for example those described in U.S. Pat. Nos. 5,910,816 and 5,423,321. The disclosures of the above-cited patents and patent publications are incorporated herein in their entirety by reference thereto.

An expandable member, such as an inflatable balloon, is preferably used to deploy the stent at the treatment site. As the balloon is expanded, the radial force of the balloon overcomes the initial resistance of the constraining mechanism, thereby allowing the stent to expand. As the balloon is inflated, the radial elements slide with respect to each other along the surface of the balloon until the stent has been expanded to a desired diameter.

The stent of embodiments of the inventions are adapted for deployment using conventional methods known in the art and employing percutaneous transluminal catheter devices. This includes deployment in a body lumen by means of a balloon expandable design whereby expansion is driven by the balloon expanding. Alternatively, the stent may be mounted onto a catheter that holds the stent as it is delivered through the body lumen and then releases the stent and allows it to self-expand into contact with the body lumen. The restraining means may comprise a removable sheath and/or a mechanical aspect of the stent design.

Some embodiments of the inventions may be useful in coronary arteries, carotid arteries, vascular aneurysms (when covered with a sheath), and peripheral arteries and veins (e.g., renal, iliac, femoral, popliteal, subclavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may or may not require a sheath covering the stent.

It is desirable to have the stent radially expand in a uniform manner. Alternatively, the expanded diameter may be variable and determined by the internal diameter and anatomy of the body passageway to be treated. Accordingly, uniform and variable expansion of the stent that is controlled during deployment is not likely to cause a rupture of the body passageway. Furthermore, the stent will resist recoil because the locking means resist sliding of the mating elements. Thus, the expanded intraluminal stent will continue to exert radial pressure outward against the wall of the body passageway and will therefore, not migrate away from the desired location.

From the foregoing description, it will be appreciated that a novel approach for expanding a lumen has been disclosed. While the components, techniques and aspects of the inventions have been described with a certain degree of particularity, it is manifest that many changes may be made in the specific designs, constructions and methodology herein above described without departing from the spirit and scope of this disclosure.

While a number of preferred embodiments of the inventions and variations thereof have been described in detail, other modifications and methods of using and medical applications for the same will be apparent to those of skill in the art. Accordingly, it should be understood that various applications, modifications, materials, and substitutions may be made of equivalents without departing from the spirit of the inventions or the scope of the claims.

Various modifications and applications of the inventions may occur to those who are skilled in the art, without departing from the true spirit or scope of the inventions. It should be understood that the inventions is not limited to the embodiments set forth herein for purposes of exemplification, but is to be defined only by a fair reading of the appended claims, including the full range of equivalency to which each element thereof is entitled.

REFERENCES

Some of the references cited herein are listed below, the entirety of each one of which is hereby incorporated by reference herein:

Charles R, Sandirasegarane L, Yun J, Bourbon N, Wilson R, Rothstein R P, et al. Ceramide-Coated Balloon Catheters Limit Neointimal Hyperplasia after Stretch Injury in Carotid Arteries. Circ Res 2000; 87(4):282-288.

Coroneos E, Martinez M, McKenna S, Kester M. Differential regulation of sphingomyelinase and ceramidase activities by growth factors and cytokines. Implications for cellular proliferation and differentiation. J Biol Chem 1995; 270 (40):23305-9.

Coroneos E, Wang Y, Panuska J R, Templeton D J, Kester M. Sphingolipid metabolites differentially regulate extracellular signal-regulated kinase and stress-activated protein kinase cascades. Biochem J 1996; 316(Pt 1):13-7.

Jacobs L S, Kester M. Sphingolipids as mediators of effects of platelet-derived growth factor in vascular smooth muscle cells. Am J Physiol 1993; 265(3 Pt 1):C740-7.

Tanguay J F, Zidar J P, Phillips H R, 3rd, Stack R S. Current status of biodegradable stents. Cardiol Clin 1994; 12(4): 699-713.

Nikol S, Huehns T Y, Hofling B. Molecular biology and post-angioplasty restenosis. Atherosclerosis 1996; 123(1-2): 17-31.

Biomaterials Science: An Introduction to Materials in Medicine (29 Jul., 2004) Ratner, Hoffman, Schoen, and Lemons

What is claimed is:

1. An axially nested stent being expandable from an axially nested unexpanded state to an expanded state, the stent comprising a tubular member having a longitudinal axis, the tubular member comprising:
    a plurality of linkage sections comprising engagement apertures, the engagement apertures being disposed through the linkage sections in a circumferential direction; and
    at least one interconnector module comprising an interlink body and longitudinally spaced interconnection members,
    each interlink body having a generally curved shape and extending in a longitudinal direction,
    the longitudinally spaced interconnection members alternatingly extending from each interlink body in opposing circumferential directions, the interconnection members passing through the engagement apertures of the linkage sections,
    the at least one interconnector module being configured to allow one-way slidable movement of the linkage sections relative to at least one interlink body during expansion of the stent from the axially nested unexpanded state to the expanded state.

2. The stent of claim 1, wherein each linkage section comprises a plurality of link elements interconnected via flexible sections, the link elements each defining proximal and distal ends, the flexible sections extending intermediate the proximal end of a given link element and the distal end of another given link element to interconnect the plurality of link elements in an end-to-end manner, wherein the engagement apertures are disposed in at least one link element of the linkage section, the engagement apertures being disposed through the at least one link element in the circumferential direction.

3. The stent of claim 1, wherein at least first, second, and third linkage sections are circumferentially spaced apart from each other and connected via a plurality of interconnector modules, the interconnection members of the interconnector modules connecting the first and second linkage sections being longitudinally spaced apart from the interconnection members of the interconnector modules connecting the second and third linkage sections.

4. The stent of claim 1, wherein each interlink body has the shape of a sinusoidal curve.

5. The stent of claim 1, wherein one of the interconnection members extends from a central crest of each interlink body and a pair of the interconnection members extend from respective end troughs of each interlink body.

6. The stent of claim 1, wherein the linkage sections have the generally curved shape that is complementary to a curved shape of each interlink body.

7. The stent of claim 1, wherein a distal tip of at least one of the interconnection members passes through and passes out of the corresponding engagement aperture.

8. The stent of claim 1, wherein at least one of the interconnection members passes completely through a corresponding engagement aperture.

9. The stent of claim 1, further comprising a plurality of interconnector modules, wherein adjacent interconnector modules are spaced longitudinally from each other and are not directly connected to each other.

10. A stent comprising:
    a plurality of linkage sections each comprising one or more engagement apertures, the one or more engagement apertures being disposed through the respective linkage sections in a circumferential direction; and
    at least one interconnector module comprising:
        an interlink body extending in a longitudinal direction, and
        longitudinally spaced interconnection members that alternatingly extend from the interlink body in opposing circumferential directions, one of the interconnection members extending from a central crest of the interlink body and a pair of the interconnection members extending from respective end troughs of the interlink body,
        each of the interconnection members comprising an end that is at least partially received into a respective one of the one or more engagement apertures;
    the at least one interconnector module being configured to allow one-way slidable movement of the linkage sections relative to each interlink body of the at least one interconnector module during expansion of the stent from an axially nested unexpanded state to an expanded state.

11. The stent of claim 10, wherein each interlink body has the shape of a sinusoidal curve.

12. The stent of claim 10, wherein the linkage sections each comprise a plurality of engagement apertures.

13. The stent of claim 10, wherein each of the plurality of linkage sections has a curved shape, and wherein each interconnector module has a curved shape that is complementary to the linkage sections.

14. The stent of claim 10, further comprising at least two interconnector modules, wherein each interconnector module is spaced longitudinally from an adjacent interconnector module, and adjacent interconnector modules are not directly connected to each other.

15. An axially nested stent being expandable from an axially nested unexpanded state to an expanded state, the stent comprising a tubular member having a longitudinal axis, the tubular member comprising:
    a plurality of linkage sections comprising a plurality of linkage elements each having at least one engagement aperture, each of the at least one engagement apertures being disposed through the respective linkage elements in a circumferential direction;
    a flexible section extending intermediate longitudinally adjacent linkage elements; and a plurality of interconnector modules arranged in a generally longitudinal alignment, each of the interconnector modules comprising;
an interlink body, and
a plurality of interconnection members extending from the interlink body in opposing circumferential directions;
each of the interconnection members being configured to engage the at least one engagement aperture of a respective one of the linkage elements, each of the plurality of interconnector modules being configured to move independently relative to an adjacent one of the plurality of interconnector modules to allow one-way slidable movement of the linkage sections relative to the interlink bodies during expansion of the stent from the axially nested unexpanded state to the expanded state.

16. The stent of claim 15, wherein at least first, second, and third linkage sections are circumferentially spaced apart from each other and connected via the interconnection members of the interconnection modules, the interconnection members connecting the first and second linkage sections being longitudinally spaced apart from the interconnection members connecting the second and third linkage sections.

17. The stent of claim 15, wherein each interlink body has a generally curved shape.

18. The stent of claim 15, wherein each interlink body has the shape of a sinusoidal curve.

19. The stent of claim 15, wherein one of the interconnection members extends from a central crest of each interlink body and a pair of the interconnection members extend from respective end troughs of each interlink body.

20. The stent of claim 15, wherein the linkage sections each comprise a plurality of engagement apertures.

21. The stent of claim 15, wherein the linkage elements have a curved shape that is complementary to a curved shape of each interlink body.

22. The stent of claim 15, wherein the interconnector modules move independently relative adjacent interconnector modules in the circumferential direction.

23. The stent of claim 15, wherein the interconnector modules move independently relative to adjacent interconnector modules in a longitudinal direction.

24. The stent of claim 15, wherein the interconnector modules are aligned in a longitudinal direction and are spaced longitudinally from adjacent interconnector modules.

25. The stent of claim 15, wherein the interconnector modules are aligned in a longitudinal direction and are not joined with adjacent interconnector modules.

26. The stent of claim 15, wherein each interconnector module is spaced longitudinally from adjacent interconnector modules, and adjacent interconnector modules are not directly connected to each other.

27. A stent comprising:
a plurality of linkage sections each comprising at least one engagement aperture, the at least one engagement aperture being disposed through the respective linkage sections in a circumferential direction; and
a plurality of interconnector modules aligned in a longitudinal direction, each of the plurality of interconnector modules:
being spaced longitudinally from another, longitudinally adjacent, interconnector module of the plurality of interconnector modules, and
comprising an interlink body extending in a longitudinal direction and longitudinally spaced interconnection members extending from the interlink body in opposing circumferential directions,
the interconnection members of each respective one of the plurality of interconnector modules being received by a respective one of the at least one engagement apertures of the linkage sections to allow each of the interconnector modules to move independently relative to adjacent ones of the interconnector modules, thereby allowing the stent to define a variable diameter.

28. The stent of claim 27, wherein the interconnection members of one of the interconnector modules alternatingly extend from the interlink body in opposing circumferential directions.

29. The stent of claim 27, wherein the interconnector modules move independently relative adjacent interconnector modules in the circumferential direction.

30. The stent of claim 27, wherein the linkage sections each comprise a plurality of engagement apertures.

31. The stent of claim 27, wherein the interconnector modules are aligned in a longitudinal direction and are not joined with adjacent interconnector modules.

32. The stent of claim 27, wherein each of the plurality of linkage sections has a curved shape, and each of the plurality of interconnector modules has a curved shape that is complementary to the linkage sections.

33. The stent of claim 27, wherein each interconnector module is spaced longitudinally from adjacent interconnector modules, and adjacent interconnector modules are not directly connected to each other.

34. An axially nested stent being expandable from an axially nested unexpanded state to an expanded state, the stent comprising a tubular member having a longitudinal axis, the tubular member comprising:
a plurality of linkage sections comprising:
a plurality of longitudinally extending link elements defining proximal and distal ends;
a flexible section extending along the longitudinal axis intermediate the proximal end of a given link element and the distal end of another given link element to interconnect the plurality of link elements in an end-to-end manner; and
at least one engagement aperture disposed in at least one link element of the linkage sections, the at least one engagement aperture being disposed through the at least one link element in a circumferential direction; and
at least two interconnector modules extending in the circumferential direction, each of the at least two interconnector modules being engagable with a corresponding at least one engagement aperture of the linkage sections, each of the at least two interconnector modules comprising:
an interlink body, and
a plurality of interconnection members each having a free end;
each interlink body comprising a first side and a second side, the interconnection members extending from the first side and the second side of each interlink body, the first side of each interlink body having a number of interconnection members extending therefrom that is different from a number of interconnection members extending from the second side of each interlink body, the interconnection members of the first and second sides of each interlink body being spaced apart from each other in a longitudinal direction,
the at least two interconnector modules being configured to allow one-way slidable movement of the linkage sections relative to each interlink body during expansion of the stent from the axially nested unexpanded state to the expanded state;

wherein at least first, second, and third linkage sections are circumferentially spaced apart from each other to form the tubular member, wherein the tubular member comprises respective interconnector modules being at least partially circumferentially interposed between respective circumferentially adjacent linkage sections.

35. The stent of claim 34, wherein the linkage sections are formed separately from the at least two interconnector modules.

36. The stent of claim 34, wherein the interconnector modules connecting the first and second linkage sections and the interconnector modules connecting the second and third linkage sections at least partially define an outer surface of the tubular member.

37. The stent of claim 34, wherein in the expanded state, an end of each of the interconnection members of the at least two interconnector modules is at least partially received into a corresponding engagement aperture.

38. The stent of claim 34, wherein in the expanded state, each of the interconnection members of the at least two interconnector modules comprises an end that is substantially fixed relative to a corresponding engagement aperture.

39. The stent of claim 34, wherein in the axially nested unexpanded state, a plurality of interconnector modules are circumferentially nested.

40. The stent of claim 34, wherein each interlink body is circumferentially disposed about the longitudinal axis of the tubular member and is interposed between adjacent linkage sections.

41. The stent of claim 40, wherein each interlink body is configured with at least two interconnection members extending from the second side thereof.

42. The stent of claim 34, wherein at least one of the interconnector members comprises a plurality of teeth disposed along at least one of top and bottom surfaces thereof to engage the at least one engagement aperture for facilitating one-way expansion of the stent.

43. The stent of claim 42, wherein the teeth comprise a flexible oblique projection extending from the top surface of the at least one interconnector member.

44. The stent of claim 42, wherein the teeth comprise paddles having a free end and a fixed end, the paddles being operative to deflect during passage of the at least one interconnector member through the at least one engagement aperture and to return to an engaged position upon exiting the at least one engagement aperture to facilitate one-way expansion of the stent.

45. The stent of claim 34, wherein the at least two interconnector modules interconnect adjacent linkage sections, and wherein a length of each of the at least two interconnector modules defines a maximum distance between the adjacent linkage sections.

46. The stent of claim 34, wherein at least one of interconnection members comprises a stop member for limiting expansion of the stent.

47. The stent of claim 46, wherein the at least one engagement aperture defines a first passing profile and the stop member defines a second passing profile being greater than the first passing profile.

48. The stent of claim 34, wherein the linkage sections each comprise a plurality of engagement apertures.

49. The stent of claim 34, wherein each interlink body has a generally curved shape.

50. The stent of claim 34, wherein each interlink body has the shape of a sinusoidal curve.

51. The stent of claim 34, wherein one of the interconnection members extends from a central crest of each interlink body and a pair of the interconnection members extend from respective end troughs of each interlink body.

52. The stent of claim 34, wherein the first side of each interlink body has an odd number of interconnection members extending therefrom and the second side of each interlink body has an even number of interconnection members extending therefrom.

53. The stent of claim 52, wherein the odd number is one less than the even number.

54. The stent of claim 52, wherein the odd number is one and the even number is two.

55. The stent of claim 34, wherein the link elements have a curved shape that is complementary to a curved shape of each interlink body.

56. The stent of claim 34, wherein each of the interconnection members comprises a first end and a second end, each first end connected with one of the interlink bodies, each free end being disposed at each second end.

57. The stent of claim 34, wherein each free end of the at least two of the interconnection members comprises a stop member for limiting expansion of the stent.

58. The stent of claim 34, wherein each interconnector module is spaced longitudinally from an adjacent interconnector module, and adjacent interconnector modules are not directly connected to each other.

* * * * *